(12) United States Patent
Shukla et al.

(10) Patent No.: US 9,382,216 B2
(45) Date of Patent: Jul. 5, 2016

(54) SUBSTITUTED MORPHOLINES AS MODULATORS FOR THE CALCIUM SENSING RECEPTOR

(75) Inventors: Manojkumar Ramprasad Shukla, Maharashtra (IN); Vinod Dinkar Chaudhari, Maharashtra (IN); Majid Bashir Sayyed, Maharashtra (IN); Ramesh Dattatraya Phadtare, Maharashtra (IN); Navnath Bajirao Walke, Maharashtra (IN); Sanjeev Anant Kulkarni, Maharashtra (IN); Venkata P. Palle, Maharashtra (IN); Rajender Kumar Kamboj, Maharashtra (IN)

(73) Assignee: LUPIN LIMITED, Mumbai, Maharashtra (IN)

( * ) Notice: Subject to any disclaimer, the term of this patent is extended or adjusted under 35 U.S.C. 154(b) by 115 days.

(21) Appl. No.: 14/003,853

(22) PCT Filed: Mar. 9, 2012

(86) PCT No.: PCT/IB2012/051109
§ 371 (c)(1),
(2), (4) Date: Sep. 9, 2013

(87) PCT Pub. No.: WO2012/120476
PCT Pub. Date: Sep. 13, 2012

(65) Prior Publication Data
US 2013/0345213 A1    Dec. 26, 2013

(30) Foreign Application Priority Data
Mar. 10, 2011 (IN) .............................. 317/KOL/2011

(51) Int. Cl.
*C07D 265/30* (2006.01)
*C07D 265/32* (2006.01)
*C07D 413/04* (2006.01)

(52) U.S. Cl.
CPC ............ *C07D 265/30* (2013.01); *C07D 265/32* (2013.01); *C07D 413/04* (2013.01)

(58) Field of Classification Search
CPC ... C07D 265/30; C07D 265/32; C07D 413/07
See application file for complete search history.

(56) References Cited

U.S. PATENT DOCUMENTS

| | | |
|---|---|---|
| 2003/0199497 A1 | 10/2003 | Ruat et al. |
| 2009/0062366 A1 | 3/2009 | Hachiya et al. |
| 2010/0184805 A1 | 7/2010 | Baldwin et al. |
| 2010/0210640 A1 | 8/2010 | Lei et al. |
| 2011/0028452 A1 | 2/2011 | Didiuk et al. |

FOREIGN PATENT DOCUMENTS

| | | |
|---|---|---|
| WO | WO 97/41090 | 11/1997 |
| WO | WO 02/12181 | 2/2002 |
| WO | WO 2004/069793 | 8/2004 |
| WO | WO 2004/106280 | 12/2004 |
| WO | WO 2006/114606 | 11/2006 |
| WO | WO 2006/123725 | 11/2006 |
| WO | WO 2007/006715 | 1/2007 |
| WO | WO 2008/059854 | 5/2008 |
| WO | WO 2009/065406 | 5/2009 |
| WO | WO 2010/038895 | 4/2010 |
| WO | WO 2010/042642 | 4/2010 |
| WO | WO 2010/136037 | 12/2010 |
| WO | WO 2010/150837 | 12/2010 |

OTHER PUBLICATIONS

Brown et al., "Chiral Synthesis of 3-Substituted Morpholines via Serine Enantiomers and Reductions of 5-Oxomorpholine-3-carboxylates", *J. Chem. Soc. Perkin Trans I*, 1985, pp. 2577-2580.
Hirashima et al., "Synthesis and Biological Activity of 2-Aminothiazolines and 2-Mercaptothiazolines as Octopaminergic Agonists", *Agric. Biol. Chem.*, vol. 55, No. 10, 1991, pp. 2537-2545.
International Search Report and Written Opinion from International Application No. PCT/IB2012/051109 mailed May 7, 2012.
Kessler et al., "$N^1$-Benzoyl-$N^2$-[1-(1-naphthyl)ethyl]-*trans*-1,2-diaminocyclohexanes: Development of 4-Chlorophenylcarboxamide (Carlhex 231) as a New Calcium Sensing Receptor Ligand Demonstrating Potent Calcilytic Activity", *J. Med. Chem.*, vol. 49, 2006, pp. 5119-5128.
Leighton et al., "A Modification of Wenker's Method of Preparing Ethyleneimine", *J. Am. Chem. Soc.*, vol. 69, 1947, pp. 1540.
Miyano et al., "Kinetic Resolution of Racemic β-Hydroxy Amines by Enantioselective N-Oxide Formation", *J. Org. Chem.*, vol. 50, 1985 pp. 4350-4360.
Theoclitou et al., "Discovery of (+) N-(3-Aminopropyl)-N-[1-{5-benzyl-3-methyl-4-oxo-[1,2]thiazolo[5,4-d]pyrimidin-6-yl)-2-methylpropyl]-4-methylbenzamide {AZD4877}, a kinesin spindle protein inhibitor and potential anticancer agent", *Journal of Medicinal Chemistry, Supporting Information*, 2011, pp. S1-S44.
Yanagisawa, "Facile Synthesis of Optically Active Sulfonates of 4-*tert*-Butoxycarbonyl-2-Hydroxymethylmorpholine", *Heterocycles*, vol. 35, No. 1, 1993, pp. 105-109.

*Primary Examiner* — Rebecca Anderson
(74) *Attorney, Agent, or Firm* — Merchant & Gould P.C.

(57) ABSTRACT

Compounds of Formula (I) along with processes for their preparation that are useful for treating, managing and/or lessening the diseases, disorders, syndromes or conditions associated with the modulation of calcium sensing (CaSR) receptors. Methods of treating, managing and/or lessening the diseases, disorders, syndromes or conditions associated with the modulation of calcium sensing (CaSR) receptors of Formula (I).

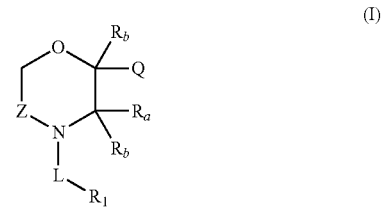

11 Claims, No Drawings

SUBSTITUTED MORPHOLINES AS MODULATORS FOR THE CALCIUM SENSING RECEPTOR

RELATED APPLICATIONS

This application is a National Stage International Application of PCT/IB2012/051109, filed Mar. 9, 2012, which claims the benefit of Indian patent application no. 0317/KOL/2011 filed on Mar. 10, 2011 and which applications are incorporated herein by reference. To the extent appropriate, a claim of priority is made to each of the above disclosed applications.

FIELD OF THE INVENTION

The present invention relates to substituted heterocyclic compounds, pharmaceutically acceptable salts thereof and pharmaceutical compositions for the treatment, management, and/or lessening the severity of diseases, disorders, syndromes or conditions associated with the modulation of calcium sensing receptors (CaSR). The invention also relates to methods of treating, managing and/or lessening the severity of diseases disorders, syndromes or conditions associated with the modulation of calcium sensing receptors (CaSR). The invention also relates to processes for the preparation of the compounds of the invention.

BACKGROUND OF THE INVENTION $Ca^{2+}$ is known to be an intracellular second messenger, with the molecular identification of an extracellular calcium sensing receptor (CaSR), it has further opened the possibility that $Ca^{2+}$ might also function as a messenger outside the cells. Information about the local changes in extracellular concentration of $Ca^{2+}$ is conveyed to the interior of many types of cells through this unique receptor.

Calcium-sensing receptor (CaSR) is a G-protein-coupled receptor (GPCR) that signals through the activation of phospholipase C, increasing levels of inositol 1,4,5-triphosphate and cytosolic calcium. The CaSR belongs to the subfamily C of the GPCR superfamily. Structurally, CaSR has an exceptionally large amino-terminal extracellular (ECD) domain (about 600 aminoacids), a feature that is shared by all of the members of the family C GPCRs.

In mammals, the expression of CaSR is quite ubiquitous and its presence in the parathyroid gland plays an important role in the secretion of parathyroid hormone (PTH). The reduction in serum calcium leads to the secretion of PTH. Consequently, PTH secretion leads to conservation of serum $Ca^{2+}$ by increasing kidney retention and intestinal absorption of $Ca^{2+}$. This happens indirectly through the PTH-induced synthesis of the active vitamin D metabolite, 25-dihydroxyvitamin D. In addition, the pulsatile action of PTH has anabolic effects on bone development and its sustained levels can lead to catabolic effects, in which the bones breakdown releasing $Ca^{2+}$ as in the case of osteoporosis. All these systems converge in maintenance of baseline serum $Ca^{2+}$ and it involves a tight regulation between serum PTH and extracellular calcium which is mediated by the remarkable receptor CaSR.

In conditions such as primary and secondary hyperparathyroidism, there is excessive secretion of parathyroid hormone due to hyperplasia of the glands. The most common cause of primary hyperparathyroidism (PHPT) is parathyroid adenoma resulting from clonal mutations (~97%) and associated hypercalcemia. In the case of secondary hyperparathyroidism (SHPT), it is most commonly seen in patients with chronic renal failure. The kidneys fail to convert enough vitamin D to its active form and also does not adequately excrete phosphorous. Excess phosphorous further depletes serum calcium forming calcium phosphate (kidney stones) leading to hypocalcemia.

Small molecules that are positive allosteric modulators called calcimimetics modulate and improve the receptors sensitivity to the already existing milieu of extracellular ionic calcium. This would eventually translate in lowering plasma PTH levels thereby improving conditions of hyperparathyroidism, calcium homeostasis and bone metabolism.

US 2011/0028452, WO 2010/150837, WO 2010/136037, WO 2010/042642, WO 2010/038895, WO 2009/065406, WO 2008/059854, WO 2006/123725, WO 2004/106280, WO 2004/069793, WO 2002/012181 and US 2003/0199497 applications disclose the compounds related to calcium sensing receptors (CaSR) for the treatment of various diseases mediated by CaSR. And also J. Med. Chem. (2006), 49, 5119-5128 discloses the compounds related to calcium sensing receptors (CaSR).

SUMMARY OF THE INVENTION

In accordance with one aspect, the invention provide compounds having the structure of Formula (I),

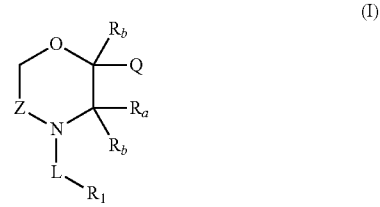

wherein,
Q is hydrogen or

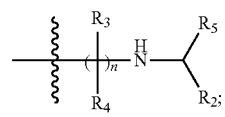

$R_a$ is selected from

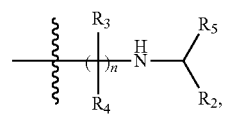

hydrogen, halogen, cyano, substituted or unsubstituted alkyl, substituted or unsubstituted cycloalkyl and substituted or unsubstituted haloalkyl;

$R_b$ is selected from hydrogen, halogen, cyano, substituted or unsubstituted alkyl, substituted or unsubstituted cycloalkyl and substituted or unsubstituted haloalkyl;

or $R_a$ and $R_b$ together attached on the same carbon form C(O) or C(S);

provided that,
when Q is

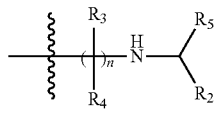

then
R$_a$ is selected from hydrogen, halogen, substituted or unsubstituted alkyl, cyano, substituted or unsubstituted cycloalkyl and substituted or unsubstituted haloalkyl; or R$_a$ and R$_b$ together attached on the same carbon atom form C(O) or C(S);
when Q is hydrogen then R$_a$ is

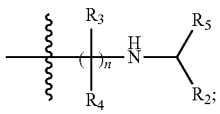

L is selected from a bond, —(CR$_c$R$_d$)$_m$—, —C(O)—, —C(S)—, —C(O)NR$_7$—, —S(O)$_2$—, —S(O)$_2$—NR$_7$, —C(O)CH$_2$—, —CH$_2$C(O)— and —C(O)O—;

R$_c$ and R$_d$, which may be same or different at each occurrence, are independently selected from hydrogen, halogen, substituted or unsubstituted alkyl and substituted or unsubstituted haloalkyl;

R$_1$ is selected from

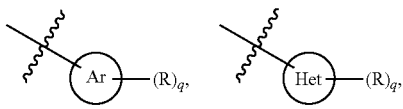

substituted or unsubstituted alkyl, —(CR$_e$R$_f$)$_{1-3}$—C(O)OR$_6$, substituted or unsubstituted haloalkyl, substituted or unsubstituted alkenyl, substituted or unsubstituted alkynyl, substituted or unsubstituted cycloalkyl and substituted or unsubstituted cycloalkenyl;

ring Ar is phenyl or naphthyl;
ring Het is heteroaryl, or heterocyclyl;
R, which may be same or different at each occurrence, is independently selected from halogen, nitro, cyano, substituted or unsubstituted alkyl, substituted or unsubstituted alkenyl, substituted or unsubstituted alkynyl, substituted or unsubstituted haloalkyl, substituted or unsubstituted hydroxyalkyl, substituted or unsubstituted cycloalkyl, —OR$_6$, —C(O)R$_6$, —(CR$_e$R$_f$)$_{0-3}$—C(O)OR$_6$, —(CR$_e$R$_f$)$_{1-2}$cycloalkylene-C(O)OR$_6$, -cycloalkylene (CR$_e$R$_f$)$_{0-2}$—C(O)OR$_6$, —O(CR$_e$R$_f$)$_{0-3}$—C(O)OR$_6$, —O-cycloalkylene-C(O)OR$_6$, —C(O)NR$_7$—(CR$_e$R$_f$)$_{1-2}$—C(O)OR$_6$, —C(O)NR$_7$R$_8$, —S(O)$_{0-2}$R$_6$, and —S(O)$_2$NR$_7$R$_8$;

R$_e$ and R$_f$, which may be same or different at each occurrence, are independently selected from hydrogen, halogen, hydroxy, cyano, nitro, substituted or unsubstituted alkyl, substituted or unsubstituted haloalkyl and substituted or unsubstituted cycloalkyl; or R$_e$ and R$_f$, together with the carbon atom to which they are attached, form a substituted or unsubstituted 3 to 7 membered saturated carbocyclic ring;

R$_2$ is selected from substituted or unsubstituted aryl, substituted or unsubstituted heteroaryl and substituted or unsubstituted heterocyclyl;

R$_3$ and R$_4$, which may be same or different at each occurrence, are independently selected from hydrogen, halogen, substituted or unsubstituted alkyl, substituted or unsubstituted haloalkyl, substituted or unsubstituted alkenyl, substituted or unsubstituted alkynyl, substituted or unsubstituted alkoxy, substituted or unsubstituted haloalkoxy and substituted or unsubstituted cycloalkyl;

R$_5$ is substituted or unsubstituted alkyl or substituted or unsubstituted haloalkyl;

R$_6$, which may be same or different at each occurrence, is independently selected from hydrogen, substituted or unsubstituted alkyl and substituted or unsubstituted haloalkyl;

R$_7$ and R$_8$, which may be same or different at each occurrence, are independently selected from hydrogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, and substituted or unsubstituted heterocyclylalkyl; or R$_7$ and R$_8$, together with the nitrogen atom to which they are attached, form a substituted or unsubstituted 4 to 12 membered cyclic ring, where the cyclic ring may be substituted or unsubstituted heteroaryl or heterocyclyl;

Z is selected from —CR$_g$R$_h$, —C(O), and —C(S);
R$_g$ and R$_h$ are independently selected from hydrogen, halogen, cyano, nitro, substituted or unsubstituted alkyl and substituted or unsubstituted haloalkyl;

'm' is an integer ranging from 1 to 3, both inclusive;
'n' is an integer ranging from 1 to 3, both inclusive; and
'q' is an integer ranging from 0 to 4, both inclusive;
or pharmaceutically acceptable salt thereof.

According to one embodiment, there is provided a compound of the formula (II):

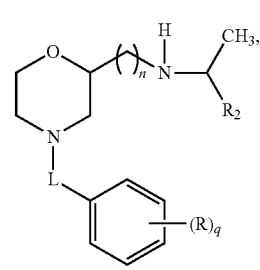

or pharmaceutically acceptable salt thereof;
wherein,
L is selected from a bond, —(CR$_c$R$_d$)$_m$—, —C(O)— and —C(O)NR$_7$—;
R$_2$ is substituted or unsubstituted phenyl or substituted or unsubstituted naphthyl;
R$_c$, R$_d$, R, R$_7$, 'm', 'n' and 'q' are as defined in Formula (I).

According to another embodiment, there is provided a compound of the formula (III):

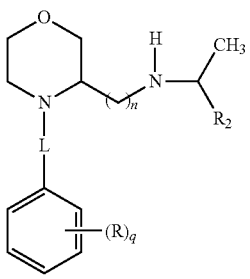

(III)

or pharmaceutically acceptable salt thereof;
wherein,
L is selected from a bond, —(CR$_c$R$_d$)$_m$, —C(O)— and —C(O)NR$_7$—;
R$_2$ is substituted or unsubstituted phenyl or substituted or unsubstituted naphthyl;
R$_c$, R$_d$, R, R$_7$, 'm', 'n' and 'q' are as defined in Formula (I).

According to another embodiment, there is provided a compound of the formula (IV):

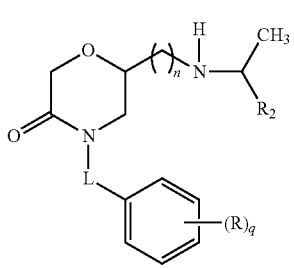

(IV)

or pharmaceutically acceptable salt thereof;
wherein,
L is selected from a bond, —(CR$_c$R$_d$)$_m$, —C(O)— and —C(O)NR$_7$—;
R$_2$ is substituted or unsubstituted phenyl or substituted or unsubstituted naphthyl;
R$_c$, R$_d$, R, R$_7$, 'm', 'n' and 'q' are as defined in Formula (I).

According to another embodiment, there is provided a compound of the formula (V):

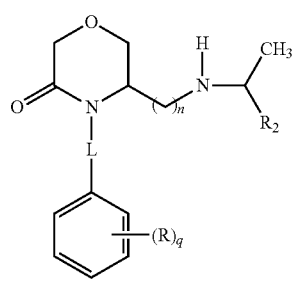

(V)

or pharmaceutically acceptable salt thereof;
wherein,
L is selected from a bond, —(CR$_c$R$_d$)$_m$, —C(O)— and —C(O)NR$_7$—;
R$_2$ is substituted or unsubstituted phenyl or substituted or unsubstituted naphthyl;
R$_c$, R$_d$, R, R$_7$, 'm', 'n' and 'q' are as defined in Formula (I).

It should be understood that the Formulae (I), (II), (III), (IV) and (V) structurally encompasses all tautomers, stereoisomers, including isotopes wherever applicable and pharmaceutically acceptable salts that may be contemplated from the chemical structure of the genera described herein.

The details of one or more embodiments of the invention set forth in the below are illustrative in nature only and not intended to limit to the scope of the invention. Other features, objects and advantages of the inventions will be apparent from the description and claims.

According to one sub embodiment, there are provided compounds of formula (I) in which L is selected from a bond, —(CR$_c$R$_d$)$_m$, —C(O)—, —C(S)—, —C(O)NR$_7$—, —S(O)$_2$—, —S(O)$_2$—NR$_7$, —C(O)CH$_2$—, —CH$_2$C(O)— and —C(O)O—; where R$_c$ and R$_d$ are independently selected from hydrogen, halogen, substituted or unsubstituted alkyl and substituted or unsubstituted haloalkyl; R$_7$ is selected from hydrogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, and substituted or unsubstituted heterocyclylalkyl; and 'm' is 1 or 2.

According to one sub embodiment, there are provided compounds of formula (I) in which L is a bond and R$_1$ is substituted or unsubstituted alkyl, substituted or unsubstituted cycloalkyl, substituted or unsubstituted heteroaryl, substituted or unsubstituted heterocyclyl, substituted or unsubstituted cycloalkylalkyl wherein the substituents are selected from halogen, substituted or unsubstituted alkyl, —C(O)OH or —C(O)Oalkyl.

According to one sub embodiment, there are provided compounds of formula (I) in which L is selected from —(CR$_c$R$_d$)$_m$, —C(S)—, —S(O)$_2$—, —S(O)$_2$—NR$_7$, —C(O)CH$_2$—, —CH$_2$C(O)— and —C(O)O—.

According to another sub embodiment, there are provided compounds of formulae (II), (III), (IV) and/or (V) in which 'n' is 1.

According to another sub embodiment, there are provided compounds of formulae (II), (III), (IV) and/or (V) in which 'n' is 2.

According to another sub embodiment, there are provided compounds of formulae (II), (III), (IV) and/or (V) in which R may be one or more, same or different and are independently selected from halogen, nitro, cyano, substituted or unsubstituted alkyl, substituted or unsubstituted alkenyl, substituted or unsubstituted alkynyl, substituted or unsubstituted haloalkyl, substituted or unsubstituted hydroxyalkyl, —OR$_6$, —C(O)R$_6$, —(CR$_e$R$_f$)$_{0-3}$—C(O)OR$_6$, —(CR$_e$R$_f$)$_{1-2}$cycloalkylene-C(O)OR$_6$, -cycloalkylene (CR$_e$R$_f$)$_{0-2}$—C(O)OR$_6$, —O(CR$_e$R$_f$)$_{0-3}$—C(O)OR$_6$, —O-cycloalkylene-C(O)OR$_6$, —C(O)NR$_7$—(CR$_e$R$_f$)$_{1-2}$—C(O)OR$_6$, —C(O)NR$_7$R$_8$, —S(O)$_{0-2}$R$_6$, and —S(O)$_2$NR$_7$R$_8$; where R$_6$ is hydrogen or alkyl; R$_e$ and R$_f$ are independently selected from hydrogen, halogen, hydroxy, cyano, nitro, substituted or unsubstituted alkyl, substituted or unsubstituted haloalkyl and substituted or unsubstituted cycloalkyl; or R$_e$ and R$_f$ together with the carbon atom to which they are attached, form a substituted or unsubstituted 3 to 7 membered saturated carbocyclic ring; R$_7$ and R$_8$ are independently selected from hydrogen, substituted or unsubstituted alkyl, substituted or unsubstituted cycloalkylalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, and substituted or unsubstituted heterocyclylalkyl; and 'q' is 0 to 3.

According to another sub embodiment, there are provided compounds of formulae (II), (III), (IV) and/or (V) in which R may be one or more, same or different and are independently selected from halogen, substituted or unsubstituted alkyl, substituted or unsubstituted haloalkyl, —$OR_6$, —$(CH_2)_{0-2}$—$C(O)OR_6$, —$C(O)NHCH_3$, —$C(O)N(CH_3)_2$, —O—$(CH_2)_{1-2}$—$COOR_6$, —$C(O)NHCH_2C(O)OR_6$ where $R_6$ is hydrogen or alkyl; and 'q' is 0 to 3.

According to another sub embodiment, there are provided compounds of formulae (II), (III), (IV) and/or (V) in which $R_2$ is substituted or unsubstituted phenyl or substituted or unsubstituted naphthyl wherein the substituent(s) may be one or more, same or different and are independently selected from halogen, substituted or unsubstituted alkyl, alkoxy, and substituted or unsubstituted alkoxy.

According to another sub embodiment, there are provided compounds of formula (I) in which Q is

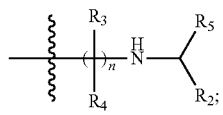

$R_a$ is hydrogen; $R_b$ is hydrogen or substituted or unsubstituted alkyl; Z is —$CH_2$— or —$C(O)$—;

L is selected from a bond, —$(CR_cR_d)_m$—, —$C(O)$—, —$C(O)NH$—, —$C(O)CH_2$— and —$CH_2C(O)$—;

$R_1$ is selected from

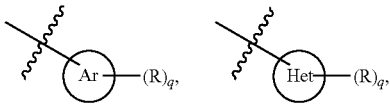

substituted or unsubstituted alkyl, —$(CR_eR_f)_{1-3}$—$C(O)OR_6$, substituted or unsubstituted haloalkyl and substituted or unsubstituted cycloalkyl;

ring Ar is phenyl or naphthyl; ring Het is heteroaryl or heterocyclyl;

R is independently selected from halogen, substituted or unsubstituted alkyl, substituted or unsubstituted haloalkyl, substituted or unsubstituted hydroxyalkyl, —$OR_6$, —$(CR_eR_f)_{0-3}$—$C(O)OR_6$, —$O(CR_eR_f)_{0-3}$—$C(O)OR_6$, —O-cycloalkylene-$C(O)OR_6$, —$C(O)NR_7$—$(CR_eR_f)_{1-2}$—$C(O)OR_6$, and —$C(O)NR_7R_8$;

$R_e$ and $R_f$ are hydrogen, halogen, substituted or unsubstituted alkyl, substituted or unsubstituted haloalkyl and substituted or unsubstituted cycloalkyl; or $R_e$ and $R_f$ together form a substituted or unsubstituted 3 to 7 membered saturated carbocyclic ring;

$R_2$ substituted or unsubstituted aryl, wherein the substituent(s) may be one or more same or different and independently selected from halogen, substituted or unsubstituted alkyl, substituted or unsubstituted haloalkyl, substituted or unsubstituted alkoxy and substituted or unsubstituted haloalkoxy;

$R_3$ and $R_4$ hydrogen; $R_5$ is substituted or unsubstituted alkyl or substituted or unsubstituted haloalkyl;

$R_6$ is hydrogen, substituted or unsubstituted alkyl and substituted or unsubstituted haloalkyl;

$R_7$ and $R_8$ are hydrogen or substituted or unsubstituted alkyl; 'n' is 1 or 2; and 'q' is 0 to 3; or pharmaceutically acceptable salt thereof.

According to another sub embodiment, there are provided compounds of formula (I) in which $R_a$ is

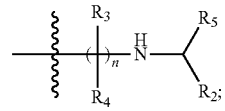

$R_b$ is hydrogen or substituted or unsubstituted alkyl; Q is hydrogen; Z is —$CH_2$— or —$C(O)$—;

L is selected from a bond, —$(CR_cR_d)_m$—, —$C(O)$—, —$C(O)NH$—, —$C(O)CH_2$— and —$CH_2C(O)$—;

$R_1$ is selected from

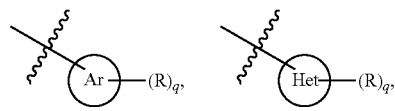

substituted or unsubstituted alkyl, —$(CR_eR_f)_{1-3}$—$C(O)OR_6$, substituted or unsubstituted haloalkyl and substituted or unsubstituted cycloalkyl;

ring Ar is phenyl or naphthyl; ring Het is heteroaryl or heterocyclyl;

R is independently selected from halogen, substituted or unsubstituted alkyl, substituted or unsubstituted haloalkyl, substituted or unsubstituted hydroxyalkyl, —$OR_6$, —$(CR_eR_f)_{0-3}$—$C(O)OR_6$, —$O(CR_eR_f)_{0-3}$—$C(O)OR_6$, —O-cycloalkylene-$C(O)OR_6$, —$C(O)NR_7$—$(CR_eR_f)_{1-2}$—$C(O)OR_6$, and —$C(O)NR_7R_8$;

$R_e$ and $R_f$ are hydrogen, halogen, substituted or unsubstituted alkyl, substituted or unsubstituted haloalkyl and substituted or unsubstituted cycloalkyl; or $R_e$ and $R_f$ together form a substituted or unsubstituted 3 to 7 membered saturated carbocyclic ring;

$R_2$ is substituted or unsubstituted aryl, wherein the substituent(s) may be one or more same or different and independently selected from halogen, substituted or unsubstituted alkyl, substituted or unsubstituted haloalkyl, substituted or unsubstituted alkoxy and substituted or unsubstituted haloalkoxy;

$R_3$ and $R_4$ hydrogen; $R_5$ is substituted or unsubstituted alkyl or substituted or unsubstituted haloalkyl;

$R_6$ is hydrogen, substituted or unsubstituted alkyl and substituted or unsubstituted haloalkyl;

$R_7$ and $R_8$ are hydrogen or substituted or unsubstituted alkyl; 'n' is 1 or 2; and 'q' is 0 to 3; or pharmaceutically acceptable salt thereof.

According to another sub embodiment, there are provided compounds of formula (I) in which the compounds are used as either free base or a pharmaceutically acceptable salt; where the pharmaceutically acceptable salt is monohydrochloride or dihydrochloride salt.

According to another sub embodiment, the provided compounds of formula (I) structurally encompasses stereoisomers including enantiomers and diastereomers.

Below are the representative compounds, which are illustrative in nature only and are not intended to limit to the scope of the invention.

(1R)-1-(Naphthalen-1-yl)-N-((4-phenylmorpholin-3-yl)methyl)ethanamine hydrochloride;
(1R)-1-(Naphthalen-1-yl)-N-((4-(3-(trifluoromethyl)phenyl)morpholin-3-yl)methyl)ethanamine;

(1R)-N-((4-(3-Fluorophenyl)morpholin-2-yl)methyl)-1-(naphthalen-1-yl)ethanamine hydrochloride;
(1R)-1-(3-Methoxy phenyl)-N-((4-(3-(trifluoromethyl)phenyl)morpholin-3-yl)methyl)ethanamine;
(1R)-N-((4-(3-Methoxyphenyl)morpholin-3-yl)methyl)-1-(naphthalen-1-yl)ethanamine hydrochloride;
(1R)-1-(3-Methoxy phenyl)-N-((4-(3-methoxyphenyl)morpholin-3-yl)methyl)ethanamine;
(1R)-1-(Naphthalen-1-yl)-N-((4-(p-tolyl)morpholin-3-yl)methyl)ethanamine;
(1R)-1-(3-Methoxy phenyl)-N-((4-(p-tolyl)morpholin-3-yl)methyl)ethanamine;
(1R)-N-((4-(3-Fluorophenyl)morpholin-3-yl)methyl)-1-(naphthalen-1-yl)ethanamine hydrochloride;
(1R)-1-(3-Methoxyphenyl)-N-((4-(m-tolyl)morpholin-3-yl)methyl)ethanamine hydrochloride;
(1R)-1-(3-Methoxy phenyl)-N-((4-phenylmorpholin-3-yl)methyl)ethanamine hydrochloride;
(1R)-N-((4-(3,4-Difluorophenyl)morpholin-3-yl)methyl)-1-(3-methoxyphenyl)ethanamine hydrochloride;
(1R)-1-(3-Methoxyphenyl)-N-((4-(3-methoxyphenyl)morpholin-3-yl)methyl)ethanamine;
(1R)-N-((4-(4-Fluorophenyl)morpholin-3-yl)methyl)-1-(3-methoxyphenyl)ethanamine hydrochloride;
(1R)-N-((4-(3-Fluorophenyl)morpholin-3-yl)methyl)-1-(3-methoxyphenyl)ethanamine hydrochloride;
(1R)-N-((4-(3-Fluoro-4-methoxyphenyl)morpholin-3-yl)methyl)-1-(3-methoxyphenyl)ethanamine hydrochloride;
(1R)-N-((4-(4-Fluorophenyl)morpholin-3-yl)methyl)-1-(naphthalen-1-yl)ethanamine hydrochloride;
N,N-Dimethyl-3-(3-((((R)-1-(naphthalen-1-yl)ethyl)amino)methyl)morpholino)benzamide hydrochloride;
N-Methyl-3-(3-((((R)-1-(naphthalen-1-yl)ethyl)amino)methyl)morpholino)benzamide hydrochloride;
Methyl 4-(3-((((R)-1-(naphthalen-1-yl)ethyl)amino)methyl)morpholino)benzoate hydrochloride;
4-(3-((((R)-1-(Naphthalen-1-yl)ethyl)amino)methyl)morpholino)benzoic acid hydrochloride;
(1R)-1-(Naphthalen-1-yl)-N-((4-(3-(trifluoromethyl)phenyl)morpholin-2-yl)methyl)ethanamine;
(1R)-1-(3-Methoxyphenyl)-N-((4-(3-methoxyphenyl)morpholin-2-yl)methyl)ethanamine;
(1R)-1-(3-Methoxyphenyl)-N-((4-(3-(trifluoromethyl)phenyl)morpholin-2-yl)methyl)ethanamine;
(1R)-N-((4-(3-Methoxyphenyl)morpholin-2-yl)methyl)-1-(naphthalen-1-yl)ethanamine;
(1R)-1-(Naphthalen-1-yl)-N-((4-phenylmorpholin-2-yl)methyl)ethanamine hydrochloride;
(1R)-1-(Naphthalen-1-yl)-N-((4-(p-tolyl)morpholin-2-yl)methyl)ethanamine hydrochloride;
(1R)-N-((4-(4-Fluorophenyl)morpholin-2-yl)methyl)-1-(naphthalen-1-yl)ethanamine hydrochloride;
(1R)-N-((4-(2-Fluorophenyl)morpholin-2-yl)methyl)-1-(naphthalen-1-yl)ethanamine hydrochloride;
(1R)-N-((4-(4-Fluoro-3-methoxyphenyl)morpholin-2-yl)methyl)-1-(naphthalen-1-yl)ethanamine hydrochloride;
(1R)-N-((4-(3-Fluorophenyl)morpholin-2-yl)methyl)-1-(3-methoxyphenyl)ethanamine dihydrochloride;
(1R)-1-(3-Methoxyphenyl)-N-((4-(3-(trifluoromethyl)phenyl)morpholin-2-yl)methyl)ethanamine hydrochloride;
(1R)-1-(Naphthalen-1-yl)-N-((4-(4-(trifluoromethyl)phenyl)morpholin-2-yl)methyl)ethanamine hydrochloride;
(1R)-N-((4-(2,4-difluorophenyl)morpholin-2-yl)methyl)-1-(3-methoxyphenyl)ethanamine hydrochloride;
(1R)-1-(Naphthalen-1-yl)-N-((4-(3-(trifluoromethyl)benzyl)morpholin-3-yl)methyl)ethanamine;
(1R)-N-((4-Benzylmorpholin-3-yl)methyl)-1-(naphthalen-1-yl)ethanamine;
(1R)-N-((4-Benzylmorpholin-3-yl)methyl)-1-(3-methoxyphenyl)ethanamine;
(1R)-1-(Naphthalen-1-yl)-N-((4-(4-(trifluoromethyl)benzyl)morpholin-3-yl)methyl)ethanamine;
(3-((((R)-1-(Naphthalen-1-yl)ethyl)amino)methyl)morpholino)(phenyl)methanone;
(3-((((R)-1-(3-Methoxyphenyl)ethyl)amino)methyl)morpholino)(phenyl)methanone;
3-((((R)-1-(Naphthalen-1-yl)ethyl)amino)methyl)-N-phenylmorpholine-4-carboxamide hydrochloride;
3-((((R)-1-(Naphthalen-1-yl)ethyl)amino)methyl)-N-(3-(trifluoromethyl)phenyl)morpholine-4-carboxamide hydrochloride;
3-((((R)-1-(Naphthalen-1-yl)ethyl)amino)methyl)-N-(p-tolyl)morpholine-4-carboxamide hydrochloride;
N-(4-Fluorophenyl)-3-((((R)-1-(naphthalen-1-yl)ethyl)amino)methyl)morpholine-4-carboxamide hydrochloride;
N-(3-Methoxyphenyl)-3-((((R)-1-(naphthalen-1-yl)ethyl)amino)methyl)morpholine-4-carboxamide hydrochloride;
3-((((R)-1-(3-Methoxyphenyl)ethyl)amino)methyl)-N-(3-(trifluoromethyl)phenyl) morpholine-4-carboxamide hydrochloride;
4-Benzyl-5-((((R)-1-(naphthalen-1-yl)ethyl)amino)methyl)morpholin-3-one;
4-Benzyl-5-((((R)-1-(3-methoxyphenyl)ethyl)amino)methyl)morpholin-3-one hydrochloride;
6-((((R)-1-(Naphthalen-1-yl)ethyl)amino)methyl)-4-phenylmorpholin-3-one hydrochloride;
4-(3-Fluoro-4-methoxyphenyl)-6-((((R)-1-(3-methoxyphenyl)ethyl)amino)methyl)morpholin-3-one;
6-((((R)-1-(Naphthalen-1-yl)ethyl)amino)methyl)-4-(m-tolyl)morpholin-3-one hydrochloride;
4-(3-Fluorophenyl)-6-((((R)-1-(naphthalen-1-yl)ethyl)amino)methyl)morpholin-3-one hydrochloride;
3-(2-((((R)-1-(Naphthalen-1-yl)ethyl)amino)methyl)-5-oxomorpholino)benzoic acid hydrochloride;
4-(2,3-Difluorophenyl)-6-((((R)-1-(naphthalen-1-yl)ethyl)amino)methyl)morpholin-3-one hydrochloride;
6-((((R)-1-(Naphthalen-1-yl)ethyl)amino)methyl)-4-(4-(trifluoromethyl)phenyl)morpholin-3-one hydrochloride;
2-Fluoro-5-(2-((((R)-1-(naphthalen-1-yl)ethyl)amino)methyl)-5-oxomorpholino)benzoic acid hydrochloride;
4-(2-((((R)-1-(Naphthalen-1-yl)ethyl)amino)methyl)-5-oxomorpholino)benzoic acid hydrochloride;
2-(3-(2-((((R)-1-(Naphthalen-1-yl)ethyl)amino)methyl)-5-oxomorpholino)phenoxy)acetic acid hydrochloride;
4-(2,2-Difluorobenzo[d][1,3]-dioxol-5-yl)-6-((((R)-1-(naphthalen-1-yl)ethyl)amino)methyl)morpholin-3-one hydrochloride;
2-(4-(2-((((R)-1-(Naphthalen-1-yl)ethyl)amino)methyl)-5-oxomorpholino)phenyl)acetic acid hydrochloride;
4-(3-Fluoro-4-methoxyphenyl)-6-((((R)-1-(naphthalen-1-yl)ethyl)amino)methyl)morpholin-3-one hydrochloride;
4-(3,4-Difluorophenyl)-6-((((R)-1-(naphthalen-1-yl)ethyl)amino)methyl)morpholin-3-one hydrochloride;
6-((((R)-1-(Naphthalen-1-yl)ethyl)amino)methyl)-4-(3-(trifluoromethyl)phenyl)morpholin-3-one hydrochloride;
3-(2-((((R)-1-(3-Methoxyphenyl)ethyl)amino)methyl)-5-oxomorpholino)-N,N-dimethylbenzamide hydrochloride;
4-(2-((((R)-1-(3-Methoxyphenyl)ethyl)amino)methyl)-5-oxomorpholino)benzoic acid hydrochloride;
3-(2-((((R)-1-(3-Methoxyphenyl)ethyl)amino)methyl)-5-oxomorpholino)benzoic acid hydrochloride;
4-(3,4-Difluorophenyl)-6-((((R)-1-(3-methoxyphenyl)ethyl)amino)methyl)morpholin-3-one hydrochloride;

6-((((R)-1-(4-Fluoro-3-methoxyphenyl)ethyl)amino)methyl)-4-(3-fluoro-4-methoxy phenyl)morpholin-3-one hydrochloride;
4-(Cyclopentylmethyl)-6-((((R)-1-(naphthalen-1-yl)ethyl)amino)methyl)morpholin-3-one;
6-((((R)-1-(Naphthalen-1-yl)ethyl)amino)methyl)-4-(3-(trifluoromethyl)benzyl)morpholin-3-one hydrochloride;
6-((((R)-1-(Naphthalen-1-yl)ethyl)amino)methyl)-4-(2,4,5-trifluorobenzyl)morpholin-3-one hydrochloride;
4-(2,5-Difluorobenzyl)-6-((((R)-1-(naphthalen-1-yl)ethyl)amino)methyl)morpholin-3-one hydrochloride;
4-((2-(((((R)-1-(Naphthalen-1-yl)ethyl)amino)methyl)-5-oxomorpholino)methyl)benzoic acid hydrochloride;
2-(4-((2-(((((R)-1-(Naphthalen-1-yl)ethyl)amino)methyl)-5-oxomorpholino)methyl)benzamido)acetic acid hydrochloride;
4-(2,6-Difluorobenzyl)-6-((((R)-1-(naphthalen-1-yl)ethyl)amino)methyl)morpholin-3-one hydrochloride;
4-Cyclopentyl-6-((((R)-1-(naphthalen-1-yl)ethyl)amino)methyl)morpholin-3-one hydrochloride;
4-Ethyl-6-((((R)-1-(naphthalen-1-yl)ethyl)amino)methyl)morpholin-3-one hydrochloride;
2-(2-((((R)-1-(Naphthalen-1-yl)ethyl)amino)methyl)-5-oxomorpholino)acetic acid hydrochloride;
6-((((R)-1-(Naphthalen-1-yl)ethyl)amino)methyl)-4-(4-(trifluoromethyl)benzyl)morpholin-3-one hydrochloride;
3-((2-((((R)-1-(Naphthalen-1-yl)ethyl)amino)methyl)-5-oxomorpholino)methyl)benzoic acid hydrochloride;
4-(2,3-Difluorobenzyl)-6-((((R)-1-(naphthalen-1-yl)ethyl)amino)methyl)morpholin-3-one hydrochloride;
4-(4-Fluoro-2-(trifluoromethyl)benzyl)-6-((((R)-1-(naphthalen-1-yl)ethyl)amino)methyl)morpholin-3-one hydrochloride;
6-((((R)-1-(Naphthalen-1-yl)ethyl)amino)methyl)-4-(3-(trifluoromethyl)phenethyl)morpholin-3-one hydrochloride;
4-(3-Chlorophenethyl)-6-((((R)-1-(naphthalen-1-yl)ethyl)amino)methyl)morpholin-3-one hydrochloride;
4-(3-Methoxyphenethyl)-6-((((R)-1-(naphthalen-1-yl)ethyl)amino)methyl)morpholin-3-one hydrochloride;
4-(4-Fluorobenzyl)-6-((((R)-1-(naphthalen-1-yl)ethyl)amino)methyl)morpholin-3-one hydrochloride;
4-(4-Fluoro-3-(trifluoromethyl)benzyl)-6-((((R)-1-(naphthalen-1-yl)ethyl)amino)methyl)morpholin-3-one;
4-(1-(4-Fluorophenyl)ethyl)-6-((((R)-1-(naphthalen-1-yl)ethyl)amino)methyl)morpholin-3-one hydrochloride;
4-(1-(3,4-Difluorophenyl)ethyl)-6-((((R)-1-(naphthalen-1-yl)ethyl)amino)methyl)morpholin-3-one hydrochloride;
4-(Cyclopentylmethyl)-6-((((R)-1-(4-fluoro-3-methoxyphenyl)ethyl)amino)methyl)morpholin-3-one hydrochloride;
4-(4-Fluoro-3-(trifluoromethyl)benzyl)-6-((((R)-1-(4-fluoro-3-methoxyphenyl)ethyl)amino)methyl)morpholin-3-one hydrochloride;
4-(2,3-Difluorobenzyl)-6-((((R)-1-(4-fluoro-3-methoxyphenyl)ethyl)amino)methyl)morpholin-3-one hydrochloride;
4-Isopropyl-6-((((R)-1-(naphthalen-1-yl)ethyl)amino)methyl)morpholin-3-one hydrochloride;
6-((((R)-1-(Naphthalen-1-yl)ethyl)amino)methyl)-4-neopentylmorpholin-3-one hydrochloride;
4-Cyclopropyl-6-((((R)-1-(naphthalen-1-yl)ethyl)amino)methyl)morpholin-3-one hydrochloride;
4-Cyclopentyl-6-((((R)-1-(4-fluoro-3-methoxyphenyl)ethyl)amino)methyl)morpholin-3-one hydrochloride;
4-(Cyclopropylmethyl)-6-((((R)-1-(naphthalen-1-yl)ethyl)amino)methyl)morpholin-3-one hydrochloride;
4-(4-Fluorophenethyl)-6-((((R)-1-(naphthalen-1-yl)ethyl)amino)methyl)morpholin-3-one hydrochloride;
4-(3,4-Difluorobenzyl)-6-((((R)-1-(4-fluoro-3-methoxyphenyl)ethyl)amino)methyl)morpholin-3-one hydrochloride;
4-(3,4-Difluorobenzyl)-6-((((R)-1-(naphthalen-1-yl)ethyl)amino)methyl)morpholin-3-one hydrochloride;
6-((((R)-1-(4-Fluoro-3-methoxyphenyl)ethyl)amino)methyl)-4-(4-fluorobenzyl)morpholin-3-one hydrochloride;
2-(4-(2-(2-(((R)-1-(Naphthalen-1-yl)ethyl)amino)ethyl)morpholino)phenoxy) acetic acid hydrochloride;
2-Methyl-5-(2-(2-(((R)-1-(naphthalen-1-yl)ethyl)amino)ethyl)morpholino)benzoic acid;
2-Methyl-4-(2-(2-(((R)-1-(naphthalen-1-yl)ethyl)amino)ethyl)morpholino)benzoic acid;
(1R)-1-(Naphthalen-1-yl) N (2 (4 (4 (trifluoromethyl)phenyl) morpholin-2-yl)ethyl)ethanamine;
2-(2-Methyl-4-(2-(2-(((R)-1-(naphthalen-1-yl)ethyl)amino)ethyl)morpholino)phenoxy)acetic acid hydrochloride;
2-(2-Methyl-5-(2-(2-(((R)-1-(naphthalen-1-yl)ethyl)amino)ethyl)morpholino)phenoxy)acetic acid hydrochloride;
3-(2-Methyl-5-(2-(2-(((R)-1-(naphthalen-1-yl)ethyl)amino)ethyl)morpholino)phenyl)propanoic acid hydrochloride;
4-(2-(2-(((R)-1-(Naphthalen-1-yl)ethyl)amino)ethyl)morpholino)-2-(trifluoromethyl)benzoic acid hydrochloride;
5-(2-(2-(((R)-1-(Naphthalen-1-yl)ethyl)amino)ethyl)morpholino)-2-(trifluoromethyl)benzoic acid hydrochloride;
3-(2-(2-(((R)-1-(Naphthalen-1-yl)ethyl)amino)ethyl)morpholino)benzoicacid hydrochloride;
4-(2-(2-(((R)-1-(Naphthalen-1-yl)ethyl)amino)ethyl)morpholino)benzoicacid hydrochloride;
2-(3-(2-(2-(((R)-1-(Naphthalen-1-yl)ethyl)amino)ethyl)morpholino)phenoxy)acetic acid hydrochloride;
2,6-Dimethyl-3-(2-(2-(((R)-1-(naphthalen-1-yl)amino)ethyl)morpholino)benzoic acid;
4-((2-(2-(((R)-1-(Naphthalen-1-yl)ethyl)amino)ethyl)morpholino)methyl)benzoic acid hydrochloride;
3-((2-(2-(((R)-1-(Naphthalen-1-yl)ethyl)amino)ethyl)morpholino)methyl)benzoic acid dihydrochloride;
3-(3-(2-(((R)-1-(Naphthalen-1-yl)ethyl)amino)ethyl)morpholino)-5-(trifluoromethyl)benzoic acid hydrochloride;
2-Methyl-4-(3-((((R)-1-(naphthalen-1-yl)ethyl)amino)methyl)morpholino)benzoic acid hydrochloride;
2-Methyl-5-(3-((((R)-1-(naphthalen-1-yl)ethyl)amino)methyl)morpholino)benzoic acid hydrochloride;
(1R)-1-(Naphthalen-1-yl)-N-((4-(m-tolyl)morpholin-3-yl)methyl)ethanamine;
Methyl-3-(3-((((R)-1-(3-methoxyphenyl)ethyl)amino)methyl)morpholino)benzoate;
Methyl-3-(3-((((R)-1-(naphthalen-1-yl)ethyl)amino)methyl)morpholino)benzoate;
Methyl-4-(3-((((R)-1-(3-methoxyphenyl)ethyl)amino)methyl)morpholino)benzoate;
3-(3-((((R)-1-(3-Methoxyphenyl)ethyl)amino)methyl)morpholino)-N,N-dimethyl benzamide;
4-(3-((((R)-1-(3-Methoxyphenyl)ethyl)amino)methyl)morpholino)-N,N-dimethyl benzamide;
N,N-Dimethyl-4-(3-((((R)-1-(naphthalen-1-yl)ethyl)amino)methyl)morpholino)benzamide;
3-(3-((((R)-1-(3-Methoxyphenyl)ethyl)amino)methyl)morpholino)benzoic acid;
3-(3-((((R)-1-(Naphthalen-1-yl)ethyl)amino)methyl)morpholino)benzoic acid;
4-(3-((((R)-1-(3-Methoxyphenyl)ethyl)amino)methyl)morpholino)benzoic acid;
3-Methoxy-4-(2-((((R)-1-(naphthalen-1-yl)ethyl)amino)methyl)morpholino)benzoic acid hydrochloride;
4-(2-((((R)-1-(Naphthalen-1-yl)ethyl)amino)methyl)morpholino)-2-(trifluoromethyl)benzoic acid hydrochloride;

3,5-Difluoro-4-(2-((((R)-1-(naphthalen-1-yl)ethyl)amino) methyl)morpholino)benzoic acid hydrochloride;
(1R)-1-(3-Methoxyphenyl)-N-((4-(p-tolyl)morpholin-2-yl) methyl)ethanamine hydrochloride;
(1R)-1-(3-Methoxyphenyl)-N-((4-(m-tolyl)morpholin-2-yl) methyl)ethanamine hydrochloride;
(1R)-N-((4-(3,4-Difluorophenyl)morpholin-2-yl)methyl)-1-(3-methoxyphenyl)ethanamine hydrochloride;
2-Methyl-4-(2-((((R)-1-(naphthalen-1-yl)ethyl)amino)methyl)morpholino)benzoic acid hydrochloride;
4-(2-((((R)-1-(3-Methoxyphenyl)ethyl)amino)methyl)morpholino)-N-methylbenzamide hydrochloride;
Methyl 3-(2-((((R)-1-(3-methoxyphenyl)ethyl)amino)methyl)morpholino)benzoate;
Methyl 3-(2-((((R)-1-(naphthalen-1-yl)ethyl)amino)methyl) morpholino)benzoate;
Methyl 4-(2-((((R)-1-(naphthalen-1-yl)ethyl)amino)methyl) morpholino)benzoate;
3-(2-((((R)-1-(3-Methoxyphenyl)ethyl)amino)methyl)morpholino)-N,N-dimethyl benzamide;
N,N-Dimethyl-3-(2-((((R)-1-(naphthalen-1-yl)ethyl)amino) methyl) morpholino)benzamide;
4-(2-((((R)-1-(3-Methoxyphenyl)ethyl)amino)methyl)morpholino)-N,N-dimethyl benzamide hydrochloride;
N,N-Dimethyl-4-(2-((((R)-1-(naphthalen-1-yl)ethyl)amino) methyl)morpholino)benzamide;
3-(2-((((R)-1-(3-methoxyphenyl)ethyl)amino)methyl)morpholino)benzoic acid hydrochloride;
3-(2-((((R)-1-(Naphthalen-1-yl)ethyl)amino)methyl)morpholino)benzoicacid hydrochloride;
4-(2-((((R)-1-(Naphthalen-1-yl)ethyl)amino)methyl)morpholino)benzoic acid hydrochloride;
4-(2-((((R)-1-(3-Methoxyphenyl)ethyl)amino)methyl)morpholino)benzoic acid hydrochloride;
2-(4-(2-((((R)-1-(Naphthalen-1-yl)ethyl)amino)methyl) morpholino)phenyl)acetic acid hydrochloride;
3-(2-((((R)-1-(Naphthalen-1-yl)ethyl)amino)methyl)morpholino)-5-(trifluoromethyl)benzoic acid hydrochloride;
6-((((R)-1-Phenylethyl)amino)methyl)-4-(4-(trifluoromethyl)phenyl)morpholin-3-one hydrochloride;
4-(3,4-Difluorophenyl)-6-((((R)-1-(4-fluoro-3-methoxyphenyl)ethyl)amino)methyl)morpholin-3-one hydrochloride;
6-((((R)-1-(3-Methoxyphenyl)ethyl)amino)methyl)-4-phenylmorpholin-3-one;
Methyl 4-(2-((((R)-1-(naphthalen-1-yl)ethyl)amino)methyl)-5-oxomorpholino)benzoate;
3-(2-((((R)-1-(3-Methoxyphenyl)ethyl)amino)methyl)-5-oxomorpholino)-N-methyl benzamide;
N-Methyl-4-(2-((((R)-1-(naphthalen-1-yl)ethyl)amino)methyl)-5-oxomorpholino)benzamide;
4-(Cyclopropylmethyl)-6-((((R)-1-phenylethyl)amino)methyl)morpholin-3-one hydrochloride;
6-((((R)-1-(4-Fluoro-3-methoxyphenyl)ethyl)amino)methyl)-4-(4-fluorophenethyl)morpholin-3-one hydrochloride;
4-(2,6-Difluorobenzyl)-6-((((R)-1-(4-fluoro-3-methoxyphenyl)ethyl)amino)methyl)morpholin-3-one hydrochloride;
4-(2,5-Difluorobenzyl)-6-((((R)-1-(4-fluoro-3-methoxyphenyl)ethyl)amino)methyl)morpholin-3-one hydrochloride;
6-((((S)-1-(Naphthalen-1-yl)ethyl)amino)methyl)-4-(4-(trifluoromethyl)phenyl)morpholin-3-one hydrochloride;
6-((((S)-1-(Naphthalen-1-yl)ethyl)amino)methyl)-4-(4-(trifluoromethyl)phenyl)morpholin-3-one hydrochloride;
(1R)-N-((4-(Cyclopentylmethyl)morpholin-2-yl)methyl)-1-(4-fluoro-3-methoxyphenyl)ethanamine hydrochloride;
2-Methyl-4-((2-((((R)-1-(naphthalen-1-yl)ethyl)amino)methyl)morpholino)methyl)benzoic acid hydrochloride;
3-(2-((((R)-1-(Naphthalen-1-yl)ethyl)amino)methyl)morpholino)-5-(trifluoromethoxy)benzoic acid;
2-(3-(2-((((R)-1-(Naphthalen-1-yl)ethyl)amino)methyl) morpholino)-5-(trifluoromethyl)phenoxy)acetic acid;
3-Methyl-5-(2-((((R)-1-(naphthalen-1-yl)ethyl)amino)methyl)morpholino)benzoic acid;
3-Fluoro-5-(2-((((R)-1-(naphthalen-1-yl)ethyl)amino)methyl)morpholino)benzoic acid;
2-(3-Methyl-5-(2-((((R)-1-(naphthalen-1-yl)ethyl)amino) methyl)morpholino)phenoxy)acetic acid;
2-(3-Fluoro-5-(2-((((R)-1-(naphthalen-1-yl)ethyl)amino) methyl)morpholino)phenoxy)acetic acid;
3-(2-((((R)-1-(Naphthalen-1-yl)ethyl)amino)methyl)morpholino)-4-(trifluoromethyl)benzoic acid;
5-(2-((((R)-1-(Naphthalen-1-yl)ethyl)amino)methyl)morpholino)-2-(trifluoromethyl)benzoic acid;
4-(2-((((R)-1-(Naphthalen-1-yl)ethyl)amino)methyl)morpholino)-2-(trifluoromethyl)benzoic acid;
2-(5-(2-((((R)-1-(Naphthalen-1-yl)ethyl)amino)methyl) morpholino)-2-(trifluoromethyl)phenoxy)acetic acid;
2-(4-(2-((((R)-1-(Naphthalen-1-yl)ethyl)amino)methyl) morpholino)-2-(trifluoromethyl)phenoxy)acetic acid;
2-(3-(2-((((R)-1-(Naphthalen-1-yl)ethyl)amino)methyl) morpholino)-2-(trifluoromethyl)phenoxy)acetic acid;
2-(4-(2-((((R)-1-(Naphthalen-1-yl)ethyl)amino)methyl) morpholino)-3-(trifluoromethyl)phenoxy)acetic acid;
2-(2-Fluoro-5-(2-((((R)-1-(naphthalen-1-yl)ethyl)amino) methyl)morpholino)phenoxy)acetic acid;
2-(2,6-Difluoro-3-(2-((((R)-1-(naphthalen-1-yl)ethyl) amino)methyl)morpholino)phenoxy)acetic acid;
2-(2-Fluoro-3-(2-((((R)-1-(naphthalen-1-yl)ethyl)amino) methyl)morpholino)phenoxy)acetic acid;
2-(4-Fluoro-3-(2-((((R)-1-(naphthalen-1-yl)ethyl)amino) methyl)morpholino)phenoxy)acetic acid;
2-Fluoro-5-(2-((((R)-1-(naphthalen-1-yl)ethyl)amino)methyl)morpholino)benzoic acid;
2,6-Difluoro-3-(2-((((R)-1-(naphthalen-1-yl)ethyl)amino) methyl)morpholino)benzoic acid;
2-Fluoro-3-(2-((((R)-1-(naphthalen-1-yl)ethyl)amino)methyl)morpholino)benzoic acid;
4-Fluoro-3-(2-((((R)-1-(naphthalen-1-yl)ethyl)amino)methyl)morpholino)benzoic acid;
2-Methyl-3-(2-((((R)-1-(naphthalen-1-yl)ethyl)amino)methyl)morpholino)benzoic acid;
4-Methyl-3-(2-((((R)-1-(naphthalen-1-yl)ethyl)amino)methyl)morpholino)benzoic acid;
2-Fluoro-4-(2-((((R)-1-(naphthalen-1-yl)ethyl)amino)methyl)morpholino)benzoic acid;
3-Fluoro-4-(2-((((R)-1-(naphthalen-1-yl)ethyl)amino)methyl)morpholino)benzoic acid;
3-Methyl-4-(2-((((R)-1-(naphthalen-1-yl)ethyl)amino)methyl)morpholino)benzoic acid;
2-(3-Methyl-4-(2-((((R)-1-(naphthalen-1-yl)ethyl)amino) methyl)morpholino)phenoxy)acetic acid;
2-(2-Methyl-4-(2-((((R)-1-(naphthalen-1-yl)ethyl)amino) methyl)morpholino)phenoxy)acetic acid;
2-(2-Methyl-5-(2-((((R)-1-(naphthalen-1-yl)ethyl)amino) methyl)morpholino)phenoxy)acetic acid;
2,3-Difluoro-5-(2-((((R)-1-(naphthalen-1-yl)ethyl)amino) methyl)morpholino)benzoic acid;
2,4-Difluoro-5-(2-((((R)-1-(naphthalen-1-yl)ethyl)amino) methyl)morpholino)benzoic acid;
6-Fluoro-2-methyl-3-(2-((((R)-1-(naphthalen-1-1)ethyl) amino)methyl)morpholino)benzoic acid;
3-(tert-butyl)-5-(2-((((R)-1-(Naphthalen-1-yl)ethyl)amino) methyl)morpholino)benzoic acid;

3-((2-((((R)-1-(Naphthalen-1-yl)ethyl)amino)methyl)morpholino)methyl)-5-(trifluoromethyl)benzoic acid;
3-Methyl-5-(2-((((R)-1-(naphthalen-1-yl)ethyl)amino)methyl)morpholino)methyl)benzoic acid;
3-(2-((((R)-1-(4-Fluoro-3-methoxyphenyl)ethyl)amino)methyl)morpholino)-5-(trifluoromethoxy)benzoic acid;
2-(3-(2-((((R)-1-(4-Fluoro-3-methoxyphenyl)ethyl)amino)methyl)morpholino)-5-(trifluoromethyl)phenoxy)acetic acid;
3-(2-((((R)-1-(4-Fluoro-3-methoxyphenyl)ethyl)amino)methyl)morpholino)-5-methylbenzoic acid;
3-Fluoro-5-(2-((((R)-1-(4-fluoro-3-methoxyphenyl)ethyl)amino)methyl)morpholino)benzoic acid;
5-(2-((((R)-1-(4-Fluoro-3-methoxyphenyl)ethyl)amino)methyl)morpholino)-2-(trifluoromethyl)benzoic acid;
4-(2-((((R)-1-(4-Fluoro-3-methoxyphenyl)ethyl)amino)methyl)morpholino)-2-(trifluoromethyl)benzoic acid;
3-(2-((((R)-1-(4-Fluoro-3-methoxyphenyl)ethyl)amino)methyl)morpholino)-5-(trifluoromethyl)benzoic acid;
3-(3-((((R)-1-(Naphthalen-1-yl)ethyl)amino)methyl)morpholino)-5-(trifluoromethyl)benzoic acid;
2-(3-(3-((((R)-1-(Naphthalen-1-yl)ethyl)amino)methyl)morpholino)-5-(trifluoromethyl) phenoxy)acetic acid;
4-(3-((((R)-1-(Naphthalen-1-yl)ethyl)amino)methyl)morpholino)-2-(trifluoromethyl)benzoic acid; and
5-(3-((((R)-1-(Naphthalen-1-yl)ethyl)amino)methyl)morpholino)-2-(trifluoromethyl)benzoic acid;
or pharmaceutically acceptable salts thereof or stereoisomers thereof.

In another aspect of the invention, there is provided a compound of formula (I) useful in treating, managing or lessening the severity of diseases, disorders, syndromes or conditions associated with calcium sensing receptor (CaSR) modulators.

In another aspect, the invention provides a pharmaceutical composition comprising at least one compound of Formula (I) and at least one pharmaceutically acceptable excipient.

In another aspect, the invention provides a pharmaceutical composition of compound of formula (I) useful in treating, managing or lessening the severity of the diseases disorders, syndromes or conditions associated with calcium sensing receptor (CaSR) modulators in a subject, in need thereof, by administering to the subject, one or more compounds described herein in a therapeutically effective amount to cause modulation of such receptor.

In another aspect, the invention provides a pharmaceutical composition comprising a compound of formula (I) or a pharmaceutically acceptable stereoisomer, salt, or in vivo hydrolysable ester thereof together with a pharmaceutically acceptable excipient.

In another aspect, there are provided processes for the preparation compounds of formula (Ia):

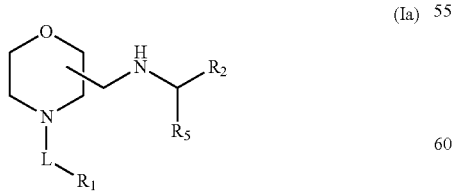

(Ia)

where L, $R_1$, $R_2$, and $R_5$ are as described herein above, the process comprising:
a) coupling of compound of formula (67) with formula (11) where L' is leaving group, to get compound of formula (68) wherein the coupling reaction is carried out using suitable coupling reagents mentioned herein in the detailed description;

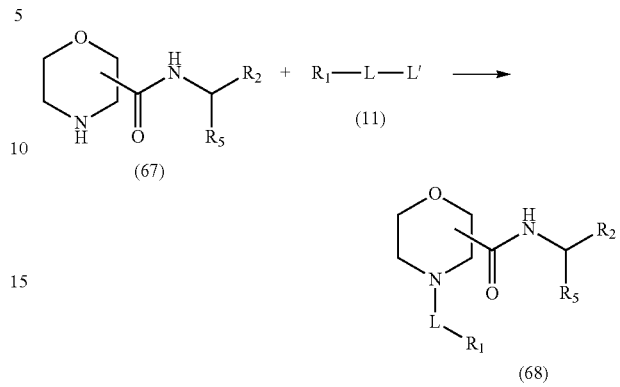

b) reducing a compound of formula (68) using suitable reducing agents for example borane-dimethyl sulfide complex to get compound of formula (Ia)

c) reducing a compound of formula (67) using suitable reducing agents for example borane-dimethyl sulfide complex to get compound of formula (69);

d) coupling of compound of formula (69) with formula (11) where L' is leaving group, to give compound of formula (Ia) wherein the coupling reaction is carried out using suitable coupling reagents mentioned herein in the detailed description;

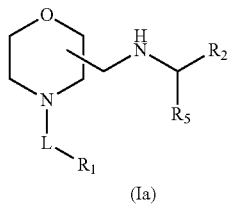

(Ia)

e) hydrolyzing the compound of formula (Ia) using suitable base such as NaOH, LiOH etc., to give corresponding acid compound
when $R_1$ is (when formula Ia is an ester derivative)

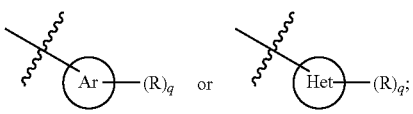

ring Ar is phenyl or naphthyl;
ring Het is heteroaryl or heterocyclyl;
R is —$(CR_eR_f)_{0-3}$—C(O)OR$_6$, —$(CR_eR_f)_{1-2}$cycloalkylene-C(O)OR$_6$, -cycloalkylene $(CR_eR_f)_{0-2}$—C(O)OR$_6$, —O$(CR_eR_f)_{0-3}$—C(O)OR$_6$, —O-cycloalkylene-C(O)OR$_6$, or —C(O)NR$_7$—$(CR_eR_f)_{1-2}$—C(O)OR$_6$;
$R_e$ and $R_f$ are independently selected from hydrogen, halogen, hydroxy, cyano, nitro, substituted or unsubstituted alkyl, substituted or unsubstituted haloalkyl and substituted or unsubstituted cycloalkyl; or $R_e$ and $R_f$, together with the carbon atom to which they are attached, form a substituted or unsubstituted 3 to 7 membered saturated carbocyclic ring; and
$R_6$ is substituted or unsubstituted alkyl.

In another aspect, there are provided processes for the preparation of compounds of formula (Ib):

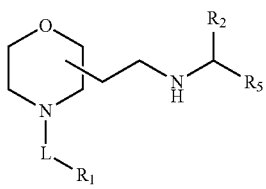

(Ib)

where L, $R_1$, $R_2$, and $R_5$ are as described herein above, the process comprising:

a) coupling of compound of formula (70) with formula (11) where L' is leaving group, to give compound of formula (Ib), wherein the coupling reaction is carried out using suitable coupling reagents mentioned herein in the detailed description;

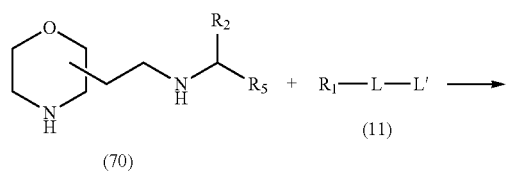

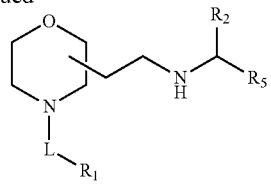

(Ib)

b) hydrolyzing the compound of formula (Ib) using suitable base such as NaOH, LiOH etc., to give corresponding acid compound
when $R_1$ is (when formula Ia is an ester derivative)

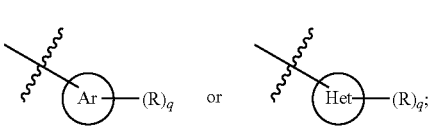

ring Ar is phenyl or naphthyl;
ring Het is heteroaryl or heterocyclyl;
R is —$(CR_eR_f)_{0-3}$—C(O)OR$_6$, —$(CR_eR_f)_{1-2}$cycloalkylene-C(O)OR$_6$, -cycloalkylene $(CR_eR_f)_{0-2}$—C(O)OR$_6$, —O$(CR_eR_f)_{0-3}$—C(O)OR$_6$, —O-cycloalkylene-C(O)OR$_6$, or —C(O)NR$_7$—$(CR_eR_f)_{1-2}$—C(O)OR$_6$;
$R_e$ and $R_f$ are independently selected from hydrogen, halogen, hydroxy, cyano, nitro, substituted or unsubstituted alkyl, substituted or unsubstituted haloalkyl and substituted or unsubstituted cycloalkyl; or $R_e$ and $R_f$, together with the carbon atom to which they are attached, form a substituted or unsubstituted 3 to 7 membered saturated carbocyclic ring; and $R_6$ is substituted or unsubstituted alkyl.

DETAILED DESCRIPTION OF THE INVENTION

Definitions and Abbreviations

Unless otherwise stated, the following terms used in the specification and claims have the meanings given below.

For purposes of interpreting the specification, the following definitions will apply and whenever appropriate, terms used in the singular will also include the plural and vice versa.

The terms "halogen" or "halo" means fluorine, chlorine, bromine, or iodine.

Unless otherwise stated, in the present application "oxo" means C(=O) group. Such an oxo group may be a part of either a cycle or a chain in the compounds of the present invention.

The term "alkyl" refers to an alkane derived hydrocarbon radical that includes solely carbon and hydrogen atoms in the backbone, contains no unsaturation, has from one to six carbon atoms, and is attached to the remainder of the molecule by a single bond, e.g., methyl, ethyl, n-propyl, 1-methylethyl (isopropyl), n-butyl, n-pentyl, 1,1-dimethylethyl (t-butyl) and the like. Unless set forth or recited to the contrary, all alkyl groups described or claimed herein may be straight chain or branched, substituted or unsubstituted.

The term "alkenyl" refers to a hydrocarbon radical containing from 2 to 10 carbon atoms and including at least one carbon-carbon double bond. Non-limiting examples of alkenyl groups include ethenyl, 1-propenyl, 2-propenyl (allyl), iso-propenyl, 2-methyl-1-propenyl, 1-butenyl, 2-butenyl and the like. Unless set forth or recited to the contrary, all alkenyl groups described or claimed herein may be straight chain or branched, substituted or unsubstituted.

The term "alkynyl" refers to a hydrocarbon radical containing 2 to 10 carbon atoms and including at least one carbon-carbon triple bond. Non-limiting examples of alkynyl groups include ethynyl, propynyl, butynyl and the like. Unless set forth or recited to the contrary, all alkynyl groups described or claimed herein may be straight chain or branched, substituted or unsubstituted.

The term "alkoxy" refers to an alkyl group attached via an oxygen linkage. Non-limiting examples of such groups are methoxy, ethoxy and propoxy and the like. Unless set forth or recited to the contrary, all alkoxy groups described or claimed herein may be straight chain or branched, substituted or unsubstituted.

The term "haloalkyl" refers to an alkyl group as defined above that is substituted by one or more halogen atoms as defined above. Preferably, the haloalkyl may be monohaloalkyl, dihaloalkyl or polyhaloalkyl including perhaloalkyl. A monohaloalkyl can have one iodine, bromine, chlorine or fluorine atom. Dihaloalkyl and polyhaloalkyl groups can be substituted with two or more of the same halogen atoms or a combination of different halogen atoms. Preferably, a polyhaloalkyl is substituted with up to 12 halogen atoms. Non-limiting examples of a haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl and the like. A perhaloalkyl refers to an alkyl having all hydrogen atoms replaced with halogen atoms. Unless set forth or recited to the contrary, all haloalkyl groups described or claimed herein may be straight chain or branched, substituted or unsubstituted.

The term "haloalkoxy" refers to a haloalkyl, defined herein, group attached via an oxygen linkage. Non-limiting examples of such groups are monohaloalkoxy, dihaloalkoxy or polyhaloalkoxy including perhaloalkoxy. Unless set forth or recited to the contrary, all haloalkoxy group described or claimed herein may be straight chain or branched, substituted or unsubstituted.

The term "hydroxyalkyl" refers to an alkyl group, as defined above that is substituted by one or more hydroxy groups. Preferably, the hydroxyalkyl is monohydroxyalkyl or dihydroxyalkyl. Non-limiting examples of a hydroxyalkyl include 2-hydroxyethyl, 3-hydroxypropyl, 2-hydroxypropyl, and the like. Unless set forth or recited to the contrary, all hydroxyalkyl group described or claimed herein may be straight chain or branched, substituted or unsubstituted.

The term "cycloalkyl" refers to a non-aromatic mono or multicyclic ring system having 3 to 12 carbon atoms, such as cyclopropyl, cyclobutyl, cyclopentyl, cyclohexyl and the like. Examples of multicyclic cycloalkyl groups include, but are not limited to, perhydronapththyl, adamantyl and norbornyl groups, bridged cyclic groups or spirobicyclic groups, e.g., spiro(4,4)non-2-yl and the like. Unless set forth or recited to the contrary, all cycloalkyl groups described or claimed herein may be substituted or unsubstituted.

The term "cycloalkylene" refers to a saturated divalent cyclic hydrocarbon radical that includes solely carbon and hydrogen atoms in the backbone. In particular, "$C_3$-$C_7$ cycloalkylene" means a saturated divalent cyclic hydrocarbon radical with 3 to 7 carbon atoms e.g. cyclopropylene, cyclobutylene, cyclopentylene, cyclohexylene and the like. Unless set forth or recited to the contrary, all cycloalkylene groups described or claimed herein may be substituted or unsubstituted.

The term "cycloalkenyl" refers to a non-aromatic mono or multicyclic ring system having 3 to 12 carbon atoms and including at least one carbon-carbon double bond, such as cyclopentenyl, cyclohexenyl, cycloheptenyl and the like. Unless set forth or recited to the contrary, all cycloalkenyl groups described or claimed herein may be substituted or unsubstituted.

The term "cycloalkylalkyl" refers to a cycloalkyl group as defined above, directly bonded to an alkyl group as defined above, e.g., cyclopropylmethyl, cyclobutylmethyl, cyclopentylmethyl, cyclohexylmethyl, cyclohexylethyl, etc. Unless set forth or recited to the contrary, all cycloalkylalkyl groups described or claimed herein may be substituted or unsubstituted.

The term "aryl" refers to an aromatic radical having 6- to 14-carbon atoms, including monocyclic, bicyclic and tricyclic aromatic systems, such as phenyl, naphthyl, tetrahydronaphthyl, indanyl, and biphenyl and the like. Unless set forth or recited to the contrary, all aryl groups described or claimed herein may be substituted or unsubstituted.

The term "arylalkyl" refers to an aryl group as defined above directly bonded to an alkyl group as defined above, e.g., —$CH_2C_6H_5$ and —$C_2H_4C_6H_5$. Unless set forth or recited to the contrary, all arylalkyl groups described or claimed herein may be substituted or unsubstituted.

A "carbocyclic ring" or "carbocycle" as used herein refers to a 3- to 10-membered saturated or unsaturated, monocyclic, fused bicyclic, spirocyclic or bridged polycyclic ring containing carbon atoms, which may optionally be substituted, for example, carbocyclic rings include but are not limited to cyclopropyl, cyclobutyl, cyclopentyl, cyclohexyl, cyclopropylene, cyclohexanone, aryl, naphthyl, adamentyl etc. Unless set forth or recited to the contrary, all carbocyclic groups or rings described or claimed herein may be aromatic or non aromatic.

The term "heterocyclic ring" or "heterocyclyl ring" or "heterocyclyl", unless otherwise specified, refers to substituted or unsubstituted non-aromatic 3- to 15-membered ring which consists of carbon atoms and with one or more heteroatom(s) independently selected from N, O or S. The heterocyclic ring may be a mono-, bi- or tricyclic ring system, which may include fused, bridged or spiro ring systems and the nitrogen, carbon, oxygen or sulfur atoms in the heterocyclic ring may be optionally oxidized to various oxidation states. In addition, the nitrogen atom may be optionally quaternized, the heterocyclic ring or heterocyclyl may optionally contain one or more olefinic bond(s), and one or two carbon atoms(s) in the heterocyclic ring or heterocyclyl may be interrupted with —$CF_2$—, —C(O)—, —S(O)—, S(O)$_2$, —C(=N-alkyl)-, or —C(=N-cycloalkyl), etc. In addition heterocyclic ring may also be fused with aromatic ring. Non-limiting examples of heterocyclic rings include azetidinyl, benzopyranyl, chromanyl, decahydroisoquinolyl, indanyl, indolinyl, isoindolinyl, isochromanyl, isothiazolidinyl, isoxazolidinyl, morpholinyl, oxazolinyl, oxazolidinyl, 2-oxopiperazinyl, 2-oxopiperidinyl, 2-oxopyrrolidinyl, 2-oxoazepinyl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisquinolyl, tetrahydrofuryl, tetrahydropyranyl, thiazolinyl, thiazolidinyl, thiamorpholinyl, thiamorpholinyl sulfoxide, thiamorpholinyl sulfone indoline, benzodioxole, tetrahydroquinoline, tetrahydrobenzopyran and the like. The heterocyclic ring may be attached to the main structure at any heteroatom or carbon atom that results in the creation of a stable structure. Unless set forth or recited to the contrary, all heterocyclyl groups described or claimed herein may be substituted or unsubstituted; substituents may be on same or different ring atom.

The term "heteroaryl" unless otherwise specified, refers to a substituted or unsubstituted 5- to 14-membered aromatic heterocyclic ring with one or more heteroatom(s) independently selected from N, O or S. The heteroaryl may be a mono-, bi- or tricyclic ring system. The heteroaryl ring may be attached to the main structure at any heteroatom or carbon atom that results in the creation of a stable structure. Non-limiting examples of a heteroaryl ring include oxazolyl, isoxazolyl, imidazolyl, furyl, indolyl, isoindolyl, pyrrolyl, triazolyl, triazinyl, tetrazolyl, thienyl, thiazolyl, isothiazolyl, pyridyl, pyrimidinyl, pyrazinyl, pyridazinyl, benzofuranyl, benzothiazolyl, benzoxazolyl, benzimidazolyl, benzothienyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl, phthalazinyl and the like. Unless set forth or recited to the contrary, all heteroaryl groups described or claimed herein may be substituted or unsubstituted.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure. Unless set forth or recited to the contrary, all heterocyclylalkyl groups described or claimed herein may be substituted or unsubstituted.

The term "heteroarylalkyl" refers to a heteroaryl ring radical directly bonded to an alkyl group. The heteroarylalkyl radical may be attached to the main structure at any carbon atom in the alkyl group that results in the creation of a stable structure. Unless set forth or recited to the contrary, all heteroarylalkyl groups described or claimed herein may be substituted or unsubstituted.

Unless otherwise specified, the term "substituted" as used herein refers to a group or moiety having one or more substituents attached to the structural skeleton of the group or moiety. Such substituents include, but are not limited to hydroxy, halogen, carboxyl, cyano, nitro, oxo (=O), thio (=S), alkyl, haloalkyl, alkenyl, alkynyl, aryl, arylalkyl, cycloalkyl, cycloalkylalkyl, cycloalkenyl, heteroaryl, heterocyclic ring, heterocyclylalkyl, heteroarylalkyl, —C(O)OR$^x$, —C(O)R$^x$, —C(S)R$^x$, —C(O)NR$^x$R$^y$, —NR$^x$C(O)NR$^y$R$^z$, —N(R$^x$)S(O)R$^y$, —N(R$^x$)S(O)$_2$R$^y$, —NR$^x$R$^y$, —NR$^x$C(O) R$^y$, —NR$^x$C(S)R$^y$, —NR$^x$C(S)NR$^y$R$^z$, —S(O)$_2$NR$^x$R$^y$, —OR$^x$, —OC(O)R$^x$, —OC(O)NR$^x$R$^y$, —R$^x$C(O)OR$^y$, —R$^x$C(O)NR$^y$R$^z$, —R$^x$C(O)R$^y$, —SR$^x$, and —S(O)$_2$R$^x$; wherein each occurrence of R$^x$, R$^y$ and R$^z$ are independently selected from hydrogen, halogen, alkyl, haloalkyl, alkenyl, alkynyl, aryl, arylalkyl, cycloalkyl, cycloalkenyl, heteroaryl, heterocyclic ring, heterocyclylalkyl ring and heteroarylalkyl. The aforementioned "substituted" groups cannot be further substituted. For example, when the substituent on "substituted alkyl" is "aryl" or "alkenyl", the aryl or alkenyl can not be substituted aryl or substituted alkenyl, respectively.

The compounds of the present invention may have one or more chiral centers. The absolute stereochemistry at each chiral centre may be 'R' or 'S'. The compounds of the invention include all diastereomers and enantiomers and mixtures thereof. Unless specifically mentioned otherwise, reference to one stereoisomer applies to any of the possible stereoisomers. Whenever the stereoisomeric composition is unspecified, it is to be understood that all possible stereoisomers are included.

The term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. The terms "racemate" or "racemic mixture" refer to a mixture of equal parts of enantiomers.

A "tautomer" refers to a compound that undergoes rapid proton shifts from one atom of the compound to another atom of the compound. Some of the compounds described herein may exist as tautomers with different points of attachment of hydrogen. The individual tautomers as well as mixture thereof are encompassed with compounds of formula (I).

The term "treating" or "treatment" of a state, disorder or condition includes: (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof; c) lessening the severity of a disease disorder or condition or at least one of its clinical or subclinical symptoms or (d) relieving the disease, i.e., causing regression of the state, disorder or condition or at least one of its clinical or subclinical symptoms.

The term "modulate" or "modulating" or "modulation" or "modulator" refers to an increase in the amount, quality, or effect of a particular activity or function of the receptor. By way of illustration and not limitation, it includes agonists, partial agonists, allosteric modulators of calcium sensing receptor (CaSR) of the present invention. Such modulation may be contingent on the occurrence of a specific event, such as activation of a signal transduction pathway.

The term "allosteric modulators of calcium-sensing receptor", refers to the ability of a compound that binds to calcium sensing receptors and induces a conformational change that reduces the threshold for calcium sensing receptor activation by the endogenous ligand $Ca^{2+}$ depending on the concentration of the compound exposed to the calcium-sensing receptor.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a disease, disorder, syndrome or condition, is sufficient to cause the effect in the subject which is the purpose of the administration. The "therapeutically effective amount" will vary depending on the compound, the disease and its severity and the age, weight, physical condition and responsiveness of the subject to be treated.

The compound of the invention may form salts. Non-limiting examples of pharmaceutically acceptable salts include salts derived from inorganic bases, salts of organic bases, salts of chiral bases, salts of natural amino acids and salts of non-natural amino acids.

With respect to the overall compounds described by the Formula (I), the invention extends to these stereoisomeric forms and to mixtures thereof. To the extent prior art teaches synthesis or separation of particular stereoisomers, the different stereoisomeric forms of the invention may be separated from one another by a method known in the art, or a given isomer may be obtained by stereospecific or asymmetric synthesis or chiral HPLC (high performance liquid chromatography. Tautomeric forms and mixtures of compounds described herein are also contemplated.

Screening of compounds of invention for calcium sensing receptor (CaSR) modulation activity can be achieved by using various in vitro and in vivo protocols mentioned herein below or methods known in the art.

Pharmaceutical Compositions

The invention relates to pharmaceutical compositions containing the compounds of the Formula (I) disclosed herein. In particular, pharmaceutical compositions containing a therapeutically effective amount of at least one compound of formula (I) described herein and at least one pharmaceutically acceptable excipient (such as a carrier or diluent). Preferably, the contemplated pharmaceutical compositions include the compound(s) described herein in an amount sufficient to modulate calcium sensing receptor (CaSR) mediated diseases described herein when administered to a subject.

The subjects contemplated include, for example, a living cell and a mammal, including human mammal. The compound of the invention may be associated with a pharmaceutically acceptable excipient (such as a carrier or a diluent) or be diluted by a carrier, or enclosed within a carrier which can be in the form of a capsule, sachet, paper or other container. The pharmaceutically acceptable excipient includes pharmaceutical agent that does not itself induce the production of antibodies harmful to the individual receiving the composition, and which may be administered without undue toxicity.

Examples of suitable carriers or excipients include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, salicylic acid, fatty acids, fatty acid amines, fatty acid monoglycerides and diglycerides, pentaerythritol fatty acid esters, polyoxyethylene, hydroxymethylcellulose and polyvinylpyrrolidone.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions described herein may be prepared by conventional techniques known in the art. For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be in conventional forms, for example, capsules, tablets, caplets, orally disintegrating tablets, aerosols, solutions, suspensions or products for topical application.

The route of administration may be any route which effectively transports the active compound of the invention to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment).

Solid oral formulations include, but are not limited to, tablets, caplets, capsules (soft or hard gelatin), orally disintegrating tablets, dragees (containing the active ingredient in powder or pellet form), troches and lozenges. Tablets, dragees, or capsules having talc and/or a carbohydrate carrier or binder or the like are particularly suitable for oral application. Liquid formulations include, but are not limited to, syrups, emulsions, soft gelatin and sterile injectable liquids, such as aqueous or non-aqueous liquid suspensions or solutions. For parenteral application, particularly suitable are injectable solutions or suspensions formulation.

Liquid formulations include, but are not limited to, syrups, emulsions, suspensions, solutions, soft gelatin and sterile injectable liquids, such as aqueous or non-aqueous liquid suspensions or solutions.

For parenteral application, particularly suitable are injectable solutions or suspensions, preferably aqueous solutions with the active compound dissolved in polyhydroxylated castor oil.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as pocketed tablets, capsules, and powders in vials or ampoules. Also, the unit dosage form can be a capsule, tablet, caplet, cachet, or lozenge itself, or it can be the appropriate number of any of these in packaged form.

For administration to subject patients, the total daily dose of the compounds of the invention depends, of course, on the mode of administration. For example, oral administration may require a higher total daily dose, than an intravenous (direct into blood). The quantity of active component in a unit dose preparation may be varied or adjusted from 0.1 mg to 10000 mg according to the potency of the active component or mode of administration.

Suitable doses of the compounds for use in treating the diseases and disorders described herein can be determined by those skilled in the relevant art. Therapeutic doses are generally identified through a dose ranging study in subject based on preliminary evidence derived from the animal studies. Doses must be sufficient to result in a desired therapeutic benefit without causing unwanted side effects for the patient. For example, the daily dosage of the CaSR modulator can range from about 0.1 to about 30.0 mg/kg. Mode of administration, dosage forms, suitable pharmaceutical excipients, diluents or carriers can also be well used and adjusted by those skilled in the art. All changes and modifications are envisioned within the scope of the invention.

Methods of Treatment

In an embodiment, the invention provides compounds and pharmaceutical compositions thereof that are useful in treating, managing or lessening the severity of diseases, disorders, syndromes or conditions modulated by calcium sensing receptor (CaSR).

The invention further provides method of treating diseases, disorders, syndromes or conditions modulated by CaSR in a subject in need thereof by administering to the subject a therapeutically effective amount of a compound or a pharmaceutical composition of the invention.

In another aspect of the invention, the methods provided are also useful for diagnosis of conditions that can be treated by modulating CaSR for determining if a patient will be responsible to therapeutic agents.

In another aspect, the invention provides a method for the treatment of diseases, disorders or conditions through modulating CaSR. In this method, a subject in need of such treatment is administered a therapeutically effective amount of a compound of formula (I) described herein.

The compound and pharmaceutical composition of the present invention is useful to a subject in need of the treatment having a disease, disorder, syndrome or condition characterized by one or more of the following: (a) abnormal calcium ion homeostasis, (b) an abnormal level of a messenger whose production or secretion is affected by the calcium sensing receptor (CaSR) activity or (c) an abnormal level of activity of a messenger whose function is affected by the calcium sensing receptor activity. In one aspect, the patient has a disease, disorder, syndrome or condition characterized by an abnormal level of one or more calcium sensing receptor-regulated components and the compound is active on a CaSR of a cell including parathyroid cell, bone cells (pre-osteoclast, osteoclast, pre-osteoblast, osteoblast), juxtaglomerular kidney cell, kidney messengial cell, glomerular kidney cell, proximal tubule kidney cell, distal tubule kidney cell, cell of the thick ascending limb of Henle's loop and/or collecting duct, parafollicular cell in the thyroid (C-cell), intestinal cell, platelet, vascular smooth muscle cell, gastrointestinal tract cell, pituitary cell or hypothalamic cell. The messenger of the calcium sensing receptor is Calcium.

The compound of Formula (I), being modulators of CaSR, is potentially useful in treating, managing or lessening the severity, morbidity/mortality or complications of diseases, disorders, syndromes or conditions include but are not limited to primary hyperparathyroidism, secondary hyperparathyroidism, tertiary hyperparathyroidism, chronic renal failure (with or without dialysis), chronic kidney disease (with or without dialysis) parathyroid adenoma, parathyroid hyperplasia, parathyroid carcinoma, vascular & valvular calcification, abnormal calcium homeostasis such as hypercalcemia, abnormal phosphorous homeostasis such as hypophosphatemia, bone related diseases or complications arising due to hyperparathyroidism, chronic kidney disease or parathyroid carcinoma, bone loss post renal transplantation, osteitis fibrosa cystica, adynamic bone disease, renal bone diseases, cardiovascular complications arising due to hyperparathyroidism or chronic kidney disease, certain malignancies in which $(Ca^{2+})_e$ ions are abnormally high, cardiac, renal or intestinal dysfunctions, podocyte-related diseases, abnormal intestinal motility, diarrhea, augmenting gastrin or gastric acid secretion to directly or indirectly benefit in atrophic gastritis or to improve absorption of pharmacological compounds, drugs or supplements from gastrointestinal tract by augmenting gastric acidity.

Primary hyperparathyroidism, is a disorder of one or more of the parathyroid glands, resulting from a hyper function of the parathyroid glands themselves (acquired sporadically or familial) resulting in PTH over secretion which could be due to single or double adenoma, hyperplasia, multigland disease or rarely, carcinoma of the parathyroid glands. As a result, the blood calcium rises to a level that is higher than normal (called hypercalcemia). This elevated calcium level can cause many short-term and long-term complications.

Secondary hyperparathyroidism occurs when a decrease in circulating levels of $Ca^{2+}$ level stimulates PTH secretion. One cause of secondary hyperparathyroidism is chronic renal insufficiency (also referred to as chronic kidney disease or CKD), such as that in renal polycystic disease or chronic pyelonephritis, or chronic renal failure, such as that in hemodialysis patients (also referred to as end stage renal disease or ESRD). Excess PTH may be produced in response to hypocalcemia resulting from low calcium intake, GI disorders, renal insufficiency, vitamin D deficiency, magnesium deficiency and renal hypercalciuria. Tertiary hyperparathyroidism may occur after a long period of secondary hyperparathyroidism and hypercalcemia.

In one aspect, the compound and composition of the present invention can be used in treating, managing or lessening the vascular or valvular calcification in a subject. In one aspect, administration of the compound of the invention retards or reverses the formation, growth or deposition of extracellular matrix hydroxyapatite crystal deposits. In another aspect of the invention, administration of the compound of the invention prevents the formation, growth or deposition of extracellular matrix hydroxyapatite crystal deposits. In one aspect, the compounds of the invention may also be used to prevent or treat atherosclerotic calcification and medial calcification and other conditions characterized by vascular calcification. In one aspect, vascular calcification may be associated with chronic renal insufficiency or end-stage renal disease or excess calcium or PTH itself. In another aspect, vascular calcification may be associated with pre- or post-dialysis or uremia. In a further aspect, vascular calcification may be associated with diabetes mellitus I or II. In yet another aspect, vascular calcification may be associated with a cardiovascular disorder.

Abnormal calcium homeostasis such as hyperparathyroidism related diseases can be characterized as described in standard medical textbooks, but not limited to Harrison's Principles of Internal Medicine. The compound and composition of the present invention can be used, in particular, to participate in a reduction of the serum levels in the parathyroid hormone known as PTH: these products could thus be useful for the treatment of diseases such as hyperparathyroidism.

Abnormal phosphorous homeostasis such as hypophosphatemia can be characterized as described in standard medical textbooks, but not limited to Harrison's Principles of Internal Medicine. The compound and composition of the present invention can be used, in particular, to participate in a reduction of the serum levels in the parathyroid hormone known as PTH: these products could thus be useful for the treatment of diseases such as hypophosphatemia.

In one aspect, the podocyte diseases or disorders treated by methods of the present invention stem from the perturbations in one or more functions of podocytes. These functions of podocytes include: (i) a size barrier to protein; (ii) charge barrier to protein; (iii) maintenance of the capillary loop shape; (iv) counteracting the intraglomerular pressure; (v) synthesis and maintenance of the glomerular basement membrane (GMB); (vi) production and secretion of vascular endothelial growth factor (VEGF) required for the glomerular endothelial cell (GEN) integrity. Such disorders or diseases include but are not limited to loss of podocytes (podocytopenia), podocyte mutation, an increase in foot process width, or a decrease in slit diaphragm length. In one aspect, the podocyte-related disease or disorder can be effacement or a diminution of podocyte density. In one aspect, the diminution of podocyte density could be due to a decrease in a podocyte number, for example, due to apoptosis, detachment, lack of proliferation, DNA damage or hypertrophy.

In one aspect, the podocyte-related disease or disorder can be due to a podocyte injury. In one aspect, the podocyte injury can be due to mechanical stress such as high blood pressure, hypertension, or ischemia, lack of oxygen supply, a toxic substance, an endocrinologic disorder, an infection, a contrast agent, a mechanical trauma, a cytotoxic agent (cis-platinum, adriamycin, puromycin), calcineurin inhibitors, an inflammation (e.g., due to an infection, a trauma, anoxia, obstruction, or ischemia), radiation, an infection (e.g., bacterial, fungal, or viral), a dysfunction of the immune system (e.g., an autoimmune disease, a systemic disease, or IgA nephropathy), a genetic disorder, a medication (e.g., anti-bacterial agent, anti-viral agent, anti-fungal agent, immunosuppressive agent, anti-inflammatory agent, analgestic or anticancer agent), an organ failure, an organ transplantation, or uropathy. In one aspect, ischemia can be sickle-cell anemia, thrombosis, transplantation, obstruction, shock or blood loss. In one aspect, the genetic disorders may include congenital nephritic syndrome of the Finnish type, the fetal membranous nephropathy or mutations in podocyte-specific proteins.

In one aspect, the compounds of the invention can be used for treating abnormal intestinal motilities disorders such as diarrhea. The methods of the invention comprise administering to the subject a therapeutically effective amount of the compounds of Formula I. In a further aspect, diarrhea can be exudative diarrhea, i.e., resulting from direct damage to the small or large intestinal mucosa. This type of diarrhea can be caused by infectious or inflammatory disorders of the gut. In one aspect, exudative diarrhea can be associated with gastrointestinal or abdominal surgery, chemotherapy, radiation treatment, inflammation or toxic traumatic injury. In another aspect, diarrhea can be secretary, means that there is an increase in the active secretion, or there is an inhibition of absorption. There is little to no structural damage. The most common cause of this type of diarrhea is cholera. In another aspect, diarrhea can be due to acceleration of intestinal transit (rapid transit diarrhea). Such condition may occur because the rapid flow-through impairs the ability of the gut to absorb water.

The compound and composition of the present invention can be used, in particular, to participate in an augmenting gastrin or gastric acid secretion to directly or indirectly benefit certain medical conditions such as but not limited to atrophic gastritis or to improve absorption of pharmacological compounds, drugs or supplements from gastro-intestinal tract by augmenting gastric acidity.

All of the patent, patent application and non-patent publications referred to in this specification are incorporated herein by reference in their entireties.

General Methods of Preparation

The compounds described herein may be prepared by techniques known in the art. In addition, the compounds described herein may be prepared by following one or more reaction sequences as depicted in Scheme-1 to Scheme-10. Further, in the following schemes, where specific bases, acids, reagents, solvents, coupling agents, etc., are mentioned, it is understood that other bases, acids, reagents, solvents, coupling agents etc., known in the art may also be used and are therefore included within the scope of the present invention. Variations in reaction conditions, for example, temperature and/or duration of the reaction, which may be used as known in the art are also within the scope of the present invention. All the isomers of the compounds are described in these schemes, unless otherwise specified, are also encompassed within the scope of this invention.

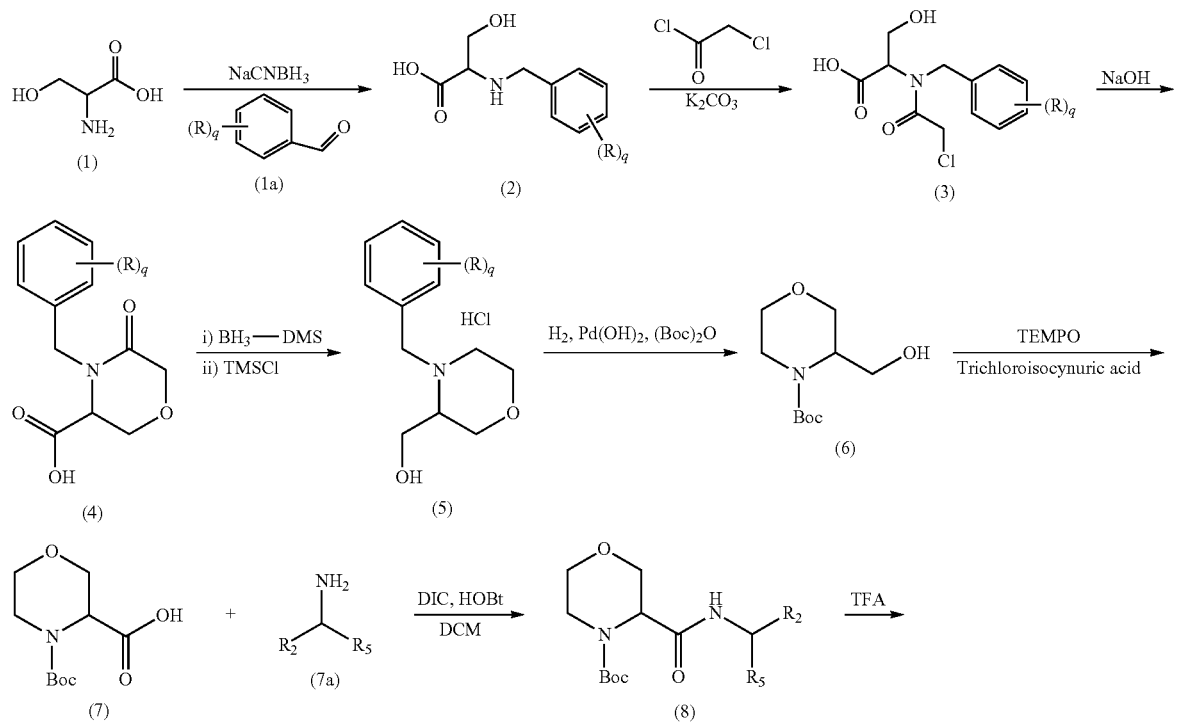

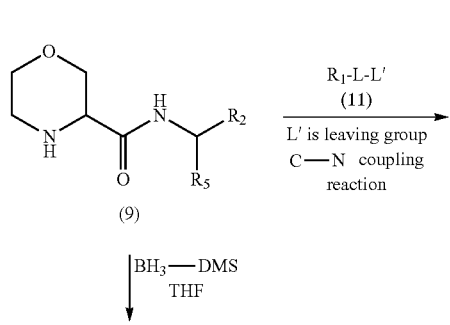
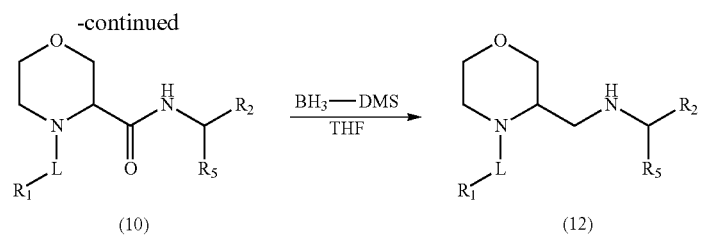

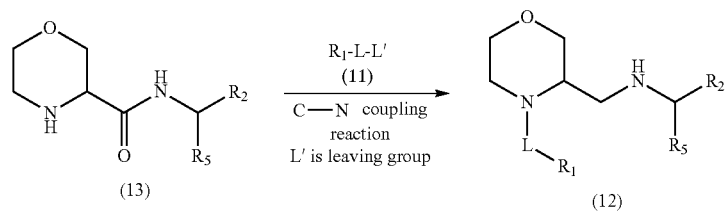

The compound of formula (12) where L, $R_1$, $R_2$, and $R_5$ are as defined herein above, can be prepared by following the procedure as depicted in Scheme-1 starting from commercially available DL-Serine of formula (1). Thus, DL-Serine of formula (1) undergoes reductive amination with benzaldehyde of formula (1a) using suitable reducing agents such as sodium cyanoborohydride or sodium triacetoxyborohydride in presence of a base for example NaOH (2M NaOH solution) to give compound of formula (2). The compound of formula (2) undergoes N-acetylation using chloroacetyl chloride, in presence of suitable base, followed by cyclization in the presence of a base to give compound of formula (4). Further, this acid and amide groups in formula (4) are reduced using suitable reducing agents for example borane-dimethyl sulfide complex in tetrahydrofuran to afford compound of formula (5). Debenzylation and N-Boc protection (Boc is tert-butoxycarbonyl) of compound of formula (5) is done in single pot using $H_2$, $Pd(OH)_2$ and $(Boc)_2O$ in ethyl acetate to give compound of formula (6) (*Organic and Bio-Organic Chemistry* (1972-1999); (1985); 2577-2580, WO 2006/114606 and US 2010/210640). The compound of formula (6) is oxidised to give compound of formula (7) using (2,2,6,6-Tetramethyl-piperidin-1-yl)oxyl (TEMPO) and trichloroisocyanuric acid. This acid compound of formula (7) is coupled with amine of formula (7a) by using suitable coupling reagents such as N,N-diisopropylcarbodiimide (DIPC) or 1-Ethyl-3-(3-dimethylaminopropyl)carbodiimide Hydrochloride (EDCI) and 1-hydroxybenzotriazole (HOBT) in suitable solvent such as dichloromethane or tetrahydrofuran to give compound of formula (8). N-Boc deprotection is done using suitable reagent for example Trifluoroacetic acid (TFA) in dichloromethane to give compound of formula (9). Compound of formula (9) undergoes carbon-nitrogen (C—N) coupling reaction with formula (11) by following the methods known in the art for example Buchwald coupling reaction (when L is a bond) using suitable reagents known in the art, or the coupling reaction (when L is not a bond) carried out by using suitable base for example triethylamine (TEA), N,N-Diisopropylethylamine (DIPEA) etc., and in suitable solvent for example DCM (dichloromethane), THF (tetrahydrofuran) etc., to give compound of formula (10). This compound of formula (10) undergoes amide group reduction by using suitable reagent for example borane-dimethyl sulfide complex to afford final compound of formula (12). Alternatively, the compound of formula (9) is reduced to formula (13) by using suitable reagent for example borane-dimethyl sulfide complex. This compound of formula (13) undergoes carbon-nitrogen (C—N) coupling reaction with formula (11) by following the methods known in the art for example Buchwald coupling reaction (when L is a bond) using suitable reagents known in the art, or the coupling reaction (when L is not a bond) carried out by using suitable base for example TEA, DIPEA etc., and in suitable solvent for example DCM, THF etc., to give compound of formula (12). If the compound of formula (12) is an ester derivative it can be further converted to corresponding acid by using the procedures known in the art for example using base such as NaOH or LiOH.

Scheme-2

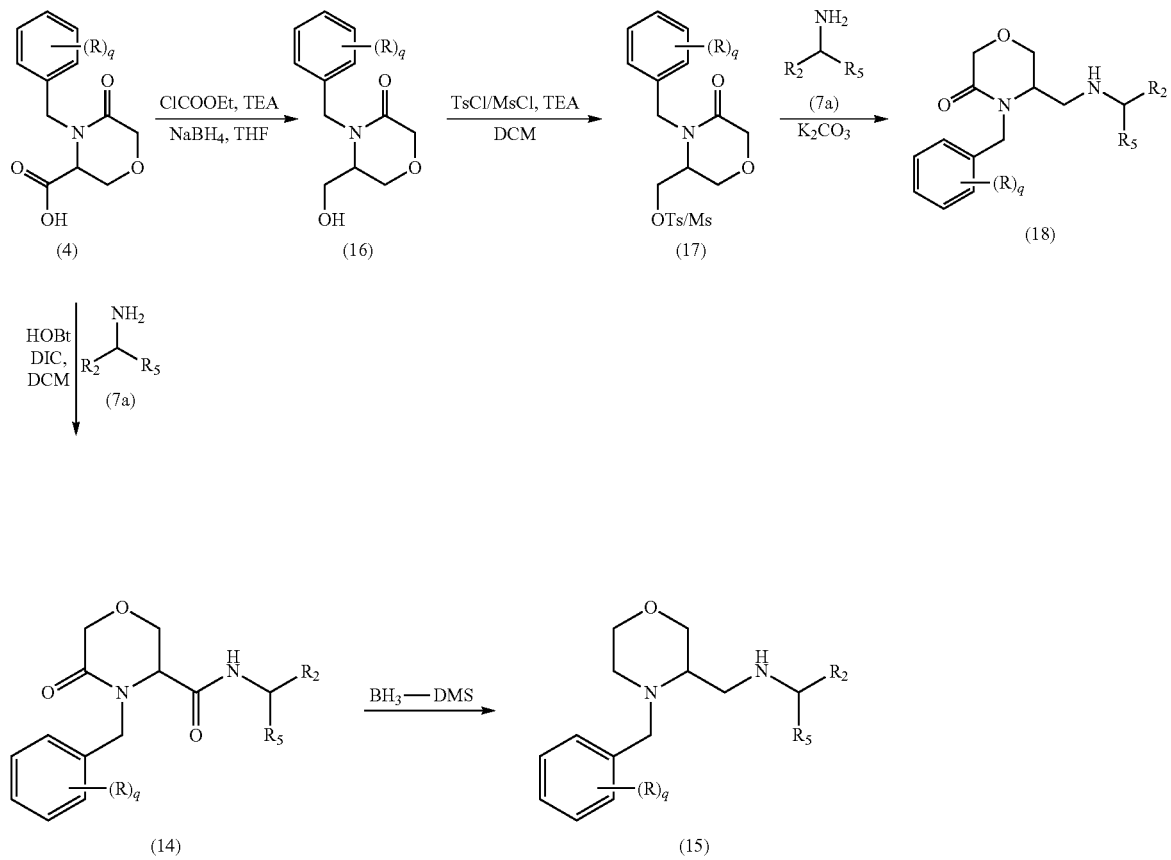

The compound of formula (18) where R, $R_2$, $R_5$ and 'q' are as described herein above, can be prepared by following sequential conversions of compound of formula (4). Selective reduction of compound of formula (4) using suitable reducing agents for example sodium borohydride in presence of ethyl chloroformate and base such as triethylamine or N,N'-diisopropyl ethylamine (mix anhydride formation with ethyl chloroformate in basic conditions) gives compound of formula (16). Tosylation or mesylation of compound of formula (16) is carried out in presence of base such as pyridine or triethylamine to give compound of formula (17), which on coupling with amine of formula (7a) in basic conditions such as $K_2CO_3$ or $Cs_2CO_3$ or Hunig's bases in solvents like toluene, DMF (Dimethylformamide) or acetonitrile gives compound of formula (18).

Also, compound of formula (4) can be coupled with amine of formula (7a) by using suitable coupling reagents such as N,N-diisopropylcarbodiimide or EDCI and 1-hydroxy benzotriazole in suitable solvent to afford compound of formula (14). This compound of formula (14) is then reduced using suitable reducing agents for example borane-dimethyl sulfide complex to get compound of formula (15). If the compound for formula (15) is an ester derivative it can be further converted to corresponding acid by using the procedures known in the art for example using base such as NaOH or LiOH.

Scheme-3

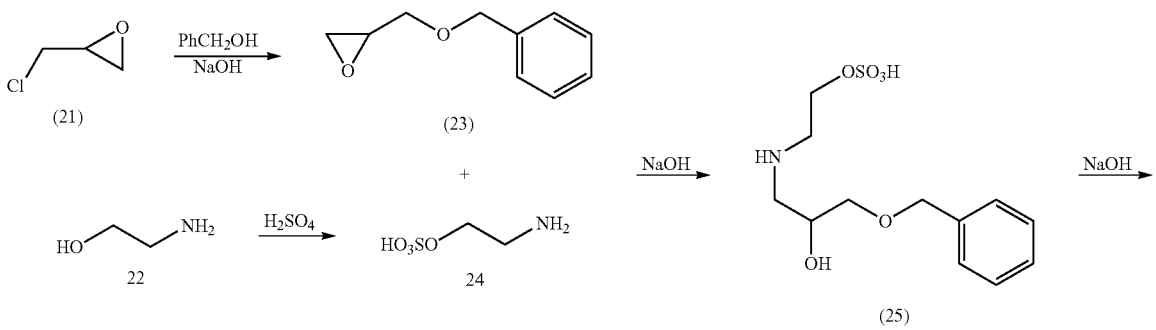

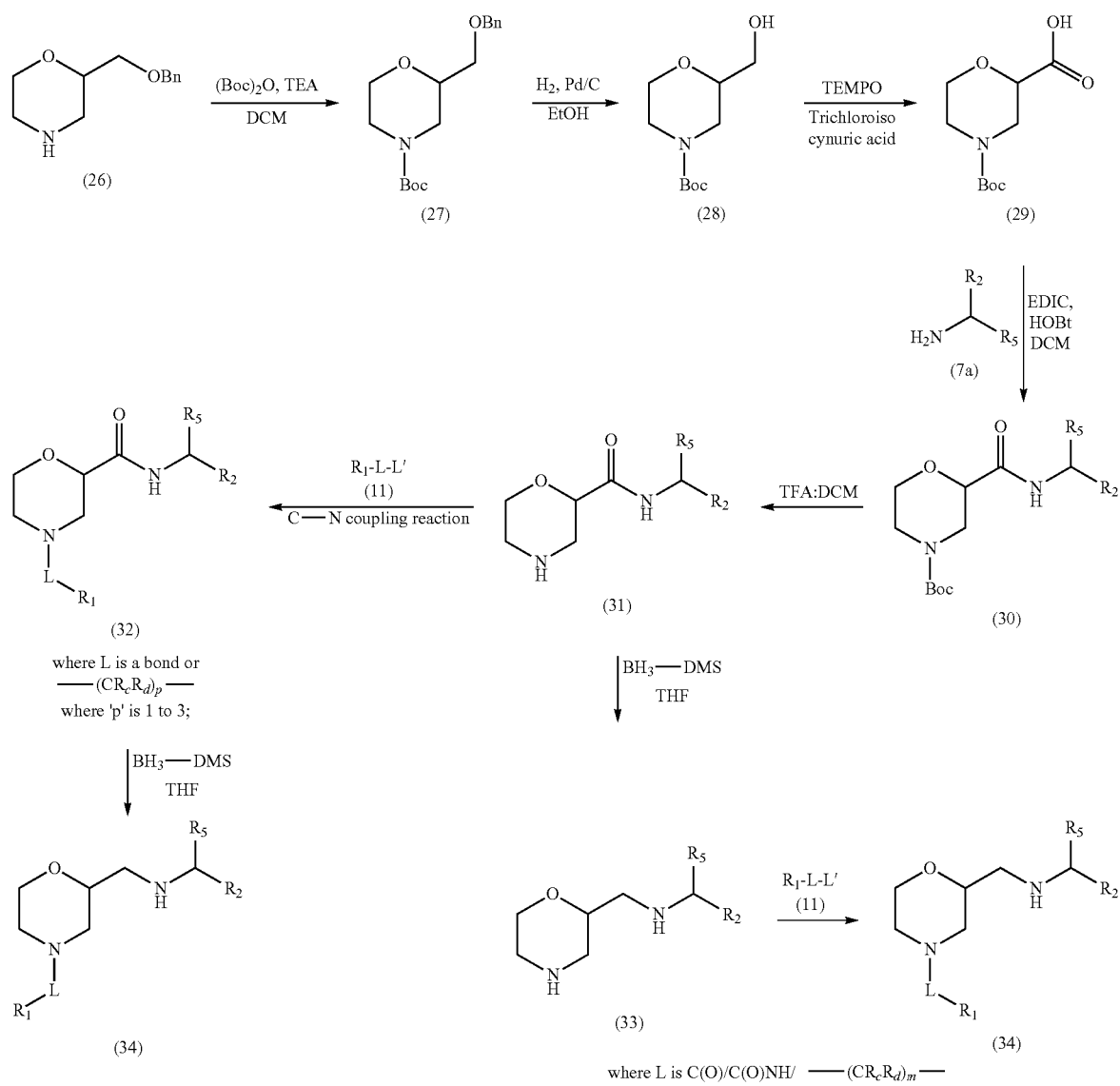

As depicted in Scheme-3, morpholine of formula (26) (US 2010/184805 and WO 2007/6715) can be prepared by coupling of 2-(benzyloxymethyl)-oxirane (23) (*J. Org. Chem.*, 1985, 50, 4350) and 2-aminomethyl hydrogen sulfate (24) (*Agricultural and Biological Chemistry*, 1991, 55(10), 2537; *J. Am. Chem. Soc.*, 1947, 69, 1540) in presence of aqueous NaOH followed by cyclisation in presence of base. The compound of formula (26) on N-Boc protection using (Boc)$_2$O in presence of base such as Hunig's base and in suitable solvent like dichloromethane gives compound (27) which is debenzylated using H$_2$, Pd(OH)$_2$/C in suitable solvent such as ethanol, methanol, acetone etc., to give compound of formula (28) (heterocycles, (1993), 35, 105 and WO 2007/06715). Compound of formula (28) converted to compound of formula (29) by using TEMPO and trichloroisocyanuric acid. Coupling of formula (29) with amine of formula (7a) in presence of N,N-diisopropylcarbodiimide or EDCI and 1-hydroxy benzotriazole in suitable solvent such as dichloromethane or tetrahydrofuran gives compound of formula (30). This compound of formula (30) is deprotected using suitable reagents for example TFA and in suitable solvent to give compound of formula (31). Compound of formula (31) undergoes carbon-nitrogen (C—N) coupling reaction with formula (11) by following the methods known in the art for example Buchwald coupling reaction (when L is a bond) using suitable reagents known in the art, or the coupling reaction (when L is not a bond) carried out by using suitable base for example TEA, DIPEA etc., and in suitable solvent for example DCM, THF etc., to give compound of formula (32). This compound of formula (32) undergoes amide group reduction by using suitable reagent for example borane-dimethyl sulfide complex to afford final compound of formula (34) where L, R$_1$, R$_2$ and R$_5$ are as defined herein above. Alternatively, the compound of formula (31) is converted to formula (33) by using suitable reagent for example borane-dimethyl sulfide complex. Compound of formula (33) undergoes carbon-nitrogen (C—N) coupling reaction with formula (11) by following the methods known in the art for example Buchwald coupling reaction (when L is a bond) using suitable reagents known in the art, or the coupling reaction (when L is not a bond) carried out by using suitable base for example TEA, DIPEA etc., and in suitable solvent for example DCM, THF etc., to give compound of formula (34). If the compound for formula (34) is an ester derivative it can be further converted to corresponding acid by using the procedures known in the art for example using base such as NaOH or LiOH.

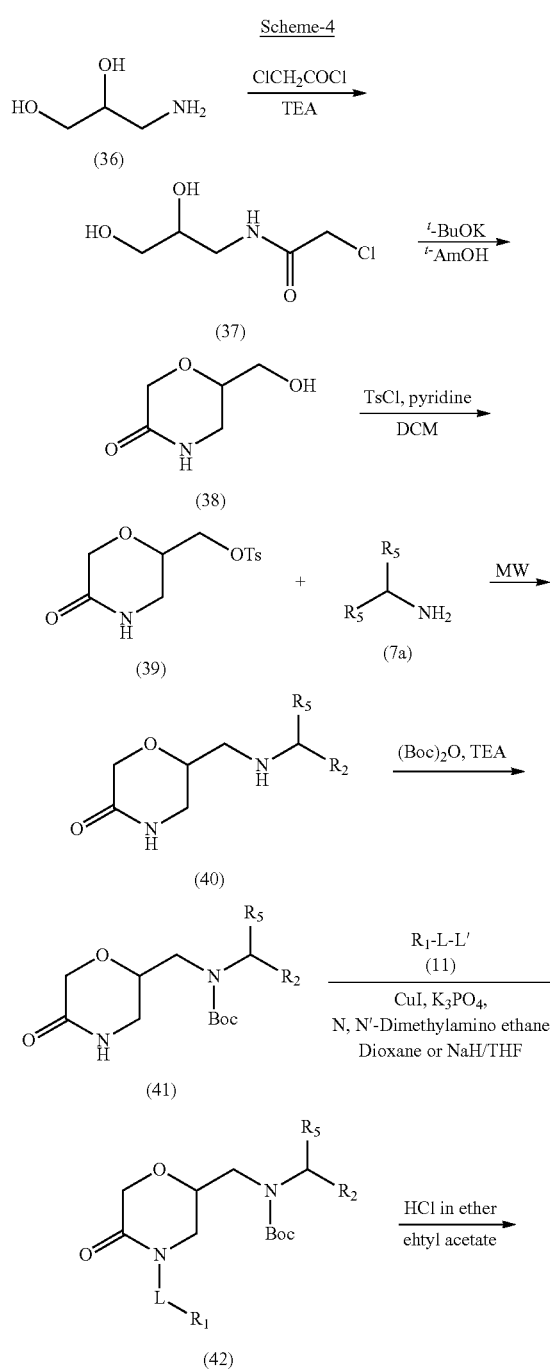

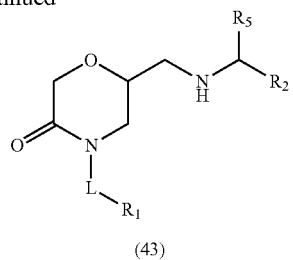

Commercially available 3-aminopropane-1,2-diol (36) undergoes acylation reaction with 2-chloroacetyl chloride in presence of base for example triethylamine to give compound of formula (37). It is further cyclised to give lactam compound of formula (38) in presence of tert-amyl alcohol and a base for example potassium tert-butoxide. The hydroxy group in formula (38) is O-tosylated in presence of base such as pyridine, TEA to give compound formula (39). The compound of formula (39) undergoes coupling reaction with amine of formula (7a) to give compound of formula (40) under microwave irradiation (MW) which is further protected with Boc in presence of a base to give compound of formula (41). This compound of formula (41) is coupled with formula (11) using suitable reagents using potassium phosphate and copper iodide or bases such as NaH, $K_2CO_3$ to give compound of formula (42) which on N-Boc deprotection in acidic conditions such as ethereal HCl to give compound of formula (43), where L, $R_1$, $R_2$ and $R_5$ are as defined herein above. If the compound for formula (43) is an ester derivative it can be further converted to corresponding acid by using the procedures known in the art for example using base such as NaOH or LiOH.

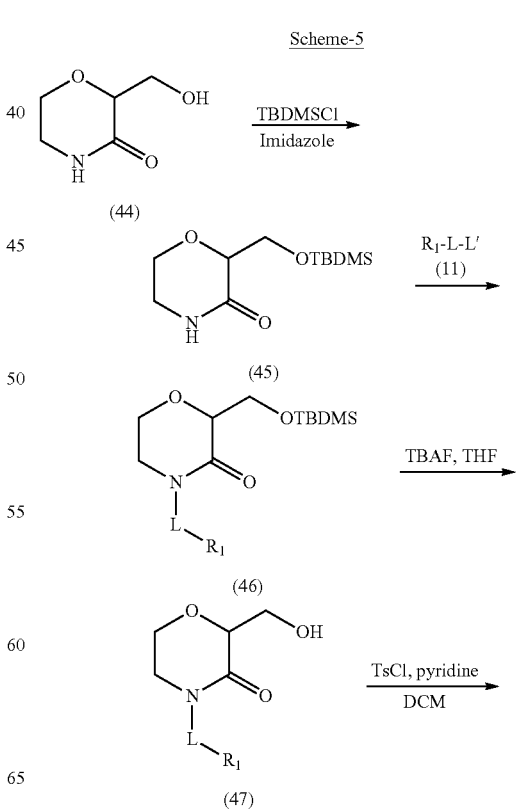

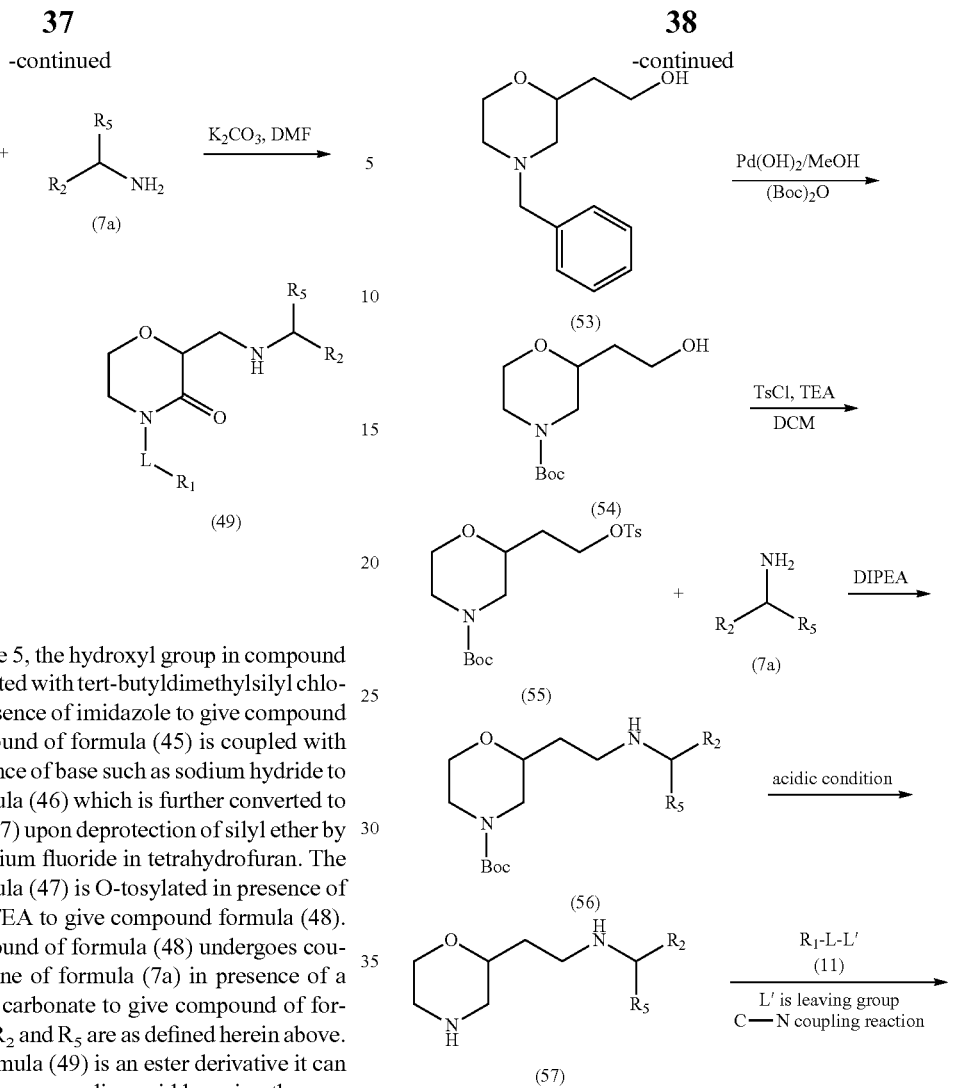

As depicted in scheme 5, the hydroxyl group in compound of formula (44) is protected with tert-butyldimethylsilyl chloride (TBDMSCl) in presence of imidazole to give compound of formula (45). Compound of formula (45) is coupled with formula of (11) in presence of base such as sodium hydride to give compound of formula (46) which is further converted to compound of formula (47) upon deprotection of silyl ether by using tetra butylammonium fluoride in tetrahydrofuran. The hydroxyl group in formula (47) is O-tosylated in presence of base such as pyridine, TEA to give compound formula (48). This O-tosylated compound of formula (48) undergoes coupling reaction with amine of formula (7a) in presence of a base such as potassium carbonate to give compound of formula (49) where L, $R_1$, $R_2$ and $R_5$ are as defined herein above. If the compound for formula (49) is an ester derivative it can be further converted to corresponding acid by using the procedures known in the art for example using base such as NaOH or LiOH.

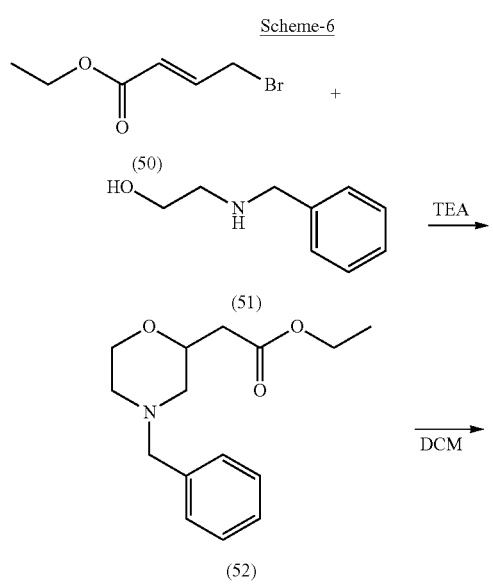

The reaction of commercially available 2-(benzylamino) ethanol of formula (51) with (E)-ethyl 4-bromobut-2-enoate (50) in presence of a base such as triethylamine gives compound of formula (52). Compound of formula (52) is further reduced to give alcohol compound of formula (53) using suitable reducing agents such as LiAlH$_4$, NaBH$_4$, Diisobutylaluminium hydride (DIBAL-H) etc. Compound of formula (53) undergoes debenzylation and N-Boc protection in single pot using H$_2$, Pd(OH)$_2$ and (Boc)$_2$O in suitable solvent to give compound of formula (54). The hydroxy group in formula (54) is O-tosylated in presence of base such as triethylamine to give compound formula (55). This compound of formula (55) is coupled with amine of formula (7a) to give compound of formula (56) followed by Boc deprotection in acidic conditions to give compound of formula (57). this compound of formula (57) undergoes carbon-nitrogen (C—N) coupling reaction with formula (11) by following the methods known in the art for example Buchwald coupling reaction (when L is a bond) using suitable reagents known in the art, or the coupling reaction (when L is not a bond) carried out by using suitable base for example TEA, DIPEA etc., and in suitable solvent for example DCM, THF etc., to give compound of formula (58) where L, $R_1$, $R_2$ and $R_5$ are as defined herein above. If the compound for formula (58) is an ester derivative it can be further converted to corresponding acid by using the procedures known in the art for example using base such as NaOH or LiOH.

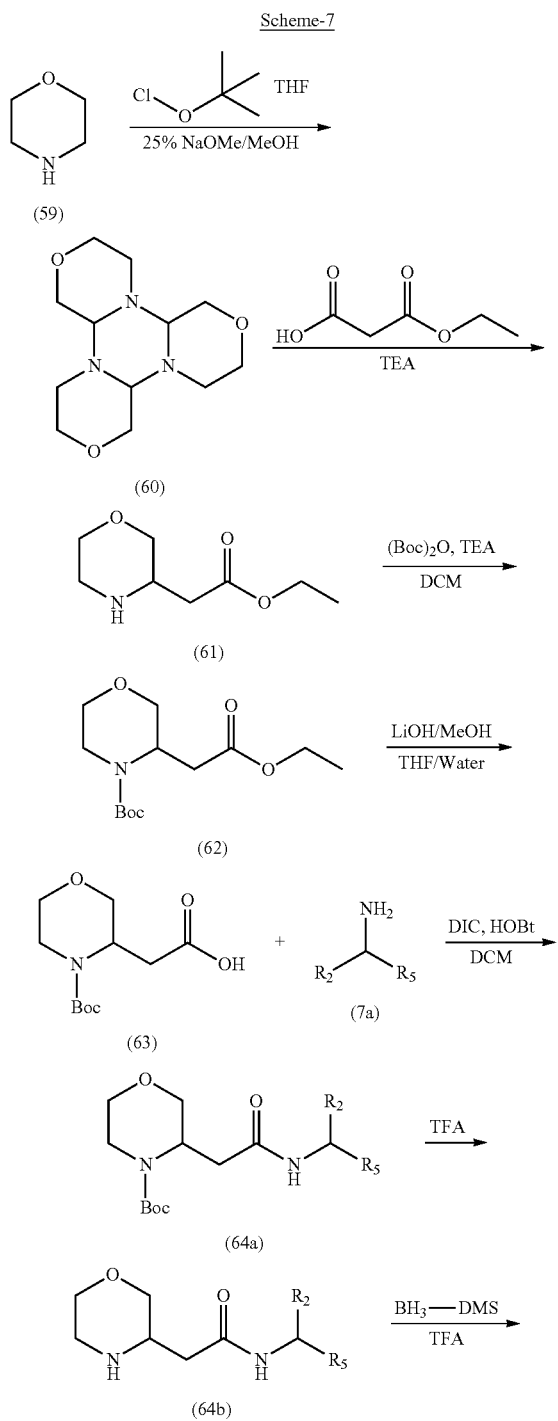

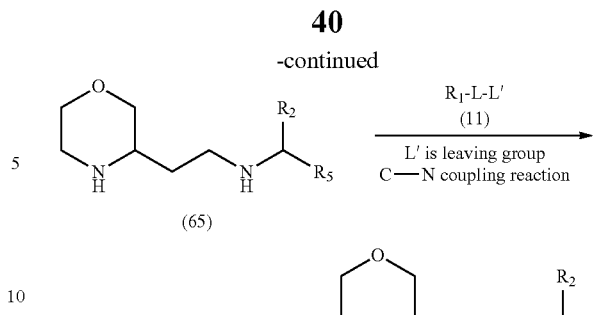

Morpholine compound of formula (59) is reacted with tert-butyl hypochlorite in THF to give compound of formula (60), which is further reacted with 2-(ethoxycarbonyl)acetic acid in the presence of TEA to give compound of formula (61). This compound of formula (61) is N-BOC protected with Boc anhydride in presence of TEA to give compound of formula (62). Compound of formula (62) undergoes hydrolysis to give compound of formula (63) using suitable base for example lithium hydroxide. Compound of formula (63) is reacted with amine compound of formula (7a) to give compound of formula (64a) in the presence of suitable reagent for example DIPC and HOBT, and this amide compound is first deprotected then reduced (amide group) in presence of suitable reagent for example borane-dimethyl sulfide complex in THF to give compound of formula (65). This compound of formula (65) undergoes carbon-nitrogen (C—N) coupling reaction with formula (11) by following the methods known in the art for example Buchwald coupling reaction (when L is a bond) using suitable reagents known in the art, or the coupling reaction (when L is not a bond) carried out by using suitable base for example TEA, DIPEA etc., and in suitable solvent for example DCM, THF etc., to give compound of formula (66) where L, $R_1$, $R_2$ and $R_5$ are as defined herein above. If the compound for formula (66) is an ester derivative it can be further converted to corresponding acid by using the procedures known in the art for example using base such as NaOH or LiOH.

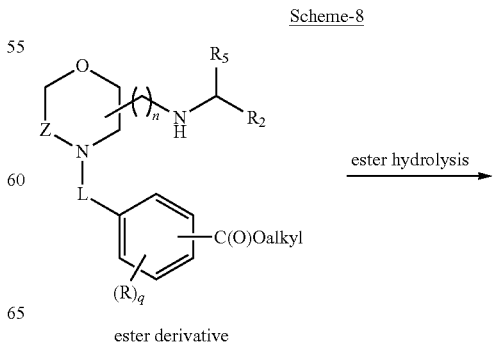

ester derivative

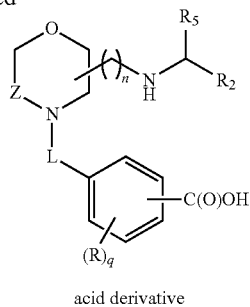

acid derivative

The ester derivative in Scheme-8, which can be prepared in any of the above schemes, undergoes hydrolysis in presence of a base such as NaOH, LiOH etc., to give corresponding acid derivative of the final compound where L, Z, R, $R_2$, $R_5$, 'n', and 'q' are as defined herein above.

Scheme-9

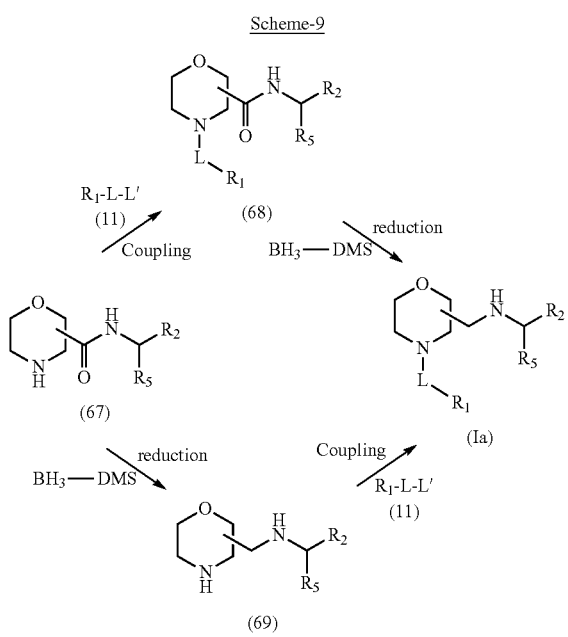

The compound of formula (Ia) can be prepared by C—N coupling of compound of formula (67) with formula (11) as mentioned in scheme-1 and scheme-3, followed by amide reduction as depicted in scheme-9.

Alternatively, the compound of formula (Ia) can be prepared from compound of formula (67) by carrying out amide reduction followed by coupling with formula (11) as mentioned in scheme-1 and scheme-3. If the compound for formula (Ia) is an ester derivative it can be further converted to corresponding acid by using the procedures known in the art for example using base such as NaOH or LiOH.

Scheme-10

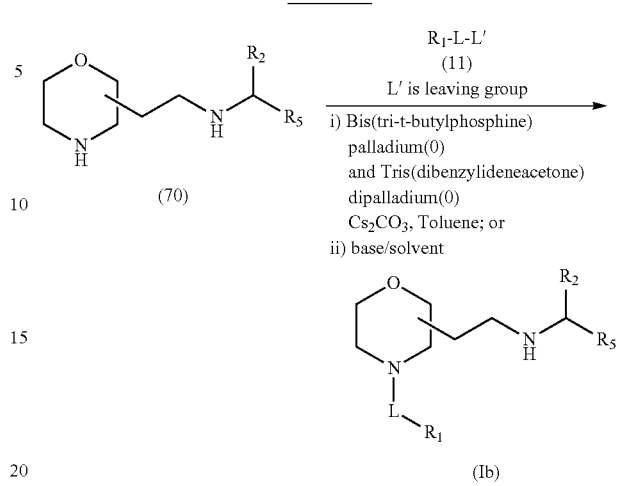

This compound of formula (70) (which derived from formula (57) and (65) as depicted in scheme-6 and scheme-7) is coupled with formula (11) in presence of Buchwald coupling reaction conditions (C—N bond formation) (when L is a bond) using suitable reagents known in the art, or the coupling reaction (when L is not a bond) carried out by using suitable base for example TEA, DIPEA etc., and in suitable solvent for example DCM, THF etc., to give compound of formula (Ib). If the compound for formula (Ib) is an ester derivative it can be further converted to corresponding acid by using the procedures known in the art for example using base such as NaOH or LiOH.

EXPERIMENTAL

The invention is further illustrated by the following examples which are provided merely to be exemplary of the invention and do not limit the scope of the invention. The examples set forth below demonstrate the synthetic procedures for the preparation of the representative compounds. Certain modifications and equivalents will be apparent to those skilled in the art and are intended to be included within the scope of the invention. The aforementioned patents and patent applications are incorporated herein by reference.

Intermediates

Intermediate-1

N-((R)-1-(Naphthalen-1-yl)ethyl)morpholine-3-carboxamide

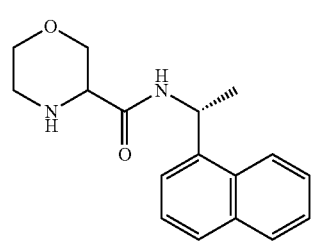 [SMILES: C[C@@H](NC(=O)C1COCCN1)c1cccc2ccccc12]

Step-1: 4-(tert-Butoxycarbonyl)morpholine-3-carboxylic acid

Saturated aqueous NaHCO₃ (15 mL) was added to a stirred solution of tert-butyl 3-(hydroxymethyl)morpholine-4-carboxylate (1.09 g, 5.0 mmol) (*Organic and Bio-Organic Chemistry* (1972-1999); (1985); 2577-2580, WO 2006/114606 and US 2010/210640) in acetone (50 mL) at 0° C. Solid NaBr (0.1 g, 1 mmol) and TEMPO (0.015 g, 0.1 mmol) were added. Trichloroisocyanuric acid (2.32 g, 10.0 mmol) was then added for 20 min at 0° C. After addition, the reaction mixture was allowed to room temperature (RT) and further maintained overnight. 2-Propanol (3 mL) was added and the resulting solution was stirred at RT for 30 min, filtered through a pad of Celite, concentrated under vacuum, and treated with saturated aqueous Na₂CO₃ solution (15 mL) The aqueous solution was extracted with EtOAc (5 mL), acidified with 6N HCl and extracted with EtOAc (5×10 mL). The combined organic layers were dried over Na₂SO₄ and the solvent was concentrated to give title compound as a white solid (760 mg). (M–H)–229.9.

Step-2: tert-Butyl 3-(((R)-1-(naphthalen-1-yl)ethyl)carbamoyl)morpholine-4-carboxylate To a stirred solution of Step-1 of Intermediate-1 (1.8 g, 7.79 mmole) in dichloromethane, HOBt (1.57 g, 11.6 mmole) was added followed by DIPC (1.05 mL, 11.6 mmole) at RT. The reaction mixture was stirred for 15 min and (R)-1-(naphthalen-1-yl)ethanamine (1.49 mL, 9.35 mmole) was added to the reaction mixture and then stirred overnight. Solid separated out was filtered, washed with dichloromethane (2×15 mL), filtrate collected and washed with brine (2×15 mL) and demineralised water (DM water) to get crude amide, which was further purified by flash chromatography (n-hexane:ethyl acetate, 8:2) to get title compound as a white solid (2.6 gm) (m/z-Boc) 285.1

Step-3: N-((R)-1-(Naphthalen-1-yl)ethyl)morpholine-3-carboxamide

To a stirred solution of Step-2 of Intermediate-1 (360 mg) in dichloromethane (3 mL), TFA (2 mL) was added dropwise at 0° C. and stirred for 3 h. Reaction mixture was concentrated under reduced pressure, further dried using high vacuum, the resultant oily mass diluted with dichloromethane and sodium bicarbonate solution, organic layer separated, dried over Na₂SO₄ concentrated to get the title compound as a white solid (300 mg) m/z 285.1

Intermediate-2

N-((R)-1-(Naphthalen-1-yl)ethyl)morpholine-2-carboxamide

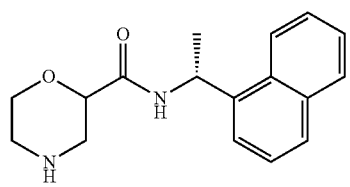 [SMILES: C[C@@H](NC(=O)C1CNCCO1)c1cccc2ccccc12]

Step-1: 4-(tert-Butoxycarbonyl)morpholine-2-carboxylic acid

Saturated aqueous NaHCO₃ (15 mL) was added to a stirred solution of tert-butyl 2-(hydroxymethyl)morpholine-4-carboxylate (1.09 g, 5.0 mmol) (heterocycles, (1993), 35, 105 and WO 2007/06715) in acetone (50 mL) at 0° C. Solid NaBr (0.1 g, 1 mmol) and TEMPO (0.015 g, 0.1 mmol) were added. trichloroisocyanuric acid (2.32 g, 10.0 mmol) was then added for 20 min at 0° C. After addition the reaction mixture was allowed to rise to RT and stirred overnight. 2-Propanol (3 mL) was added and the resulting solution was stirred at RT for 30 min, filtered through a pad of Celite, concentrated under vacuum, and treated with saturated aqueous Na₂CO₃ solution (15 mL) The aqueous solution was extracted with EtOAc (5 mL), acidified with 6N HCl and extracted with EtOAc (5×10 mL). The combined organic layers were dried over Na₂SO₄ and the solvent was concentrated to give the title compound as a white solid (1.1 g crude) (M–H) 230.

Step-2: tert-Butyl-2-(((R)-1-(naphthalen-1-yl)ethyl)carbamoyl)morpholine-4-carboxylate To a stirred solution of Step-1 of Intermediate-2 (2.9 g, 12.55 mmole) in dichloromethane (100 ml), HOBt (2.54 g, 18.83 mmole) was added followed by DIPC (2.92 mL, 18.83 mmole) at RT (room temperature). The reaction mixture was stirred for 15 min and (R)-1-(naphthalen-1-yl)ethanamine (2.41 mL, 15.06 mmole) was added to the reaction mixture and stirred overnight. Solid separated out was filtered, washed with dichloromethane (2×30 mL), filtrate collected and washed with brine (2×30 mL) and DM water to get crude amide which was further purified by flash chromatography (n-Hexane:ethyl acetate, 8:2) to get the title compound as a white solid (3.4 gm) (m/z-Boc) 285.2

Step-3: N-((R)-1-(Naphthalen-1-yl)ethyl)morpholine-2-carboxamide

To a stirred solution of Step-2 of Intermediate-2 (28) (3.4 g, 11.97 mmole) in dichloromethane (100 mL), TFA (20 mL) was added dropwise at 0° C. and stirred for 3 h. Reaction mixture was concentrated under reduced pressure, further dried using high vacuum, resultant crude oil diluted with dichloromethane and added sodium bicarbonate solution, organic layer separated, dried over Na₂SO₄ and concentrated to get the title compound as a white solid (2.4 g). m/z 285.1

Intermediate-3

N-((R)-1-(3-Methoxyphenyl)ethyl)morpholine-3-carboxamide

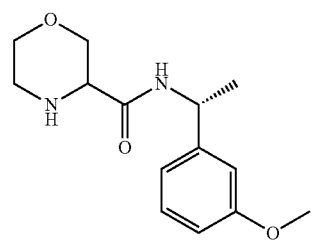 [SMILES: COc1cccc([C@@H](C)NC(=O)C2COCCN2)c1]

The title compound was prepared by following the similar procedure as described in Step-2 of Intermediate-1 by using Step-1 of Intermediate-1 and (R)-1-(3-methoxyphenyl) ethanamine followed by deprotection of resultant Boc protected compound as described in Step-3 of Intermediate-1.

Intermediate-4

(1R)-N-(Morpholin-3-ylmethyl)-1-(naphthalen-1-yl)ethanamine

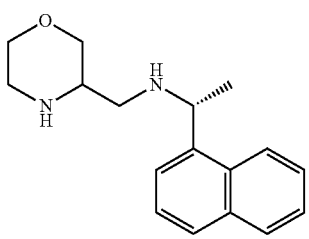 [SMILES: C[C@@H](NCC1COCCN1)c1cccc2ccccc12]

To a stirred solution of Intermediate-1 (1.9 gm, 6.68 mmole) in THF (35 mL), borane-dimethyl sulfide complex (1.26 mL, 16.7 mmole) was added at RT, heated to reflux and further maintained for 6 h at the same temperature. After reaction completion, the reaction mass was concentrated under reduced pressure to get crude oily mass. This was diluted with 10N hydrochloric acid (20 mL) and heated to 100° C. for 1 h. Reaction mixture was basified with aqueous NaOH solution (pH 10) and extracted in ethyl acetate (2×25 mL), washed with brine solution, dried over $Na_2SO_4$, and concentrated to get the title compound as an oily mass (1.6 gm). m/z 271.1

Intermediate-5

(1R)-1-(3-Methoxyphenyl)-N-(morpholin-3-ylmethyl)ethanamine

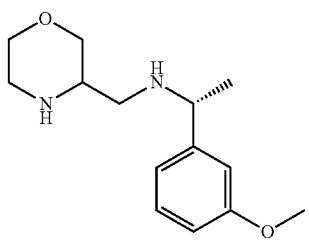 [SMILES: COc1cccc([C@@H](C)NCC2COCCN2)c1]

The title compound was prepared by following the similar procedure as described in Intermediate-4 by using Intermediate-3.

Intermediate-6

N-((R)-1-(3-Methoxyphenyl)ethyl)morpholine-2-carboxamide

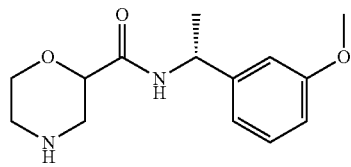 [SMILES: COc1cccc([C@@H](C)NC(=O)C2CNCCO2)c1]

The title compound was prepared by following the similar procedure as described in Step-2 of Intermediate-2 by using 4-(tert-butoxycarbonyl)morpholine-2-carboxylic acid (Step-1 of Intermediate-2) and (R)-1-(3-methoxyphenyl) ethanamine followed by deprotection of resultant Boc protected compound by following the similar procedure as described in Step-3 of Intermediate-2.

Intermediate-7

4-Benzyl-N-((R)-1-(naphthalen-1-yl)ethyl)-5-oxomorpholine-3-carboxamide

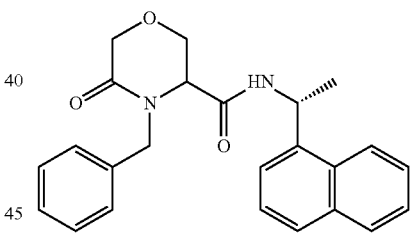

To a stirred solution of 4-benzyl-5-oxomorpholine-3-carboxylic acid (*Organic and Bio-Organic Chemistry* (1972-1999); (1985); 2577-2580) (500 mg, 2.12 mmole) in dichloromethane (15 mL), HOBt (430 mg, 3.19 mmole) and DIPC (287 μL, 3.19 mmole) were added at room temperature. The reaction mixture was stirred for 15 min, then (R)-1-(naphthalen-1-yl)ethanamine (400 μL, 2.57 mmole) was added to the reaction mixture and stirred overnight. Solid separated out was filtered, washed with dichloromethane (2×15 mL), filtrate collected and washed with brine solution (2×15 mL) and DM water. The organic layer was concentrated to get crude amide and which was further purified by flash chromatography (n-Hexane:ethyl acetate, 8:3) to get title compound (500 mg). m/z 389.2

Intermediate-8

4-Benzyl-N-((R)-1-(3-methoxyphenyl)ethyl)-5-oxo-morpholine-3-carboxamide

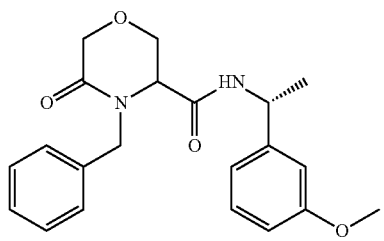 [SMILES: COc1cccc([C@@H](C)NC(=O)C2COCC(=O)N2Cc2ccccc2)c1]

The title compound was prepared by following the similar procedure as described in Intermediate-7 by using 4-benzyl-5-oxomorpholine-3-carboxylic acid (*Organic and Bio-Organic Chemistry* (1972-1999); (1985); 2577-2580) and (R)-1-(3-methoxyphenyl) ethanamine. m/z 369.2.

Intermediate-9 tert-Butyl ((R)-1-(naphthalen-1-yl)ethyl)((5-oxomorpholin-2-yl)methyl)carbamate

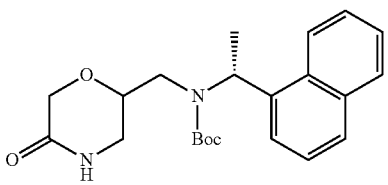 [SMILES: C[C@H](c1cccc2ccccc12)N(CC1CNC(=O)CO1)C(=O)OC(C)(C)C]

Step-1: 2-Chloro-N-(2,3-dihydroxypropyl)acetamide

3-Amino-1,2-propanediol (16.8 g, 184 mmol) was dissolved in MeOH (90 mL) at RT and the solution was diluted with ACN (acetonitrile) (550 mL) TEA (30.5 mL, 219 mmol) was added and the reaction mixture was cooled to −10° C. Chloroacetyl chloride (22.2 g, 15.6 mL, 197 mmol) was added dropwise at −10° C. for 2 h under nitrogen atmosphere and further maintained at −10° C. for 1 h and the reaction mixture was allowed to RT and stirred overnight (15 h). The solvents were removed under vacuo. The residue was purified by flash column chromatography (normal phase, gradient 1 percent to 20 percent MeOH in EtOAc) to afford the title compound (20 g) as a colorless oil m/z 168.

Step-2: 6-(Hydroxymethyl)morpholin-3-one

To a stirred solution of potassium tert-butoxide (23.4 g, 299.4 mmol) in 200 mL tert-amyl alcohol at room temperature was added 2-chloro-N-(2,3-dihydroxypropyl) acetamide (Step-1 of Intermediate-9) (20 g, 119.6 mmol) in 460 mL tert-amyl alcohol for 2 h under nitrogen atmosphere. After one hour, MeOH (100 mL) and H₂O (3 mL) were added and further stirred for 20 min. The reaction mixture was concentrated under vacuum and purified by flash chromatography on silica gel with MeOH/EtOAc (20:80) to give the title compound as a white solid (14.4 g). m/z 132.1

Step-3: (5-Oxomorpholin-2-yl)methyl 4-methylbenzenesulfonate

To a stirred solution of 6-(hydroxymethyl)morpholin-3-one (Step-2 of Intermediate-9) (4.1 g, 31.29 mmole) in dichloromethane (25 mL), triethylamine (8.31 mL, 62.59 mmole) and TsCl (tosyl chloride) (6.56 g, 34.42 mmole) were added at 0° C. The reaction mixture was allowed to RT and further stirred overnight. Reaction mixture was diluted with dichloromethane (30 mL), and washed with brine solution (2×30 mL) and DM water, separated the organic layer, dried over Na₂SO₄, concentrated and further purified by flash chromatography (n-hexane:ethyl acetate, 1:4) to get the title compound as a white solid (3.8 gm). m/z 286.1

Step-4: 6-((((R)-1-(Naphthalen-1-yl)ethyl)amino) methyl)morpholin-3-one

The above Step-3 of Intermediate-9 (3.0 g, 10.52 mmole) and (R)-1-(naphthalen-1-yl)ethanamine (3.37 mL, 21.05 mmole) mixed together in microwave vial and irradiated in microwave (Biotage Microwave) at 120° C. for 2 h. Reaction mixture purified through flash chromatography (using eluent 1:4, MeOH:DCM) to get the title compound as an oil (2.7 g). m/z 285.1

Step-5: tert-Butyl ((R)-1-(naphthalen-1-yl)ethyl)((5-oxomorpholin-2-yl)methyl) carbamate To a stirred solution of the above Step-4 of Intermediate-9 (2.7 g, 9.5 mmole) in dichloromethane (20 ml), triethylamine (2.9 mL, 20.91 mmole) and (Boc)₂O (2.28 g, 10.4 mmole) were added at 0° C. The reaction mixture was allowed to RT and further stirred overnight. Reaction mixture was diluted with dichloromethane (30 mL), and washed with brine solution (2×30 mL) and DM water. Separated organic layer, dried over Na₂SO₄, concentrated and it was further purified by flash chromatography (n-Hexane:ethyl acetate, 1:1) to get the title compound as a sticky oil (2.5 g). nth 385.2

Intermediate-10 tert-Butyl ((R)-1-(3-methoxyphenyl)ethyl)((5-oxomorpholin-2-yl)methyl)carbamate

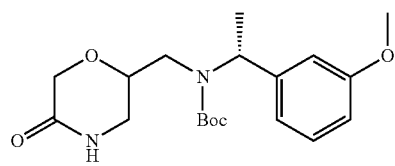 [SMILES: COc1cccc([C@@H](C)N(CC2CNC(=O)CO2)C(=O)OC(C)(C)C)c1]

The title compound was prepared by following the similar procedure as described in Step-4 of Intermediate-9 followed by N-Boc protection by following the procedure as described in Step-5 of Intermediate-9 by using (5-oxomorpholin-2-yl) methyl-4-methylbenzenesulfonate (step-3 of Intermediate-9) and (R)-1-(3-methoxyphenyl)ethanamine.

Intermediate-11

2-(Morpholin-2-yl)-N-((R)-1-(naphthalen-1-yl)ethyl)ethanamine

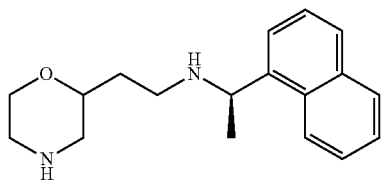 [SMILES: C[C@@H](NCCC1CNCCO1)c1cccc2ccccc12]

Step-1: Ethyl 2-(4-benzylmorpholin-2-yl)acetate 2-(Benzylamino)ethanol (19.05 ml, 132 mmol) and triethylamine (18.44 ml, 132 mmol) was added to water (150 ml) and the resulting mixture was heated to reflux temperature. (E)-Ethyl 4-bromobut-2-enoate (18.24 ml, 132 mmol) was added dropwise for 10 min The resulting mixture was further maintained at reflux temperature for 5 h. The reaction mixture was cooled to 25° C. and added NaOH (5.29 g, 132 mmol) after that the solvent was removed by distillation under reduced pressure to give orange oil. Ethyl acetate (150 mL) was added and the resulting solution was washed with water (2×50 mL). Ethyl acetate was distilled off under reduced pressure to give crude compound (15 g). This crude compound was purified by flash chromatography (Biotage) using eluent 20% ethyl acetate in hexane to yield 13 g of pure title compound as colorless viscous oil. m/z 264.08.

Step-2: 2-(4-Benzylmorpholin-2-yl)ethanol

A solution of Step-1 intermediate (13 g, 49.4 mmol) in THF (100 ml) was added dropwise to a stirred suspension of LiAlH$_4$ (LAH) (1.874 g, 49.4 mmol). The reaction mixture is stirred at 25° C. for 1 h. The excess of LAH is decomposed by the successive addition of ethyl acetate and water. The insoluble materials were filtered and the filtrate is evaporated to give the title compound (10 g, 45.2 mmol, 92% yield) as oily mass. This compound was purified by flash chromatography (Biotage) using eluent 80% ethyl acetate in hexane to yield 10 g of pure compound as colorless, viscous oil. m/z 222.17

Step-3: tert-Butyl 2-(2-hydroxyethyl)morpholine-4-carboxylate

To a stirred solution of Step-2 intermediate (10 g, 45.2 mmol) and (Boc)$_2$O (31.5 ml, 136 mmol) in MeOH (50 ml), 10% Pd/C (1 g, 7.12 mmol) was added and the reaction mixture was stirred under pressure (balloon of hydrogen) for 8 h. Reaction mixture was filtered through celite bed and concentrated to get crude product (8 g). This crude compound was purified by flash chromatography (Biotage) using eluent 80% ethyl acetate in hexane to yield 7.3 g of pure compound as colorless viscous oil. m/z-Boc 132.1

Step-4: tert-Butyl 2-(2-(tosyloxy)ethyl)morpholine-4-carboxylate

To a stirred solution of Step-3 intermediate (7.3 g, 31.6 mmol) in dichloromethane (10 ml), triethylamine (11.00 ml, 79 mmol) was added. Cooled the reaction mixture to 0° C., then tosyl chloride (9.03 g, 47.3 mmol) was added at the same temperature. The reaction mixture was allowed to RT and stirred overnight. Reaction mixture diluted with dichloromethane (30 mL), and washed with brine (2×30 mL) and DM water (demineralized water), separated the organic layer, dried over Na$_2$SO$_4$, and concentrated which was further purified by flash chromatography (n-hexane:ethyl acetate, 1:4) to get title compound (10.7 g). m/z-Boc 286.02

Step-5: tert-Butyl 2-(2-(((R)-1-(naphthalen-1-yl)ethyl)amino)ethyl)morpholine-4-carboxylate To a stirred solution of Step-4 intermediate (10.3 g, 26.7 mmol), (R)-1-(naphthalen-1-yl)ethanamine (8.63 ml, 53.4 mmol) and N,N-diisopropylethylamine (50 ml, 286 mmol) in dichloromethane (10 ml) was heated at 120° C. and maintained for 8 h, concentrated reaction mixture and further purified by flash chromatography to get the title compound (9.5 g). m/z 385.22.

Step-6: 2-(Morpholin-2-yl)-N-((R)-1-(naphthalen-1-yl)ethyl)ethanamine

To a stirred solution of Step-5 intermediate (9.5 g, 24.71 mmol) in ethyl acetate (10 ml), HCl in dioxane (6.18 ml, 24.71 mmol) was added and the reaction mixture was heated at 60° C. and further maintained for 8 h in closed vessel. Solid separated out was filtered and washed with ethylacetate, basified with saturated NaHCO$_3$ and extracted with dichloromethane, dried over Na$_2$SO$_4$, and concentrated to get title product (6.5 g, 22.86 mmol, 93% yield) as white solid (6.5 g, 93%). m/z 285.2.

Intermediate-12

2-(Morpholin-3-yl)-N-((R)-1-(naphthalen-1-yl)ethyl)ethanamine

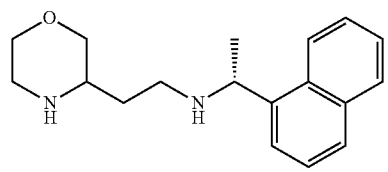 [SMILES: C[C@@H](NCCC1COCCN1)c1cccc2ccccc12]

Step-1: Dodecahydrotris([1,4]oxazino)[4,3-a:4',3'-c:4'',3''-e][1,3,5]triazine In a flask fitted with a condenser and a thermocouple THF (10 mL) was added and cooled to −15° C. To this, tert-butyl hypochlorite (5 g, 46.1 mmol) was added for 15 minutes at below 0° C. Maintained the reaction mixture at the same temperature for 30 min. 25% NaOMe/MeOH (11 mL, 0.5 mol) was added for 15 min at below 3° C. The mixture was allowed to 45° C. and further maintained for 1 h, then cooled to RT. The reaction mixture was filtered through celite bed and evaporated the filtrate to get the title compound (5 g).

Step-2: Ethyl 2-(morpholin-3-yl)acetate

To a solution of monoethyl malonate (0.12 mol) and triethylamine (0.12 mol) acetonitrile (40 mL) and Step-1 intermediate was added (0.02 mol). The mixture was heated to a sufficient temperature to cause considerable evolution of CO$_2$ gas. After 5 h, the solution was concentrated under reduced pressure. The residue was treated with 30% aqueous K$_2$CO$_3$ solution and extracted with diethyl ether, dried over Na$_2$SO$_4$ and concentrated to get the title compound.

Step-3: tert-Butyl 3-(2-ethoxy-2-oxoethyl)morpholine-4-carboxylate

To a stirred solution of ethyl 2-(morpholin-3-yl)acetate (Step-2 intermediate) (1.4 g, 8.08 mmol) in dichloromethane (20 mL), triethylamine (1.690 mL, 12.12 mmol) and followed by (Boc)$_2$O was added (2.81 mL, 12.12 mmol) at 0° C. The reaction mixture was allowed to RT and further stirred overnight. The reaction mixture was diluted with dichloromethane (15 mL), and washed with brine solution (2×8 mL) followed by DM water. The organic layer was separated, dried over Na$_2$SO$_4$ and concentrated. The crude compound was further purified by flash chromatography to give the title compound (700 mg, yield: 31.7%, three steps), m/z-boc 173.94.

Step-4: 2-(4-(tert-Butoxycarbonyl)morpholin-3-yl)acetic acid

To a stirred solution of Step-3 intermediate (800 mg, 2.93 mmol) in THF (5 mL) ethanol (3 mL) and water (1 mL) in single neck round bottom flask LiOH (350 mg, 14.63 mmol) was added. The reaction mixture was heated to 80° C. and further maintained for 4 h. After reaction completion, the reaction mixture was concentrated and washed with diethyl ether (2×10 mL). The aqueous layer was acidified with 6N HCl, extracted with dichloromethane (2×30 mL), washed with DM water, dried over Na$_2$SO$_4$ and concentrated to get the title compound (700 mg, 98% yield), m/z 246.14.

Step-5: tert-Butyl 3-(2-(((R)-1-(naphthalen-1-yl) ethyl)amino)-2-oxoethyl)morpholine-4-carboxylate To a stirred solution of Step-5 intermediate (30 ml), HOBt (0.749 g, 4.89 mmol) and DIPC (0.762 ml, 4.89 mmol) were added at RT. The reaction mixture was stirred for 15 min, then (R)-1-(naphthalen-1-yl)ethanamine (0.670 g, 3.91 mmol) was added to the reaction mixture and further stirred overnight. Solid separated out was filtered and filtrate extracted with dichloromethane (2×30 mL), washed with brine solution (2×30 mL) and DM water. The solvent was evaporated to get the crude compound and it was further purified by flash chromatography (n-Hexane:ethyl acetate, 4:1) to get the title compound as a white solid (930 mg, 71.6%), m/z 399.

Step-6: 2-(morpholin-3-yl)-N-((R)-1-(naphthalen-1-yl)ethyl)acetamide

To a stirred solution of Step-5 intermediate (930 mg, 2.334 mmol) in dichloromethane (15 mL), TFA (3 mL, 38.9 mmol) was added dropwise at 0° C. and stirred for 3 h at RT. After reaction completion, the reaction mixture was concentrated under reduced pressure, further dried using high vacuum. The resulted oily crude mass was diluted with dichloromethane and washed with sodium bicarbonate solution. Organic layer was separated, dried over Na$_2$SO$_4$ and concentrated to get the title compound (600 mg, 86%), m/z 299.15.

Step-7: 2-(Morpholin-3-yl)-N-((R)-1-(naphthalen-1-yl)ethyl)ethanamine

To a stirred solution of Step-6 intermediate (600 mg, 2.011 mmol) in THF (9 mL), borane-dimethyl sulfide complex (2.0 ml, 4.02 mmol) was added to the reaction mixture at RT. The reaction mixture was heated to reflux temperature and maintained for 6 h. After reaction completion, the reaction mixture was concentrated under reduced pressure to get crude oily mass. This was diluted with 10N hydrochloric acid (10 mL), then heated to 100° C. and maintained for 1 h. Reaction mixture was basified with aqueous NaOH solution (pH 10) and extracted into ethyl acetate (2×20 mL), washed with brine solution, dried over Na$_2$SO$_4$, and concentrated to get the title compound as oily mass (400 mg, 69.9%), 284.7.

Intermediate-13

(1R)-N-(morpholin-2-ylmethyl)-1-(naphthalen-1-yl) ethanamine

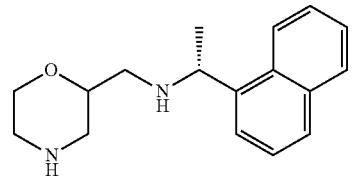 [SMILES: C[C@@H](NCC1CNCCO1)c1cccc2ccccc12]

The title compound was prepared by following the similar reduction procedure as described in Intermediate-4 by using Intermediate-2 and borane-dimethyl sulfide complex.

Intermediate-14 tert-Butyl((R)-1-(4-fluoro-3-methoxyphenyl)ethyl) ((5-oxomorpholin-2-yl)methyl)carbamate

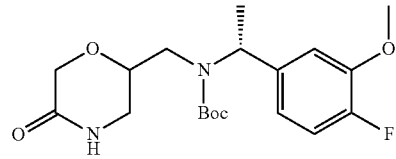 [SMILES: COc1cc([C@@H](C)N(CC2CNC(=O)CO2)C(=O)OC(C)(C)C)ccc1F]

The title compound was prepared by following the similar procedure as described in Step-4 of Intermediate-9 followed by N-Boc protection by following the procedure as described in Step-5 of Intermediate-9 by using (5-oxomorpholin-2-yl) methyl-4-methylbenzenesulfonate (step-3 of Intermediate-9) and (R)-1-(4-fluoro-3-methoxyphenyl)ethanamine.

Intermediate-15 tert-Butyl ((5-oxomorpholin-2-yl)methyl)((R)-1-phenylethyl)carbamate

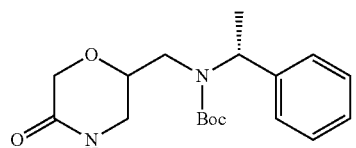

The title compound was prepared by following the similar procedure as described in Step-4 of Intermediate-9 by taking step-3 of Intermediate-9 and (R)-1-phenylethanamine, followed by N-Boc protection by following the similar procedure as described in Step-5 of Intermediate-9.

Intermediate-16

(1R)-1-(3-Methoxyphenyl)-N-(morpholin-2-ylmethyl)ethanamine

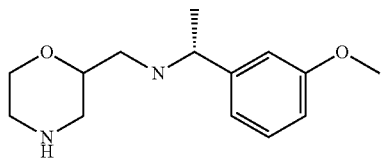 [SMILES: COc1cccc([C@@H](C)NCC2CNCCO2)c1]

The title compound was prepared by following the similar reduction procedure as described in Intermediate-4 by using Intermediate-6 and borane-dimethyl sulfide complex.

Intermediate-17 tert-Butyl ((S)-1-(naphthalen-1-yl)ethyl)((5-oxomorpholin-2-yl)methyl)carbamate

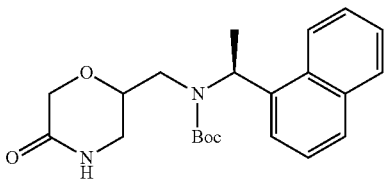 [SMILES: C[C@@H](c1cccc2ccccc12)N(CC1CNC(=O)CO1)C(=O)OC(C)(C)C]

The title compound was prepared by following the similar procedure as described in Step-4 of Intermediate-9 by taking step-3 of Intermediate-9 and (S)-1-(naphthalen-1-yl)ethanamine, followed by N-Boc protection by following the similar procedure as described in Step-5 of Intermediate-9.

EXAMPLES

Example-1a, 1b (1R)-1-(Naphthalen-1-yl)-N-((4-phenylmorpholin-3-yl)methyl)ethanamine hydrochloride

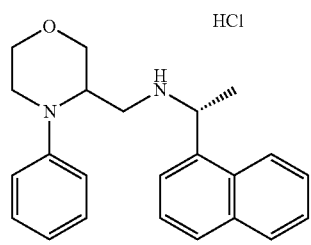 [SMILES: Cl ; C[C@@H](NCC1COCCN1c1ccccc1)c1cccc2ccccc12]

Step-1: N-((R)-1-(Naphthalen-1-yl)ethyl)-4-phenyl-morpholine-3-carboxamide

A mixture of N-((R)-1-(Naphthalen-1-yl)ethyl)morpholine-3-carboxamide (Intermediate-1) (300 mg, 1.056 mmol), trisdibenzylidene acetone dipalladium(0) (14.5 mg, 0.0158 mmole), xantphos (27.5 mg, 0.047 mmole), bromobenzene (144 µL, 1.37 mmole), and $Cs_2CO_3$ (516 mg, 1.58 mmole) in toluene (10 mL) was stirred at 110° C. for 20 h under nitrogen atmosphere. The mixture was diluted with diethyl ether, filtered through Celite, and concentrated in vacuum. The residue was purified by column chromatography on silica gel using a mixture of ethyl acetate and hexane as eluent afforded the title compound as an oil (150 mg), m/z 361.2.

Step-2: (1R)-1-(Naphthalen-1-yl)-N-((4-phenylmorpholin-3-yl)methyl)ethanamine

To a stirred solution of above Step-1 intermediate (140 mg, 0.388 mmole) in THF (5 mL), borane-dimethyl sulfide complex (147 µL, 1.94 mmole) was added to the reaction mixture at room temperature and refluxed for 6 h. After reaction completion reaction mixture was concentrated under reduced pressure to get crude oily product, which was diluted with 10N hydrochloric acid (20 mL), heated to 100° C. and further maintained for 1 h. Reaction mixture was basified with aqueous NaOH solution (pH 10) and extracted in ethyl acetate (2×25 mL), washed with brine solution, dried over $Na_2SO_4$, concentrated to get crude oily product, which was further purified by preparative HPLC to give mixture of diastereomers of the title compound (35 mg). Further, these diastereomers were separated by preparative HPLC (ACQUITY BEH C18, 50×2.1 mm, 1.7µ, water:ACN (90:10) V/V %+0.1% $NH_4OH$). Further, hydrochloride salt of Example-1a and Example-1b were prepared by following the procedure as described below.

Preparation of Hydrochloride Salt(s) of the Amino Examples:

Amino compound was dissolved in dry DCM, then slowly added with 2 Methereal HCl solution and further maintained for few minutes. The reaction mixture was distilled off completely to give hydrochloride salt of the desired compound.

Example-1a: $t_R$ (retention time)=2.56; $^1$H NMR (400 MHz, DMSO): δ 9.9 (bs, 1H), 9.65 (bs, 1H), 8.12 (d, J=8 Hz, 1H), 7.96-7.90 (m, 3H), 7.61-7.53 (m, 3H), 7.14 (t, J=7.2 Hz, 2H), 6.85 (d, J=8 Hz, 2H), 6.71 (t, J=7.2 Hz, 1H), 5.30 (q, J=6 Hz, 1H), 4.28-4.22 (m, 2H), 3.87-3.84 (m, 1H), 3.65 (d, J=10.4 Hz, 1H), 3.57 (m, 2H), 3.30-3.27 (m, 1H), 2.91-2.84 (m, 1H), 2.66-2.50 (m, 1H), 1.67 (d, J=6.4 Hz, 3H); m/z 347.3.

Example-1b: $t_R$=2.58; $^1$H NMR (400 MHz, DMSO): δ 10.0 (bs, 1H), 9.4 (bs, 1H), 8.17 (d, J=8 Hz, 1H), 8.02-7.96 (m, 3H), 7.61-7.57 (m, 2H), 7.09 (t, J=7.2 Hz, 2H), 6.83 (d, J=8 Hz, 2H), 6.72 (t, J=7.2 Hz, 1H), 5.38 (q, J=6.8 Hz, 1H), 3.82-3.78 (m, 2H), 3.64 (d, J=13.2 Hz, 1H), 3.53-3.46 (m, 2H), 3.24 (d, J=11.6 Hz, 2H), 2.99-2.85 (m, 3H), 1.66 (d, J=6.8 Hz, 3H); m/z 347.3.

Example-2a, 2b (1R)-1-(Naphthalen-1-yl)-N-((4-(3-(trifluoromethyl)phenyl)morpholin-3-yl)methyl) ethanamine

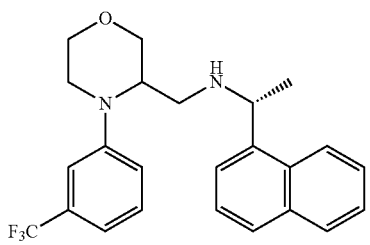 [SMILES: C[C@@H](NCC1COCCN1c1cccc(C(F)(F)F)c1)c1cccc2ccccc12]

Step-1: N-((R)-1-(Naphthalen-1-yl)ethyl)-4-(3-(trifluoromethyl)phenyl)morpholine-3-carboxamide To a mixture solution of N-((R)-1-(naphthalen-1-yl)ethyl) morpholine-3-carboxamide (Intermediate-1) (400 mg, 1.4 mmol) in toluene (10 mL), bis(tri-tert-butylphosphine palladium(0) (19.3 mg, 0.021 mmol), xantphos (36.67 mg, 0.047 mmol), 1-bromo-3-(trifluoromethyl)benzene (244 µL, 1.69 mmol) and $Cs_2CO_3$ (688 mg, 2.11 mmol) were added. The reaction mass was heated to 110° C. and further maintained for 20 h under nitrogen atmosphere. After reaction completion the mixture was diluted with diethylether, filtered through celite, and concentrated under vacuum. The residue was purified by column chromatography on silica gel using a mixture of ethyl acetate and hexane as eluent to afford the title compound (200 mg), m/z 429.1.

Step-2: (1R)-1-(Naphthalen-1-yl)-N-((4-(3-(trifluoromethylphenyl)morpholin-3-yl)methyl)ethanamine To a stirred solution of above Step-1 intermediate (200 mg, 0.46 mmole) in THF (6 mL), borane-dimethyl sulfide complex (130 µL, 1.4 mmole) was added at room temperature. The reaction mixture was heated to reflux and maintained for 6 h. Reaction mixture was concentrated under reduced pressure to get crude oily mass, which was diluted with 10N hydrochloric acid (20 mL) then heated to 95° C. and maintained for 1 h. Reaction mixture was basified with aqueous NaOH solution (pH 10) and extracted with ethyl acetate (2×25 mL), washed with brine solution, dried over $Na_2SO_4$, concentrated to get crude oily compound. Further diastereomers were separated by preparative HPLC (ACQUITY BEH C18, 50×2.1 mm, 1.7µ, water:ACN (90:10) V/V %+0.1% $NH_4OH$) to give Example-2a (20 mg) and Example-2b (20 mg).

Example-2a: $t_R$=2.40; $^1$H NMR (400 MHz, $CDCl_3$): δ 8.11 (d, J=2.4 Hz, 1H), 7.86-7.83 (m, 1H), 7.71 (d, J=8.0 Hz, 1H), 7.53 (d, J=6.8 Hz, 1H), 7.49-7.39 (m, 3H), 7.25-7.19 (m, 1H), 7.01-6.98 (m, 2H), 6.91-6.88 (m, 1H), 4.56 (q, J=6.8 Hz, 1H), 4.18 (d, J=11.2 Hz, 1H), 3.93 (d, J=11.2 Hz, 1H), 3.75 (dd, J=2.4, 11.6 Hz, 1H), 3.70-3.61 (m, 2H), 3.16-3.13 (m, 2H), 2.95 (dd, J=8.8, 12 Hz, 1H), 2.62 (dd, J=4, 12 Hz, 1H), 1.42 (d, J=6.8 Hz, 3H); (M+H) 415.2

Example-2b: $t_R$=2.56; $^1$H NMR (400 MHz, $CDCl_3$): δ 8.13 (d, J=8.4 Hz, 1H), 7.85 (d, J=7.2 Hz, 1H), 7.72 (d, J=8.0 Hz, 1H), 7.55 (d, J=7.2 Hz, 1H), 7.50-7.40 (m, 3H), 7.16 (t, J=8 Hz, 1H), 6.98-6.95 (m, 2H), 6.73 (d, J=8.4 Hz, 1H), 4.52 (q, J=6.4 Hz, 1H), 4.15 (d, J=11.2 Hz, 1H), 3.95 (d, J=10.4 Hz, 1H), 3.71-3.61 (m, 3H), 3.19-2.97 (m, 3H), 2.63 (dd, J=4, 12 Hz, 1H), 1.39 (d, J=6.4 Hz, 3H); (M+H) 415.2.

Example-3

(1R)-N-((4-(3-Fluorophenyl)morpholin-2-yl)methyl)-1-(naphthalen-1-yl)ethanamine hydrochloride

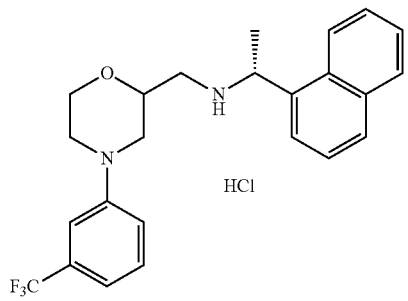 [SMILES: C[C@@H](NCC1CN(c2cccc(C(F)(F)F)c2)CCO1)c1cccc2ccccc12 ; Cl]

Step-1: 4-(3-Fluorophenyl)-N-((R)-1-(naphthalen-1-yl)ethyl)morpholine-2-carboxamide A mixture solution of N-((R)-1-(naphthalen-1-yl)ethyl) morpholine-2-carboxamide (Intermediate-2) (300 mg, 1.056 mmol) in toluene (10 mL), bis(tri-tert butyl phosphine) Pd(0) (0.10, 54 mg), trisdibenzylidene acetone dipalladium(0) (48 mg, 0.0528 mmol), 1-fluoro-3-iodobenzene (0.15 ml, 1.26 mmol) and $Cs_2CO_3$ (516 mg, 1.58 mmol) were added. The reaction mass was heated to 110° C. and further maintained for 15 h under nitrogen atmosphere. The mixture was diluted with ethyl acetate, filtered through celite bed, and concentrated under vacuum. It was further purified by column chromatography on silica gel using a mixture of ethyl acetate and hexane as eluent to afford title compound as oily mass (250 mg), m/z: 379.2.

Step-2: (1R)-N-((4-(3-Fluorophenyl)morpholin-2-yl)methyl)-1-(naphthalen-1-yl)ethanamine To a stirred solution of above Step-1 intermediate (250 mg, 0.660 mmole) in THF (5 mL), borane-dimethyl sulfide complex (0.12 ml, 1.65 mmole) was added at room temperature. The reaction mixture was heated to reflux and maintained for 6 h. Reaction mixture was concentrated under reduced pressure to get crude oil, which was diluted with 10N hydrochloric acid (20 mL) then heated to 100° C. and maintained for 1 h. Reaction mixture was basified with aqueous NaOH solution (pH 10) and extracted with ethyl acetate (2×30 mL), washed with brine solution, dried over $Na_2SO_4$, concentrated to get crude oily compound, which was further purified by preparative HPLC to give title compound as mixture of diastereomers, and which was further dissolved in dry DCM (2 mL) and 2M ethereal HCl (2 mL) was added, solvent was evaporated to get title compound as HCl salt (200 mg). m/z 365.3. $^1$H NMR (400 MHz, CDCl$_3$): δ 10.21 (bs, 1H), 9.8 (bs, 1H), 9.60 (bs, 1H), 9.1 (bs, 1H), 8.22 (J=8.4 Hz, 1H), 8.14 (d, J=7.2 Hz, 1H), 8.03-8.0 (m, 1H), 7.944-7.92 (m, 2H), 7.67-7.58 (m, 2H), 7.12-7.05 (m, 1H), 6.57-6.46 (m, 3H), 5.5 (m, 1H), 3.96-3.94 (m, 1H), 3.83-3.80 (m, 1H), 3.53-3.35 (m, 2H), 3.27-3.24 (m, 2H), 2.89-2.87 (m, 2H), 2.0 (d, J=6.8 Hz, 3H).

The below list of examples 4 to 16 given in Table-1 were prepared in two steps:

Step-1: Preparation Amide Derivatives

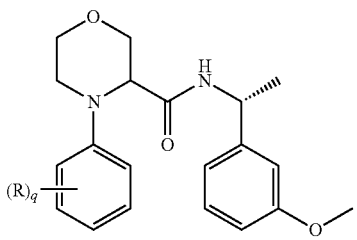

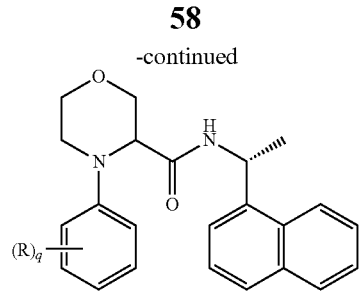

R and 'q' are as defined herein above;

The appropriately substituted amide derivatives were prepared by following the similar procedure as described in Step-1 of Example-3 by taking any one of Intermediate-1 or Intermediate-3 and appropriately substituted halobenzene.

Step-2: Reduction of Amide Derivative

The above Step-1 amide derivative was reduced to give corresponding amine by following the similar procedure as described in Step-2 of Example-3. Further HCl salt of these examples were prepared by following the similar hydrochloride salt procedure as described in Example-1.

TABLE 1

| Example | Structure | Mass (m/z) and NMR |
|---|---|---|
| 4a, 4b | (1R)-1-(3-Methoxyphenyl)-N-((4-(3-(trifluoromethyl)phenyl)morpholin-3-yl)methyl)ethanamine | m/z 395.2; 4a: $^1$H NMR (400 MHz, CDCl$_3$): δ 7.29 (t, J = 8 Hz, 1H), 7.18 (t, J = 8 Hz, 1H), 6.94-7.03 (m, 3H), 6.73-.679 (m, 3H), 4.14 (d, J = 11.2 Hz, 1H), 3.92 (d, J = 11.2 Hz, 1H), 3.71-3.78 (m, 4H), 3.06-3.67 (m, 3H), 3.12-3.16 (m, 2H), 2.83 (m, 1H), 2.49 (dd, 12 & 4.4 Hz, 1H), 1.25 (d, J = 6.8 Hz, 3H); (M + H) 395.2<br>4b: $^1$H NMR (400 MHz, CDCl$_3$): δ 7.18-7.25 (m, 2H), 6.93-6.98 (m, 2H), 6.74-6.83 (m, 4H), 4.13 (d, J = 11.2 Hz, 1H), 3.86 (d, J = 11.2 Hz, 1H), 3.8 (s, 3H), 3.60-3.70 (m, 3H), 3.54-3.56 (m, 1H), 3.09-3.19 (m, 2H), 2.92 (m, 1H), 2.49 (dd, 12 & 4.4 Hz, 1H), 1.25 (d, J = 6.8 Hz, 3H). |
| 5a, 5b | (1R)-N-((4-(3-methoxyphenyl)morpholin-3-yl)methyl)-1-(naphthalen-1-yl)ethanamine hydrochloride | m/z 377.3; 5a: $^1$H NMR (400 MHz, DMSO): δ 9.9 (bs, 1H), 9.65 (bs, 1H), 8.12 (d, J = 8 Hz, 1H), 8.05 (d, J = 7.2 Hz, 1H), 7.96-7.89 (m, 2H), 7.61-7.49 (m, 3H), 7.035 (t, J = 8 Hz, 1H), 6.43-6.41 (m, 2H), 6.30 (d, J = 7.2 Hz, 1H), 5.30 (m, 1H), 3.86-3.83 (m, 1H), 3.72(s, 3H), 3.60-3.63 (m, 1H), 3.56-3.45 (m, 3H), 3.82-3.25 (m, 1H), 2.90-2.83 (m, 1H), 2.67-2.66 (m, 2H), 1.66 (d, J = 6.8 Hz, 3H).<br>5b: $^1$H NMR (400 MHz, CDCl$_3$): δ 8.11 (d, J = 2.4 Hz, 1H), 7.83-7.86 (m, 1H), 7.71 (d, J = 8.0 Hz, 1H), 7.53 (d, J = 6.8 Hz, 1H), 7.41-7.49 (m, 3H), 7.19-7.25 (m, 1H), 6.36-6.45 (m, 3H), 4.56 (q, J = 6.8 Hz, 1H), 4.18 (d, J = 11.2 Hz, 1H), 3.93 (d, J = 11.2 Hz, 1H), 3.79 (dd, J = 2.4, 11.6 Hz, 1H), 3.74 (s, 3H) 3.61-3.70 (m, 2H), 3.13-3.16 (m, 2H), 2.95 (dd, J = 8.8, 12 Hz, 1H), 2.62 (dd, J = 4, 12 Hz, 1H), 1.42 (d, J = 6.8 Hz, 3H). |

TABLE 1-continued

| Example | Structure | Mass (m/z) and NMR |
|---|---|---|
| 6a, 6b | 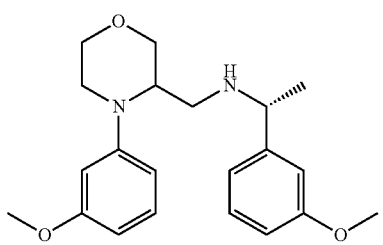<br>(1R)-1-(3-Methoxy phenyl)-N-((4-(3-methoxyphenyl)morpholin-3-yl)methyl)ethanamine | m/z 357.3; 6a: $^1$H NMR (400 MHz, CDCl$_3$): δ 7.25 (t, J = 8 Hz, 1H), 7.18 (t, J = 8 Hz, 1H), 6.84-6.86 (m, 2H), 6.78 (dd, J = 8, 1.8 Hz, 1H), 6.34-6.38 (m, 3H), 4.11 (d, J = 11.2 Hz, 1H), 3.93 (d, J = 11.2 Hz, 1H), 3.81 (s, 3H), 3.78 (s, 3H), 3.64-3.74 (m, 3H), 3.51-3.64 (m, 1H), 3.11-3.15 (m, 2H), 2.88 (m, 1H), 2.65 (dd, J = 12.0, 4.4 Hz, 1H), 1.25 (d, J = 6.8 Hz, 3H).<br>6b: $^1$H NMR (400 MHz, CDCl$_3$): δ 7.15-7.23 (m, 2H), 6.76-6.84 (m, 3H), 6.5 (d, 1H), 6.4 (m, 2H), 4.11 (d, J = 11.2 Hz, 1H), 3.90 (d, J = 11.2 Hz, 1H), 3.80 (s, 6H), 3.60-3.70 (m, 3H), 3.51 (s, 1H), 3.09-3.13 (m, 2H), 2.82 (m ,1H), 2.56 (dd, J = 12, 4.4 Hz, 1H), 1.25 (d, J = 6.8 Hz, 3H). |
| 7a, 7b | 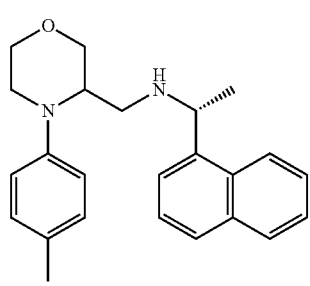<br>(1R)-1-(Naphthalen-1-yl)-N-((4-(p-tolyl)morpholin-3-yl)methyl)ethanamine | m/z 361.3; 7a: $^1$H NMR (400 MHz, CDCl$_3$): δ 8.11 (d, J = 2.4 Hz, 1H), 7.83-7.86 (m, 1H), 7.70 (d, J = 8.0 Hz, 1H), 7.37-7.497.52 (m, 4H), 6.94 (d, J = 2 Hz, 2H), 6.64 (d, J = 2.1 Hz, 2H), 4.43 (q, J = 6.8 Hz, 1H), 4.06 (d, J = 11.2 Hz, 1H), 3.88 (d, J = 11.2 Hz, 1H), 3.62-3.73 (m, 2H), 3.45-3.49 (m, 1H), 3.03-3.05 (m, 2H), 2.88 (dd, J = 8.8, 12 Hz, 1H), 2.62 (dd, J = 4, 12 Hz, 1H), 2.23 (s, 3H), 1.35 (d, J = 6.8 Hz, 3H).<br>7b: $^1$H NMR (400 MHz, CDCl$_3$): δ 8.11 (d, J = 2.4 Hz, 1H), 7.84-7.86 (m, 1H), 7.71 (d, J = 8.0 Hz, 1H), 7.39-7.497.53 (m, 4H), 6.99 (d, J = 2 Hz, 2H), 6.75 (d, J = 2.1 Hz, 2H), 4.5 (q, J = 6.8 Hz, 1H), 4.11 (d, J = 11.2 Hz, 1H), 3.80-3.88 (m, 2H), 3.66-3.71 (m, 1H), 3.55-3.58 (m, 1H), 3.03-3.06 (m, 2H), 2.86 (dd, J = 8.8, 12 Hz, 1H), 2.61 (dd, J = 4, 12 Hz, 1H), 2.23 (s, 3H), 1.35 (d, J = 6.8 Hz, 3H). |
| 8 | 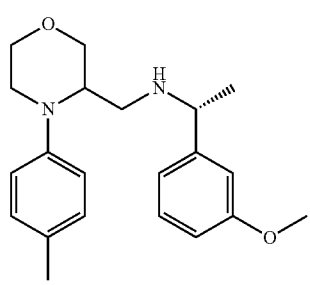<br>(1R)-1-(3-Methoxy phenyl)-N-((4-(p-tolyl)morpholin-3-yl)methyl)ethanamine | m/z 341.3; $^1$H NMR (400 MHz, CDCl$_3$): δ 7.22 (q, J = 8 Hz, 1H), 7.04 (d, J = 8.4 Hz, 2H), 6.82-6.73 (m, 4H), 6.88 (d, J = 8.4 Hz, 1H), 4.03 (d, J = 11.2 Hz, 1H), 3.39-3.85 (m, 1H), 3.78 (s, 3H), 3.71-3.61 (m, 2H), 3.60-3.47 (m, 1H), 3.08-3.03 (m, 2H), 2.84-2.70 (m, 1H), 2.59-2.50 (m, 1H), 2.25 (s, 3H), 1.24 (d, J = 6.8 Hz, 3H). |

TABLE 1-continued

| Example | Structure | Mass (m/z) and NMR |
|---|---|---|
| 9 | 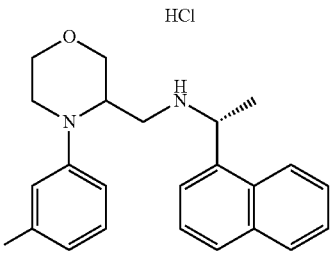<br>(1R)-N-((4-(3-Fluorophenyl)morpholin-3-yl)methyl)-1-(naphthalen-1-yl)ethanamine hydrochloride | m/z 365.2; $^1$H NMR (400 MHz, DMSO): δ 10.1 (bs, 1H), 9.6 (bs, 1H), 8.19-8.14 (m, 1H), 8.05-7.91 (m, 3H), 7.62-7.53 (m, 3H), 7.16-7.07 (m, 1H), 6.78-6.66 (m, 2H), 6.54-6.50 (m, 1H), 5.35 (m, 1H), 4.29-4.19 (m, 2H), 3.9-3.77 (m, 1H), 3.55-3.47 (m, 2H), 3.38-3.30 (m, 2H), 2.92-2.68 (m, 1H), 2.66 (m, 1H), 1.68 (d, J = 6.8 Hz, 3H). |
| 10a, 10b | 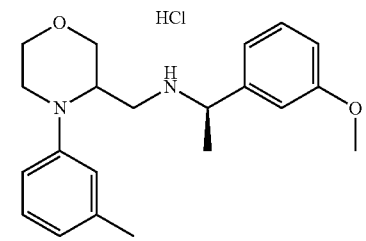<br>(1R)-1-(3-Methoxyphenyl)-N-((4-(m-tolyl)morpholin-3-yl)methyl)ethanamine hydrochloride | m/z 341.3; 10a: $^1$H NMR (400 MHz, DMSO): δ 9.55 (bs, 2H), 7.27-7.23 (m, 2H), 7.08 (d, J = 8 Hz, 1H), 6.99 (t, J = 8 Hz, 1H), 6.88 (dd, J = 8 & 2 Hz, 1H), 6.71 (m, 1H), 6.62 (d, J = 8.4 Hz, 1H), 6.53 (d, J = 7.6 Hz, 1H), 4.28 (m, 1H), 4.20 (d, J = 12 Hz, 1H), 4.11 (d, J = 8 Hz, 1H), 3.85 (d, J = 8.8 Hz, 1H), 3.75 (s, 3H), 3.61-3.56 (m, 1H), 3.55-3.49 (m, 1H), 3.40-3.22 (m, 2H), 2.89-2.82 (m, 1H), 2.50-2.46 (m, 1H), 2.20 (s, 3H), 1.57 (d, J = 6.8 Hz, 3H).<br>10b: $^1$H NMR (400 MHz, DMSO): δ 10.9 (bs, 1H), 9.29 (bs, 1H), 7.30 (t, J = 8 Hz, 1H), 7.23-7.22 (m, 1H), 7.09-7.05 (m, 2H), 6.94 (dd, J = 8 & 2 Hz, 1H), 6.80 (m, 1H), 6.73-6.71 (m, 1H), 6.59 (d, J = 7.2 Hz, 1H), 4.37-4.33 (m, 1H), 4.17 (d, J = 11.6 Hz, 2H), 3.83-3.78 (m, 1H), 3.75 (s, 3H), 3.62-3.57 (m, 1H), 3.52-3.45 (m, 1H), 3.25 (d, J = 12 H, 1H), 3.01-2.98 (m, 1H), 2.90-2.83 (m, 1H), 2.67-2.61 (m, 1H), 2.24 (s, 3H), 1.58 (d, J = 6.8 Hz, 3H). |
| 11a, 11b | 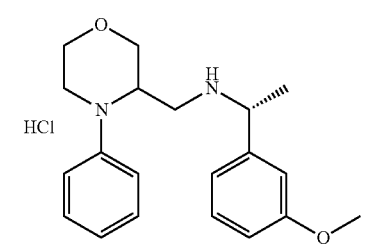<br>(1R)-1-(3-Methoxyphenyl)-N-((4-phenylmorpholin-3-yl)methyl)ethanamine hydrochloride | m/z 327.3; 11a: $^1$H NMR (400 MHz, DMSO): δ 9.67 (bs, 1H), 9.53 (bs, 1H), 7.31-7.30 (m, 1H), 7.27 (t, J = 7.6 Hz, 1H), 7.13-7.06 (m, 3H), 6.88-6.82 (m, 3H), 6.71 (t, J = 7.2 Hz, 1H), 4.30 (m, 1H), 4.21-4.14 (m, 3H), 3.83 (s, 3H), 3.64-3.50 (m, 3H), 3.30-3.23 (m, 2H), 2.90-2.83 (m, 1H), 1.58 (d, J = 6.8 Hz, 3H).<br>11b: $^1$H NMR (400 MHz, DMSO): δ 9.95 (bs, 1H), 9.32 (bs, 1H), 7.30 (t, J = 8 Hz, 1H), 7.24-7.14 (m, 3H), 7.07 (d, J = 7.6 Hz, 1H), 6.97-6.91 (m, 3H), 6.77 (t, J = 7.2 Hz, 1H), 4.37-4.36 (m, 1H), 4.18-4.15 (m, 2H), 3.80 (m, 1H), 3.75 (s, 3H), 3.53-3.47 (m, 2H), 3.27 (d, J = 12 Hz, 1H), 3.02-3.00 (m, 1H), 2.92-2.84 (m, 1H), 2.67-2.61 (m, 1H), 1.58 (d, J = 6.8 Hz, 3H). |

TABLE 1-continued

| Example | Structure | Mass (m/z) and NMR |
|---|---|---|
| 12 | 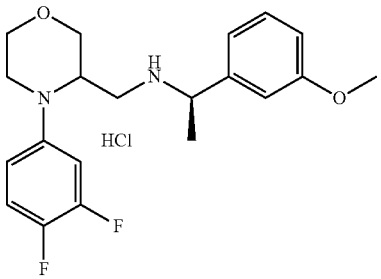<br>(1R)-N-((4-(3,4-Difluorophenyl)morpholin-3-yl)methyl)-1-(3-methoxyphenyl)ethanamine hydrochloride | m/z 363.43; $^1$H NMR (400 MHz, CDCl$_3$): δ 10.32 (bs, 1H), 9.95 (bs, 1H), 7.30-7.12 (m, 3H), 7.02-6.97 (m, 2H), 6.89-6.84 (m, 2H), 4.49 (m, 3H), 4.16 (m, 2H), 3.85 (s, 3H), 3.29-3.19 (m, 3H), 3.04 (m, 2H), 1.86 (d, J = 6.8 Hz, 3H). |
| 13a, 13b | 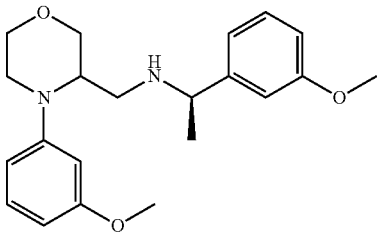<br>(1R)-1-(3-methoxyphenyl)-N-((4-(3-methoxyphenyl)morpholin-3-yl)methyl)ethanamine | m/z 357.3; 13a: $^1$H NMR (400 MHz, CDCl$_3$): δ 7.23 (t, J = 8 Hz, 1H), 7.12 (t, J = 8 Hz, 1H), 6.86-6.84 (m, 2H), 6.79-6.76 (m, 1H), 6.38-6.34 (m, 3H), 4.10 (d, J = 11.2 Hz, 1H), 3.96-3.92 (m, 1H), 3.81 (s, 3H), 3.78 (s, 3H), 3.74-3.64 (m, 3H), 3.58-3.51 (m, 1H), 3.15-3.11 (m, 2H), 2.91-2.86 (m, 1H), 2.62 (dd, J = 4.4 & 12.2 Hz, 1H), 1.25 (d, J = 6.4 Hz, 3H).<br>13b: $^1$H NMR (400 MHz, CDCl$_3$): δ 7.32-7.15 (m, 2H), 6.48-6.76 (m, 3H), 6.50-6.48 (m, 1H), 6.42-6.39 (m, 2H), 4.10 (d, J = 11.2 Hz, 1H), 3.92-3.89 (m, 1H), 3.78 (s, 6H), 3.70-3.60 (m, 3H), 3.51 (s, 1H), 3.13-3.09 (m, 2H), 2.84-2.79 (m, 1H), 2.56 (dd, J = 3.6 & 9.8 Hz, 1H), 1.25 (d, J = 6.4 Hz, 3H). |
| 14 | 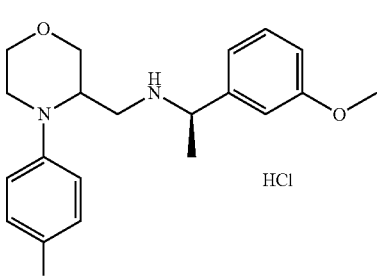<br>(1R)-N-((4-(4-Fluorophenyl)morpholin-3-yl)methyl)-1-(3-methoxyphenyl)ethanamine hydrochloride | m/z 345.41; $^1$H NMR (400 MHz, DMSO): δ 9.9 (bs, 1H), 9.45 (bs, 1H), 7.30-7.23 (m, 2H), 7.07-7.02 (m, 2H), 6.96-6.91 (m, 2H), 6.88-6.83 (m, 2H), 4.13 (m, 2H), 3.84-3.77 (m, 1H), 3.75 (s, 3H), 3.67-3.61 (m, 1H), 3.57-3.47 (m, 1H), 3.24-3.14 (m, 2H), 2.99-2.82 (m, 2H), 2.49-2.32 (m, 1H), 1.57 (d, J = 5.2 Hz, 3H). |

TABLE 1-continued

| Example | Structure | Mass (m/z) and NMR |
|---|---|---|
| 15 | 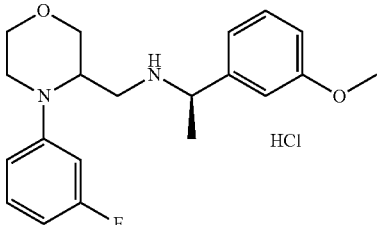<br>(1R)-N-((4-(3-Fluorophenyl)morpholin-3-yl)methyl)-1-(3-methoxyphenyl)ethanamine hydrochloride | m/z 345.43; $^1$H NMR (400 MHz, CDCl$_3$): δ 10.3 (bs, 1H), 9.88 (bs, 1H), 7.27-7.15 (m, 3H), 6.97 (d, J = 7.6 Hz, 2H), 6.89-6.82 (m, 2H), 6.68 (m, 1H), 4.61-4.53 (m, 1H), 4.44 (m, 1H), 4.16-4.01 (m, 2H), 3.85 (s, 3H), 3.76-3.66 (m, 1H), 3.26-3.03 (m, 3H), 2.18 (m, 1H), 2.70 (m, 1H), 1.87 (d, J = 6.8 Hz, 3H). |
| 16a, 16b | 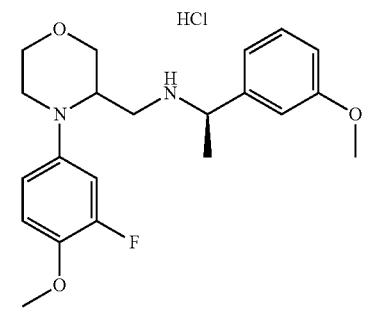<br>(1R)-N-((4-(3-Fluoro-4-methoxyphenyl)morpholin-3-yl)methyl)-1-(3-methoxyphenyl)ethanamine hydrochloride | m/z 375.2; 16a: $^1$H NMR (400 MHz, CDCl$_3$): & 10.3 (bs, 1H), 9.9 (bs, 1H), 7.31-7.27 (m, 1H), 7.19 (m, 1H), 6.94-6.89 (m, 2H), 6.82 (d, J = 8.8 Hz, 3H), 6.71 (dd, J = 6.8 & 13.6 Hz, 1H), 4.78 (m, 1H), 4.50 (d, J = 12.4 Hz, 1H), 4.22-4.14 (m, 2H), 3.88 (s, 7H), 3.66-3.60 (m, 1H), 3.21-3.16 (m, 1H), 2.97 (m, 1H), 2.90-2.83 (m, 1H), 2.67-2.63 (m, 1H), 1.90 (d, J = 6.8 Hz, 3H).<br>16b: $^1$H NMR (400 MHz, CDCl$_3$): δ 10.3 (bs, 1H), 9.9 (bs, 1H), 7.30-7.23 (m, 1H), 7.17 (m, 1H), 7.00 (d, J = 7.2 Hz, 1H), 6.89-6.81 (m, 2H), 6.68-6.60 (m, 2H), 4.82-4.79 (m, 1H), 4.39 (d, J = 6.4 Hz, 1H), 4.14-4.11 (m, 2H), 3.86 (s, 6H), 3.81 (m, 1H), 3.67-3.62 (m, 1H), 3.24-3.18 (m, 1H), 2.99-2.87 (m, 2H), 2.73-2.69 (m, 1H), 1.87 (d, J = 6.8 Hz, 3H). |

The below list of examples 17 to 21 given in Table-2 were prepared by following the similar procedure as described in Step-1 of Example-3 by taking Intermediate-4 appropriately substituted halobenzene. Further, hydrochloride salts of these compounds were prepared by following the similar hydrochloride salt procedure as described in Example-1.

TABLE 2

| Example | Structure | Mass (m/z) and $^1$H NMR |
|---|---|---|
| 17 | 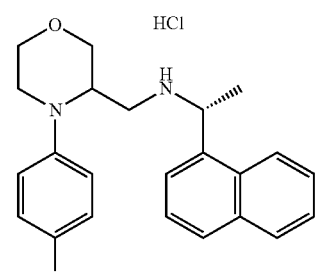<br>(1R)-N-((4-(4-Fluorophenyl)morpholin-3-yl)methyl)-1-(naphthalen-1-yl)ethanamine hydrochloride | m/z 365.2; $^1$H NMR (400 MHz, DMSO): δ 10.1 (bs, 1H), 9.5 (bs, 1H), 8.13 (m, 1H), 8.02-7.92 (m, 3H), 7.60-7.52 (m, 3H), 6.98-6.83 (m, 4H), 5.35 (m, 1H), 4.24-4.13 (m, 2H), 3.85-3.49 (m, 3H), 3.17-3.11 (m, 2H), 2.88-2.84 (m, 2H), 1.67 (d, J = 6.8 Hz, 3H). |

TABLE 2-continued

| Example | Structure | Mass (m/z) and ¹H NMR |
|---|---|---|
| 18 | 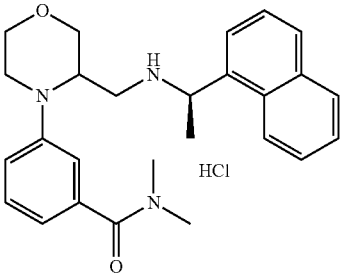<br>N,N-Dimethyl-3-(3-((((R)-1-(naphthalen-1-yl)ethyl)amino)methyl)morpholino)benzamide hydrochloride | m/z 418.32; ¹H NMR (400 MHz, DMSO): δ 10.25 (bs, 1H), 9.6 (bs, 1H), 8.5 (d, J = 8 Hz, 1H), 8.02-7.94 (m, 3H), 7.90 (d, J = 8.4 Hz, 1H), 7.61-7.52 (m, 3H), 7.18 (t, J = 8.4 Hz, 1H), 6.96-6.93 (m, 1H), 6.71 (d, J = 7.6 Hz, 1H), 5.35 (m, 1H), 4.19 (m, 2H), 3.86-3.78 (m, 1H), 3.66-3.60 (m, 1H), 3.53-3.46 (m, 2H), 3.33-3.29 (m, 2H), 2.91 (s, 3H), 2.88 (s, 3H), 1.67 (d, J = 6.8 Hz, 3H). |
| 19 | 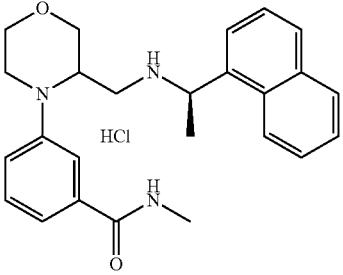<br>N-Methyl-3-(3-((((R)-1-(naphthalen-1-yl)ethyl)amino)methyl)morpholino)benzamide hydrochloride | m/z 404.3; ¹H NMR (400 MHz, DMSO): δ 10.3 (bs, 1H), 9.3 (bs, 1H), 8.4 (m, 1H), 8.12 (m, 1H), 8.04-7.92 (m, 2H), 7.87 (d, J = 8.4 Hz, 1H), 7.63-7.54 (m, 2H), 7.44-7.40 (m, 1H), 7.25-7.17 (m, 2H), 7.01-6.97 (m, 1H), 5.36 (m, 1H), 4.36 (m, 1H), 4.29-4.20 (m, 1H), 3.85-3.80 (m, 1H), 3.68-3.62 (m, 1H), 3.54-3.48 (m, 1H), 3.32-3.29 (m, 2H), 2.92-2.89 (m, 1H), 2.80-2.76 (m, 3H), 1.67 (d, J = 6.8 Hz, 3H). |
| 20 | 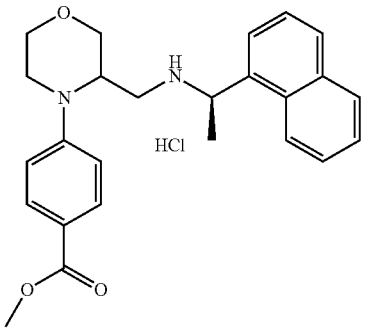<br>Methyl 4-(3-((((R)-1-(naphthalen-1-yl)ethyl)amino)methyl)morpholino)benzoate hydrochloride | m/z 405.32; ¹H NMR (400 MHz, DMSO): δ 10.9 (bs, 1H), 10.2 (bs, 1H), 8.11 (d, J = 8 Hz, 1H), 7.96 (d, J = 6.4 Hz, 1H), 7.94-7.81 (m, 3H), 7.75 (d, J = 8.4 Hz, 1H), 7.62-7.57 (m, 1H), 7.55-7.52 (m, 1H), 7.42-7.38 (m, 2H), 7.24-7.22 (m, 1H), 5.23 (m, 1H), 4.73-4.59 (m, 2H), 4.28 (m, 1H), 3.91 (s, 3H), 3.82-3.76 (m, 1H), 3.50-3.45 (m, 1H), 3.13-3.07 (m, 2H), 2.69 (m, 1H), 2.05 (d, J = 6.4 Hz, 3H). |

TABLE 2-continued

| Example | Structure | Mass (m/z) and $^1$H NMR |
|---|---|---|
| 21 | 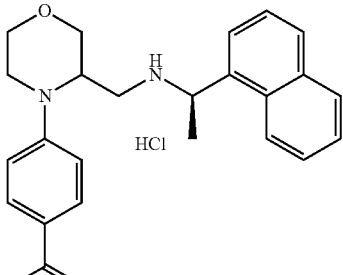<br>4-(3-((((R)-1-(Naphthalen-1-yl)ethyl)amino)methyl)morpholino)benzoic acid hydrochloride | m/z 391.2; $^1$H NMR (400 MHz, DMSO): δ 13.1 (bs, 1H), 10.3 (bs, 1H), 9.5 (bs, 1H), 8.17-8.10 (m, 1H), 8.04-7.90 (m, 3H), 7.71-7.64 (m, 2H), 7.62-7.52 (m, 3H), 6.99-6.91 (m, 2H), 5.3 (m, 1H), 4.38-4.27 (m, 2H), 3.61-3.59 (m, 1H), 3.52-3.51 (m, 1H), 3.48-3.45 (m, 2H), 3.30-3.10 (m, 2H), 2.96-2.93 (m, 1H), 1.69 (d, J = 6.4 Hz, 3H) |

The below list of examples 22 to 33 given in Table-3 were prepared in two steps:

Step-1: Preparation Amide Derivatives

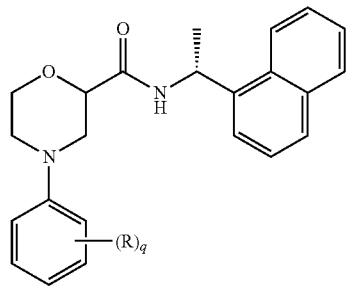

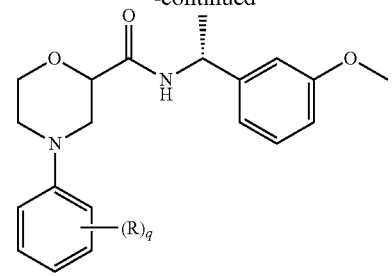

R and 'q' are as defined herein above;

The appropriately substituted amide derivatives were prepared by following the similar procedure as described in Step-1 of Example-3 by taking Intermediate-2 or Intermediate-6 and appropriately substituted halobenzene.

Step-2: Reduction of Amide Derivative

The above Step-1 amide derivatives were reduced to give corresponding amine by following the similar procedure as described in Step-2 of Example-3. Further HCl salt of these examples were prepared by following the similar hydrochloride salt procedure as described in Example-1.

TABLE 3

| Example | Structure | Mass (m/z) and $^1$H NMR |
|---|---|---|
| 22 | 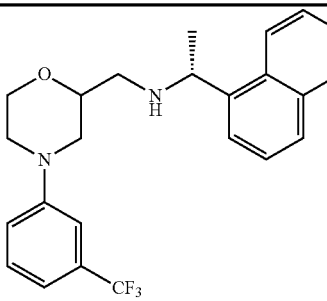<br>(1R)-1-(Naphthalen-1-yl)-N-((4-(3-(trifluoromethyl)phenyl)morpholin-2-yl)methyl)ethanamine | m/z 415.2; $^1$H NMR (400 MHz, CDCl$_3$): δ 8.20 (m, 1H), 8.87 (d, J = 8 Hz, 1H), 7.76-7.63 (m, 2H), 7.52-7.46 (m, 3H), 7.33-7.31 (m, 1H), 7.08-6.98 (m, 3H), 4.64 (q, J = 6.8 Hz, 1H), 4.06-4.03 (m, 1H), 3.81-3.76 (m, 2H), 3.45-3.37 (m, 2H), 2.87-2.84 (m, 1H), 2.75-2.63 (m, 2H), 2.56-2.53 (m, 1H), 1.52 (d, J = 6.8 Hz, 3H). |

TABLE 3-continued

| Example | Structure | Mass (m/z) and ¹H NMR |
|---|---|---|
| 23 | (1R)-1-(3-Methoxyphenyl)-N-((4-(3-methoxyphenyl)morpholin-2-yl)methyl)ethanamine | m/z 357.3; ¹H NMR (400 MHz, CDCl₃): δ 7.22 (m, 1H), 7.15 (m, 1H), 6.93-6.89 (m, 2H), 6.79 (d, J = 8.4 Hz, 1H), 6.49-6.47 (m, 1H), 6.42-6.40 (m, 2H), 4.02-3.99 (m, 1H), 3.81-3.73 (m, 8H), 3.41 (d, J = 11.2 Hz, 2H), 2.83-2.78 (m, 1H), 2.65-2.57 (m, 2H), 2.53-2.45 (m, 2H), 1.36 (d, J = 6.8 Hz, 3H). |
| 24 | (1R)-1-(3-Methoxyphenyl)-N-((4-(3-(trifluoromethyl)phenyl)morpholin-2-yl)methyl)ethanamine | m/z 395.2; |
| 25a, 25b | (1R)-N-((4-(3-Methoxyphenyl)morpholin-2-yl)methyl)-1-(naphthalen-1-yl)ethanamine hydrochloride | m/z 377.2; 25a: ¹H NMR (400 MHz, CDCl₃): δ 10.86 (bs, 1H), 9.54 (bs, 1H), 8.23 (d, J = 8 Hz, 1H), 8.86 (d, J = 8 Hz, 1H), 7.71-7.76 (m, 2H), 7.46-7.52 (m, 3H), 7.14 (t, J = 8 Hz, 1H), 6.47 (dd, J = 2, 11.2 Hz, 1H), 6.40-6.42 (m, 2H), 4.62 (q, J = 6.8 Hz, 1H), 4.03 (dd, J = 2, 11.2 Hz, 1H), 3.76-3.83 (m, 5H), 3.41 (d, J = 11.6 Hz, 2H), 2.77-2.84 (m, 1H), 2.67-2.72 (m, 1H), 2.61 (dd, J = 3.6, 12 Hz, 1H), 2.49 (t, J = 11.6 Hz, 1H), 1.52 (d, J = 6.8 Hz, 3H).<br>25b: ¹H NMR (400 MHz, CDCl₃): δ 10.70 (bs, 1H), 9.55 (bs, 1H), 8.16-8.15 (m, 1H), 8.04 (m, 2H), 7.95-7.89 (m, 2H), 7.63-7.52 (m, 4H), 6.81 (d, J = 8 Hz, 2H), 5.42-5.40 (m, 1H), 4.97 (m, 1H), 4.52 (m, 1H), 4.07 (m, 2H), 3.80 (s, 3H), 3.49-3.45 (m, 2H), 3.20-3.08 (m, 1H), 1.25 (d, J = 6.8 Hz, 3H). |

TABLE 3-continued

| Example | Structure | Mass (m/z) and ¹H NMR |
|---|---|---|
| 26a, 26b | 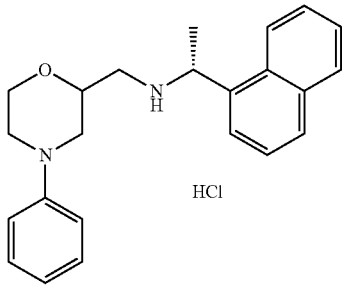<br>(1R)-1-(Naphthalen-1-yl)-N-((4-phenylmorpholin-2-yl)methyl)ethanamine hydrochloride | m/z 347.2; 26a: ¹H NMR (400 MHz, CDCl₃): δ 10.54 (bs, 1H), 9.0 (bs, 1H), 8.23 (d, J = 8 Hz, 1H), 8.87 (d, J = 8 Hz, 1H), 7.76-7.71 (m, 2H), 7.53-7.46 (m, 3H), 7.26-7.22 (m, 3H), 6.85 (t, J = 7.2 Hz, 2H), 4.63 (q, J = 6.8 Hz, 1H), 3.85-3.79 (m, 2H), 3.71-3.57 (t, J = 6 Hz, 1H), 3.41 (d, J = 12.4 Hz, 1H), 2.84-2.81 (m, 1H), 2.72-2.61 (m, 2H), 2.49 (t, J = 10.4 Hz, 1H), 1.52 (d, J = 6.8 Hz, 3H).<br>26b: ¹H NMR (400 MHz, CDCl₃): δ 10.54 (bs, 1H), 9.0 (bs, 1H), 8.20 (d, J = 7.2 Hz, 1H), 8.04 (d, J = 8 Hz, 1H), 7.88-7.93 (m, 2H), 7.50-7.63 (m, 4H), 7.35 (t, J = 10.4 Hz, 2H), 7.19 (t, J = 10.4 Hz, 1H), 5.45 (bs, 1H), 4.87 (bs, 1H), 4.38 (bs, 1H), 4.05 (d, J = 11.6 Hz, 1H), 3.80 (d, J = 6 Hz, 1H), 3.31-3.48 (m, 3H), 3.16 (bs, 1H), 3.04 (bs, 1H), 2.02 (d, J = 6.8 Hz, 3H). |
| 27a, 27b | 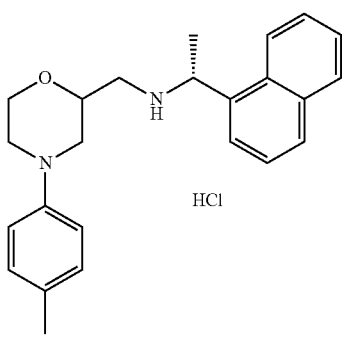<br>(1R)-1-(Naphthalen-1-yl)-N-((4-(p-tolyl)morpholin-2-yl)methyl)ethanamine hydrochloride | m/z 361.3; 27a: ¹H NMR (400 MHz, CDCl₃): δ 10.85 (bs, 1H), 9.9 (bs, 1H), 8.23 (d, J = 7.2 Hz, 1H), 8.07 (d, J = 8 Hz, 1H), 7.95-7.88 (m, 2H), 7.77 (d, J = 7.6 Hz, 2H), 7.64-7.55 (m, 3H), 7.25 (d, J = 7.2 Hz, 2H), 5.46 (s, 1H), 5.19 (s, 1H), 4.74-4.69 (m, 1H), 4.17-4.05 (m, 2H), 3.66 (m, 2H), 3.28 (s, 1H), 3.08 (s, 1H), 2.33 (s, 3H), 1.23 (d, J = 6.8 Hz, 3H).<br>27b: ¹H NMR (400 MHz, CDCl₃): δ 10.18 (bs, 2H), 8.22 (s, 1H), 8.04 (s, 1H), 7.87-7.92 (m, 2H), 7.80 (s, 2H), 7.54-7.62 (m, 3H), 7.25 (d, J = 11.6 Hz, 2H), 5.37 (bs, 1H), 4.96 (bs, 1H), 4.63 (bs, 1H), 4.07 (bs, 2H), 3.68 (d, J = 11.6 Hz, 1H), 3.52 (bs, 1H), 3.45 (bs, 1H), 3.21 (bs, 1H), 2.93 (bs, 1H), 2.34 (s, 3H), 1.24 (d, J = 6.8 Hz, 3H). |
| 28 | 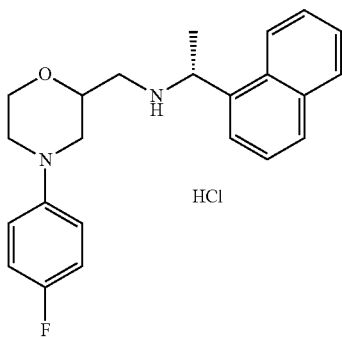<br>(1R)-N-((4-(4-Fluorophenyl)morpholin-2-yl)methyl)-1-(naphthalen-1-yl)ethanamine hydrochloride | m/z 365.3; ¹H NMR (400 MHz, DMSO): δ 10.21 (bs, 1H), 9.1 (bs, 1H), 8.23 (d, J = 8 Hz, 1H), 8.00-7.93 (m, 2H), 7.65-7.63 (m, 4H), 7.09-6.96 (m, 4H), 5.36 (m, 1H), 4.0-3.98 (m, 2H), 3.87 (m, 2H), 3.65-3.50 (m, 2H), 2.98-2.87 (m, 2H), 2.40 (m, 1H), 1.72 (d, J = 6.8 Hz, 3H). |

TABLE 3-continued

| Example | Structure | Mass (m/z) and ¹H NMR |
|---|---|---|
| 29 | 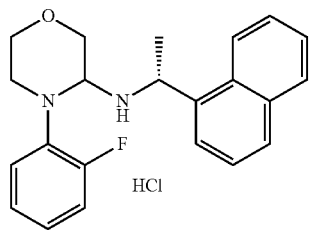<br>(1R)-N-((4-(2-Fluorophenyl)morpholin-2-yl)methyl)-1-(naphthalen-1-yl)ethanamine hydrochloride | m/z 365.3; ¹H NMR (400 MHz, DMSO): δ 9.8 (bs, 1H), 9.60 (bs, 1H), 8.25 (m, 1H), 8.00 (t, J = 8.4 Hz, 2H), 7.92 (m, 2H), 7.67-7.58 (m, 2H), 7.12-6.95 (m, 4H), 5.35 (m, 1H), 4.0-3.98 (m, 2H), 3.25-3.18 (m, 3H), 2.83-2.75 (m, 2H), 2.54-2.32 (m, 2H), 1.735 (d, J = 6.8 Hz, 3H). |
| 30 | 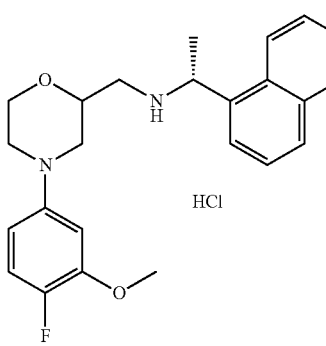<br>(1R)-N-((4-(4-Fluoro-3-methoxyphenyl)morpholin-2-yl)methyl)-1-(naphthalen-1-yl)ethanamine hydrochloride | m/z 395.4; ¹H NMR (400 MHz, DMSO): δ 10.2 (bs, 1H), 9.0 (bs, 1H) 8.22 (m, 1H), 8.00 (t, J = 8.4 Hz, 2H), 7.9 (m, 1H), 7.65-7.58 (m, 2H), 7.1-6.95 (m, 4H), 5.35 (m, 1H), 4.0-3.98 (m, 2H), 3.90 (s, 3H), 3.25-3.18 (m, 3H), 3.21-3.18 (m, 2H), 2.83-2.75 (m, 2H), 1.735 (d, J = 6.8 Hz, 3H). |
| 31 | 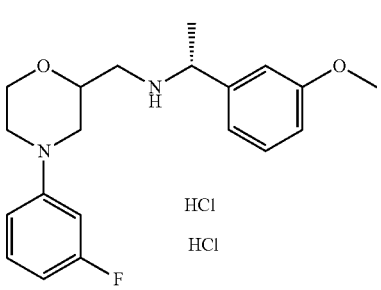<br>(1R)-N-((4-(3-Fluorophenyl)morpholin-2-yl)methyl)-1-(3-methoxyphenyl)ethanamine dihydrochloride | m/z 345.3; ¹H NMR (400 MHz, DMSO): δ 10.1 (bs, 1H), 9.78 (bs, 1H), 9.59 (bs, 1H), 8.8 (bs, 1H), 7.35-7.34 (m, 1H), 7.32-7.30 (m, 3H), 7.09-7.08 (m, 1H), 6.98-6.95 (m, 2H), 6.76-6.72 (m, 1H), 4.34 (m, 1H), 4.0 (m, 2H), 3.95 (s, 3H), 3.6 (m, 2H), 3.1 (m, 2H), 3.05 (m, 2H), 2.54 (m, 1H), 1.58 (d, J = 6.4 Hz, 3H). |

TABLE 3-continued

| Example | Structure | Mass (m/z) and ¹H NMR |
|---|---|---|
| 32 | 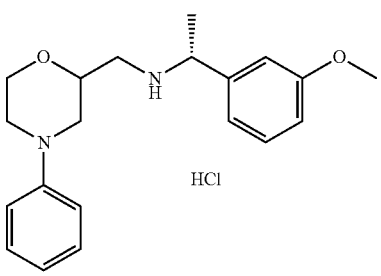<br>(1R)-1-(3-Methoxyphenyl)-N-((4-(3-(trifluoromethyl)phenyl)morpholin-2-yl)methyl)ethanamine hydrochloride | m/z 327.3; ¹H NMR (400 MHz, DMSO): δ 9.59 (bs, 1H), 8.8 (bs, 1H), 7.35-7.34 (m, 1H), 7.27-7.23 (m, 2H), 7.17-7.12 (m, 2H), 7.11 (d, J = 7.6 Hz, 1H), 7.01-6.97 (m, 3H), 6.89-6.87 (m, 1H), 4.34 (m, 1H), 4.1 (m, 2H), 3.95 (s, 3H), 3.72 (m, 2H), 3.12 (m, 2H), 3.02 (m, 1H), 2.52 (m, 1H), 1.59 (d, J = 6.4 Hz, 3H). |
| 33a, 33b | 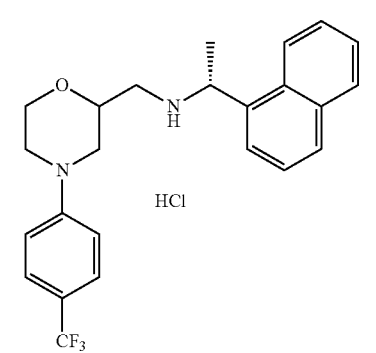<br>(1R)-1-(Naphthalen-1-yl)-N-((4-(4-(trifluoromethyl)phenyl)morpholin-2-yl)methyl)ethanamine hydrochloride | m/z 414.97; 33a: ¹H NMR (400 MHz, DMSO): δ 10.25 (bs, 1H), 9.25 (bs, 1H), 8.24 (d, J = 6.8 Hz, 1H), 8.03-7.98 (m, 3H), 7.67-7.58 (m, 3H), 7.51 (d, J = 8.8 Hz, 2H), 7.04 (d, J = 8.8 Hz, 2H), 5.37 (q, J = 6.8 Hz, 1H), 4.03-4.01 (m, 2H), 3.77 (d, J = 12 Hz, 2H), 3.68-3.61 (m, 2H), 3.21-3.15 (m, 1H), 2.82-2.76 (m, 2H), 1.72 (d, J = 6.8 Hz, 3H).<br>33b: ¹H NMR (400 MHz, DMSO): δ 9.69 (bs, 1H), 9.49 (bs, 1H), 8.25 (d, J = 6.8 Hz, 1H), 8.03-7.98 (m, 3H), 7.67-7.58 (m, 3H), 7.51 (d, J = 8.4 Hz, 2H), 7.05 (d, J = 8.8 Hz, 2H), 5.35 (q, J = 6.4 Hz, 1H), 3.79 (m, 2H), 3.66 (d, J = 11.2 Hz, 3H), 3.11-3.08 (m, 3H), 2.82-2.76 (m, 1H), 1.72 (d, J = 6.8 Hz, 3H). |
| 34 | 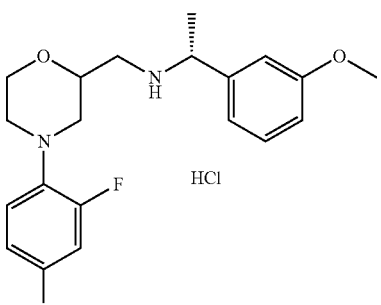<br>(1R)-N-((4-(2,4-difluorophenyl)morpholin-2-yl)methyl)-1-(3-methoxyphenyl)ethanamine hydrochloride | m/z = 363.2; ¹H NMR (400 MHz, CDCl3): δ 10.1 (bs, 1H), 9.75 (bs, 1H), 9.55 (bs, 1H), 8.80 (bs, 1H), 7.33-7.30 (m, 2H), 7.28-7.25 (m, 1H), 7.05-7.0 (m, 1H), 6.95-6.90 (m, 1H), 6.72-6.70 (m, 1H), 6.52-6.5 (m ,1H), 5.0 (m, 1H), 4.21-4.18 (m, 1H), 4.12-4.08 (m, 1H), 3.99 (m, 1H), 3.90 (s, 3H), 3.82-3.80 (m, 1H), 3.48-3.46 (m, 1H), 3.19 (m, 1H), 2.95-2.90 (m, 2H), 2.48-2.42 (m, 1H), 1.98 (d, J = 6.4 Hz, 3H). |

Example-35a, 35b (1R)-1-(Naphthalen-1-yl)-N-((4-(3-(trifluoromethyl)benzyl)morpholin-3-yl)methyl)ethanamine

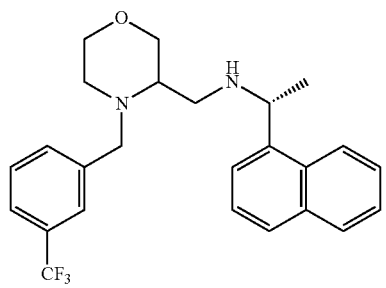 [SMILES: C[C@@H](NCC1COCCN1Cc1cccc(C(F)(F)F)c1)c1cccc2ccccc12]

Step-1: N-((R)-1-(Naphthalen-1-yl)ethyl)-4-(3-(trifluoromethyl)benzyl)morpholine-3-carboxamide To a stirred solution of Intermediate-1 (200 mg, 0.703 mmole) in toluene, $K_2CO_3$ (194 mg, 0.844 mmole) was added followed by 1-(bromomethyl)-3-(trifluoromethyl)benzene. The reaction mixture was heated to 110° C. and further maintained for 20 h. The reaction mixture was diluted with ethyl acetate and washed with DM water (2×15 mL). Organic layer was separated, dried over $Na_2SO_4$, and concentrated to give crude compound. The resultant crude compound was further purified by flash chromatography (210 mg), m/z 443.2.

Step-2: (1R)-1-(Naphthalen-1-yl)-N-((4-(3-(trifluoromethyl)benzyl)morpholin-3-yl)methyl)ethanamine To a stirred solution of above Step-1 intermediate (200 mg, 0.452 mmole) in THF (5 mL), borane-dimethyl sulfide complex (85 µL, 1.13 mmole) was added at room temperature The reaction mass was heated to reflux and further maintained for 6 h. After reaction completion reaction mixture was concentrated under reduced pressure to get crude oil, which was diluted with 10N hydrochloric acid (20 mL) again heated to 100° C. and maintained for 1 h. Reaction mixture was basified with aqueous NaOH solution (pH 10) and extracted in ethyl acetate (2×30 mL), washed with brine solution, dried over $Na_2SO_4$, concentrated to get crude oily product, which was further purified by preparative HPLC and further diastereomers were separated by preparative HPLC (ACQUITY BEH C18, 50×2.1 mm, 1.7µ; water:ACN (90:10) V/V %+0.1% $NH_4OH$) to give title compound of Example-35a (36 mg) and Example-35b: (45 mg)

Example-35a: $t_R$=2.27; $^1$H NMR (400 MHz, $CDCl_3$): δ 8.15 (m, 1H), 7.83-7.85 (m, 1H), 7.71 (d, J=8.4 Hz, 1H), 7.53 (m, 2H), 7.38-7.46 (m, 6H), 4.51 (q, J=6.8 Hz, 1H), 4.0 (d, J=14 Hz, 1H), 3.88 (dd, J=7.2, 2.8 Hz, 2H), 3.65-3.70 (m, 2H), 3.52-3.58 (m, 1H), 3.16 (d, J=14 Hz, 1H), 2.73 (d, J=4.8 Hz, 1H), 2.49-2.2.59 (m, 2H), 2.16-2.22 (m, 1H), 1.42 (d, J=6.8 Hz, 3H); (M+H) 429.2

Example-35b: $t_R$=2.38; $^1$H NMR (400 MHz, $CDCl_3$): δ 8.18 (m, 1H), 7.84-7.86 (m, 1H), 7.73 (d, J=8.4 Hz, 1H), 7.76 (d, J=6.8 Hz, 1H), 7.52-7.58 (m, 2H), 7.46-7.49 (m, 5H), 4.39 (q, J=6.8 Hz, 1H), 4.07 (d, J=14 Hz, 1H), 3.71-3.85 (m, 3H), 3.58-3.64 (m, 1H), 3.25 (d, J=14 Hz, 1H), 2.80 (dd, J=5.2, 12.4 Hz, 1H), 2.56-2.67 (m, 2H), 2.50-2.52 (m, 1H), 2.27-2.30 (m, 1H), 1.42 (d, J=6.8 Hz, 3H); (M+H) 429.2

Example-36a, 36b (1R)-N-((4-Benzylmorpholin-3-yl)methyl)-1-(naphthalen-1-yl)ethanamine

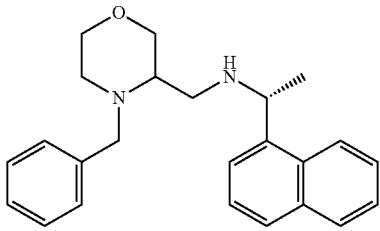 [SMILES: C[C@@H](NCC1COCCN1Cc1ccccc1)c1cccc2ccccc12]

To a stirred solution of Intermediate-7 (300 mg, 0.77 mmole) in THF (5 mL), borane-dimethyl sulfide complex (117 µL, 1.54 mmole) was added at room temperature. The reaction mass was heated to reflux and maintained for 6 h. After reaction completion the reaction mixture was concentrated under reduced pressure to get crude oily product, which was diluted with 10N hydrochloric acid (10 mL) again heated to 100° C. and maintained for 1.5 h. Reaction mixture was basified with aqueous NaOH solution (pH 10) and extracted in ethyl acetate (2×25 mL), washed with brine solution, dried over $Na_2SO_4$, concentrated to get oily product, which was further purified by preparative HPLC (ACQUITY BEH C18, 50×2.1 mm, 1.7µ, ACN:water(90:10) V/V %+0.1% $NH_4OH$) to afford title compound of Example-36a (34 mg) and Example-36b (47 mg).

Example-36a: $t_R$=1.63; $^1$H NMR (400 MHz, $CDCl_3$): δ 8.22-8.19 (m, 1H), 7.90-7.87 (m, 1H), 7.75 (d, J=8.0 Hz, 1H), 7.61 (d, J=7.2 Hz, 1H), 7.50-7.47 (m, 2H), 7.43-7.39 (m, 1H), 7.28-7.23 (m, 5H), 4.58-4.53 (m, 1H), 3.99-3.91 (m, 2H), 3.76-3.70 (m, 2H), 3.60-3.55 (m, 1H), 3.14 (d, J=13.2 Hz, 1H), 2.80-2.76 (m, 2H), 2.65-2.52 (m, 2H), 2.24-2.19 (m, 1H), 1.51 (d, J=6.4 Hz, 3H); m/z: 361.2

Example-36b: $t_R$=1.71; $^1$H NMR (400 MHz, $CDCl_3$): δ 8.17 (d, J=8 Hz, 1H), 7.85 (d, J=8.0 Hz, 1H), 7.72 (d, J=8.0 Hz, 1H), 7.65 (d, J=6.8 Hz, 1H), 7.51-7.43 (m, 3H), 7.34-7.22 (m, 5H), 4.35 (q, J=6.4 Hz, 1H), 4.02 (d, J=13.2 Hz, 1H), 3.83-3.88 (m, 2H), 3.63-3.48 (m, 1H), 3.19 (d, J=13.2 Hz, 1H), 2.81 (dd, J=4.8, 12.4 Hz, 1H), 2.79 (d, J=11.6 Hz, 1H), 2.55 (d, J=12.4 Hz, 1H), 2.46-2.47 (m, 1H), 2.28-2.22 (m, 1H), 1.43 (d, J=6.4 Hz, 3H); m/z: 361.2

Example-37a, 37b (1R)-N-((4-Benzylmorpholin-3-yl)methyl)-1-(3-methoxyphenyl)ethanamine

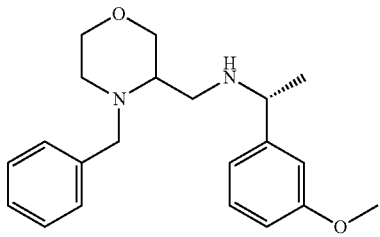 [SMILES: COc1cccc([C@@H](C)NCC2COCCN2Cc2ccccc2)c1]

The title compounds were prepared by following the similar procedure as described in Example-36a and 36b by using Intermediate-8. Further, diastereomers were separated by preparative HPLC (ACQUITY BEH C18, 50×2.1 mm, 1.7μ, ACN:water:(90:10) v/v %+0.1% NH$_4$OH) to get title compound of Example-37a (76 mg) and Example-37b (37 mg).

Example-37a: $t_R$=2.25; $^1$H NMR (400 MHz, CDCl$_3$): δ 7.32-7.18 (m 6H), 6.88 (m, 2H), 6.76 (dd, J=1.6, 7.2 Hz, 1H), 4.02 (d, J=13.6 Hz, 1H), 3.80-3.68 (m, 6H), 3.61-3.49 (m, 2H), 3.18 (d, J=13.2 Hz, 1H), 2.75 (dd, J=5.2, 12.4 Hz, 1H), 2.68-2.63 (m, 1H), 2.48-2.43 (m, 2H), 2.27-2.20 (m, 1H), 1.27 (d, J=6.4 Hz, 1H); m/z: 341.2.

Example-37b: $t_R$=2.27; $^1$H NMR (400 MHz, CDCl$_3$): δ 7.28-7.15 (m 6H), 6.84-6.82 (m, 2H), 6.76-6.74 (m, 1H), 3.92 (d, J=13.2 Hz, 1H), 3.87-3.50 (m, 8H), 3.11 (d, J=13.6 Hz, 1H), 2.69-2.58 (m, 3H), 2.49-2.48 (m, 1H), 2.20-2.17 (m, 1H), 1.35 (d, J=6.8 Hz, 1H); m/z: 341.2.

Example-38a, 38b (1R)-1-(Naphthalen-1-yl)-N-((4-(4-(trifluoromethyl)benzyl)morpholin-3-yl)methyl)ethanamine

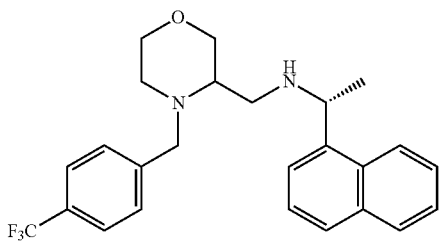

Step-1: N-((R)-1-(Naphthalen-1-yl)ethyl)-4-(4-(trifluoromethyl)benzyl)morpholine-3-carboxamide

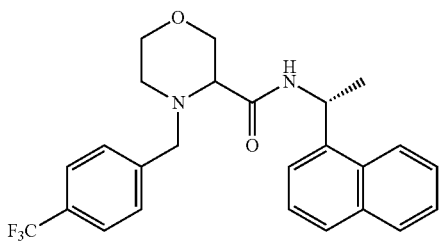 [SMILES: C[C@@H](NC(=O)C1COCCN1Cc1ccc(C(F)(F)F)cc1)c1cccc2ccccc12]

The title compound was prepared by following the similar procedure as described in Step-1 of Example-35a, 35b by using Intermediate-1 and 1-(bromomethyl)-4-(trifluoromethyl)benzene, m/z: 443.2.

Step-2: (1R)-1-(Naphthalen-1-yl)-N-((4-(4-(trifluoromethyl)benzyl)morpholin-3-yl)methyl)ethanamine The title compound was prepared by following the similar procedure as described in step-2 Example-35a, 35b by using above Step-1 intermediate.

Further, diastereomers were separated by preparative HPLC (ACQUITY BEH C18, 50×2.1 mm, 1.7μ, ACN:water (90:10) V/V %+0.1% NH$_4$OH) to get the compound of Example-38a (47 mg) and Example-38b (27 mg).

Example-38a: $t_R$=1.99; $^1$H NMR (400 MHz, CDCl$_3$): δ 8.17 (m, 1H), 7.837-7.89 (m, 1H), 7.75 (d, J=8 Hz, 1H), 7.58 (d, J=8 Hz, 1H), 7.45-7.56 (m, 4H), 7.36-7.42 (m, 3H), 4.51 (q, J=6.8 Hz, 1H), 4.0 (d, J=14 Hz, 1H), 3.92 (dd, J=7.2, 2.8 Hz, 1H), 3.69-3.74 (m, 2H), 3.49-3.61 (m, 2H), 3.19 (d, J=14 Hz, 1H), 2.77-2.78 (m, 2H), 2.54-2.62 (m, 2H), 2.19-2.25 (m, 1H), 1.42 (d, J=6.8 Hz, 3H); m/z 429.3.

Example-38b: $t_R$=2.05; $^1$H NMR (400 MHz, CDCl$_3$): δ 8.18 (m, 1H), 7.86-7.88 (m, 1H), 7.75 (d, J=8.4 Hz, 1H), 7.57-7.65 (m, 3H), 7.44-7.50 (m, 5H), 4.39 (q, J=6.8 Hz, 1H), 4.07 (d, J=14 Hz, 1H), 3.72-3.87 (m, 3H), 3.61-3.66 (m, 1H), 3.49-3.51 (m, 1H), 3.27 (d, J=14 Hz, 1H), 2.80 (dd, J=5.2, 12.4 Hz, 1H), 2.66-2.69 (m, 1H), 2.60 (dd, J=15.2, 12.4 Hz, 1H), 2.51 (m, 1H), 2.27-2.31 (m, 1H), 1.42 (d, J=6.8 Hz, 3H); m/z 429.3.

Example-39a, 39b (3-((((R)-1-(Naphthalen-1-yl)ethyl)amino)methyl)morpholino)(phenyl)methanone

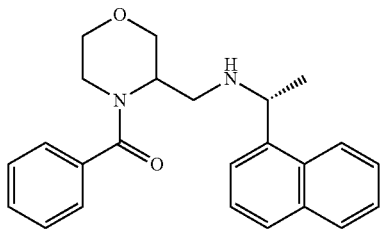 [SMILES: C[C@@H](NCC1COCCN1C(=O)c1ccccc1)c1cccc2ccccc12]

To a stirred solution of Intermediate-4 (140 mg, 0.51 mmol) in DCM (5 mL), triethylamine (52 mg, 0.51 mmol) was added at 0° C. and benzoylchloride (57 mg, 0.41 mmol) in DCM (2 mL) was added dropwise at 0° C. and stirred for 5 min at the same temperature. Reaction mixture was diluted with DCM (20 mL) and washed with water (2×15 mL). Organic layer separated, dried over Na$_2$SO$_4$ and concentrated under vacuum. This crude compound was further purified by using chiral HPLC [CELLULOSE 2, 250 mm×4.6, 5μ, A:B (70:30) A=hexane:IPA (isopropyl alcohol) (90:10) B=IPA (100%)] to get the compound of Example-39a; $t_R$=9.80 (70 mg) M/z 375.3 and Example-39b; $t_R$=12.42 (61 mg) m/z 375.3.

Example-40a, 40b (3-((((R)-1-(3-Methoxyphenyl)ethyl)amino)methyl)morpholino)(phenyl)methanone

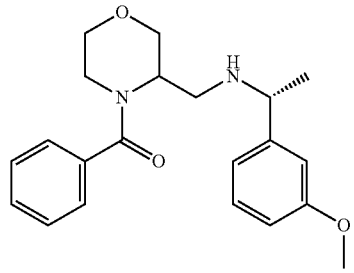 [SMILES: COc1cccc([C@@H](C)NCC2COCCN2C(=O)c2ccccc2)c1]

The title compounds were prepared by following the similar procedure as described in Example-39a, 39b by using Intermediate-5 and benzoylchloride, m/z: 355.3.

Example-41a, 41b 3-((((R)-1-(Naphthalen-1-yl)ethyl)amino)methyl)-N-phenylmorpholine-4-carboxamide hydrochloride

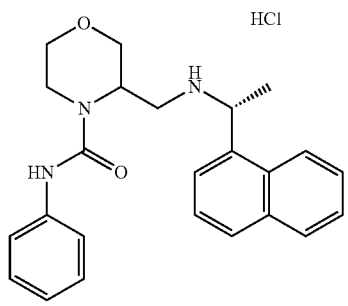 [SMILES: Cl ; C[C@@H](NCC1COCCN1C(=O)Nc1ccccc1)c1cccc2ccccc12]

To a stirred solution of Intermediate-4 (200 mg, 0.73 mmol) in DCM (6 mL), phenylisocyanate (88 mg, 0.73 mmol) in DCM (2 mL) was added dropwise at 0° C. and stirred for 5 min at the same temperature. Reaction mixture was diluted with DCM (20 mL) and washed with water (2×15 mL). Organic layer was separated, dried over $Na_2SO_4$ and concentrated in vacuum. Crude compound was purified by using preparative HPLC to get the title compound.

Further, diastereomers were separated using Chiral HPLC [CELLULOSE 2 250×4.6 mm, 5μ, A:B (70:30) A=hexane: IPA (90:10) B=IPA (100%)],) to get the compound of Example-41a, $t_R$=8.23 and Example-41b, $t_R$=10.06. Hydrochloride salts of these compounds were prepared by using the procedure as described in Example-1 (Example-41a, 72 mg HCl salt and Example-41b, 70 mg HCl salt).

Example-41a: $^1$H NMR (400 MHz, DMSO): δ 9.1 (bs, 1H), 9.0 (bs, 1H), 8.24 (d, J=8 Hz, 1H), 7.96-8.02 (m, 3H), 7.57-7.65 (m, 3H), 7.52 (d, J=7.6 Hz, 2H), 7.23 (t, J=7.6 Hz, 2H), 6.95 (t, J=7.6 Hz, 1H), 5.40 (q, J=6 Hz, 1H), 4.55 (bs, 1H), 3.87-3.91 (m, 2H), 3.76-3.79 (m, 1H), 3.53 (dd, J=3.2 Hz & 12 Hz, 1H), 3.30-3.46 (m, 3H), 3.10-3.11 (m, 1H), 1.70 (d, J=6.4 Hz, 3H); m/z 390.3.

Example-41b: $^1$H NMR (400 MHz, DMSO): δ 9.50 (bs, 1H), 9.40 (bs, 1H), 8.24 (d, J=8 Hz, 1H), 7.98-8.02 (m, 3H), 7.58-7.65 (m, 1H), 7.51-7.56 (m, 4H), 7.23 (t, J=7.6 Hz, 2H), 6.96 (t, J=7.6 Hz, 1H), 5.44 (q, J=6 Hz, 1H), 4.57 (bs, 1H), 3.86-3.92 (m, 2H), 3.79 (dd, J=3.2 Hz & 12 Hz, 1H), 3.49 (dd, J=3.2 Hz & 12 Hz, 2H), 3.36-3.41 (m, 1H), 3.17-3.30 (m, 2H), 1.70 (d, J=6.4 Hz, 3H); m/z 390.3.

The below list of Examples-42 to 45 given in Table-4 were prepared by following the similar procedure as described in Example-41a and 41b using Intermediate-4 and appropriately substituted phenylisocyanate. Further hydrochloride salts of these compounds were prepared by following the similar hydrochloride salt procedure as described in Example-1.

TABLE 4

| Example | Structure | Mass (m/z) and $^1$H NMR |
|---|---|---|
| 42 | 3-((((R)-1-(Naphthalen-1-yl)ethyl)amino)methyl)-N-(3-(trifluoromethyl)phenyl)morpholine-4-carboxamide hydrochloride | m/z 458.2; $^1$H NMR (400 MHz, DMSO): δ 9.45-9.19 (m, 3H), 8.22 (d, J = 8.0 Hz, 1H), 8.10-7.939 (m, 3H), 7.78 (d, J = 8.4 Hz, 1H), 7.65-7.52 (m, 3H), 7.48 (t, J = 7.6 Hz, 1H), 7.29 (t, J = 6.8 Hz, 1H), 5.43-5.40 (m, 1H), 4.59 (bs, 1H), 3.92-3.80 (m, 3H), 3.56-3.10 (m, 5H), 1.70 (d, J = 6.4 Hz, 3H). |

TABLE 4-continued

| Example | Structure | Mass (m/z) and ¹H NMR |
|---|---|---|
| 43 | 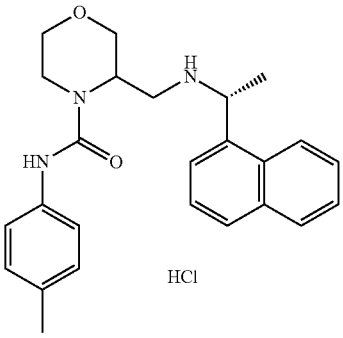 [SMILES: Cc1ccc(NC(=O)N2CCOCC2CN[C@H](C)c2cccc3ccccc23)cc1 ; Cl]<br>3-((((R)-1-(Naphthalen-1-yl)ethyl)amino)methyl)-N-(p-tolyl)morpholine-4-carboxamide hydrochloride | m/z 404.3; ¹H NMR (400 MHz, DMSO): δ 9.50 (bs, 1H), 9.00 (bs, 1H), 8.21 (m, 1H), 8.027-7.97 (m, 3H), 7.65-7.51 (m, 3H), 7.40 (d, J = 8.4 Hz, 1H), 7.04 (d, J = 8.4 Hz, 1H), 5.45-5.43 (m, 1H), 4.56 (bs, 1H), 3.90-3.86 (m, 1H), 3.78-3.76 (m, 1H), 3.54-3.35 (m, 5H), 3.18-2.99 (m, 1H), 2.23 (s, 3H), 1.71 (d, J = 6.8 Hz, 3H). |
| 44 | 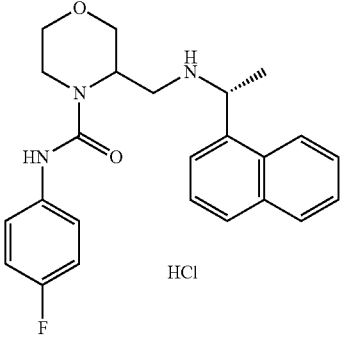 [SMILES: C[C@@H](NCC1COCCN1C(=O)Nc1ccc(F)cc1)c1cccc2ccccc12 ; Cl]<br>N-(4-Fluorophenyl)-3-((((R)-1-(naphthalen-1-yl)ethyl)amino)methyl) morpholine-4-carboxamide hydrochloride | m/z 408.2; ¹H NMR (400 MHz, DMSO): δ 9.47 (bs, 1H), 9.36 (bs, 1H), 8.85 (bs, 1H), 8.24 (d, J = 9.2 Hz, 1H), 8.027-7.94 (m, 3H), 7.65-7.50 (m, 5H), 7.085 (t, J = 8.8 Hz, 2H), 5.44-5.41 (m, 1H), 4.56 (bs, 1H), 3.88 (dd, J = 6.0, 12.8 Hz, 2H), 3.79 (d, J = 9.2 Hz, 1H), 3.53-3.35 (m, 3H), 3.20-3.07 (m, 2H), 1.70 (d, J = 6.8 Hz, 3H). |
| 45 | 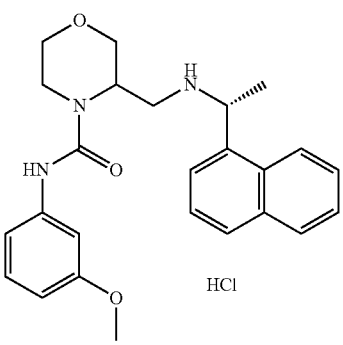 [SMILES: COc1cccc(NC(=O)N2CCOCC2CN[C@H](C)c2cccc3ccccc23)c1 ; Cl]<br>N-(3-Methoxyphenyl)-3-((((R)-1-(naphthalen-1-yl)ethyl)amino)methyl) morpholine-4-carboxamide hydrochloride | m/z 420.2; ¹H NMR (400 MHz, DMSO): δ 10.0 (bs, 1H), 9.4(bs, 1H), 8.24 (d, J = 8 Hz, 1H), 8.02-7.95 (m, 3H), 7.64-7.56 (m, 3H), 7.26-7.24 (m, 1H), 7.13-7.12 (m, 2H), 6.45-6.52 (m, 1H), 5.44-5.39 (m, 1H), 4.57-4.55 (m, 1H), 3.91-3.80 (m, 2H), 3.78-3.71 (m, 1H), 3.68 (s, 3H), 3.43-3.35 (m, 3H), 3.20-3.04 (m, 2H), 1.71 (d, J = 6.8 Hz, 3H) |

Example-46a, 46b 3-((((R)-1-(3-Methoxyphenyl)ethyl)amino)methyl)-N-(3-(trifluoromethyl)phenyl)morpholine-4-carboxamide hydrochloride

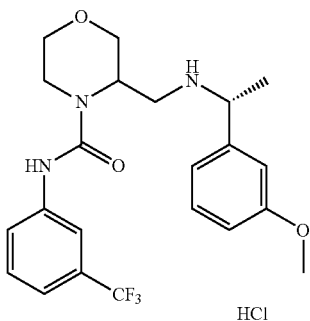 [SMILES: COc1cccc([C@@H](C)NCC2COCCN2C(=O)Nc2cccc(C(F)(F)F)c2)c1 ; Cl]

The title compound was prepared by following the similar procedure as described in Example-41a and 41b by using Intermediate-5 and 1-isocyanato-3-(trifluoromethyl)benzene. Diastereomers were separated using chiral HPLC [CHIRAL PAK 1A, 250 mm×4.6, 5μ, hexane+0.1% DEA (diethylamine) Example-46a, $t_R$=10.30 and Example-46b, $t_R$=11.55. (90):IPA (10)] and further proceeded to prepare hydrochloride salt by following the hydrochloride salt procedure as described in Example-1.

Example-46a: $^1$H NMR (400 MHz, DMSO): 9.30 (bs, 1H), 9.15 (bs, 1H), 9.04 (bs, 1H), 8.05 (s, 1H), 7.81-7.79 (m, 1H), 7.50 (t, J=8.4 Hz, 1H), 7.37-7.30 (m, 3H), 7.24 (bs, 1H), 7.14 (d, J=7.6 Hz, 1H), 6.98 (dd, J=2.0, 8.4 Hz, 1H), 4.48-4.45 (m, 2H), 3.96-3.79 (m, 3H), 3.76 (s, 3H), 3.51-3.39 (m, 3H), 3.23-3.19 (m, 1H), 2.91 (m, 1H), 1.60 (d, J=6.8 Hz, 3H); m/z 438.2.

Example-46a: $^1$H NMR (400 MHz, DMSO): 9.63 (bs, 1H), 9.21 (bs, 1H), 8.63 (bs, 1H), 8.06 (s, 1H), 7.80 (d, J=8.8 Hz, 1H), 7.48 (t, J=8.0 Hz, 1H), 7.36 (t, J=8.0 Hz, 1H), 7.29 (d, J=7.6 Hz, 1H), 7.21 (bs, 1H), 7.12 (d, J=7.6 Hz, 1H), 6.97 (dd, J=2.0, 8.0 Hz, 1H), 4.52-4.39 (m, 2H), 3.93-3.75 (m, 2H), 3.76 (s, 3H), 3.54-3.35 (m, 3H), 3.22-2.99 (m, 1H), 1.59 (d, J=6.8 Hz, 3H); m/z 438.2.

Example-47a, 47b

4-Benzyl-5-((((R)-1-(naphthalen-1-yl)ethyl)amino)methyl)morpholin-3-one

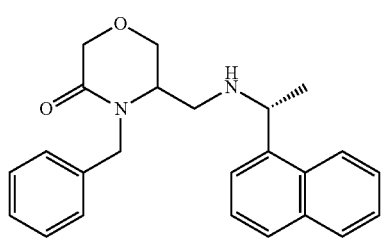 [SMILES: C[C@@H](NCC1COCC(=O)N1Cc1ccccc1)c1cccc2ccccc12]

Step-1:
4-Benzyl-5-(hydroxymethyl)morpholin-3-one

To a stirred solution of 4-benzyl-5-oxomorpholine-3-carboxylic acid (450 mg, 1.91 mmole) and triethylamine (0.28 mL, 2.5 mmole) in THF, ethylchloroformate (0.2 mL) was added dropwise for 20 min at −10° C. The reaction mixture was stirred for additional 30 min and filtered. The filtrate was added for 30 min to a solution of NaBH$_4$ (200 mg, 5.28 mmole) in water (15 mL) at 0° C. The reaction mixture was stirred for 4 h at 10° C. and acidified with 2M HCl. THF was evaporated under reduced pressure and the aqueous residue extracted into DCM, washed with saturated NaHCO$_3$ (20 mL), dried over Na$_2$SO$_4$, concentrated and purified by flash chromatography using eluent 5% MeOH in DCM to get the title compound (170 mg) as oily mass, m/z 222.

Step-2: (4-Benzyl-5-oxomorpholin-3-yl)methyl-4-methylbenzenesulfonate

To a stirred solution of Step-1 intermediate (400 mg, 1.8 mmole) and triethylamine (0.55 mL, 3.98 mmole) in dichloromethane, tosyl chloride (423 mg, 2.17 mmole) was added at 0° C. Reaction mixture was stirred for 8 h at room temperature then diluted with water (25 mL) The reaction mass was extracted into dichloromethane (2×20 mL), dried over Na$_2$SO$_4$, concentrated and purified using flash chromatography to get the title compound (510 mg) as white solid, m/z 376.1.

Step-3: 4-Benzyl-5-((((R)-1-(naphthalen-1-yl)ethyl)amino)methyl)morpholin-3-one

To a stirred solution of Step-2 intermediate (200 mg, 0.533 mmole) in acetonitrile, K$_2$CO$_3$ (147 mg, 1.06 mmole) was added followed by (R)-1-(naphthalen-1-yl)ethanamine (0.1 mL, 0.586 mmole). The reaction mixture was heated to reflux and further maintained for 2 days. The reaction mixture was filtered, washed with ethyl acetate (2×10 mL), and the filtrate was washed with DM water (2×15 mL) Organic layer was separated, dried over Na$_2$SO$_4$, concentrated and the resultant crude product was further purified by preparative HPLC (CHIRAL PAK IA, 250 mm×4.6, 5μ to get the title compound (59a) (40 mg) m/z 375.2 and (59b) 32 mg, m/z 375.2.

Further, diastereomers were separated using chiral HPLC (CHIRAL PAK 1A, 250 mm×4.6, 5μ, n-hexane:IPA (90:10% v/v)) to get the compound of Example-47a, $t_R$=13.73 (40 mg) and Example-47b, $t_R$=17.17 (32 mg).

Example-47a: $^1$H NMR (400 MHz, CDCl$_3$): δ 8.18 (d, J=9.2 Hz, 1H), 7.90-7.88 (m, 1H), 7.76 (d, J=8.0 Hz, 1H), 7.56-7.43 (m, 3H), 7.57-7.65 (m, 4H), 7.29-7.26 (m, 3H), 7.055-7.044 (m, 2H), 5.10 (d, J=14.8 Hz, 1H), 4.52 (q, J=6.4 Hz, 1H), 4.23 (q, J=16.4 Hz, 2H), 4.09 (dd, J=1.6, 12.0 Hz, 1H), 3.86 (d, J=14.8 Hz, 1H), 3.59 (dd, J=2.8 Hz & 12 Hz, 1H), 3.97-3.06 (m, 1H), 2.99-2.94 (m, 1H), 2.68 (dd, J=3.2 Hz & 12.4 Hz, 1H), 1.43 (d, J=6.4 Hz, 3H); m/z 375.2

Example-47b: $^1$H NMR (400 MHz, CDCl$_3$): δ 8.15 (d, J=8.8 Hz, 1H), 7.90-7.88 (m, 1H), 7.77 (d, J=8.4 Hz, 1H), 7.58 (d, J=6.8 Hz, 1H), 7.52-7.47 (m, 3H), 7.25-7.22 (m, 3H), 7.05-7.04 (m, 2H), 5.32-5.28 (m, 2H), 4.58 (q, J=6.8 Hz, 1H), 4.24 (q, J=16.8 Hz, 2H), 4.10 (d, J=12.0 Hz, 1H), 3.72 (d, J=14.8 Hz, 1H), 3.65 (dd, J=2.8 Hz, 12 Hz, 1H), 3.14-3.12 (m, 1H), 2.91-2.86 (m, 1H), 2.77 (dd, J=2.8 Hz & 12.0 Hz, 1H), 1.45 (d, J=6.8 Hz, 3H); m/z 375.2

Example-48a, 48b

4-Benzyl-5-((((R)-1-(3-methoxyphenyl)ethyl)amino)methyl)morpholin-3-one hydrochloride

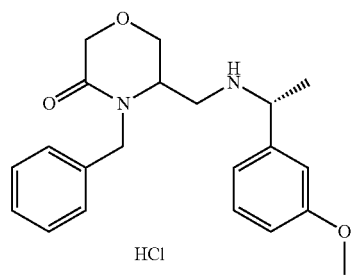 [SMILES: COc1cccc([C@@H](C)NCC2COCC(=O)N2Cc2ccccc2)c1 ; Cl]

HCl

The title compound was prepared by following the similar procedure as described in Step-3 of Example-47a and 47b using (4-benzyl-5-oxomorpholin-3-yl)methyl-4-methylbenzenesulfonate (Step-2 intermediate of Example-47a, 47b) and (R)-1-(3-methoxyphenyl)ethanamine.
Diastereomers were separated using chiral HPLC [CHIRAL PAK 1A, 250 mm×4.6, 5μ, hexane:IPA (90:10% v/v)] and further proceeded to prepare hydrochloride salt by following the similar hydrochloride salt procedure as described in Example-1. Example-48a, $t_R$=13.17 (HCl salt) and Example-48b: $t_R$=16.95 (HCl salt).

Example-48a: $^1$H NMR (400 MHz, CDCl$_3$): δ 10.19 (bs, 1H), 9.97 (bs, 1H), 7.35 (t, J=5.6 Hz, 2H), 7.23-7.7.15 (m, 6H), 7.05 (d, J=7.2 Hz, 1H), 6.95 (d, J=8.4 Hz, 1H), 4.91 (d, J=14.8 Hz, 1H), 4.60 (d, J=12.4 Hz, 1H), 4.20-4.04 (m, 3H), 3.91 (d, J=14.8 Hz, 1H), 3.87 (s, 3H), 3.75 (d, J=12.4 Hz, 1H), 3.34 (d, J=12.4 Hz, 1H), 3.15-3.14 (m, 1H), 2.69 (m, 1H), 1.66 (d, J=6.8 Hz, 3H); m/z: 355.2

Example-48b: $^1$H NMR (400 MHz, CDCl$_3$): δ 10.52 (bs, 1H), 9.57 (bs, 1H), 7.36-7.26 (m, 6H), 7.12 (bs, 1H), 7.01 (d, J=6.8 Hz, 1H), 6.95 (d, J=8.0 Hz, 1H), 5.04 (d, J=14.8 Hz, 1H), 4.48-4.46 (m, 1H), 4.10-3.98 (m, 4H), 3.85 (s, 3H), 3.75 (m, 1H), 3.23-3.21 (m, 1H), 2.08 (m, 1H), 2.74 (m, 1H), 1.73 (d, J=6.8 Hz, 3H); m/z: 355.2

Example-49a, 49b

6-((((R)-1-(Naphthalen-1-yl)ethyl)amino)methyl)-4-phenylmorpholin-3-one hydrochloride

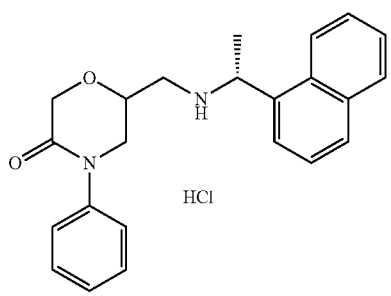 [SMILES: C[C@@H](NCC1CN(c2ccccc2)C(=O)CO1)c1cccc2ccccc12 ; Cl]

HCl

Step-1: tert-Butyl-((R)-1-(naphthalen-1-yl)ethyl)((5-oxo-4-phenylmorpholin-2-yl) methyl)carbamate tert-Butyl ((R)-1-(naphthalen-1-yl)ethyl)((5-oxomorpholin-2-yl)methyl)carbamate (300 mg, 0.78 mmol) (Intermediate-9), iodobenzene (104 μL, 0.93 mmol), potassium phosphate (330 mg, 1.56 mmol), copper iodide (14.8 mg, 0.078 mmol) and N,N'-dimethylaminoethane (17 μL, 0.15 mmol) were added in 1,4-dioxane. The reaction mixture was heated to 110° C. and further stirred overnight at the same temperature. After reaction completion the reaction mixture was concentrated and the residue was purified through silica gel column chromatography (ethyl acetate/hexane=1/4) to obtain the title compound (375 mg) as an oil. m/z 461.08

Step-2: 6-((((R)-1-(Naphthalen-1-yl)ethyl)amino)methyl)-4-phenylmorpholin-3-one

To a stirred solution of above Step-1 intermediate (250 mg, 0.69 mmol) in ethyl acetate (4 mL), HCl in diethyl ether (2M, 2 mL) was added and the reaction mixture was heated to 55° C. and maintained for 5 h in closed vessel. Solid separated out was filtered and washed with diethyl ether, basified with saturated NaHCO$_3$ and extracted into ethyl acetate, dried over Na$_2$SO$_4$, concentrated to get the title compound as white solid (80 mg).
Further, diastereomers were separated using chiral HPLC (CHIRAL PAK 1A, 250 mm×4.6, 5μ; A=Hexane:IPA (90/10% v/v)). B=Isopropanol, Isocratic A:B 70/30% v/v) and further proceeded to prepare hydrochloride salt by following the similar hydrochloride salt procedure as described in Example-1. Example-49a, $t_R$=8.57 (25 mg, HCl salt) and Example-49b: $t_R$=11.8 (30 mg, HCl salt).

Example-49a: $^1$H NMR (400 MHz, DMSO): δ 9.88 (bs, 1H), 9.52 (bs, 1H), 8.24 (d, J=8.4 Hz, 1H), 7.95-8.03 (m, 3H), 7.58-7.67 (m, 3H), 7.27-7.43 (m, 5H), 5.38-5.39 (m, 1H), 4.46 (m, 1H), 4.33 (m, 2H), 3.68 (m, 2H), 3.17 (m, 2H), 1.70 (d, J=6.4 Hz, 3H); m/z 361.31

Example-49b: $^1$H NMR (400 MHz, DMSO): δ 10.14 (bs, 1H), 9.30 (bs, 1H), 8.24 (d, J=8.4 Hz, 1H), 8.01 (t, J=8 Hz, 2H), 7.94 (d, J=7.2 Hz, 1H), 7.58-7.66 (m, 3H), 7.38-7.42 (m, 2H), 7.25-7.33 (m, 3H), 5.38 (m, 1H), 4.27-4.47 (m, 3H), 3.66-3.72 (m, 1H), 3.60 (dd, J=3.2, 12 Hz, 1H), 3.33 (m, 1H), 2.93 (m, 1H), 1.71 (d, J=6.8 Hz, 3H); m/z 361.43

Example-50a, 50b

4-(3-Fluoro-4-methoxyphenyl)-6-((((R)-1-(3-methoxyphenyl)ethyl)amino)methyl) morpholin-3-one

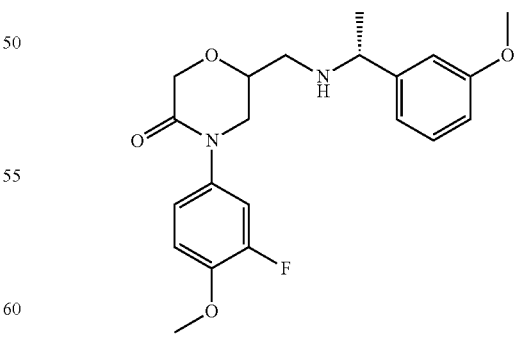

The title compound was prepared by following the similar procedure as described in step-1 Example-49a, 49b by using Intermediate-10 and 4-bromo-2-fluoro-1-methoxybenzene then Boc deprotection as described in step-2 Example-49a, 49b.

¹H NMR (400 MHz, DMSO): δ 9.55 (bs, 2H), 7.38-7.27 (m, 2H), 7.22-7.11 (m, 4H), 6.98-6.96 (m, 1H), 4.40-4.22 (m, 4H), 3.83 (s, 3H), 3.77 (s, 3H), 3.76-3.56 (m, 2H), 3.10-2.49 (m, 2H), 1.60 (t, J=6.8 Hz, 3H); m/z 389.1.

The below list of Examples-51 to 68 given in Table-5 were prepared by following the similar procedure as described in Step-1 of Example-49a, 49b then Boc deprotection by following the similar procedure as described in Step-2 of Example-49a, 49b using Intermediate-9 or Intermediate-10 or Intermediate-14. Further, hydrochloride salts of these compounds were prepared by following the similar hydrochloride salt procedure as described in Example-1.

TABLE 5

| Example | Structure | Mass (m/z) and ¹H NMR |
|---|---|---|
| 51 | 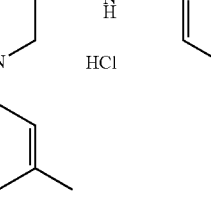<br>6-((((R)-1-(Naphthalen-1-yl)ethyl)amino)methyl)-4-(m-tolyl)morpholin-3-one hydrochloride | m/z 375.47; ¹H NMR (400 MHz, DMSO): δ 9.80 (bs, 1H), 9.31 (bs, 1H), 8.25-8.22 (m, 2H), 8.03-7.95 (m, 6H), 7.67-7.58 (m, 6H), 7.32-7.25 (m, 2H), 7.15-7.07 (m, 6H), 5.38 (m, 2H), 4.32-4.25 (m, 3H), 3.69-3.56 (m, 4H), 3.34 (m, 2H), 3.16-3.15 (m, 3H), 2.90 (m, 2H), 2.29 (s, 6H), 1.71 (t, J = 6.8 Hz, 6H). |
| 52 | 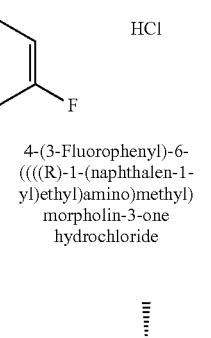<br>4-(3-Fluorophenyl)-6-((((R)-1-(naphthalen-1-yl)ethyl)amino)methyl)morpholin-3-one hydrochloride | m/z 379.41; ¹H NMR (400 MHz, DMSO): δ 10.25 (bs, 1H), 9.6 (bs, 1H), 8.23 (d, J = 8 Hz, 1H), 8.03-7.95 (m, 3H), 7.66-7.58 (m, 3H), 7.45-7.43 (m, 1H), 7.31-7.20 (m, 2H), 7.14-7.09 (m, 1H), 5.4 (m, 1H), 4.48-4.45 (m, 1H), 4.34-4.27 (m, 2H), 3.74-3.61 (m, 2H), 3.27-3.24 (m, 1H), 3.14 (m, 1H), 1.71 (d, J = 6.4 Hz, 3H). |
| 53 | 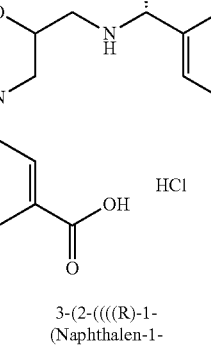<br>3-(2-((((R)-1-(Naphthalen-1-yl)ethyl)amino)methyl)-5-oxomorpholino)benzoic acid hydrochloride | m/z 405.10; ¹H NMR (400 MHz, DMSO): δ 13.15 (bs, 1H), 10.2 (bs, 1H), 9.65 (bs, 1H), 8.23 (d, J = 8.8 Hz, 1H), 8.03-7.95 (m, 3H), 7.93-7.91 (m, 1H), 7.82 (dd, J = 2.8 & 8 Hz, 1H), 7.67-7.58 (m, 4H), 7.55-7.54 (m, 1H), 5.39-5.38 (m, 1H), 4.50-4.40 (m, 1H), 4.36-4.29 (m, 2H), 3.78-3.71(m, 1H), 3.67-3.63 (m, 1H), 3.16 (m, 1H), 2.95 (m, 1H), 1.71 (d, J = 6.8 Hz, 3H). |

TABLE 5-continued

| Example | Structure | Mass (m/z) and ¹H NMR |
|---|---|---|
| 54 | 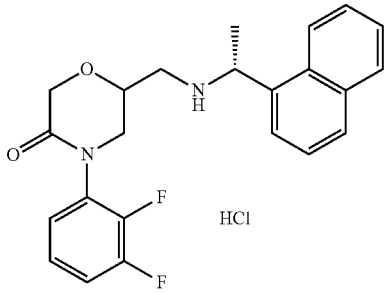 [SMILES: C[C@@H](NCC1CN(c2cccc(F)c2F)C(=O)CO1)c1cccc2ccccc12 ; Cl]<br>4-(2,3-Difluorophenyl)-6-((((R)-1-(naphthalen-1-yl)ethyl)amino)methyl) morpholin-3-one hydrochloride | m/z 397.1; ¹H NMR (400 MHz, DMSO): δ 10.1 (bs, 1H), 9.9 (bs, 1H), 8.26-8.22 (m, 1H), 8.03-7.92 (m, 3H), 7.67-7.56 (m, 3H), 7.54-7.42 (m, 1H), 7.32-7.29 (m, 2H), 5.40-5.38 (m, 1H), 4.46-4.41 (m, 2H), 4.37-4.31 (m, 1H), 3.69-3.62 (m, 2H), 3.25 (m, 1H), 2.9 (m, 1H), 1.70 (d, J = 6.8 Hz, 3H). |
| 55 | 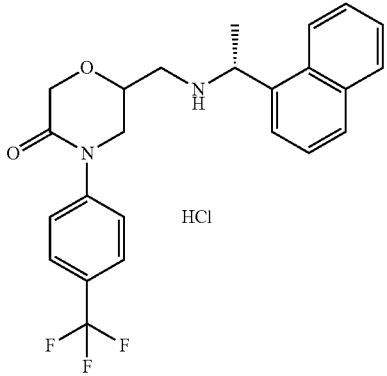 [SMILES: C[C@@H](NCC1CN(c2ccc(C(F)(F)F)cc2)C(=O)CO1)c1cccc2ccccc12 ; Cl]<br>6-((((R)-1-(Naphthalen-1-yl)ethyl)amino) methyl)-4-(4-(trifluoromethyl)phenyl) morpholin-3-one hydrochloride | m/z 429.1; ¹H NMR (400 MHz, DMSO): δ 10.5 (bs, 1H), 9.75 (bs, 1H), 8.24 (d, J = 8 Hz, 1H), 8.03-7.95 (m, 3H), 7.78 (d, J = 8 Hz, 2H), 7.67-7.58 (m, 5H), 5.40-5.39 (m, 1H), 4.49 (m, 1H), 4.41-4.31 (m, 1H), 3.80-3.68 (m, 2H), 3.31-3.29 (m, 1H), 3.15 (m, 1H), 2.95-2.91 (m, 1H), 1.70 (d, J = 6.4 Hz, 3H). |
| 56 | 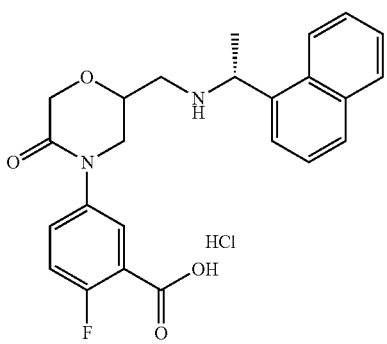 [SMILES: C[C@@H](NCC1CN(c2ccc(F)c(C(=O)O)c2)C(=O)CO1)c1cccc2ccccc12 ; Cl]<br>2-Fluoro-5-(2-((((R)-1-(naphthalen-1-yl)ethyl)amino)methyl)-5-oxomorpholino) benzoic acid hydrochloride | m/z 421.1; ¹H NMR (400 MHz, DMSO): δ 13.43 (bs, 1H), 10.34 (bs, 1H), 9.65 (bs, 1H), 8.23 (d, J = 8.4 Hz, 1H), 8.02-7.96 (m, 3H), 7.85-7.82 (m, 1H), 7.66-7.57 (m, 4H), 7.38-7.33 (m, 1H), 5.37 (m, 1H), 4.49-4.48 (m, 1H), 4.38-4.26 (m, 2H), 3.74-3.67 (m, 2H), 3.14 (m, 1H), 2.91 (m, 1H), 1.71 (d, J = 6.4 Hz, 3H). |

TABLE 5-continued

| Example | Structure | Mass (m/z) and ¹H NMR |
|---|---|---|
| 57 | 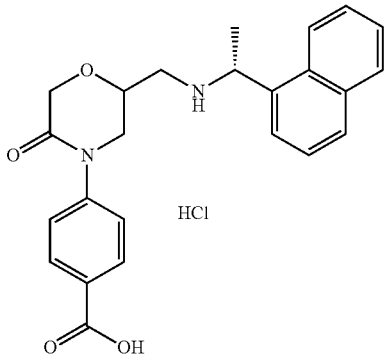 [SMILES: C[C@@H](NCC1CN(c2ccc(C(=O)O)cc2)C(=O)CO1)c1cccc2ccccc12 ; Cl]<br>4-(2-((((R)-1-(Naphthalen-1-yl)ethyl)amino)methyl)-5-oxomorpholino) benzoic acid hydrochloride | m/z 405.10; ¹H NMR (400 MHz, DMSO): δ 12.9 (bs, 1H), 10.28 (bs, 1H), 9.6 (bs, 1H), 8.24 (d, J = 8.4 Hz, 1H), 8.13-7.93 (m, 5H), 7.67-7.63 (m, 3H), 7.52-7.49 (m, 2H), 5.38 (m, 1H), 4.48 (m, 1H), 4.47-4.30 (m, 2H), 3.78-3.66 (m, 2H), 1.71 (d, J = 6.8 Hz, 3H). |
| 58 | 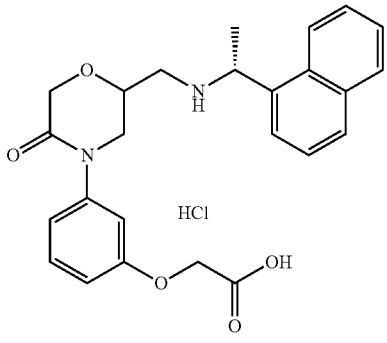 [SMILES: C[C@@H](NCC1CN(c2cccc(OCC(=O)O)c2)C(=O)CO1)c1cccc2ccccc12 ; Cl]<br>2-(3-(2-((((R)-1-(Naphthalen-1-yl)ethyl)amino)methyl)-5-oxomorpholino) phenoxy)acetic acid hydrochloride | m/z 434.35; ¹H NMR (400 MHz, DMSO): δ 13.0 (bs, 1H), 10.6 (bs, 1H), 9.5 (bs, 1H), 8.25 (d, J = 8.4 Hz, 1H), 8.03-7.97 (m, 3H), 7.97-7.57 (m, 3H), 7.29 (t, J = 8 Hz 1H), 6.94-6.92 (m, 2H), 6.82 (d, J = 6.8 Hz, 1H), 5.35 (m, 1H), 4.65 (s, 2H), 4.48-4.47 (m, 1H), 4.36-4.25 (m, 2H), 3.67-3.61 (m, 2H), 3.12-3.10 (m, 1H), 2.9 (m, 1H), 1.71 (d, J = 6 Hz, 3H). |
| 59 | 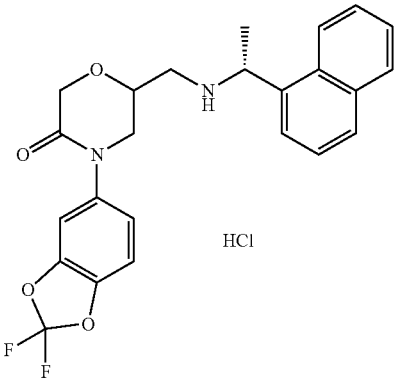 [SMILES: C[C@@H](NCC1CN(c2ccc3c(c2)OC(F)(F)O3)C(=O)CO1)c1cccc2ccccc12 ; Cl]<br>4-(2,2-Difluorobenzo[d][1,3]dioxol-5-yl)-6-((((R)-1-(naphthalen-1-yl)ethyl)amino)methyl) morpholin-3-one hydrochloride | m/z 441.1; ¹H NMR (400 MHz, DMSO): δ 10.4 (bs, 1H), 9.8 (bs, 1H), 8.23 (d, J = 8.4 Hz, 1H), 8.03-7.96 (m, 2H), 7.67-7.58 (m, 3H), 7.50-7.44 (m, 2H), 7.19-7.16 (m, 1H), 5.38 (m, 1H), 4.50-4.45 (m, 1H), 4.38-4.26 (m, 2H), 3.70-3.57 (m, 2H), 3.16-3.13 (m, 1H), 2.90-2.88 (m, 1H), 1.171 (d, J = 6.8 Hz, 3H). |

TABLE 5-continued

| Example | Structure | Mass (m/z) and ¹H NMR |
|---|---|---|
| 60 | 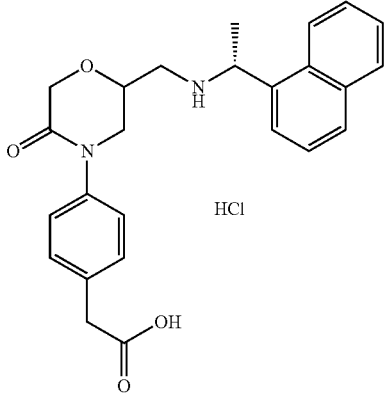 [SMILES: C[C@@H](NCC1CN(c2ccc(CC(=O)O)cc2)C(=O)CO1)c1cccc2ccccc12 ; Cl]<br>2-(4-(2-((((R)-1-(Naphthalen-1-yl)ethyl)amino)methyl)-5-oxomorpholino)phenyl)acetic acid hydrochloride | m/z 419.1; ¹H NMR (400 MHz, DMSO): δ 13.1 (bs, 1H), 10.1 (bs, 1H), 9.45 (bs, 1H), 8.25-8.22 (m, 1H), 8.02-8.00 (m, 3H), 7.72-7.59 (m, 3H), 7.27 (d, J = 5.2 Hz, 4H), 5.38 (m, 1H), 4.36-4.25 (m, 3H), 3.69-3.65 (m, 2H), 3.59-3.50 (m, 2H), 3.16 (m, 1H), 1.72 (d, J = 6.8 Hz, 3H) |
| 61 | 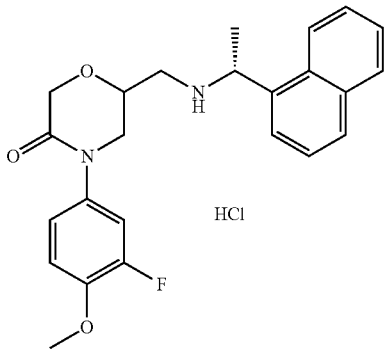 [SMILES: COc1ccc(N2CC(CN[C@H](C)c3cccc4ccccc34)OCC2=O)cc1F ; Cl]<br>4-(3-Fluoro-4-methoxyphenyl)-6-((((R)-1-(naphthalen-1-yl)ethyl)amino)methyl)morpholin-3-one hydrochloride | m/z 409.1; ¹H NMR (400 MHz, DMSO): δ 10.45 (bs, 1H), 9.8 (bs, 1H), 8.24 (d, J = 8 Hz, 1H), 8.03-7.98 (m, 3H), 7.67-7.58 (m, 3H), 7.27-7.16 (m, 2H), 6.90-6.86 (m, 1H), 5.4 (m, 1H), 4.49-4.47 (m, 1H), 4.37-4.29 (m, 2H), 3.83 (s, 3H), 3.67-3.60 (m, 2H), 3.13-3.12 (m, 1H), 2.9 (m, 1H), 1.72 (d, J = 6.8 Hz, 3H). |
| 62a, 62b | 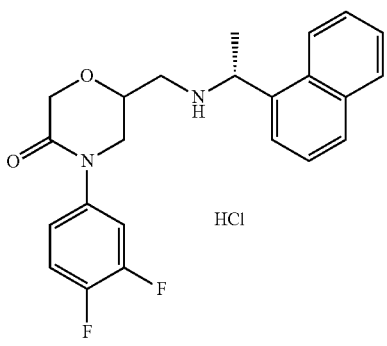 [SMILES: C[C@@H](NCC1CN(c2ccc(F)c(F)c2)C(=O)CO1)c1cccc2ccccc12 ; Cl]<br>4-(3,4-Difluorophenyl)-6-((((R)-1-(naphthalen-1-yl)ethyl)amino)methyl)morpholin-3-one hydrochloride | m/z 397.1; 62a: ¹H NMR (400 MHz, DMSO): δ 10.19 (bs, 1H), 9.30 (bs, 1H), 8.24 (d, J = 8.0 Hz, 1H), 8.01 (t, J = 8.4 Hz, 2H), 7.94 (d, J = 7.2 Hz, 1H), 7.67-7.45 (m, 5H), 7.24-7.22 (m, 1H), 5.39 (m, 1H), 4.29-4.26 (m, 3H), 3.71-3.58 (m, 2H), 3.32-3.26 (m, 1H), 2.93-2.88 (m, 1H), 1.71 (d, J = 6.8 Hz, 3H).<br>62b: ¹H NMR (400 MHz, DMSO): δ 9.80 (bs, 1H), 9.58 (bs, 1H), 8.23 (d, J = 8.0 Hz, 1H), 8.03-7.97 (m, 3H), 7.66-7.45 (m, 5H), 7.25-7.22 (m, 1H), 5.38 (m, 1H), 4.38-4.28 (m, 3H), 3.68-3.66 (m, 2H), 3.19-3.14 (m, 2H), 1.70 (d, J = 6.8 Hz, 3H). |

TABLE 5-continued

| Example | Structure | Mass (m/z) and $^1$H NMR |
|---|---|---|
| 63 | 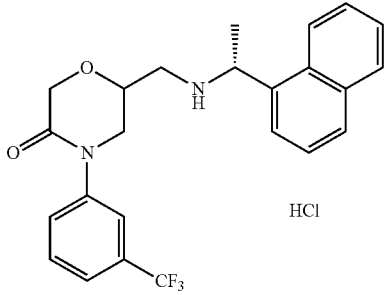 [SMILES: C[C@@H](NCC1CN(c2cccc(C(F)(F)F)c2)C(=O)CO1)c1cccc2ccccc12 ; Cl]<br>6-((((R)-1-(Naphthalen-1-yl)ethyl)amino)methyl)-4-(3-(trifluoromethyl)phenyl)morpholin-3-one hydrochloride | m/z 429.16; $^1$H NMR (400 MHz, DMSO): δ 10.38 (bs, 1H), 9.35 (bs, 1H), 8.22 (d, J = 8.0 Hz, 1H), 8.03-7.95 (m, 3H), 7.78 (m, 1H), 7.70-7.61 (m, 5H), 5.39 (m, 1H), 4.52-4.29 (m, 3H), 3.80-3.65 (m, 2H), 3.46-2.90 (m, 2H), 1.73-1.70 (m, 3H). |
| 64 | 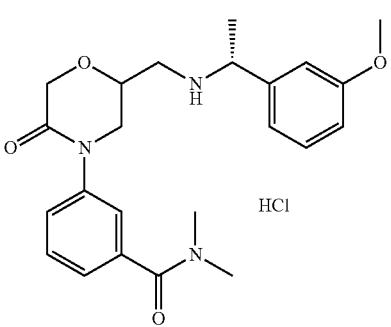 [SMILES: COc1cccc([C@@H](C)NCC2CN(c3cccc(C(=O)N(C)C)c3)C(=O)CO2)c1 ; Cl]<br>3-(2-((((R)-1-(3-Methoxyphenyl)ethyl)amino)methyl)-5-oxomorpholino)-N,N-dimethylbenzamide hydrochloride | m/z 412.2; $^1$H NMR (400 MHz, DMSO): δ 9.89 (bs, 1H), 9.19 (bs, 1H), 7.48-7.34 (m, 4H), 7.30-7.28 (m, 1H), 7.19 (m, 1H), 7.11-7.09 (m, 1H), 6.98-6.96 (m, 1H), 4.39-4.25 (m, 4H), 3.77-3.61 (m, 1H), 2.97 (s, 3H), 2.89 (s, 3H), 1.60-1.58 (m, 3H). |
| 65 | 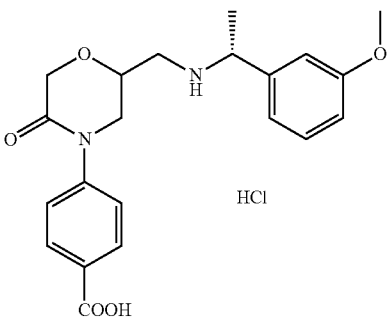 [SMILES: COc1cccc([C@@H](C)NCC2CN(c3ccc(C(=O)O)cc3)C(=O)CO2)c1 ; Cl]<br>4-(2-((((R)-1-(3-Methoxyphenyl)ethyl)amino)methyl)-5-oxomorpholino)benzoic acid hydrochloride | m/z 385.1; $^1$H NMR (400 MHz, DMSO): δ 12.90 (bs, 1H), 9.59 (bs, 1H), 9.23 (bs, 1H), 7.96 (d, J = 8.4 Hz, 1H), 7.58-7.51 (m, 2H), 7.39-7.34 (m, 1H), 7.25-7.11 (m, 3H), 6.98-6.96 (m, 1H), 4.43-4.28 (m, 4H), 3.81-3.65 (m, 5H), 3.12-2.66 (m, 2H), 1.60-1.58 (m, 3H). |

TABLE 5-continued

| Example | Structure | Mass (m/z) and ¹H NMR |
|---|---|---|
| 66 | 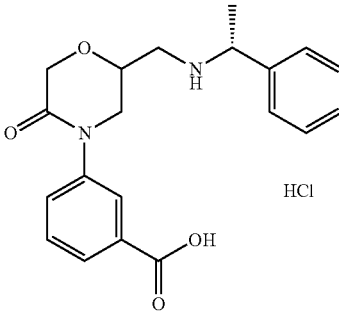<br>3-(2-((((R)-1-(3-Methoxyphenyl)ethyl)amino)methyl)-5-oxomorpholino)benzoic acid hydrochloride | m/z 385.1; ¹H NMR (400 MHz, DMSO): δ 12.90 (bs, 1H), 9.55 (bs, 1H), 9.18 (bs, 1H), 7.94-7.93 (m, 1H), 7.92-7.82 (m, 1H), 7.63-7.61 (m, 1H), 7.54 (t, J = 8.0 Hz, 1H), 7.36-7.34 (m, 1H), 7.23-7.21 (m, 1H), 7.13-7.11 (m, 1H), 6.98-6.96 (m, 1H), 4.45-4.27 (m, 4H), 3.85-3.62 (m, 4H), 3.10-2.95 (m, 2H), 2.74-2.66 (m, 1H), 1.61-1.59 (m, 3H). |
| 67 | 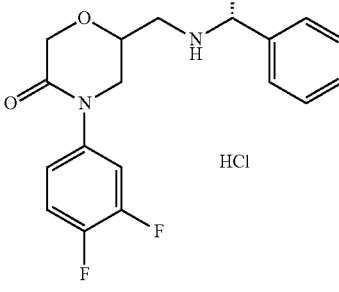<br>4-(3,4-Difluorophenyl)-6-((((R)-1-(3-methoxyphenyl)ethyl)amino)methyl)morpholin-3-one hydrochloride | m/z 377.44; ¹H NMR (400 MHz, DMSO): δ 10.18 (bs, 1H), 9.24 (bs, 1H), 7.57-7.45 (m, 2H), 7.38-7.34 (m, 1H), 7.33-7.21 (m, 2H), 7.13-7.11 (m, 1H), 6.97-6.95 (m, 1H), 4.45-4.24 (m, 4H), 3.77-3.57 (m, 5H), 3.08-2.66 (m, 2H), 1.60-1.58 (m, 3H). |
| 68 | 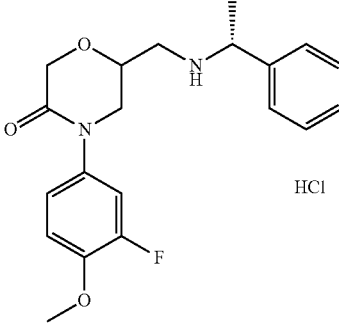<br>6-((((R)-1-(4-Fluoro-3-methoxyphenyl)ethyl)amino)methyl)-4-(3-fluoro-4-methoxyphenyl)morpholin-3-one hydrochloride | m/z 407.1; ¹H NMR (400 MHz, DMSO): δ 10.08 (bs, 1H), 9.25 (bs, 1H), 7.58-7.50 (m, 1H), 7.30-7.23 (m, 2H), 7.20-7.09 (m, 3H), 4.40-4.21 (m, 4H), 3.86-3.80 (m, 6H), 3.68-3.53 (m, 2H), 3.25-2.52 (m, 2H), 1.60 (d, J = 6.4 Hz, 3H). |

Example-69a, 69b

4-(Cyclopentylmethyl)-6-((((R)-1-(naphthalen-1-yl)ethyl)amino)methyl)morpholin-3-one

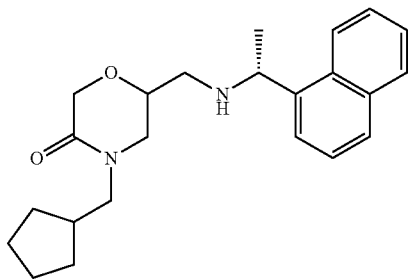 [SMILES: C[C@@H](NCC1CN(CC2CCCC2)C(=O)CO1)c1cccc2ccccc12]

Step-1: tert-Butyl ((4-(cyclopentylmethyl)-5-oxo-morpholin-2-yl)methyl)((R)-1-(naphthalen-1-yl)ethyl)carbamate In a 50 ml round bottom flask added sodium hydride (78 mg, 1.951 mmol) in DMF (10 ml) under nitrogen atmosphere, followed by Intermediate-9 in DMF at 0° C. Then the reaction mixture was stirred for 20 min, (iodomethyl)cyclopentane (0.251 ml, 1.951 mmol) added dropwise at 0° C., then the reaction mixture was stirred at RT overnight. Reaction was quenched by adding aqueous $NH_4Cl$ solution, extracted with ethyl acetate (10 mL×3). Organic layer was washed with DM water (10 mL×2), dried over $Na_2SO_4$ and concentrated to get crude oily mass. The crude compound was purified by column chromatography (hexane:ethyl acetate 1:1) to get tilted compound (260 mg, 42.8% yield).

Step-2: 4-(Cyclopentylmethyl)-6-((((R)-1-(naphthalen-1-yl)ethyl)amino)methyl)morpholin-3-one To a stirred solution of above Step-1 intermediate (250 mg, 0.536 mmol) in ethyl acetate (4 mL), HCl in diethyl ether (2M, 2 mL) was added and the reaction mixture was heated to 55° C. and maintained for 5 h in closed vessel. Solid separated out was filtered and washed with diethyl ether, basified with saturated $NaHCO_3$ and extracted into ethyl acetate, dried over $Na_2SO_4$, concentrated to get the title compound as white solid (80 mg).

Further, diastereomers were separated using chiral HPLC (CHIRAL PAK 1C, 250 mm×4.6, 5µ; A: hexane/IPA (90:10, % v/v, 0.1% DEA) B:IPA (100%) A:B 75/25% v/v) and further proceeded to prepare hydrochloride salt by following the similar hydrochloride salt procedure as described in Example-1. Example-69a, $t_R$=9.40 (80 mg, HCl salt) and Example-69b: $t_R$=11.45 (55 mg, HCl salt).

m/z 367.1; 69a: $^1H$ NMR (400 MHz, DMSO): δ 9.75 (bs, 1H), 9.5 (bs, 1H), 8.22 (d, J=8 Hz, 1H), 8.03-7.66 (m, 3H), 7.68-7.58 (m, 3H), 5.76 (m, 1H), 4.25-4.22 (m, 1H), 4.13 (m, 2H), 3.32-3.21 (m, 3H), 3.14-3.09 (m, 2H), 2.92-2.89 (m, 1H), 2.13-2.08 (m, 1H), 1.68 (d, J=6.4 Hz, 2H), 1.63-1.56 (m, 3H), 1.48-1.45 (m, 2H), 1.23 (m, 1H), 1.12 (d, J=6.8 Hz, 3H). 69b: $^1H$ NMR (400 MHz, DMSO): δ 10.45 (bs, 1H), 9.3 (bs, 1H), 8.22 (d, J=8 Hz, 1H), 8.02-7.96 (m, 3H), 7.66-7.57 (m, 3H), 5.3 (m, 1H), 4.2 (m, 1H), 4.16-4.06 (m, 2H), 3.24-3.22 (m, 2H), 3.11-3.07 (m, 1H), 2.89-2.84 (m, 3H), 2.09 (m, 1H), 1.66 (d, J=6.4 Hz, 2H), 1.57-1.54 (m, 3H), 1.46-1.43 (m, 2H), 1.23 (m, 1H), 1.17 (d, J=6.8 Hz, 3H).

The below list of Examples-70 to 101 given in Table-6 were prepared by following the similar procedure as described in Step-1 of Example-69a, 69b then Boc deprotection by following the similar procedure as described in Step-2 of Example-69a, 69b by taking Intermediate-9 or Intermediate-10 or Intermediate-14. Further, hydrochloride salts of these compounds were prepared by following the similar hydrochloride salt procedure as described in Example-1.

TABLE 6

| Example | Structure | Mass (m/z) and $^1H$ NMR |
|---|---|---|
| 70a, 70b | 6-((((R)-1-(Naphthalen-1-yl)ethyl)amino)methyl)-4-(3-(trifluoromethyl)benzyl)morpholin-3-one hydrochloride | m/z 443.1; 70a: $^1H$ NMR (400 MHz, DMSO): δ 10.13 (bs, 1H), 9.26 (bs, 1H), 8.20 (d, J = 8.4 Hz, 1H), 7.99 (m, 2H), 7.91-7.89 (d, J = 7.2 Hz, 1H), 7.66-7.52 (m, 6H), 5.32-5.30 (m, 1H), 4.63 (s, 2H), 4.33-4.20 (m, 3H), 3.19-3.13 (m, 4H), 2.90 (m, 1H), 1.66 (d, J = 6.8 Hz, 3H). 70b: $^1H$ NMR (400 MHz, DMSO): δ 9.67 (bs, 1H), 9.42 (bs, 1H), 8.21 (d, J = 8.4 Hz, 1H), 7.99 (t, J = 8.8 Hz, 2H), 7.93-7.91 (d, J = 8.4 Hz, 1H), 7.67-7.54 (m, 6H), 5.32-5.30 (m, 1H), 4.60 (s, 2H), 4.31-4.20(m, 3H), 3.26-3.12 (m, 4H), 2.90 (m, 1H), 1.66 (d, J = 6.4 Hz, 3H). |

TABLE 6-continued

| Example | Structure | Mass (m/z) and ¹H NMR |
|---|---|---|
| 71a, 71b | 6-((((R)-1-(Naphthalen-1-yl)ethyl)amino)methyl)-4-(2,4,5-trifluorobenzyl)morpholin-3-one hydrochloride | m/z 429.1; 71a: ¹H NMR (400 MHz, DMSO): δ 10.17 (bs, 1H), 9.27 (bs, 1H), 8.21 (d, J = 8.4 Hz, 1H), 8.00 (m, 2H), 7.92 (d, J = 7.2 Hz, 1H), 7.64-7.52 (m, 4H), 7.40-7.33 (m, 1H), 4.53 (s, 2H), 4.29-4.18 (m, 3H), 3.21-3.14 (m, 3H), 2.94-2.82 (m, 2H), 1.69 (d, J = 6.4 Hz, 3H).<br>71b; ¹H NMR (400 MHz, DMSO): δ 9.70 (bs, 1H), 9.51(bs, 1H), 8.22 (d, J = 8.4 Hz, 1H), 8.02-7.90 (m, 3H), 7.65-7.54 (m, 4H), 7.41-7.34 (m, 1H), 5.33 (m, 1H), 4.52 (s, 2H), 4.28-4.19 (m, 3H), 3.24-3.17 (m, 3H), 2.94-2.85 (m, 1H), 1.67 (d, J = 6.4 Hz, 3H). |
| 72a, 72b | 4-(2,5-Difluorobenzyl)-6-((((R)-1-(naphthalen-1-yl)ethyl)amino)methyl)morpholin-3-one hydrochloride | m/z 411.1; 72a; ¹H NMR (400 MHz, DMSO): δ 10.21 (bs, 1H), 9.26(bs, 1H), 8.20 (d, J = 7.6 Hz, 1H), 8.00 (dd, J = 7.6 Hz, J = 1.6 Hz, 2H), 7.92 (d, J = 7.2 Hz, 1H), 7.64-7.57 (m, 3H), 7.36-7.30 (m, 1H), 7.26-7.21 (m, 1H), 7.09-7.04 (m, 1H), 5.32 (q, 1H), 4.59-4.55(d, J = 14.8 Hz, 1H), 4.48-4.44 (d, J = 14.8 Hz, 1H), 4.29-4.25 (d, J = 16.4 Hz, 1H), 3.20-3.14 (m, 4H), 2.92-2.83 (m, 2H), 1.67 (d, J = 6.4 Hz, 3H).<br>72b; ¹H NMR (400 MHz, DMSO): δ 9.81 (bs, 1H), 9.55 (bs, 1H), 8.19 (d, 1H), 8.02-7.95 (m, 3H), 7.65-7.57 (m, 3H), 7.35-7.31 (m, 1H), 7.28-7.22 (m, 1H), 7.10-7.07 (m, 1H), 5.32 (m, 1H), 4.55(d, J = 14.8 Hz, 1H), 4.48 (d, J = 14.8 Hz, 1H), 4.28-4.20 (m, 3H), 3.40-3.37 (m, 1H), 3.30-3.22 (m, 1H), 3.16-3.09 (m, 2H), 1.67 (d, J = 6.4 Hz, 3H). |
| 73 | 4-((2-((((R)-1-(Naphthalen-1-yl)ethyl)amino)methyl)-5-oxomorpholino)methyl)benzoic acid hydrochloride | m/z 419.29; ¹H NMR (400 MHz, DMSO): δ 12.9 (bs, 1H), 10.2 (bs, 1H), 9.71 (bs, 1H), 9.42 (bs, 1H), 9.34 (bs, 1H), 8.18 (t, J = 8.0 Hz, 1H), 7.99 (t, J = 8.4 Hz, 2H), 7.92-7.88 (m, 3H), 7.66-7.56 (m, 3H), 7.33 (dd, J = 6.4 Hz, 1.6 Hz, 2H), 5.32 (m, 1H), 4.53 (t, J = 4.8 Hz, 1H), 4.32-4.24 (m, 2H), 3.40-3.37 (m, 2H), 3.24-3.12 (m, 3H), 1.67 (t, J = 6.0 Hz, 3H). |

TABLE 6-continued

| Example | Structure | Mass (m/z) and ¹H NMR |
|---|---|---|
| 74 | 2-(4-((2-((((R)-1-(Naphthalen-1-yl)ethyl)amino)methyl)-5-oxomorpholino)methyl)benzamido)acetic acid hydrochloride | m/z 476.11; ¹H NMR (400 MHz, DMSO): δ 12.5 (bs, 1H), 10.0 (bs, 1H), 9.72 (bs, 1H), 9.40 (bs, 1H), 9.37 (bs, 1H), 8.26 (m, 1H), 8.19 (t, J = 8.4 Hz, 1H), 7.99 (t, J = 8.4 Hz, 2H), 7.91-7.83 (m, 3H), 7.65-7.57 (m, 3H), 7.34 (t, J = 7.2 Hz, 2H), 4.62-4.49 (m, 2H), 4.33-4.24 (m, 3H), 3.90 (d, J = 6.0 Hz, 2H), 3.22-3.14 (m, 4H), 2.28 (m, 1H), 1.66 (t, J = 6.0 Hz, 3H). |
| 75 | 4-(2,6-Difluorobenzyl)-6-((((R)-1-(naphthalen-1-yl)ethyl)amino)methyl)morpholin-3-one hydrochloride | m/z 411.29; ¹H NMR (400 MHz, DMSO): δ 10.4 (bs, 1H), 9.8 (bs, 1H), 9.6 (bs, 1H), 9.25 (bs, 1H), 8.16 (t, J = 7.6 Hz, 1H), 8.01-7.91 (m, 3H), 7.64-7.56 (m, 3H), 7.44-7.39 (m, 1H), 7.13-7.06 (m, 1H), 5.29 (m, 1H), 4.75 (d, 2H), 4.29-4.10 (m, 2H), 3.23-3.08 (m, 4H), 1.66 (t, J = 6.8 Hz, 3H). |
| 76 | 4-Cyclopentyl-6-((((R)-1-(naphthalen-1-yl)ethyl)amino)methyl)morpholin-3-one hydrochloride | m/z 353.2; ¹H NMR (400 MHz, DMSO): δ 10.15 (bs, 1H), 9.57 (bs, 1H), 8.22 (d, J = 8 Hz, 1H), 8.03-7.94 (m, 3H), 7.66-7.58 (m, 3H), 5.35 (m, 1H), 4.85 (m, 1H), 4.20-4.06 (m, 3H), 3.25-3.20 (m, 1H), 3.13-3.06 (m, 2H), 2.88 (m, 1H), 1.71 (d, J = 6.8 Hz, 3H), 1.59-1.58 (m, 3H), 1.48-1.42 (m, 5H). |

TABLE 6-continued

| Example | Structure | Mass (m/z) and $^1$H NMR |
|---|---|---|
| 77 | 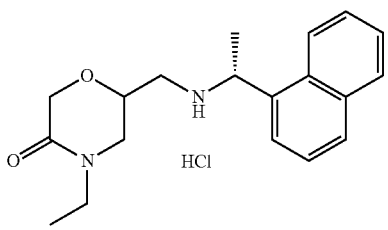 [SMILES: CCN1CC(CN[C@H](C)c2cccc3ccccc23)OCC1=O ; Cl]<br>4-Ethyl-6-((((R)-1-(naphthalen-1-yl)ethyl)amino)methyl)morpholin-3-one hydrochloride | m/z 313.46; $^1$H NMR (400 MHz, DMSO): δ 10.3 (bs, 1H), 9.65 (bs, 1H), 8.22 (d, J = 8 Hz, 1H), 8.03-7.94 (m, 3H), 7.66-7.60 (m, 3H), 5.33 (m, 1H), 4.18-4.16 (m, 1H), 4.14-4.04 (m, 2H), 3.30-3.24 (m, 2H), 3.23-3.13 (m, 3H), 3.10-3.05 (m, 1H), 1.70 (d, J = 6.8 Hz, 3H), 0.99 (t, 3H). |
| 78 | 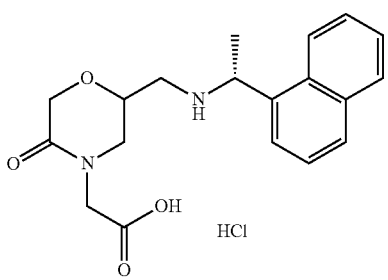 [SMILES: C[C@@H](NCC1CN(CC(=O)O)C(=O)CO1)c1cccc2ccccc12 ; Cl]<br>2-(2-((((R)-1-(Naphthalen-1-yl)ethyl)amino)methyl)-5-oxomorpholino)acetic acid hydrochloride | m/z 343.1; $^1$H NMR (400 MHz, DMSO): δ 12.9 (bs, 1H), 10.1 (bs, 1H), 9.4 (bs, 1H), 8.22-8.20 (m, 1H), 8.03-8.00 (m, 2H), 7.98-7.90 (m, 1H), 7.71-7.58 (m, 3H), 5.35 (m, 1H), 4.21-4.17 (m, 2H), 4.12-4.11 (m, 1H), 4.07-4.06 (m, 1H), 3.96-3.92 (m, 1H), 3.29-3.21 (m, 3H), 2.9 (m, 1H), 1.68 (d, J = 6.4 Hz, 3H). |
| 79a, 79b | 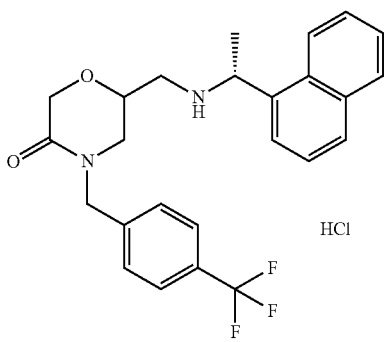 [SMILES: C[C@@H](NCC1CN(Cc2ccc(C(F)(F)F)cc2)C(=O)CO1)c1cccc2ccccc12 ; Cl]<br>6-((((R)-1-(Naphthalen-1-yl)ethyl)amino)methyl)-4-(4-(trifluoromethyl)benzyl)morpholin-3-one hydrochloride | m/z 443.29; 79a: $^1$H NMR (400 MHz, DMSO): δ 10.11 (bs, 1H), 9.26 (bs, 1H), 8.19 (d, J = 8.4 Hz, 1H), 8.01-7.96 (m, 2H), 7.90 (d, J = 7.2 Hz, 1H), 7.70 (d, J = 8 Hz, 2H), 7.64-7.56 (m, 3H), 7.44 (d, J = 8 Hz, 2H), 5.32-5.31 (m, 1H), 4.59 (d, J = 3.2 Hz, 2H), 4.33-4.20 (m, 3H), 3.17 (d, J = 6.8 Hz, 3H), 2.86-2.83 (m, 1H), 1.67 (d, J = 6.8 Hz, 3H).<br>79b: $^1$H NMR (400 MHz, DMSO): δ 9.75 (bs, 1H), 9.48 (bs, 1H), 8.21 (d, J = 8.4 Hz, 1H), 8.01-7.93 (m, 2H), 7.71 (d, J = 8 Hz, 2H), 7.63-7.57 (m, 3H), 7.45 (d, J = 8 Hz, 2H), 5.31 (d, J = 6 Hz, 1H), 4.64-4.55 (m, 2H), 4.31-4.20 (m, 3H), 3.26-3.10 (m, 2H), 2.90-2.88 (m, 2H), 1.66 (d, J = 6.8 Hz, 3H). |

TABLE 6-continued

| Example | Structure | Mass (m/z) and ¹H NMR |
|---|---|---|
| 80 | 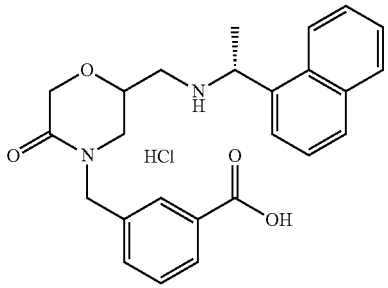 [SMILES: C[C@@H](NCC1CN(Cc2cccc(C(=O)O)c2)C(=O)CO1)c1cccc2ccccc12 ; Cl]<br>3-((2-((((R)-1-(Naphthalen-1-yl)ethyl)amino)methyl)-5-oxomorpholino)methyl)benzoic acid hydrochloride | m/z 419.1; ¹H NMR (400 MHz, DMSO): δ 13.0 (bs, 1H), 10.2 (bs, 1H), 9.5 (bs, 1H), 8.21 (t, J = 8 Hz, 1H), 8.01-7.90 (m, 3H), 7.78-7.47 (m, 2H), 5.30 (m, 1H), 4.57 (d, J = 3.6 Hz, 2H), 4.33-4.19 (m, 3H), 3.25-3.10 (m, 3H), 2.88 (m, 1H), 1.66 (d, J = 6.4 Hz, 3H). |
| 81 | 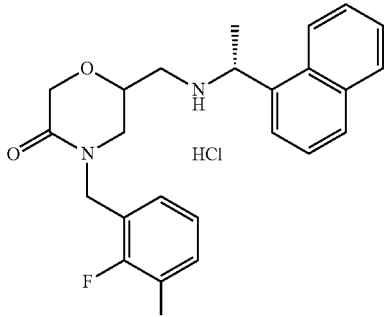<br>4-(2,3-Difluorobenzyl)-6-((((R)-1-(naphthalen-1-yl)ethyl)amino)methyl)morpholin-3-one hydrochloride | m/z 411.29; ¹H NMR (400 MHz, DMSO): δ 10.3 (bs, 1H), 9.55 (bs, 1H), 8.20 (t, J = 7.6 Hz, 1H), 8.01-7.92 (m, 3H), 7.65-7.57(m, 3H), 7.40-7.33 (m, 1H), 7.21-7.16 (m, 1H), 7.15-7.07 (m, 1H), 5.31 (m, 1H), 4.66-4.54 (m, 2H), 4.31-4.17 (m, 3H), 3.26-3.17 (m, 2H), 3.11-3.09 (m, 1H), 2.88 (m, 1H), 1.68 (d, J = 6.4 Hz, 3H). |
| 82 | 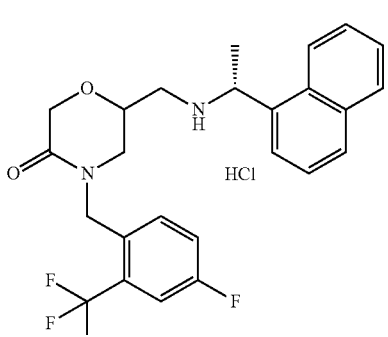<br>4-(4-Fluoro-2-(trifluoromethyl)benzyl)-6-((((R)-1-(naphthalen-1-yl)ethyl)amino)methyl)morpholin-3-one hydrochloride | m/z 461.1; ¹H NMR (400 MHz, DMSO): δ 10.3 (bs, 1H), 9.6 (bs, 1H), 8.20 (t, J = 7.6 Hz, 1H), 8.01-7.92 (m, 3H), 7.67-7.51 (m, 5H), 7.43-7.38 (m, 1H), 5.32 (m, 1H), 4.72-4.68 (m, 1H), 4.60-4.56 (m, 1H), 4.35-4.24 (m, 3H), 4.23-3.19 (m, 2H), 3.16-3.09 (m, 1H), 3.85 (m, 1H), 1.68 (d, J = 6 Hz, 3H). |

TABLE 6-continued

| Example | Structure | Mass (m/z) and $^1$H NMR |
|---|---|---|
| 83 | 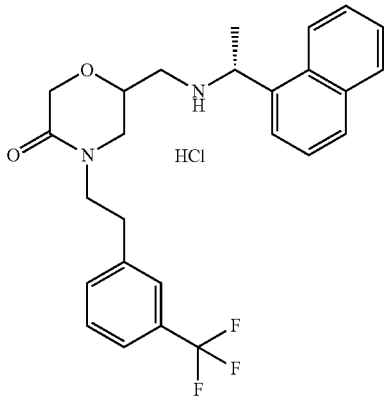 [SMILES: C[C@@H](NCC1CN(CCc2cccc(C(F)(F)F)c2)C(=O)CO1)c1cccc2ccccc12 ; Cl]<br>6-((((R)-1-(Naphthalen-1-yl)ethyl)amino)methyl)-4-(3-(trifluoromethyl)phenethyl)morpholin-3-one hydrochloride | m/z 457.04; $^1$H NMR (400 MHz, DMSO): δ 10.2 (bs, 1H), 9.55 (bs, 1H), 8.22 (d, J = 8 Hz, 1H), 8.03-7.93 (m, 3H), 7.67-7.58 (m, 3H), 7.56-7.49 (m, 4H), 5.36 (m, 1H), 4.15 (m, 1H), 4.11-4.03 (m, 2H), 7.56-7.49 (m, 1H), 3.50-3.42 (m, 1H), 3.29-3.13 (m, 3H), 2.91-2.79 (m, 3H), 1.71 (d, J = 6 Hz, 3H). |
| 84 | 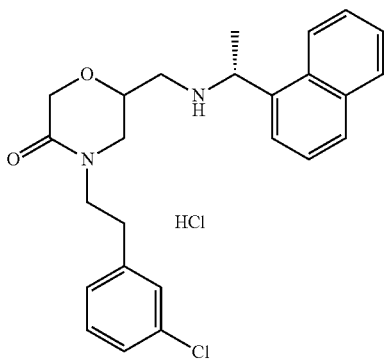 [SMILES: C[C@@H](NCC1CN(CCc2cccc(Cl)c2)C(=O)CO1)c1cccc2ccccc12 ; Cl]<br>4-(3-Chlorophenethyl)-6-((((R)-1-(naphthalen-1-yl)ethyl)amino)methyl)morpholin-3-one hydrochloride | m/z 423.16; $^1$H NMR (400 MHz, DMSO): δ 10.2 (bs, 1H), 9.2 (bs, 1H), 8.22 (d, J = 8 Hz, 1H), 8.03-7.93 (m, 3H), 7.67-7.58 (m, 3H), 7.31-7.24 (m, 3H), 7.17-7.14 (m, 1H), 5.36 (m, 1H), 4.22-4.21 (m, 1H), 4.17-4.03 (m, 2H), 3.59-3.53 (m, 1H), 3.44-3.30 (m, 1H), 3.29-3.18 (m, 3H), 2.79-2.51 (m, 2H), 1.71 (d, J = 6 Hz, 3H). |
| 85 | 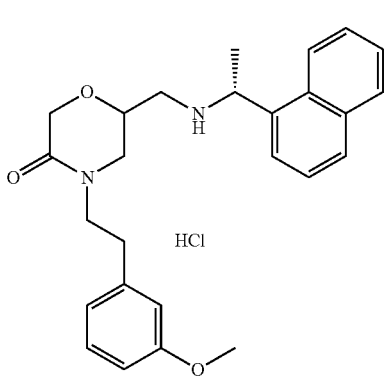 [SMILES: COc1cccc(CCN2CC(CN[C@H](C)c3cccc4ccccc34)OCC2=O)c1 ; Cl]<br>4-(3-Methoxyphenethyl)-6-((((R)-1-(naphthalen-1-yl)ethyl)amino)methyl)morpholin-3-one hydrochloride | m/z 419.23; $^1$H NMR (400 MHz, DMSO): δ 10.8 (bs, 1H), 10.55 (bs, 1H), 8.22 (d, J = 8 Hz, 1H), 7.99 (t, J = 8.4 Hz, 3H), 7.70-7.58 (m, 3H), 7.19-7.14 (m, 1H), 6.76-6.75 (m, 3H), 5.36 (m, 1H), 4.18-4.05 (m, 3H), 3.71 (s, 3H), 3.57-3.52 (m, 1H), 3.43 (s, 1H), 3.29-3.12 (m, 3H), 2.90-3.10 (m, 1H), 2.75-2.67 (m, 2H), 1.70 (d, J = 6 Hz, 3H). |

TABLE 6-continued

| Example | Structure | Mass (m/z) and ¹H NMR |
|---|---|---|
| 86 | 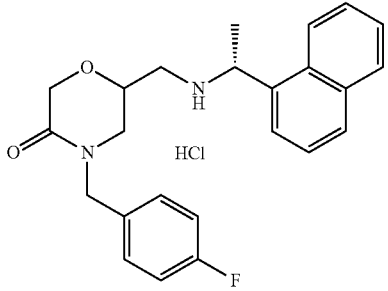<br>4-(4-Fluorobenzyl)-6-((((R)-1-(naphthalen-1-yl)ethyl)amino)methyl)morpholin-3-one hydrochloride | m/z 377.1; ¹H NMR (400 MHz, DMSO): δ 11.9 (bs, 1H), 9.39 (bs, 1H), 7.70-7.65 (m, 2H), 7.54 (d, J = 6.8 Hz, 1H), 7.30-7.22(m, 3H), 7.08-7.06 (m, 1H), 4.33-4.32 (m, 2H), 4.07-4.05 (m, 1H), 3.97-3.94 (m, 1H), 3.83 (s, 3H), 3.30-3.24 (m, 3H), 3.05-3.03 (m, 1H), 2.86-2.76 (m, 2H), 1.57 (d, J = 6.8 Hz, 3H). |
| 87 | 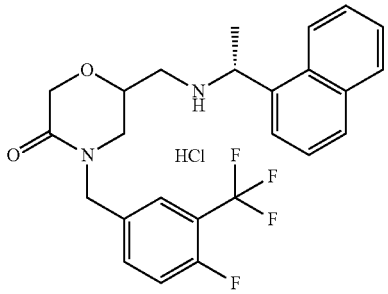 [SMILES: C[C@@H](NCC1CN(Cc2ccc(F)c(C(F)(F)F)c2)C(=O)CO1)c1cccc2ccccc12 ; Cl]<br>4-(4-Fluoro-3-(trifluoromethyl)benzyl)-6-((((R)-1-(naphthalen-1-yl)ethyl)amino)methyl)morpholin-3-one hydrochloride | m/z 461.1; ¹H NMR (400 MHz, DMSO): δ 10.1(bs, 1H), 9.41 (bs, 1H), 8.20 (t, J = 7.2 Hz, 1H), 7.99 (t, J = 8.4 Hz, 2H), 7.93-7.88 (m, 1H), 7.66-7.59 (m, 4H), 7.53-7.47 (m, 2H), 5.6 (m, 1H), 4.61-4.52 (m, 2H), 4.32-4.19 (m, 3H), 3.44-3.37 (m, 1H), 3.27-3.12 (m, 3H), 1.67 (d, J = 6.0 Hz, 3H). |
| 88 | 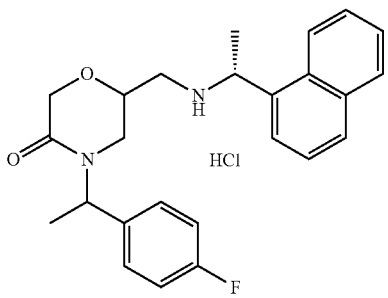 [SMILES: CC(c1ccc(F)cc1)N1CC(CN[C@H](C)c2cccc3ccccc23)OCC1=O ; Cl]<br>4-(1-(4-Fluorophenyl)ethyl)-6-((((R)-1-(naphthalen-1-yl)ethyl)amino)methyl)morpholin-3-one hydrochloride | m/z 407.1; ¹H NMR (400 MHz, DMSO): δ 10.3(bs, 1H), 9.25 (bs, 1H), 8.17 (t, J = 8 Hz, 1H), 8.01-7.93 (m, 3H), 7.63-7.56 (m, 3H), 7.31-7.25 (m, 2H), 7.20-7.11 (m, 2H), 5.77 (q, J = 6.8 Hz, 1H), 5.28 (m, 1H), 4.27-4.17 (m, 3H), 3.28-3.25 (m, 1H), 3.16-3.09 (m, 2H), 2.82-2.68 (m, 1H), 1.67 (d, J = 6.8 Hz, 3H), 1.43-1.37 (m, 3H). |

TABLE 6-continued

| Example | Structure | Mass (m/z) and ¹H NMR |
|---|---|---|
| 89 | 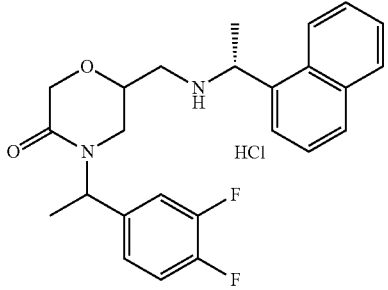 [SMILES: CC(c1ccc(F)c(F)c1)N1CC(CN[C@H](C)c2cccc3ccccc23)OCC1=O ; Cl]<br>4-(1-(3,4-Difluorophenyl)ethyl)-6-((((R)-1-(naphthalen-1-yl)ethyl)amino)methyl)morpholin-3-one hydrochloride | m/z 425.23; ¹H NMR (400 MHz, DMSO): δ 10.1(bs, 1H), 9.5 (bs, 1H), 8.21-8.13 (m, 1H), 8.01-7.91 (m, 3H), 7.65-7.57 (m, 3H), 7.43-7.29 (m, 2H), 7.12-7.10 (m, 1H), 7.74 (q, J = 2.4 Hz, 1H), 5.30 (m, 1H), 4.28-4.19 (m, 3H), 3.19-3.08 (m, 2H), 2.95-2.89 (m, 1H), 2.73-2.50 (m, 1H), 1.67(d, J = 6.8 Hz, 3H), 1.4(d, 3H). |
| 90 | 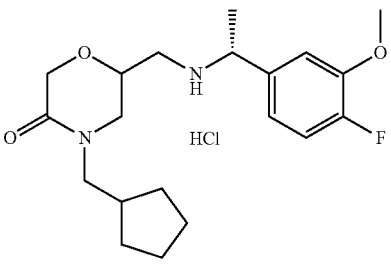 [SMILES: COc1cc([C@@H](C)NCC2CN(CC3CCCC3)C(=O)CO2)ccc1F ; Cl]<br>4-(Cyclopentylmethyl)-6-((((R)-1-(4-fluoro-3-methoxyphenyl)ethyl)amino)methyl)morpholin-3-one hydrochloride | m/z 365.34; ¹H NMR (400 MHz, DMSO): δ 10.5(bs, 1H), 9.45 (bs, 1H), 7.55 (dd, J = 8 & 2 Hz, 1H), 7.30-7.24 (m, 1H), 7.11-7.09 (m, 1H), 4.37 (m, 1H), 4.21-4.05 (m, 2H), 3.87 (s, 3H), 3.26-3.22 (m, 2H), 3.16-3.09 (m, 1H), 2.95 (m, 1H), 2.75 (m, 1H), 2.12 (m, 1H), 1.60 (d, J = 6.8 Hz, 3H), 1.47 (m, 2H), 1.23 (m, 2H), 0.84-0.85 (m, 1H). |
| 91 | 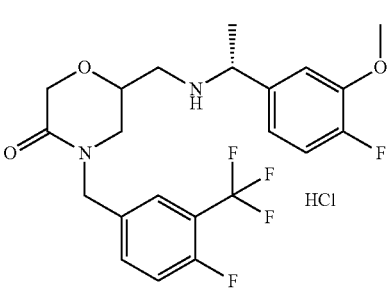 [SMILES: COc1cc([C@@H](C)NCC2CN(Cc3ccc(F)c(C(F)(F)F)c3)C(=O)CO2)ccc1F ; Cl]<br>4-(4-Fluoro-3-(trifluoromethyl)benzyl)-6-((((R)-1-(4-fluoro-3-methoxyphenyl)ethyl)amino)methyl)morpholin-3-one hydrochloride | m/z 459.0; ¹H NMR (400 MHz, DMSO): δ 9.9(bs, 1H), 9.35 (bs, 1H), 7.64-7.61 (m, 2H), 7.53-7.44 (m, 2H), 7.27-7.22 (m, 1H), 7.09-7.07 (m, 1H), 4.62-4.52 (m, 2H), 4.34-4.15 (m, 2H), 3.85 (s, 3H), 3.27-3.17 (m, 2H), 2.96 (m, 2H), 2.67-2.66 (m, 1H), 2.54 (m, 1H), 1.57 (d, J = 6.8 Hz, 3H). |

TABLE 6-continued

| Example | Structure | Mass (m/z) and ¹H NMR |
|---|---|---|
| 92a, 92b | 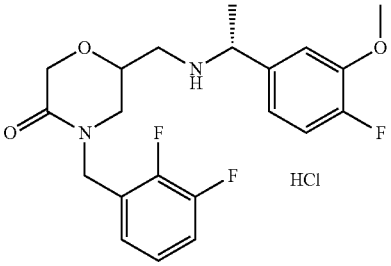 [SMILES: COc1cc([C@@H](C)NCC2CN(Cc3cccc(F)c3F)C(=O)CO2)ccc1F ; Cl]<br>4-(2,3-Difluorobenzyl)-6-((((R)-1-(4-fluoro-3-methoxyphenyl)ethyl)amino)methyl)morpholin-3-one hydrochloride | m/z 409.1; 92a: ¹H NMR (400 MHz, DMSO): δ 9.89 (bs, 1H), 9.18 (bs, 1H), 7.46-7.41 (m, 1H), 7.39-7.34 (m, 1H), 7.28-7.17 (m, 2H), 7.18 (m, 2H), 4.68 (d, J = 15.2 Hz, 1H), 4.53 (d, J = 14.8 Hz, 1H), 4.35 (s, 1H), 4.28-4.18 (m, 2H), 3.84 (s, 3H), 3.40-3.37 (m, 1H), 3.21 (d, J = 6.8 Hz, 1H), 3.00 (m, 1H), 2.68-2.66 (m, 1H), 1.58 (d, J = 6.8 Hz, 3H).<br>92b: ¹H NMR (400 MHz, DMSO): δ 9.65 (bs, 1H), 9.4 (bs, 1H), 7.51 (dd, J = 8 & 1.6 Hz, 1H), 7.45-7.34 (m, 1H), 7.27-7.17 (m, 2H), 7.13-7.06 (m, 2H), 4.66 (d, J = 15.2 Hz, 1H), 4.55 (d, J = 14.8 Hz, 1H), 4.34-4.33 (m, 1H), 4.26-4.24 (m, 1H), 4.19-4.15 (m, 2H), 3.8 (m, 3H), 3.30-3.25 (m, 1H), 3.18-3.15 (m, 1H), 2.95-2.88 (m, 2H), 1.57 (d, J = 6.8 Hz, 3H). |
| 93a, 93b | 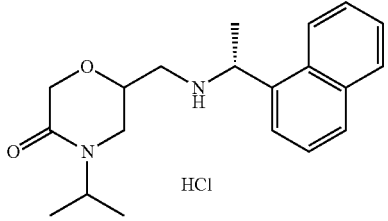 [SMILES: CC(C)N1CC(CN[C@H](C)c2cccc3ccccc23)OCC1=O ; Cl]<br>4-Isopropyl-6-((((R)-1-(naphthalen-1-yl)ethyl)amino)methyl)morpholin-3-one hydrochloride | m/z 327.1; 93a: ¹H NMR (400 MHz, DMSO): δ 10.17 (bs, 1H), 9.26 (bs, 1H), 8.21 (d, J = 8.4 Hz, 1H), 7.99 (t, J = 8.8 Hz, 2H), 7.93 (d, J = 7.2 Hz, 1H), 7.65-7.57 (m, 3H), 5.34 (m, 1H), 4.62-4.55 (m, 1H), 4.18-4.00 (m, 3H), 3.23-3.19 (m, 2H), 3.02-2.97 (m, 1H), 2.86-2.84 (m, 1H), 1.69 (d, J = 6.8 Hz, 3H), 0.98 (t, J = 6.8 Hz, 6H).<br>93b: ¹H NMR (400 MHz, DMSO): δ 9.70 (bs, 1H), 9.48 (bs, 1H), 8.24 (d, J = 8.4 Hz, 1H), 8.03-7.95 (m, 3H), 7.70-7.61 (m, 3H), 5.37-5.32 (m, 1H), 4.64-4.57 (m, 1H), 4.18-3.99 (m, 3H), 3.30-3.25 (m, 2H), 3.16-3.00 (m, 2H), 1.69 (d, J = 6.4 Hz, 3H), 1.01 (t, J = 6.8 Hz, 6H). |
| 94 | 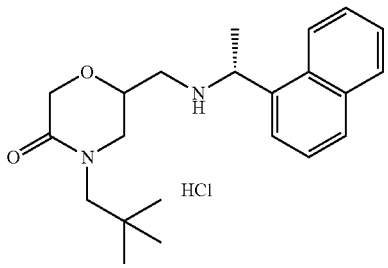 [SMILES: C[C@@H](NCC1CN(CC(C)(C)C)C(=O)CO1)c1cccc2ccccc12 ; Cl]<br>6-((((R)-1-(Naphthalen-1-yl)ethyl)amino)methyl)-4-neopentylmorpholin-3-one hydrochloride | m/z 355.2; ¹H NMR (400 MHz, DMSO): δ 9.73 (bs, 1H), 9.25 (bs, 1H), 8.23 (d, J = 8.4 Hz, 1H), 8.03-7.93 (m, 3H), 7.66-7.58 (m, 3H), 5.35 (m, 1H), 4.20-4.09 (m, 3H), 3.56-3.25 (m, 2H), 3.18-3.11 (m, 2H), 2.95-2.83 (m, 2H), 1.69 (t, J = 6.0 Hz, 3H), 0.86 (d, J = 8.0 Hz, 9H). |
| 95 | 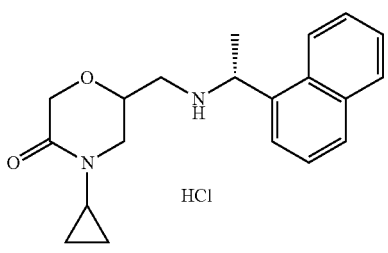 [SMILES: C[C@@H](NCC1CN(C2CC2)C(=O)CO1)c1cccc2ccccc12 ; Cl]<br>4-Cyclopropyl-6-((((R)-1-(naphthalen-1-yl)ethyl)amino)methyl)morpholin-3-one hydrochloride | m/z 325.43; ¹H NMR (400 MHz, DMSO): δ 9.59 (bs, 1H), 9.26 (bs, 1H), 8.24-8.21(m, 1H), 8.01 (t, J = 8.0 Hz, 2H), 7.88 (t, J = 6.0 Hz, 1H), 7.67-7.58 (m, 3H), 5.76-5.68 (m, 1H), 5.35 (m, 1H), 5.18-5.10 (m, 2H), 4.25-4.11 (m, 3H), 3.97-3.87 (m, 3H), 3.22-3.15 (m, 3H), 1.69-1.66 (m, 3H). |

TABLE 6-continued

| Example | Structure | Mass (m/z) and ¹H NMR |
|---|---|---|
| 96 | 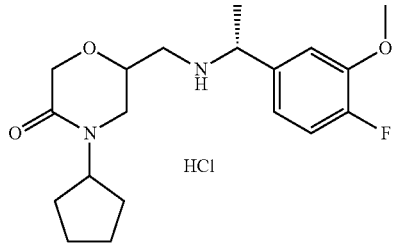 [SMILES: COc1cc([C@@H](C)NCC2CN(C3CCCC3)C(=O)CO2)ccc1F ; Cl]<br>4-Cyclopentyl-6-((((R)-1-(4-fluoro-3-methoxyphenyl)ethyl)amino)methyl)morpholin-3-one hydrochloride | m/z 350.93; ¹H NMR (400 MHz, DMSO): δ 10.05 (bs, 1H), 9.35 (bs, 1H), 7.57-7.51 (m, 1H), 7.30-7.27 (m, 1H), 7.12-7.10 (m, 1H), 4.77-4.73 (m, 1H), 4.37 (m, 1H), 4.20-4.04 (m, 3H), 3.87 (d, J = 4.4 Hz, 3H), 3.46-3.07 (m, 4H), 2.92-2.87 (m, 1H), 2.70-2.67 (m, 1H), 1.70-1.40 (m, 9H). |
| 97a, 97b | 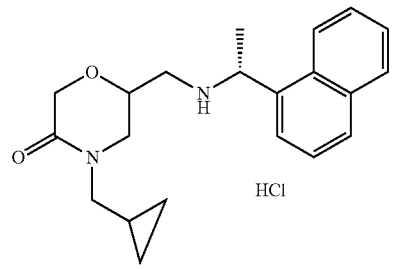 [SMILES: C[C@@H](NCC1CN(CC2CC2)C(=O)CO1)c1cccc2ccccc12 ; Cl]<br>4-(Cyclopropylmethyl)-6-((((R)-1-(naphthalen-1-yl)ethyl)amino)methyl)morpholin-3-one hydrochloride | m/z 339.2; 97a: ¹H NMR (400 MHz, DMSO): δ 10.05 (bs, 1H), 9.25 (bs, 1H), 8.22 (d, J = 8 Hz, 1H), 8.03-7.90 (m, 2H), 7.91 (d, J = 7.2 Hz, 1H), 7.67-7.58 (m, 3H), 5.38 (m, 1H), 4.24-4.08 (m, 3H), 3.90-3.22 (m, 4H), 3.023-2.87 (m, 2H), 1.70 (d, J = 6.8 Hz, 3H), 0.90-0.86 (m, 1H), 0.42-0.40 (m, 2H), 0.20-0.14 (m, 2H).<br>97b: ¹H NMR (400 MHz, DMSO): δ 9.79 (bs, 1H), 9.45 (bs, 1H), 8.22 (d, J = 8.0 Hz, 1H), 8.01 (t, J = 8.8 Hz, 2H), 7.95 (d, J = 7.2 Hz, 1H), 7.67-7.58 (m, 3H), 5.36 (m, 1H), 4.26-4.09 (m, 3H), 3.39-3.14 (m, 4H), 3.04-2.99 (m, 1H), 1.69 (d, J = 6.8 Hz, 3H), 0.93-0.89 (m, 1H), 0.44-0.42 (m, 2H), 0.20-0.17 (m, 2H). |
| 98a, 98b | 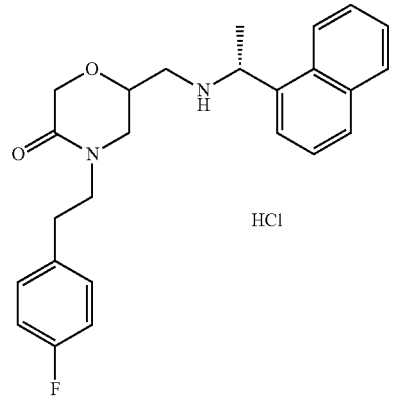 [SMILES: C[C@@H](NCC1CN(CCc2ccc(F)cc2)C(=O)CO1)c1cccc2ccccc12 ; Cl]<br>4-(4-Fluorophenethyl)-6-(((((R)-1-(naphthalen-1-yl)ethyl)amino)methyl)morpholin-3-one hydrochloride | m/z 407.35; 98a: ¹H NMR (400 MHz, DMSO): δ 10.19 (bs, 1H), 9.30 (bs, 1H), 8.23 (d, J = 8.4 Hz, 1H), 8.01 (t, J = 9.6 Hz, 2H), 7.94 (d, J = 6.8 Hz, 1H), 7.67-7.58 (m, 3H), 7.23-7.20 (m, 2H), 7.10-7.05 (m, 2H), 5.36 (m, 1H), 4.21-4.03 (m, 3H), 3.55-3.52 (m, 1H), 3.42-3.19 (m, 4H), 2.76-2.70 (m, 3H), 1.70 (d, J = 6.8 Hz, 3H).<br>98b: ¹H NMR (400 MHz, DMSO): δ 9.78 (bs, 1H), 9.55 (bs, 1H), 8.23 (d, J = 8.4 Hz, 1H), 8.03-7.97 (m, 3H), 7.67-7.58 (m, 3H), 7.24-7.21 (m, 2H), 7.10-7.06 (m, 2H), 5.35 (m, 1H), 4.20-4.04 (m, 3H), 3.54-3.26 (m, 2H), 3.22-3.05 (m, 3H), 2.92-2.87 (m, 1H), 2.77-2.72 (m, 2H), 1.69 (d, J = 6.8 Hz, 3H). |

TABLE 6-continued

| Example | Structure | Mass (m/z) and ¹H NMR |
|---|---|---|
| 99 | 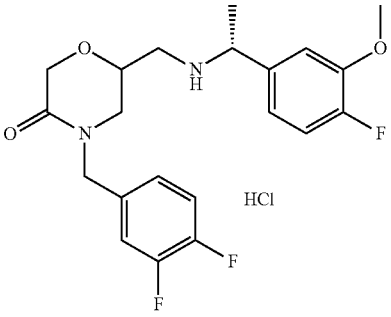 [SMILES: COc1cc([C@@H](C)NCC2CN(Cc3ccc(F)c(F)c3)C(=O)CO2)ccc1F ; Cl]<br>4-(3,4-Difluorobenzyl)-6-((((R)-1-(4-fluoro-3-methoxyphenyl)ethyl)amino)methyl)morpholin-3-one hydrochloride | m/z 409.1; ¹H NMR (400 MHz, DMSO): δ 9.68 (bs, 1H), 9.22 (bs, 1H), 7.46-7.38 (m, 2H), 7.33-7.23 (m, 2H), 7.12-7.06 (m, 2H), 4.60-4.10 (m, 5H), 3.85 (s, 3H), 3.22-3.16 (m, 2H), 2.98-2.84 (m, 2H), 2.67-2.60 (m, 1H), 1.57-1.56 (m, 3H). |
| 100 | 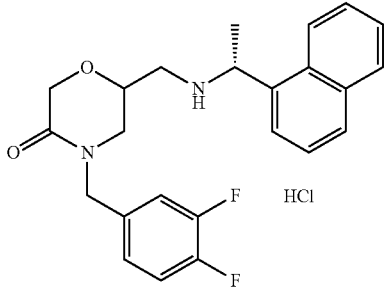 [SMILES: C[C@@H](NCC1CN(Cc2ccc(F)c(F)c2)C(=O)CO1)c1cccc2ccccc12 ; Cl]<br>4-(3,4-Difluorobenzyl)-6-((((R)-1-(naphthalen-1-yl)ethyl)amino)methyl)morpholin-3-one hydrochloride | m/z 411.29; ¹H NMR (400 MHz, DMSO): δ 10.28 (bs, 1H), 9.25 (bs, 1H), 8.20-8.18 (m, 1H), 8.01-7.91 (m, 3H), 7.65-7.57 (m, 3H), 7.44-7.36 (m, 1H), 7.32-7.27 (m, 1H), 7.09-7.08 (m, 1H), 5.32 (m, 1H), 4.48-4.42 (m, 2H), 4.30-4.18 (m, 2H), 3.56 (s, 2H), 3.34-3.08 (m, 3H), 1.69-1.66 (m, 3H). |
| 101a, 101b | 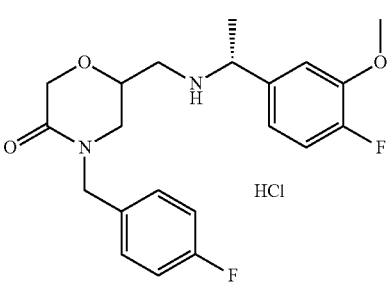 [SMILES: COc1cc([C@@H](C)NCC2CN(Cc3ccc(F)cc3)C(=O)CO2)ccc1F ; Cl]<br>6-((((R)-1-(4-Fluoro-3-methoxyphenyl)ethyl)amino)methyl)-4-(4-fluorobenzyl)morpholin-3-one hydrochloride | m/z 391.35; 101a: ¹H NMR (400 MHz, DMSO): δ 9.25-40 (m, 2H), 7.45-7.43 (m, 1H), 7.30-7.15 (m, 5H), 7.06-7.04 (m, 1H), 4.49 (s, 2H), 4.34-4.00 (m, 4H), 3.85 (s, 3H), 3.23-3.06 (m, 2H), 2.94-2.73 (m, 2H), 1.55 (d, J = 6.8 Hz, 3H).<br>101b: ¹H NMR (400 MHz, DMSO): δ 9.70 (bs, 1H), 9.14 (bs, 1H), 7.43-7.41 (m, 1H), 7.30-7.23 (m, 3H), 7.19-7.15 (m, 2H), 7.08-7.05 (m, 1H), 4.49 (ABq, J = 14.8 Hz, 2H), 4.35-4.18 (m, 4H), 3.85 (s, 3H), 3.15-3.10 (m, 2H), 3.01-2.96 (m, 1H), 2.78-2.65 (m, 1H), 1.56 (d, J = 6.8 Hz, 3H). |

Example-102a, 102b

2-(4-(2-(2-(((R)-1-(Naphthalen-1-yl)ethyl)amino)ethyl)morpholino)phenoxy)acetic acid hydrochloride

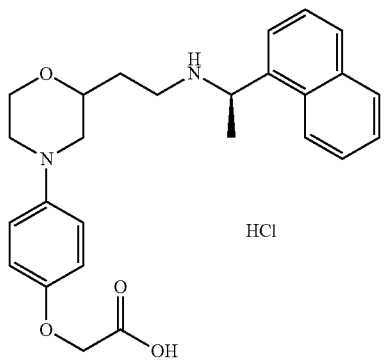 [SMILES: C[C@@H](NCCC1CN(c2ccc(OCC(=O)O)cc2)CCO1)c1cccc2ccccc12 ; Cl]

Step-1: Methyl 2-(4-(2-(2-(((R)-1-(naphthalen-1-yl)ethyl)amino)ethyl)morpholino) phenoxy)acetate Intermediate-11 (300 mg, 1.055 mmol) was dissolved in 10 ml dry toluene under $N_2$ atmosphere in sealed tube, methyl 2-(4-bromophenoxy)acetate (388 mg, 1.582 mmol) and cesium carbonate (516 mg, 1.582 mmol) were added and stirred for 10 min under $N_2$ atmosphere at RT. Then tris(dibenzylideneacetone)dipalladium(0) (48.3 mg, 0.053 mmol) and bis(tri-t-butylphosphine)palladium(0) (53.9 mg, 0.105 mmol) were added to the reaction mixture, stirred for another 20 minutes under nitrogen atmosphere. The reaction mixture was heated to 115° C. and further maintained for 15 h. After completion of reaction, solvent was evaporated, and the crude compound was purified by column chromatography by using 20% ethyl acetate in hexane to get pure compound as oily mass. Further, diastereomers were separated using CHIRAL PAK ID (250 mm×4.6, 5µ; A=n-hexane:IPA (90/10% v/v, 0.1% DEA), B=IPA, A:B=70/30% v/v) offered title compound of isomer-a, $t_R$=9.29 (110 mg) m/z 449.10 and isomer-b, $t_R$=11.29 (100 mg) m/z 449.10.

Step-2: 2-(4-(2-(2-(((R)-1-(Naphthalen-1-yl)ethyl)amino)ethyl)morpholino)phenoxy) acetic acid To a stirred solution of above Step-1 isomer-a (95 mg, 0.212 mmol) in methanol (2 ml), THF (2 ml) and water (2 ml) in single neck round bottom flask LiOH (25.4 mg, 1.059 mmol) was added and reaction mixture was heated to 65° C. and further maintained for 2 h. Reaction mixture was concentrated and neutralized with 6N HCl, the solid precipitated out was filtered, washed with DM water and n-pentane, dried to get pure product. Further, hydrochloride salt was prepared from this free base by following the similar hydrochloride salt procedure as described in Example-1 (Example-102a 70 mg). Similarly, Example-102b was also prepared from Step-1 of isomer-b (Example-102b 55 mg).

Example-102a: $^1$H NMR (400 MHz, DMSO): δ 9.73 (bs, 1H), 9.15 (bs, 1H), 8.20 (d, J=8.4 Hz, 1H), 8.00 (t, J=6.8 Hz, 2H), 7.75 (d, J=7.6 Hz, 1H), 7.67-7.58 (m, 3H), 6.98 (d, J=8.8 Hz, 2H), 6.84 (d, J=9.2 Hz, 2H), 5.30-5.35 (m, 1H), 4.58 (s, 2H), 3.63-3.59 (m, 2H), 3.39-3.29 (m, 3H), 3.15-3.12 (m, 1H), 2.98-2.96 (m, 1H), 2.69-2.67 (m, 1H), 2.50-2.33 (m, 1H), 1.86-1.80 (m, 2H), 1.62 (d, J=6.8 Hz, 3H); m/z 435.2

Example-102b: $^1$H NMR (400 MHz, DMSO): δ 9.75 (bs, 1H), 9.21 (bs, 1H), 8.18 (d, J=8.4 Hz, 1H), 7.99 (t, J=6.8 Hz, 2H), 7.73 (d, J=6.8 Hz, 1H), 7.67-7.57 (m, 3H), 6.98 (d, J=9.2 Hz, 2H), 6.83 (d, J=9.2 Hz, 2H), 5.27-5.30 (m, 1H), 4.58 (s, 2H), 3.83-3.86 (m, 1H), 3.64-3.56 (m, 2H), 3.37-3.28 (m, 2H), 3.15-3.08 (m, 1H), 2.94-2.91 (m, 1H), 2.73-2.68 (m, 2H), 1.84-1.80 (m, 2H), 1.64 (d, J=6.8 Hz, 3H); m/z 435.2.

The below list of examples 103 to 114 given in Table-7 were prepared by following the similar procedure as described in Step-1 then Step-2 of Example-102a, 102b by taking Intermediate-11 and appropriately substituted halobenzene. Further, hydrochloride salts of these compounds were prepared by following the similar hydrochloride salt procedure as described in Example-1.

TABLE 7

| Example | Structure | Mass (m/z); and $^1$H NMR |
|---|---|---|
| 103a, 103b | 2-Methyl-5-(2-(2-(((R)-1-(naphthalen-1-yl)ethyl)amino)ethyl)morpholino)benzoic acid | m/z 419.1; 103a (400 MHz, DMSO): δ 8.20 (d, J = 8.4 Hz, 1H), 8.00 (t, J = 7.2 hz, 2H), 7.76 (d, J = 7.2 Hz, 1H), 7.67-7.58 (m, 3H), 7.29 (d, J = 1.8 Hz, 1H), 7.15 (d, J = 8.4 Hz, 1H), 7.04 (dd, J = 2.4, 8.4 Hz, 1H), 5.30 (m, 1H), 3.60-3.35 (m, 5H), 3.13-3.14 (m, 1H), 2.93-2.92 (m, 1H), 2.62-2.59 (m, 1H), 2.36-2.32 (m, 4H), 1.90-1.79 (m, 2H), 1.64 (d, J = 6.8 Hz, 3H). 103b; $^1$H NMR (400 MHz, DMSO): δ 8.25 (d, J = 8.4 Hz, 1H), 8.01 (t, J = 7.6 Hz, 2H), 7.84 (d, J = 7.2 Hz, 1H), 7.67-7.59 (m, 3H), 7.34 (d, J = 2.4 Hz, 1H), 7.16 (d, J = 8.8 Hz, 1H), 7.07 (dd, J = 2.8, 8.4 Hz, 1H), 5.34-5.32 (m, 1H), 3.86 (d, J = 12.0 Hz, 1H), 3.56-3.3.34 (m, 5H), 3.16-3.13 (m, 1H), 3.00-2.98 (m, 1H), 2.66-2.35 (m, 4H), 1.91-1.84 (m, 2H), 1.67 (d, J = 6.4 Hz, 3H). |

TABLE 7-continued

| Example | Structure | Mass (m/z); and ¹H NMR |
|---|---|---|
| 104 | 2-Methyl-4-(2-(2-(((R)-1-(naphthalen-1-yl)ethyl)amino)ethyl) morpholino) benzoic acid | m/z 419.0104a:; ¹H NMR (400 MHz, DMSO): δ 8.24 (d, J = 8.0 Hz, 1H), 8.01 (t, J = 7.6 Hz, 2H), 7.76 (d, J = 7.2 Hz, 1H), 7.81-7.74 (m, 2H), 7.67-7.59 (m, 3H), 6.79-6.77 (m, 2H), 5.32 (m, 1H), 4.22-4.11 (m, 1H), 3.15 (m, 3H), 3.00-2.96 (m, 1H), 2.74-2.60 (m, 2H), 2.50-2.32 (m, 6H), 2.04-1.75 (m, 2H), 1.66 (d, J = 6.4 Hz, 3H). 104b; ¹H NMR (400 MHz, DMSO): δ 8.20 (d, J = 8.4 Hz, 1H), 8.00 (t, J = 7.6 Hz, 2H), 7.75 (t, J = 6.8 Hz, 2H), 7.67-7.58 (m, 3H), 6.77-6.75 (m, 2H), 5.33-5.29 (m, 1H), 3.68-3.47 (m, 4H), 3.17-3.13 (m, 1H), 2.96-2.90 (m, 1H), 2.73-2.67 (m, 1H), 2.50-2.46 (m, 5H), 1.90-1.76 (m, 2H), 1.65 (d, J = 6.8 Hz, 3H). |
| 105 | (1R)-1-(Naphthalen-1-yl)-N-(2-(4-(4-(trifluoromethyl) phenyl)morpholin-2-yl)ethyl)ethanamine | ¹H NMR (400 MHz, DMSO): δ 8.25 (d, J = 8.4 Hz, 1H), 8.01 (t, J = 8.8 Hz, 2H), 7.86 (d, J = 6.4 Hz, 1H), 7.67-7.59 (m, 3H), 7.51 (d, J = 8.8 Hz, 2H), 7.06 (d, J = 8.8 Hz, 2H), 5.35-5.34 (m, 1H), 3.89-3.86 (m, 1H), 3.70 (d, J = 12.4 Hz, 1H), 3.63-3.46 (m, 3H), 3.16-3.15 (m, 2H), 3.11-2.90 (m, 1H), 2.75-2.51 (m, 1H), 2.51-2.43 (m, 1H), 1.92-1.83 (m, 2H), 1.67 (d, J = 6.8 Hz, 3H). |
| 106a, 106b | 2-(2-Methyl-4-(2-(2-(((R)-1-(naphthalen-1-yl)ethyl)amino) ethyl)morpholino)phenoxy) acetic acid hydrochloride | m/z 449.10; 106a: ¹H NMR (400 MHz, DMSO): δ 9.67 (bs, 1H), 9.10 (bs, 1H), 8.27 (d, J = 8.4 Hz, 1H), 8.01 (t, J = 9.2 Hz, 2H), 7.92 (d, J = 7.2 Hz, 1H), 7.67-7.59 (m, 3H), 7.01-6.91 (m, 2H), 6.77 (d, J = 8.0 Hz, 1H), 5.34-5.32 (m, 1H), 4.64 (s, 2H), 3.89-2.54 (m, 9H), 2.17 (s, 3H), 1.91-1.85 (m, 2H), 1.67 (d, J = 6.4 Hz, 3H). 106b: ¹H NMR (400 MHz, DMSO): δ 9.63 (bs, 1H), 9.12 (bs, 1H), 8.26 (d, J = 8.4 Hz, 1H), 8.01 (t, J = 9.2 Hz, 2H), 7.92 (d, J = 6.8 Hz, 1H), 7.67-7.59 (m, 3H), 6.99-6.87 (m, 2H), 6.76 (d, J = 8.0 Hz, 1H), 5.35-5.33 (m, 1H), 4.63 (s, 2H), 3.87 (d, J = 10.4 Hz, 1H), 3.70-3.16 (m, 4H), 2.93-2.74 (m, 3H), 2.17 (s, 3H), 1.91-1.83 (m, 2H), 1.67 (d, J = 6.4 Hz, 3H). |

TABLE 7-continued

| Example | Structure | Mass (m/z); and $^1$H NMR |
|---|---|---|
| 107a, 107b | 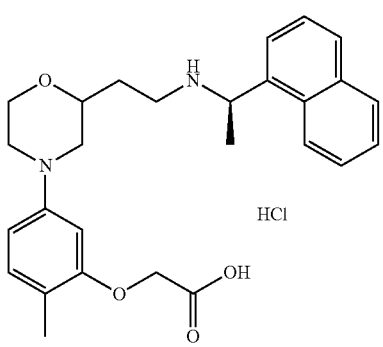 [SMILES: Cc1ccc(N2CCOC(CCN[C@H](C)c3cccc4ccccc34)C2)cc1OCC(=O)O ; Cl]<br>2-(2-Methyl-5-(2-(2-(((R)-1-(naphthalen-1-yl)ethyl)amino)ethyl)morpholino)phenoxy)acetic acid hydrochloride | m/z 449.04; 107a: $^1$H NMR (400 MHz, DMSO): δ 9.63 (bs, 1H), 9.14 (bs, 1H), 8.27 (d, J = 8.4 Hz, 1H), 8.01 (t, J = 9.6 Hz, 2H), 7.95 (d, J = 6.8 Hz, 1H), 7.67-7.59 (m, 3H), 7.00 (d, J = 8.4 Hz, 1H), 6.53-6.44 (m, 2H), 5.34-5.31 (m, 1H), 4.68 (s, 2H), 3.86 (d, J = 11.2 Hz, 1H), 3.63-3.35 (m, 4H), 3.16-2.32 (m, 4H), 2.09 (s, 3H), 1.93-1.83 (m, 2H), 1.68 (d, J = 6.4 Hz, 3H).<br>107b: $^1$H NMR (400 MHz, DMSO): δ 9.55 (bs, 1H), 9.14 (bs, 1H), 8.27 (d, J = 8.8 Hz, 1H), 8.01 (t, J = 8.4 Hz, 2H), 7.91 (d, J = 6.8 Hz, 1H), 7.67-7.59 (m, 3H), 6.98 (d, J = 8.4 Hz, 1H), 6.48-6.44 (m, 2H), 5.36-5.34 (m, 1H), 4.67 (s, 2H), 3.85 (d, J = 11.2 Hz, 1H), 3.60-3.35 (m, 4H), 3.16-2.32 (m, 4H), 2.08 (s, 3H), 1.91-1.82 (m, 2H), 1.68 (d, J = 6.4 Hz, 3H). |
| 108a, 108b | 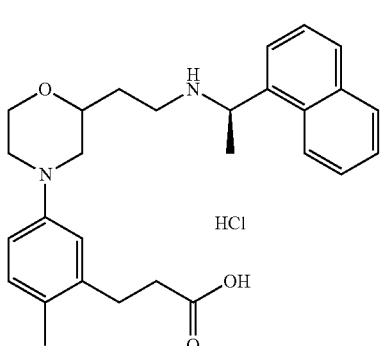<br>3-(2-Methyl-5-(2-(2-(((R)-1-(naphthalen-1-yl)ethyl)amino)ethyl)morpholino)phenyl)propanoic acid hydrochloride | m/z 447.3; 108a: $^1$H NMR (400 MHz, DMSO): δ 9.85 (bs, 1H), 9.12 (bs, 1H), 8.27 (d, J = 8.4 Hz, 1H), 8.03-7.96 (m, 3H), 7.67-7.59 (m, 3H), 7.04 (d, J = 8.4 Hz, 1H), 6.92-6.85 (m, 2H), 5.34-5.32 (m, 1H), 3.87 (d, J = 10.0 Hz, 1H), 3.63-3.13 (m, 5H), 2.97-2.77 (m, 2H), 2.75-2.67 (m, 2H), 2.55-2.44 (m, 2H), 2.18 (s, 2H), 1.96-1.84 (m, 2H), 1.68 (d, J = 6.8 Hz, 3H).<br>108b: $^1$H NMR (400 MHz, DMSO): δ 9.82 (bs, 1H), 9.25 (bs, 1H), 8.26 (d, J = 8.4 Hz, 1H), 8.03-7.97 (m, 3H), 7.67-7.58 (m, 3H), 7.05 (d, J = 8.4 Hz, 1H), 6.93-6.86 (m, 2H), 5.36-5.31 (m, 1H), 3.88-3.35 (m, 3H), 3.15-2.73 (m, 4H), 2.51-2.44 (m, 2H), 2.55-2.44 (m, 2H), 2.18 (s, 2H), 1.96-1.84 (m, 2H), 1.68 (d, J = 6.4 Hz, 3H). |
| 109a, 109b | 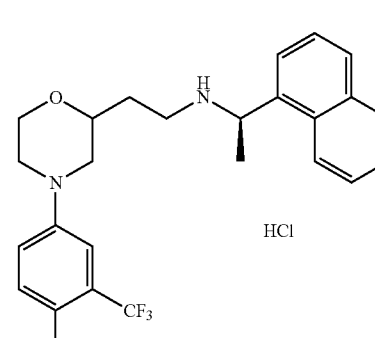<br>4-(2-(2-(((R)-1-(Naphthalen-1-yl)ethyl)amino)ethyl)morpholino)-2-(trifluoromethyl)benzoic acid hydrochloride | m/z 473.2; 109a $^1$H NMR (400 MHz, DMSO): δ 9.71 (bs, 1H), 9.10 (bs, 1H), 8.27 (d, J = 8.4 Hz, 1H), 8.04-7.99 (m, 2H), 7.93 (d, J = 7.2 Hz, 1H), 7.78 (d, J = 8.8 Hz, 1H), 7.67-7.59 (m, 3H), 7.24-7.23 (m, 2H), 5.35-5.32 (m, 1H), 3.90-3.87 (m, 1H), 3.79 (d, J = 11.6 Hz, 1H), 3.70 (d, J = 12.4 Hz, 1H), 3.61-3.50 (m, 3H), 3.16-3.15 (m, 1H), 3.0-2.9 (m, 1H), 2.83-2.67 (m, 1H), 1.98-1.90 (m, 1H), 1.89-1.85 (m, 1H), 1.68 (d, J = 6.8 Hz, 3H).<br>109b $^1$H NMR (400 MHz, DMSO): δ 9.9 (bs, 1H), 9.3 (bs, 1H), 8.26 (d, J = 8.4 Hz, 1H), 8.0-7.9 (m, 3H), 7.8 (d, J = 8.8 Hz, 1H), 7.6-7.5 (m, 3H), 7.24-7.17 (m, 2H), 5.35-5.33 (m, 1H), 3.89-3.86 (m, 1H), 3.79 (d, J = 11.6 Hz, 1H), 3.71 (d, J = 12.0 Hz, 1H), 3.59-3.35 (m, 3H), 3.16-3.14 (m, 1H), 2.82-2.77 (m, 1H), 1.98-1.90 (m, 1H), 1.89-1.85 (m, 1H), 1.68 (d, J = 6.8 Hz, 3H). |

TABLE 7-continued

| Example | Structure | Mass (m/z); and $^1$H NMR |
|---|---|---|
| 110a, 110b | 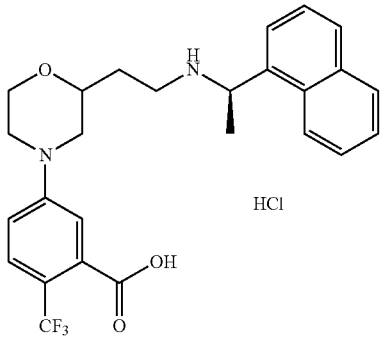 [SMILES: C[C@@H](NCCC1CN(c2ccc(C(F)(F)F)c(C(=O)O)c2)CCO1)c1cccc2ccccc12 ; Cl]

5-(2-(2-(((R)-1-(Naphthalen-1-yl)ethyl)amino)ethyl)morpholino)-2-(trifluoromethyl)benzoic acid hydrochloride | m/z 473.11; 110a $^1$H NMR (400 MHz, DMSO): δ 9.89 (bs, 1H), 9.3 (bs, 1H), 8.26 (d, J = 8.0 Hz, 1H), 8.03-7.98 (m, 3H), 7.67-7.57 (m, 4H), 7.21 (d, J = 2.4 Hz, 1H), 7.14-7.12 (m, 1H), 5.36-5.31 (m, 1H), 3.88-3.85 (m, 1H), 3.75 (d, J = 12 Hz, 1H), 3.68-3.51 (m, 4H), 3.16-3.13 (m, 1H), 2.90-2.80 (m, 1H), 2.79-2.76 (m, 1H), 1.96-1.88 (m, 1H), 1.68 (d, J = 6.8 Hz, 3H). 110b $^1$H NMR (400 MHz, DMSO): δ 9.9 (bs, 1H), 9.2 (bs, 1H), 8.27 (d, J = 8.4 Hz, 1H), 8.03-7.97 (m, 3H), 7.61-7.57 (m, 4H), 7.21 (d, J = 2.4 Hz, 1H), 7.14-7.12 (m, 1H), 5.35-5.31(m, 1H), 3.89-3.86 (m, 1H), 3.76 (d, J = 11.6 Hz, 1H), 3.68-3.40 (m, 4H), 3.16-3.13 (m, 1H), 2.98-2.85 (m, 1H), 2.80-2.76 (m, 1H), 1.99-1.96 (m, 1H), 1.89-1.85 (m, 1H), 1.69 (d, J = 6.8 Hz, 3H). |
| 111a, 111b | 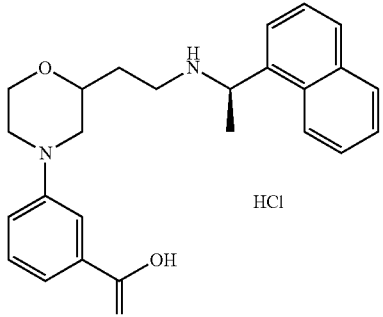

3-(2-(2-(((R)-1-(Naphthalen-1-yl)ethyl)amino)ethyl)morpholino)benzoic acid hydrochloride | m/z 404.66; 111a; $^1$H NMR (400 MHz, DMSO): δ 9.9 (bs,1H), 9.2(bs, 1H), 8.27 (d, J = 8.8 Hz, 1H), 8.03-7.98 (m, 3H), 7.67-7.58 (m, 3H), 7.46 (s, 1H), 7.40-7.32 (m, 2H), 7.22 (dd, J = 1.6, 8.0 Hz, 1H), 5.34-5.32 (m, 1H), 3.89-3.86 (m, 1H), 3.60-3.40 (m, 3H), 3.38-3.35 (m, 1H), 3.16-3.13 (m, 1H), 2.98-2.85 (m, 1H), 2.71-2.64 (m, 1H), 2.44-2.38 (m, 1H), 2.02-1.96 (m, 1H), 1.90-1.84 (m, 1H), 1.69 (d, J = 6.4 Hz, 3H). 111b; $^1$H NMR (400 MHz, DMSO): δ 9.9 (bs, 1H), 9.3 (bs, 1H), 8.27 (d, J = 8.8 Hz, 1H), 8.03-7.98 (m, 3H), 7.66-7.58 (m, 3H), 7.47 (s, 1H), 7.41-7.32 (m, 2H), 7.24 (m, 1H), 5.35-5.33 (m, 1H), 3.88-3.74 (m, 1H), 3.64-3.56 (m, 3H), 3.51-3.35 (m, 1H), 3.16-3.13 (m, 1H), 2.90-2.80 (m, 1H), 2.71-2.64 (m, 1H), 2.46-2.40 (m, 1H), 2.00-1.95 (m, 1H), 1.91-1.87 (m, 1H), 1.69 (d, J = 6.4 Hz, 3H). |
| 112a, 112b | 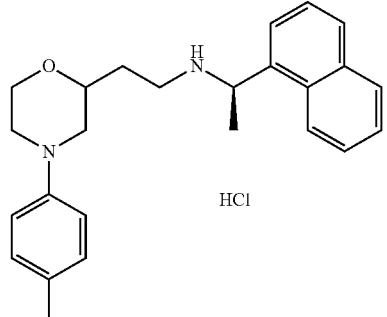

4-(2-(2-(((R)-1-(Naphthalen-1-yl)ethyl)amino)ethyl)morpholino)benzoic acid hydrochloride | m/z 405.1; 112a $^1$H NMR (400 MHz, DMSO): δ 9.90 (bs, 1H), 9.21 (bs, 1H), 8.27 (d, J = 8.0 Hz, 1H), 8.03-7.97 (m, 3H), 7.77 (d, J = 9.2 Hz, 2H), 7.67-7.58 (m, 3H), 6.97 (d, J = 9.2 Hz, 2H), 5.33-5.30 (m, 1H), 3.88 (dd, J$_1$ = 2.4 Hz, J$_2$ = 11.6 Hz, 1H), 3.74-3.72 (m, 2H), 3.66-3.62 (m, 2H), 3.16-3.13 (m, 1H), 2.98-2.88 (m, 1H), 2.78-2.71 (m, 1H), 2.45-2.33 (m, 1H), 1.99-1.95 (m, 1H), 1.89-1.86 (m, 1H), 1.69 (d, J = 6.8 Hz, 3H). 112b $^1$H NMR (400 MHz, DMSO): δ 9.84 (bs, 1H), 9.26 (bs, 1H), 8.26 (d, J = 8.4 Hz, 1H), 8.03-7.98 (m, 3H), 7.77 (d, J = 8.8 Hz, 2H), 7.67-7.58 (m, 3H), 6.97 (d, J = 9.2 Hz, 2H), 5.36-5.31 (m, 1H), 3.85-3.84 (m, 1H), 3.74-3.71 (m, 3H), 3.40-3.35 (m, 2H), 3.16-3.14 (m, 1H), 2.91-2.88 (m, 1H), 2.78-2.71 (m, 1H), 1.97-1.87 (m, 2H), 1.69 (d, J = 6.4 Hz, 3H). |

TABLE 7-continued

| Example | Structure | Mass (m/z); and $^1$H NMR |
|---|---|---|
| 113a, 113b | 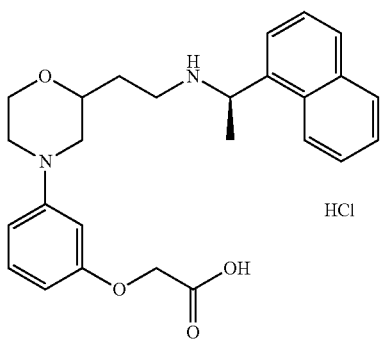 [SMILES: C[C@@H](NCCC1CN(c2cccc(OCC(=O)O)c2)CCO1)c1cccc2ccccc12 ; Cl]<br>2-(3-(2-(2-(((R)-1-(Naphthalen-1-yl)ethyl)amino)ethyl)morpholino)phenoxy)acetic acid hydrochloride | m/z 435.2; 113a $^1$H NMR (400 MHz, DMSO): δ 9.88 (bs, 1H), 9.27 (bs, 1H), 7.41 (d, J = 8.4 Hz, 1H), 8.03-7.98 (m, 3H), 7.67-7.58 (m, 3H), 7.13 (t, J = 8.4 Hz, 1H), 6.60 (d, J = 8.4 Hz, 1H), 6.53 (s, 1H), 6.39-6.37 (m, 1H), 5.36-4.63 (m, 1H), 3.86-3.35 (m, 5H), 3.16-2.69 (m, 2H), 2.67-2.64 (m, 1H), 2.50-2.39 (m, 1H), 1.95-1.86 (m, 2H), 1.69 (d, J = 6.4 Hz, 3H).<br>113b: $^1$H NMR (400 MHz, DMSO): δ 9.99 (bs, 1H), 9.27 (bs, 1H), 8.27 (d, J = 8.4 Hz, 1H), 8.03-7.98 (m, 3H), 7.66-7.58 (m, 3H), 7.13 (t, J = 8.4 Hz, 1H), 6.61 (d, J = 8.0 Hz, 1H), 6.54 (s, 1H), 6.39 (d, J = 8.4 Hz, 1H), 5.34-4.63 (m, 1H), 3.87-3.35 (m, 5H), 3.16-2.70 (m, 2H), 2.67-2.65 (m, 1H), 2.50-2.38 (m, 1H), 1.98-1.85 (m, 2H), 1.69 (d, J = 6.4 Hz, 3H) |
| 114a, 114b | 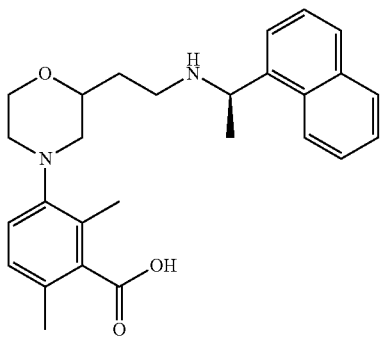 [SMILES: Cc1ccc(N2CCOC(CCN[C@H](C)c3cccc4ccccc34)C2)c(C)c1C(=O)O]<br>2,6-Dimethyl-3-(2-(2-(((R)-1-(naphthalen-1-yl)ethyl)amino)ethyl)morpholino)benzoic acid | 114a: m/z 433.3; 114a: $^1$H NMR (400 MHz, DMSO): δ 8.27 (d, J = 8.4 Hz, 1H), 8.02-7.97 (m, 2H), 7.81 (d, J = 6.4 Hz, 1H), 7.66-7.58 (m, 3H), 7.04 (d, J = 8.4 Hz, 1H), 6.97 (d, J = 8.0 Hz, 1H), 5.26-5.23 (m, 1H), 3.83-3.80 (m, 1H), 3.63-3.58 (m, 3H), 2.94-2.90 (m, 3H), 2.84 (d, J = 11.6 Hz, 1H), 2.78 (d, J = 11.2 Hz, 2H), 2.67-2.65 (m, 1H), 2.33-2.32 (m, 1H), 2.19-2.18 (m, 3H), 1.80-1.70 (m, 2H), 1.63 (d, J = 4.4 Hz, 3H).<br>114b: $^1$H NMR (400 MHz, DMSO): δ 8.26 (d, J = 8.4 Hz, 1H), 8.03-7.99 (m, 2H), 7.92 (d, J = 7.2 Hz, 1H), 7.68-7.58 (m, 3H), 7.03 (dd, $J_1$ = 8.4 Hz, $J_2$ = 24.4 Hz, 2H), 5.34-5.32 (m, 1H), 3.81-3.79 (m, 1H), 3.66-3.62 (m, 3H), 3.16-3.01 (m, 3H), 2.84-2.76 (m, 2H), 2.33-2.30 (m, 1H), 2.19-2.18 (m, 3H), 1.88-1.83 (m, 2H), 1.67 (d, J = 6.4 Hz, 3H). |

Example-115a, 115b 4-((2-(2-(((R)-1-(Naphthalen-1-yl)ethyl)amino)ethyl)morpholino)methyl)benzoic acid hydrochloride

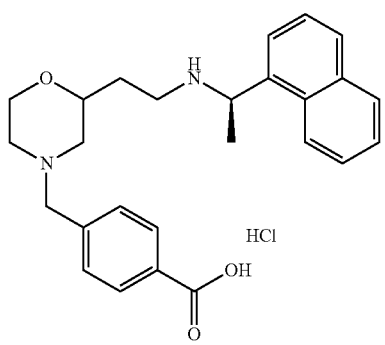 [SMILES: C[C@@H](NCCC1CN(Cc2ccc(C(=O)O)cc2)CCO1)c1cccc2ccccc12 ; Cl]

Step-1: Methyl 4-((2-(2-(((R)-1-(naphthalen-1-yl)ethyl)amino)ethyl)morpholino)methyl)benzoate To a stirred solution of Intermediate-11 (0.2 g, 0.740 mmol) in dichloromethane (5 ml), triethylamine (0.155 ml, 1.110 mmol) at 0° C., ethyl 4-(bromomethyl)-2-methylbenzoate (0.228 g, 0.888 mmol) was added. The reaction mixture stirred for 2 h at room temperature. Reaction mixture quenched with water and extracted with dichloromethane to get crude oil. Further compound was purified by prep HPLC and diasteromers were separated by chiral HPLC [CHIRAL PAK IA, 250 mm×4.6, 5μ; A=n-hexane:IPA (90:10% v/v, 0.1% DEA), B=IPA, A: B=70/30% V/V] offered title compound of isomer-a, $t_R$=5.63 (120 mg) m/z 419.04 and isomer-b, $t_R$=7.45 (130 mg) m/z 419.04.

Step-2: 4-((2-(2-(((R)-1-(naphthalen-1-yl)ethyl)amino)ethyl)morpholino)methyl)benzoic acid hydrochloride To a stirred solution of above Step-1 isomer-a (120 mg, 0.277 mmol) in methanol (2 ml), THF (2 ml) and water (2 ml) in single neck round bottom flask LiOH (150 mg, 6.26 mmol) was added and reaction mixture was heated to 65° C. and further maintained for 2 h. Reaction mixture was concentrated and neutralized with 6N HCl, the solid precipitated out was filtered, washed with DM water and n-pentane, dried to get pure product. Further, hydrochloride salt was prepared from this free base by following the similar hydrochloride salt procedure as described in Example-1 (Example-115a, 70 mg). Similarly, Example-115b was also prepared from Step-1 of isomer-b (Example-115b, 100 mg).

115a: m/z 419.04; $^1$H NMR (400 MHz, DMSO): δ 11.58 (bs, 1H), 9.99 (bs, 1H), 9.23 (bs, 1H), 8.23 (d, J=8.0 Hz, 1H), 8.02-7.96 (m, 5H), 7.73-7.71 (m, 2H), 7.65-7.57 (m, 3H), 5.29-5.28 (m, 1H), 4.35 (s, 2H), 3.88-3.80 (m, 2H), 3.23-3.08 (m, 2H), 3.03-2.50 (m, 3H), 1.98-1.93 (m, 2H), 1.92-1.80 (m, 2H), 1.77 (d, J=4.8 Hz, 3H).

115b: m/z 419.10; $^1$H NMR (400 MHz, DMSO): δ 13.17 (bs, 1H), 11.66 (bs, 1H), 9.94 (bs, 1H), 9.32 (bs, 1H), 8.22 (d, J=8.4 Hz, 1H), 8.02-7.97 (m, 5H), 7.74-7.57 (m, 5H), 5.29-5.28 (m, 1H), 4.35 (s, 2H), 3.87-3.81 (m, 3H), 3.18-3.15 (m, 2H), 3.04-2.90 (m, 2H), 2.85-2.73 (m, 2H), 1.98-1.65 (m, 5H).

Example-116a, 116b 3-((2-(2-(((R)-1-(Naphthalen-1-yl)ethyl)amino) ethyl)morpholino)methyl)benzoic acid dihydrochloride

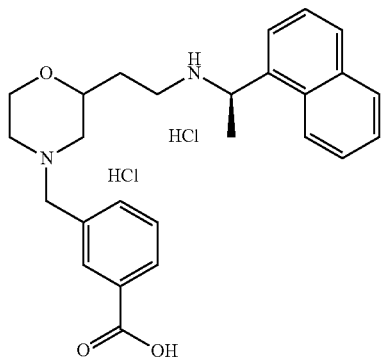 [SMILES: C[C@@H](NCCC1CN(Cc2cccc(C(=O)O)c2)CCO1)c1cccc2ccccc12 ; Cl ; Cl]

The title compound was prepared by following the similar procedure as described in step-1 Example-115a, 115b by using Intermediate-11 and 4 ethyl 3-(bromomethyl)-2-methylbenzoate then hydrolysis as described in step-2 Example-115a, 115b. Further, hydrochloride salt was prepared from this free base by following the similar hydrochloride salt procedure as described in Example-1

116a: m/z 419.16; $^1$H NMR (400 MHz, DMSO): δ 13.15 (bs, 1H), 11.60 (bs, 1H), 10.19 (bs, 1H), 9.37 (bs, 1H), 8.22-8.20 (m, 2H), 8.14-8.10 (m, 1H), 8.04-7.92 (m, 4H), 7.91-7.90 (m, 1H), 7.65-7.57 (m, 3H), 5.28-5.27 (m, 1H), 4.36 (s, 2H), 3.87-3.78 (m, 3H), 3.27-3.24 (m, 2H), 3.16-3.04 (m, 2H), 2.88-2.81 (m, 2H), 1.98-1.90 (m, 1H), 1.81-1.75 (m, 1H), 1.67 (d, J=8.0 Hz, 3H).

116b: m/z 419.10; $^1$H NMR (400 MHz, DMSO): δ 13.20 (bs, 1H), 11.48 (bs, 1H), 10.02 (bs, 1H), 9.38 (bs, 1H), 8.23-8.21 (m, 1H), 8.14-8.10 (m, 1H), 8.02-7.97 (m, 4H), 7.91-7.89 (m, 1H), 7.65-7.56 (m, 4H), 5.31-5.28 (m, 1H), 4.37 (s, 2H), 3.87-3.75 (m, 3H), 3.22-3.16 (m, 2H), 3.04-3.02 (m, 2H), 2.90-2.85 (m, 2H), 1.98-1.90 (m, 1H), 1.82-1.75 (m, 1H), 1.66 (d. J=8.0 Hz, 3H).

Example-117a, 117b 3-(3-(2-(((R)-1-(Naphthalen-1-yl)ethyl)amino)ethyl) morpholino)-5-(trifluoromethyl)benzoic acid hydrochloride

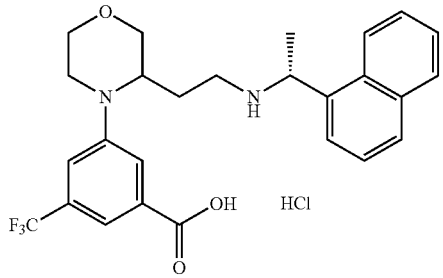 [SMILES: C[C@@H](NCCC1COCCN1c1cc(C(=O)O)cc(C(F)(F)F)c1)c1cccc2ccccc12 ; Cl]

Step-1: Methyl 3-(3-(2-(((R)-1-(naphthalen-1-yl) ethyl)amino)ethyl)morpholino)-5-(trifluoromethyl) benzoate Intermediate-12 (200 mg, 0.703 mmol) was dissolved in 10 ml dry toluene under N$_2$ atmosphere in sealed tube then methyl 3-bromo-5-(trifluoromethyl)benzoate (239 mg, 0.844 mmol) and cesium carbonate (344 mg, 1.055 mmol) were added. After that the reaction mixture was stirred for 10 min under N$_2$ atmosphere at RT then tris(dibenzylideneacetone) dipalladium(0) (32.2 mg, 0.035 mmol) and bis(tri-t-butylphosphine)palladium(0) (35.9 mg, 0.070 mmol) were added and stirred for 20 minutes under N$_2$ atmosphere. The reaction mixture was heated to reflux temperature and further maintained for 15 h. After completion of the reaction, solvent was evaporated and the resultant crude compound was purified by column chromatography by using 20% ethyl acetate in hexane to get pure title compound. Further, diastereomers were separated by preparative HPLC (ACQUITY BEH C18, 50×2.1 mm, 1.7μ, water:ACN (90:10) v/v %+0.1% NH$_4$OH) to get two diastereomers (Isomer-a; t$_R$=2.77, 25 mg, Isomer-b; t$_R$=2.82, 25 mg); m/z 487.2.

Step-2: 3-(3-(2-(((R)-1-(Naphthalen-1-yl)ethyl) amino)ethyl)morpholino)-5-(trifluoro methyl)benzoic acid hydrochloride To a stirred solution of Step-1 isomer-a, (25 mg, 0.056 mmol) in methanol (2 ml), THF (2 ml) and water (2 ml) in single neck round bottom flask LiOH (26.7 mg, 1.115 mmol) was added and the reaction mixture was heated to 65° C. and further maintained for 2 h. Reaction mixture was concentrated and neutralized with 6N HCl solution, extracted with dichloromethane (2×30 mL), dried over Na$_2$SO$_4$, concentrated to get the title compound of Example-117a (20 mg, 83%). Similarly, Example-117b was prepared from Step-1 of isomer-b.

Example-117a: $^1$H NMR (400 MHz, DMSO): δ 13.1 (bs, 1H), 9.8 (bs, 1H), 9.2 (bs, 1H), 8.11 (d, J=8 Hz, 1H), 7.97-7.92 (m, 2H), 7.86 (d, J=7.2 Hz, 1H), 7.57-7.49 (m, 4H), 7.42 (s, 1H), 7.26 (s, 1H), 5.24 (q, J=6.4 Hz, 1H), 4.06-4.04 (m, 3H), 3.70 (d, J=12 Hz, 1H), 3.58-3.55 (m, 1H), 3.50-3.45 (m, 1H), 3.38-3.30 (m, 2H), 3.07-3.03 (m, 1H), 2.80-2.72 (m, 2H), 2.45-2.10 (m, 1H), 1.88 (m, 1H), 1.60 (d, J=6.4 Hz, 3H), m/z 473.11

Example 117b: ¹H NMR (400 MHz, DMSO): δ 13.0 (bs, 1H), 9.65 (bs, 1H), 9.25 (bs, 1H), 8.10-8.08 (m, 1H), 7.98-7.92 (m, 2H), 7.81 (d, J=7.2 Hz, 1H), 7.57-7.51 (m, 4H), 7.43 (s, 1H), 7.29 (s, 1H), 5.21 (q, J=6.4 Hz, 1H), 4.04 (m, 1H), 3.87-3.76 (m, 1H), 3.73-3.58 (m, 2H), 3.55-3.46 (m, 1H), 3.07-2.94 (m, 3H), 2.67 (m, 1H), 2.14-2.11 (m, 1H), 1.78 (m, 1H), 1.60 (d, J=6.4 Hz, 3H), m/z 473.1.

The below list of examples 118 to 120 given in Table-8a were prepared by following the similar procedure as described in Step-1 then Step-2 of Example-102a, 102b by taking Intermediate-4 and appropriately substituted halobenzene. Further, hydrochloride salts of these compounds were prepared by following the similar hydrochloride salt procedure as described in Example-1.

TABLE 8a

| Example | Structure | Mass (m/z) and ¹H NMR |
|---|---|---|
| 118 | 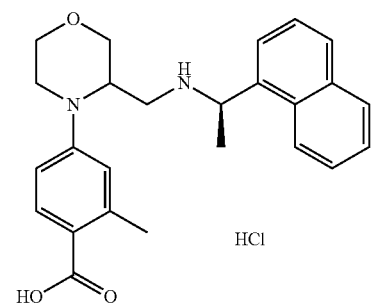 [SMILES: Cc1cc(N2CCOCC2CN[C@H](C)c2cccc3ccccc23)ccc1C(=O)O ; Cl]<br>2-Methyl-4-(3-((((R)-1-(naphthalen-1-yl)ethyl)amino)methyl)morpholino)benzoic acid hydrochloride | m/z 405.2; ¹H NMR (400 MHz, DMSO): δ 13.1 (bs, 1H), 10.2 (bs, 1H), 9.65 (bs, 1H), 8.16-8.15 (m, 1H), 8.10 (d, J = 7.2 Hz, 1H), 8.024-7.90 (m, 2H), 7.69 (dd, J = 2.4 & 8 Hz, 1H), 7.63-7.52 (m, 3H), 6.87-6.82 (m, 1H), 6.79-6.73 (m, 1H), 5.35 (s, 1H), 4.37 (s, 1H), 3.89-3.79 (m, 2H), 3.52-3.38 (m, 2H), 3.11-3.26 (m, 1H), 2.96-2.89 (m, 2H), 2.70-2.67 (m, 1H), 2.49 (s, 3H), 1.70 (d, J = 6.8 Hz, 3H). |
| 119 | 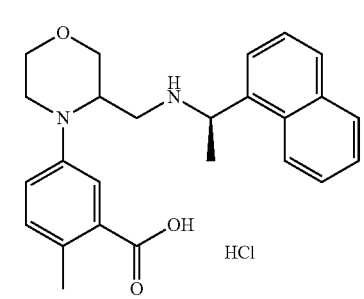 [SMILES: Cc1ccc(N2CCOCC2CN[C@H](C)c2cccc3ccccc23)cc1C(=O)O ; Cl]<br>2-Methyl-5-(3-((((R)-1-(naphthalen-1-yl)ethyl)amino)methyl)morpholino)benzoic acid hydrochloride | m/z 404.97; ¹H NMR (400 MHz, DMSO): δ 13.2 (bs, 1H), 9.9 (bs, 1H), 9.3 (bs, 1H), 8.15-8.13 (m, 1H), 8.02-8.79 (m, 3H), 7.60-7.49 (m, 2H), 7.28-7.26 (m, 2H), 7.02-6.94 (m, 2H), 5.35 (s, 1H), 4.18-4.16 (m, 2H), 3.53-3.46 (m, 2H), 3.22-3.15 (m, 2H), 2.95-2.85 (m, 2H), 2.67 (m, 1H), 2.38 (s, 3H), 1.65 (d, J = 6.8 Hz, 3H). |
| 120 | 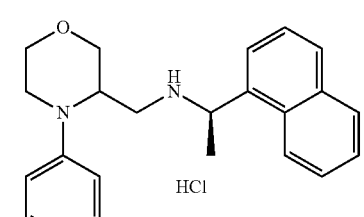<br>(1R)-1-(Naphthalen-1-yl)-N-((4-(m-tolyl)morpholin-3-yl)methyl)ethanamine hydrochloride | m/z 361.3; ¹H NMR (400 MHz, DMSO): δ 10.0 (bs, 1H), 9.5 (bs, 1H), 8.17-8.12 (m, 1H), 8.02-7.90 (m, 3H), 7.61-7.51 (m, 3H), 7.04-6.96 (m, 1H), 6.74 (d, J = 8.4 Hz, 1H), 6.63 (d, J = 8.4 Hz, 1H), 6.57-6.54 (m, 1H), 5.33 (q, J = 6.8 Hz, 1H), 4.26-3.81 (m, 2H), 3.67-3.61 (m, 1H), 3.53-3.45 (m, 1H), 3.28-3.22 (m, 2H), 2.19-2.84 (m, 2H), 2.67-2.66 (m, 1H), 2.3 (s, 3H), 1.66 (d, J = 6.8 Hz, 3H). |

The below list of examples 121 to 129 given in Table-8b can be prepared by following the similar procedure as described in Step-1 then Step-2 of Example-102a, 102b by taking Intermediate-4 or Intermediate-5 and appropriately substituted halobenzene.

TABLE 8b

| Example | Structure | Chemical name |
|---|---|---|
| 121 | 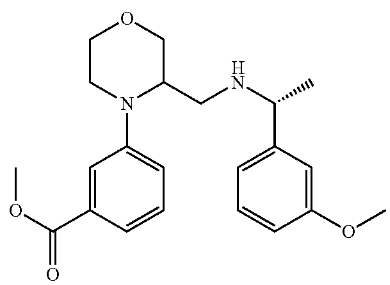 [SMILES: COC(=O)c1cccc(N2CCOCC2CN[C@H](C)c2cccc(OC)c2)c1] | Methyl-3-(3-((((R)-1-(3-methoxyphenyl)ethyl)amino)methyl)morpholino)benzoate |
| 122 | 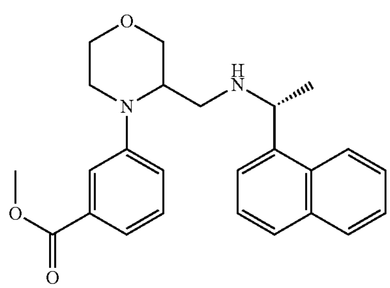 [SMILES: COC(=O)c1cccc(N2CCOCC2CN[C@H](C)c2cccc3ccccc23)c1] | Methyl-3-(3-((((R)-1-(naphthalen-1-yl)ethyl)amino)methyl)morpholino)benzoate |
| 123 | 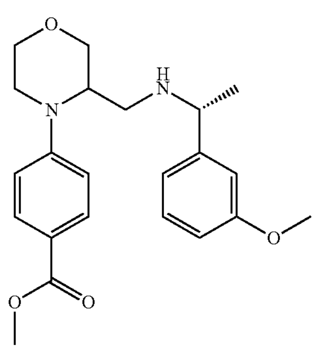 [SMILES: COC(=O)c1ccc(N2CCOCC2CN[C@H](C)c2cccc(OC)c2)cc1] | Methyl- 4-(3-((((R)-1-(3-methoxyphenyl)ethyl)amino)methyl)morpholino)benzoate |
| 124 | 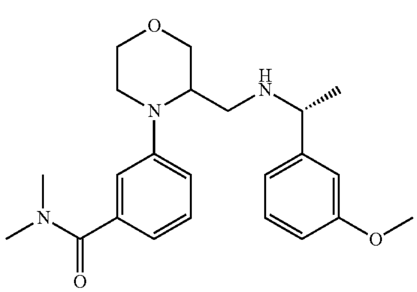 | 3-(3-((((R)-1-(3-Methoxyphenyl)ethyl)amino)methyl)morpholino)-N,N-dimethylbenzamide |

TABLE 8b-continued

| Example | Structure | Chemical name |
|---|---|---|
| 125 | 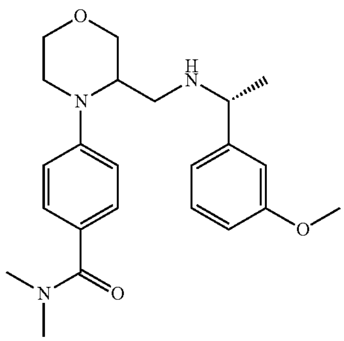 | 4-(3-((((R)-1-(3-Methoxyphenyl)ethyl)amino)methyl)morpholino)-N,N-dimethylbenzamide |
| 126 | 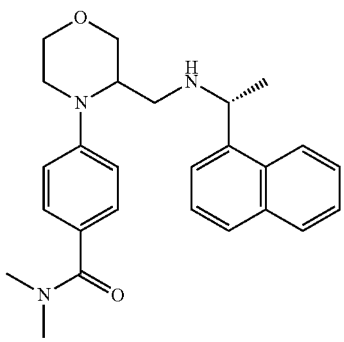 [SMILES: C[C@@H](NCC1COCCN1c1ccc(C(=O)N(C)C)cc1)c1cccc2ccccc12] | N,N-Dimethyl-4-(3-((((R)-1-(naphthalen-1-yl)ethyl)amino)methyl) morpholino)benzamide |
| 127 | 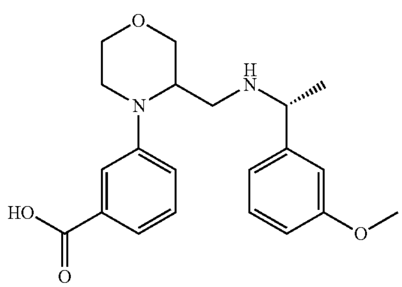 [SMILES: COc1cccc([C@@H](C)NCC2COCCN2c2cccc(C(=O)O)c2)c1] | 3-(3-((((R)-1-(3-Methoxyphenyl)ethyl)amino)methyl)morpholino)benzoic acid |
| 128 | 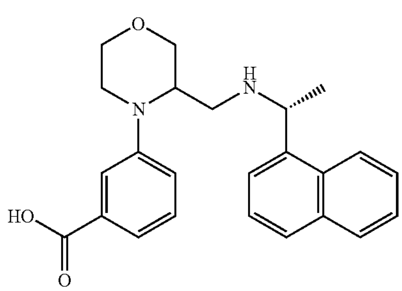 [SMILES: C[C@@H](NCC1COCCN1c1cccc(C(=O)O)c1)c1cccc2ccccc12] | 3-(3-((((R)-1-(Naphthalen-1-yl)ethyl)amino)methyl)morpholino)benzoic acid |
| 129 | 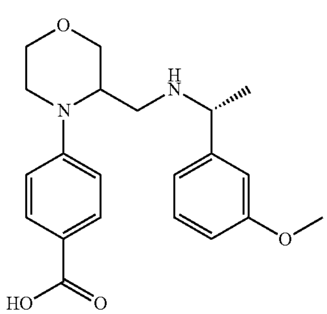 [SMILES: COc1cccc([C@@H](C)NCC2COCCN2c2ccc(C(=O)O)cc2)c1] | 4-(3-((((R)-1-(3-Methoxyphenyl)ethyl)amino)methyl)morpholino)benzoic acid |

The below list of examples 130 to 150 given in Table-9 were prepared by following the similar procedure as described in Step-1 of Example-102a, 102b by taking Intermediate-13 or Intermediate-16 appropriately substituted halobenzene. Further, hydrochloride salts of these compounds were prepared by following the similar hydrochloride salt procedure as described in Example-1.

TABLE 9

| Example | Structure | Mass (m/z) and $^1$H NMR |
| --- | --- | --- |
| 130 | 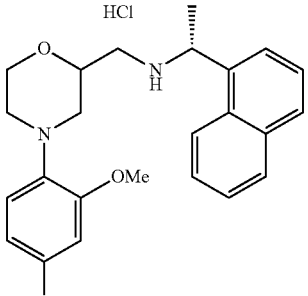<br>3-Methoxy-4-(2-((((R)-1-(naphthalen-1-yl)ethyl)amino)methyl)morpholino)benzoic acid hydrochloride | m/z 420.98; $^1$H NMR (400 MHz, DMSO): δ 12.5 (bs, 1H), 10.1 (bs, 1H), 9.1 (bs, 1H), 8.2 (m, 1H), 8.012-7.978 (m, 3H), 7.66-7.58 (m, 3H), 7.50-7.47 (m, 1H), 7.37-7.35 (m, 1H), 6.91-6.86 (m, 1H), 5.2 (m, 1H), 3.97 (m, 1H), 3.94 (m, 1H), 3.8 (s, 3H), 3.48-3.33 (m, 3H), 3.27-3.18 (m, 2H), 2.84-2.70 (m, 2H), 1.67 (d, J = 8 Hz, 3H). |
| 131a, 131b | 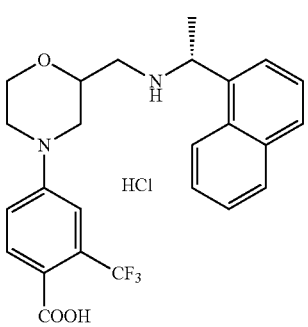 [SMILES: C[C@@H](NCC1CN(c2ccc(C(=O)O)c(C(F)(F)F)c2)CCO1)c1cccc2ccccc12 ; Cl]<br>4-(2-((((R)-1-(Naphthalen-1-yl)ethyl)amino)methyl)morpholino)-2-(trifluoromethyl)benzoic acid hydrochloride | m/z 459.29; 131a: $^1$H NMR (400 MHz, DMSO): δ 12.1 (bs, 1H), 9.8 (bs, 1H), 9.60 (bs, 1H), 8.22 (d, J = 8.4 Hz, 1H), 8.0 (t, J = 8 Hz, 2H), 7.86 (m, 1H), 7.84-7.76 (d, J = 8.8 Hz, 1H), 7.65-7.55 (m, 3H), 7.16-7.12 (m, 2H), 5.4 (m, 1H), 4.0-3.98 (m, 1H), 3.90 (m, 1H), 3.76-3.50 (m, 2H), 3.36 (m, 1H), 3.18 (m, 1H), 2.86 (m, 2H), 2.48 (m, 1H), 1.7 (d, J = 6.4 Hz, 3H). 131b: $^1$H NMR (400 MHz, DMSO): δ12.1 (bs, 1H), 9.60 (bs, 1H), 9.1 (bs, 1H), 8.24 (d, J = 8.4 Hz, 1H), 8.01 (t, J = 8 Hz, 2H), 7.89 (m, 1H), 7.84-7.762 (d, J = 8.8 Hz, 1H), 7.67-7.58 (m, 3H), 7.19-7.14 (m, 2H), 5.4 (m, 1H), 4.05-4.03 (m, 1H), 3.92 (m, 1H), 3.79-3.53 (m, 2H), 3.39 (m, 1H), 3.21(m, 1H), 2.88 (m, 2H), 2.50 (m, 1H), 1.7 (d, J = 6.4 Hz, 3H). |
| 132 | 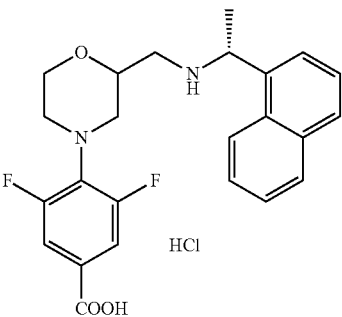 [SMILES: C[C@@H](NCC1CN(c2c(F)cc(C(=O)O)cc2F)CCO1)c1cccc2ccccc12 ; Cl]<br>3,5-Difluoro-4-(2-((((R)-1-(naphthalen-1-yl)ethyl)amino)methyl)morpholino)benzoic acid hydrochloride | m/z 427.0; $^1$H NMR (400 MHz, DMSO: δ 11.1 (bs, 1H), 9.6 (bs, 1H), 9.1 (bs, 1H), 8.19-8.16 (m, 1H), 8.00-7.98 (t, J = 8 Hz, 2H), 7.82 (d, J = 7.2 Hz, 1H), 7.64-7.54 (m, 3H), 7.49-7.40 (m, 2H), 5.28 (m, 1H), 4.0-3.9 (m, 2H), 3.68-3.63 (m, 1H), 3.38-3.33 (m, 3H), 3.27-3.18 (m, 1H), 2.84-2.70 (m, 2H), 1.67 (d, J = 8 Hz, 3H). |

TABLE 9-continued

| Example | Structure | Mass (m/z) and ¹H NMR |
|---|---|---|
| 133 | 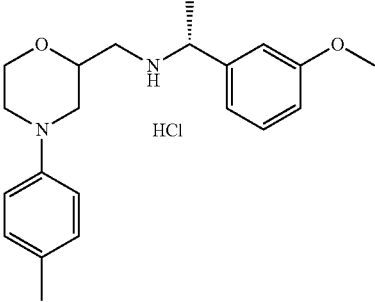 [SMILES: COc1cccc([C@@H](C)NCC2CN(c3ccc(C)cc3)CCO2)c1 ; Cl]<br>(1R)-1-(3-Methoxyphenyl)-N-((4-(p-tolyl)morpholin-2-yl)methyl)ethanamine hydrochloride | m/z 341.3; ¹H NMR (400 MHz, DMSO): δ 10.1 (bs, 1H), 9.1 (bs, 1H), 7.34 (t, J = 8 Hz, 1H ), 7.27-7.23 (m, 4H), 7.17-7.12 (m, 3H), 4.32 (m, 1H), 4.10 (m, 2H), 3.92 (s, 3H), 3.68 (m, 1H), 3.10 (m, 2H), 3.0 (s, 3H), 2.85 (m, 2H), 2.5 (m, 2H), 1.59 (d, J = 6.4 Hz, 3H). |
| 134 | 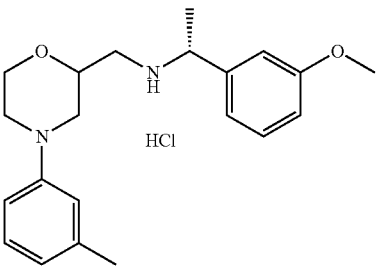 [SMILES: COc1cccc([C@@H](C)NCC2CN(c3cccc(C)c3)CCO2)c1 ; Cl]<br>(1R)-1-(3-Methoxyphenyl)-N-((4-(m-tolyl)morpholin-2-yl)methyl)ethanamine hydrochloride | m/z 341.3; ¹H NMR (400 MHz, DMSO): δ 10.1 (bs, 1H), 8.8 (bs, 1H), 7.37 (t, J = 8 Hz, 1H ), 7.27-7.23 (m, 2H), 7.17-7.12 (m, 1H), 7.11 (d, J = 7.6 Hz, 1H), 7.01-6.97 (m, 2H), 6.89 (t, J = 6.4 Hz, 1H), 4.34 (m, 1H), 4.1 (m, 2H), 3.95 (s, 3H), 3.72 (m, 1H), 3.12 (m, 2H), 3.02 (m, 3H), 2.85 (m, 2H), 2.52 (m, 2H), 1.59 (d, J = 6.4 Hz, 3H). |
| 135 | 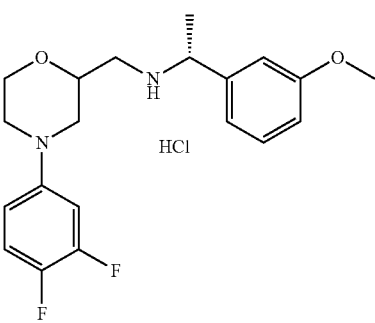 [SMILES: COc1cccc([C@@H](C)NCC2CN(c3ccc(F)c(F)c3)CCO2)c1 ; Cl]<br>(1R)-N-((4-(3,4-Difluorophenyl)morpholin-2-yl)methyl)-1-(3-methoxyphenyl)ethanamine hydrochloride | m/z 363.3; ¹H NMR (400 MHz, CDCl3): δ 10.1 (bs, 1H), 9.89 (bs, 1H), 7.35-7.34 (m, 2H), 7.32-7.30 (m, 1H), 7.09-7.06 (m, 1H), 6.98-6.95 (m, 1H), 6.76-6.72 (m, 1H), 6.54-6.51 (m, 1H), 5.01 (m, 1H), 4.21-4.18 (m, 1H), 4.15-4.12 (m, 1H), 4.01 (m, 1H), 3.95 (s, 3H), 3.87-3.85 (m, 1H), 3.52-3.50 (m, 1H), 3.20 (m, 1H), 2.98-2.80 (m, 2H), 2.54-2.52 (m, 1H), 1.98 (d, J = 6.4 Hz, 3H). |

TABLE 9-continued

| Example | Structure | Mass (m/z) and ¹H NMR |
|---|---|---|
| 136a, 136b | 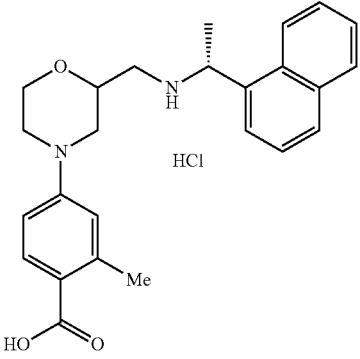 [SMILES: Cc1cc(N2CCOC(CN[C@H](C)c3cccc4ccccc34)C2)ccc1C(=O)O ; Cl]<br>2-Methyl-4-(2-((((R)-1-(naphthalen-1-yl)ethyl)amino)methyl)morpholino)benzoic acid hydrochloride | m/z 405.2; 136a: ¹H NMR (400 MHz, DMSO) δ 11.02 (bs, 1H), 9.81 (bs, 1H), 9.6 (bs, 1H), 8.16 (d, J = 7.2 Hz, 1H), 8.0 (t, J = 6.8 Hz, 2H), 7.8 (d, J = 8 Hz, 1H), 7.7 (d, J = 8 Hz, 1H), 7.6-7.57 (m, 3H), 6.7-6.72 (m, 2H), 4.5 (m, 1H), 3.92-3.86 (m, 1H), 3.85-3.80 (m, 1H), 3.5 (m, 3H), 3.09 (m, 1H), 2.9 (m, 1H), 2.6 (m, 1H), 2.52 (m, 3H), 1.88 (s, 3H), 1.75 (d, J = 6.4 Hz, 3H).<br>136b: ¹H NMR (400 MHz, DMSO) δ 12.1 (bs, 1H), 9.6 (bs, 1H), 9.1 (bs, 1H), 8.19 (d, J = 7.2 Hz, 1H), 8.0 (t, J = 6.8 Hz, 2H), 7.82 (d, J = 8 Hz, 1H), 7.74 (d, J = 8 Hz, 1H), 7.64-7.57 (m, 3H), 6.76-6.72 (m, 2H), 4.5 (m, 1H), 3.95-3.89 (m, 1H), 3.85-3.80 (m, 1H), 3.51 (m, 3H), 3.10 (m, 1H), 2.96 (m, 1H), 2.63 (m, 1H), 2.5 (m, 3H), 1.91 (s, 3H) 1.72 (d, J = 6.4 Hz, 3H). |
| 137 | 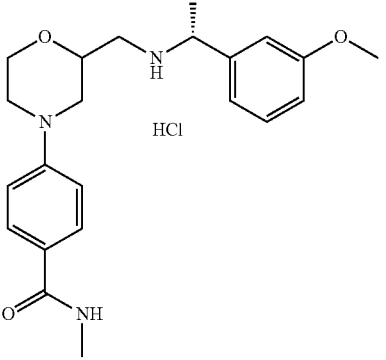<br>4-(2-((((R)-1-(3-Methoxyphenyl)ethyl)amino)methyl)morpholino)-N-methylbenzamide hydrochloride | m/z 384.2; ¹H NMR (400 MHz, DMSO): δ (11.1, bs, 1H), 10.1 (bs, 1H), 9.6 (bs, 1H), 7.78-7.75 (m, 1H), 7.38 (t, J = 8 Hz, 2H), 7.75-7.73 (m, 3H), 7.60-7.56 (m, 2H), 4.3 (m, 1H), 3.9 (s, 3H), 3.77-3.75 (m, 4H), 3.1 (s, 3H), 3.05-2.95 (m, 3H), 2.5-2.4 (m, 2H), 1.71 (d, J = 6.4 Hz, 3H). |
| 138 | 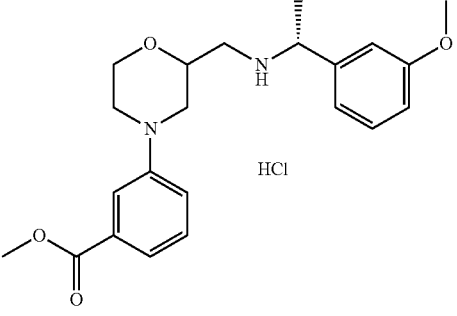<br>Methyl 3-(2-((((R)-1-(3-methoxyphenyl)ethyl)amino)methyl)morpholino)benzoate hydrochloride | m/z 382.2; ¹H NMR (400 MHz, DMSO ); δ 10.2 (bs, 1H), 9.1 (bs, 1H), 7.43-7.32 (m, 4H), 7.20-7.14 (m, 2H), 7.09-7.06 (m, 1H), 6.98-6.95 (m, 1H), 4.36 (m, 1H), 4.05-3.99 (m, 1H), 3.89 (s, 3H), 3.51-3.48 (m, 2H), 3.10-3.07 (m, 1H), 3.03-2.98 (m, 1H), 2.96-2.94 (m, 1H), 2.63-2.59 (m, 4H), 1.67 (d, J = 6.4 Hz, 3H). |

TABLE 9-continued

| Example | Structure | Mass (m/z) and ¹H NMR |
|---|---|---|
| 139 | 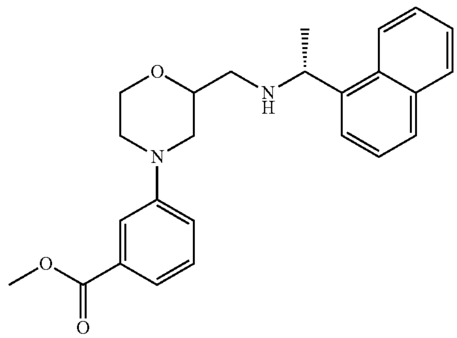 [SMILES: COC(=O)c1cccc(N2CCOC(CN[C@H](C)c3cccc4ccccc34)C2)c1] | Methyl 3-(2-((((R)-1-(naphthalen-1-yl)ethyl)amino)methyl)morpholino)benzoate |
| 140 | 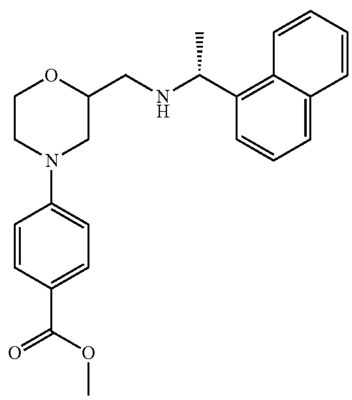 [SMILES: COC(=O)c1ccc(N2CCOC(CN[C@H](C)c3cccc4ccccc34)C2)cc1] | Methyl 4-(2-((((R)-1-(naphthalen-1-yl)ethyl)amino)methyl)morpholino)benzoate |
| 141 | 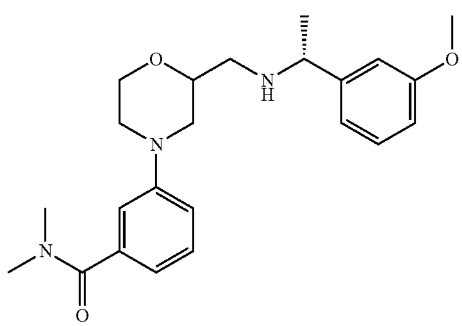 | 3-(2-((((R)-1-(3-Methoxyphenyl)ethyl)amino)methyl)morpholino)-N,N-dimethylbenzamide |
| 142 | 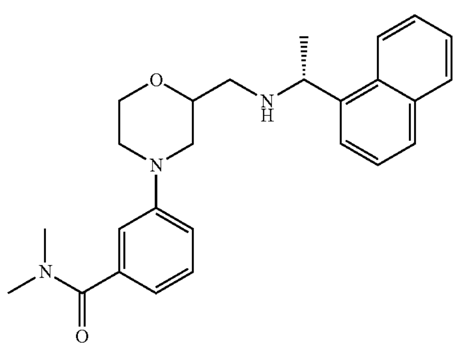 [SMILES: C[C@@H](NCC1CN(c2cccc(C(=O)N(C)C)c2)CCO1)c1cccc2ccccc12] | N,N-Dimethyl-3-(2-((((R)-1-(naphthalen-1-yl)ethyl)amino)methyl)morpholino)benzamide |

TABLE 9-continued

| Example | Structure | Mass (m/z) and ¹H NMR |
|---|---|---|
| 143 | 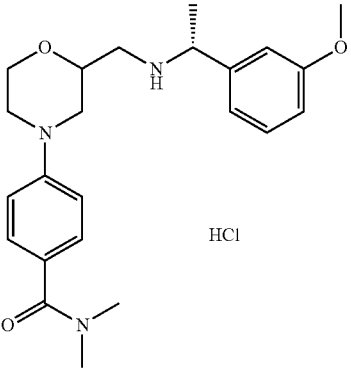 [SMILES: COc1cccc([C@@H](C)NCC2CN(c3ccc(C(=O)N(C)C)cc3)CCO2)c1 ; Cl]<br>4-(2-((((R)-1-(3-Methoxyphenyl)ethyl)amino)methyl)morpholino)-N,N-dimethylbenzamide hydrochloride | m/z 398.2; ¹H NMR (400 MHz, DMSO): δ 11.1, (bs, 1H), 9.6 (bs, 1H), 8.19 (m, 1H), 7.38 (t, J = 7.2 Hz, 2H ), 7.29-7.2 (m, 2H), 7.77-7.75 (m, 1H), 7.65-7.56 (m, 2H ), 4.32 (m, 1H), 3.98 (s, 3H), 3.77-3.75 (m, 4H), 3.1 (s, 6H), 3.05-2.95 (m, 3H), 2.5-2.45 (m, 2H), 1.71 (d, J = 6.4 Hz, 3H). |
| 144 | 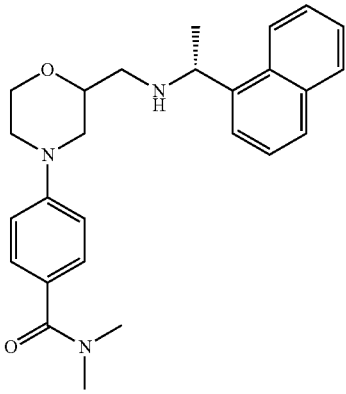 [SMILES: C[C@@H](NCC1CN(c2ccc(C(=O)N(C)C)cc2)CCO1)c1cccc2ccccc12] | N,N-Dimethyl-4-(2-((((R)-1-(naphthalen-1-yl)ethyl)amino)methyl)morpholino)benzamide |
| 145 | 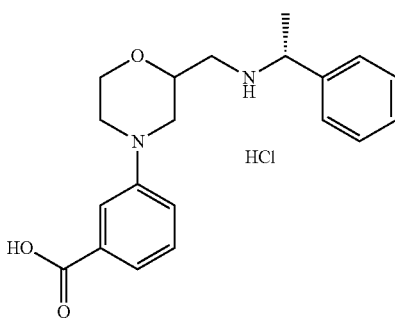<br>3-(2-((((R)-1-(3-methoxyphenyl)ethyl)amino)methyl)morpholino)benzoic acid hydrochloride | m/z 371.4; ¹H NMR (400 MHz, DMSO): δ (11.1, bs, 1H), 9.81 (bs 1H) 9.6 (bs, 1H), 8.19 (d, J = 7.2 Hz, 1H), 7.98 (t, J = 7.2 Hz, 2H), 7.88-7.85 (m, 1H), 7.75-7.73 (m, 1H), 7.65-7.56 (m, 1H ), 6.93-6.91 (m, 1H), 5.34 (m, 1H), 3.7-3.69 (m, 1H), 3.60-3.58 (m, 1H), 3.54-3.45 (m, 3H), 3.1 (s, 3H), 3.05-2.98 (m, 1H), 2.50-2.53 (m, 1H), 2.20-2.15 (m, 2H), 1.71 (d, J = 6.4 Hz, 3H) |

TABLE 9-continued

| Example | Structure | Mass (m/z) and ¹H NMR |
|---|---|---|
| 146 | 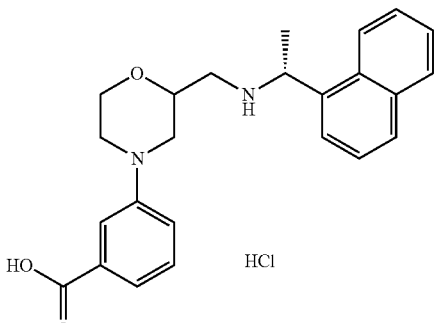<br>3-(2-((((R)-1-(Naphthalen-1-yl)ethyl)amino)methyl)morpholino)benzoic acid hydrochloride | m/z 391.41; ¹H NMR (400 MHz, DMSO ): 11.2 (bs, 1H), 9.78 (bs, 1H), 9.59 (bs, 1H), 7.38-7.32 (m, 5H), 7.20-7.14 (m, 3H), 7.11-7.09 (m, 2H), 6.98-6.95 (m, 1H), 4.5 (m, 1H), 3.95-3.89 (m, 1H), 3.51-3.48 (m, 3H), 3.10-3.08 (m, 1H), 3.03-2.98 (m, 1H), 2.96-2.94 (m, 1H), 2.63-2.60 (m, 1H), 2.45-2.43 (m, 1H), 1.67 (d, J = 6.4 Hz, 3H). |
| 147 | 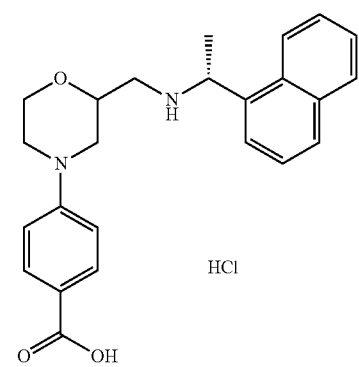 [SMILES: C[C@@H](NCC1CN(c2ccc(C(=O)O)cc2)CCO1)c1cccc2ccccc12 ; Cl]<br>4-(2-((((R)-1-(Naphthalen-1-yl)ethyl)amino)methyl)morpholino)benzoic acid hydrochloride | m/z 391.4; ¹H NMR (400 MHz, DMSO) δ 11.0 (bs, 1H), 10.5 (bs, 1H), 9.5 (bs, 1H), 7.43-7.32 (m, 5H), 7.20-7.14 (m, 3H), 7.09 (m, 2H), 6.98-6.95 (m, 1H), 4.5 (m, 1H), 3.95-3.89 (m, 1H), 3.51 (m, 3H), 3.10-3.06 (m, 1H), 3.03-3.0 (m, 1H), 2.96-2.94 (m, 1H), 2.63-2.60 (m, 1H), 2.45-2.42 (m, 1H), 1.67 (d, J = 6.4 Hz, 3H). |
| 148 | 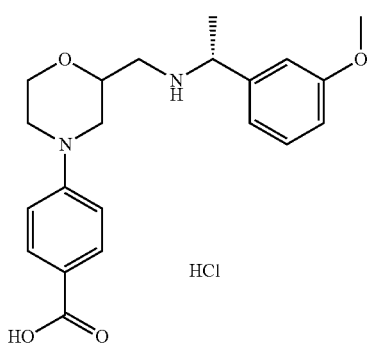 [SMILES: COc1cccc([C@@H](C)NCC2CN(c3ccc(C(=O)O)cc3)CCO2)c1 ; Cl]<br>4-(2-((((R)-1-(3-methoxyphenyl)ethyl)amino)methyl)morpholino) benzoic acid hydrochloride | m/z 371.4; ¹H NMR (400 MHz, DMSO): δ 11.1 (bs, 1H), 10.1 (bs, 1H), 9.6 (bs, 1H), 8.19 (m, 2H), 7.98 (t, J = 7.2 Hz, 1H), 7.9-7.8 (m, 1H), 7.77-7.75 (m, 1H), 7.65-7.56 (m, 2H), 6.99-6.94 (m, 1H), 5.32 (m, 1H), 3.77-3.75 (m, 1H), 3.64-3.60 (m, 1H), 3.52-3.44 (m, 3H), 3.1 (s, 3H), 3.05 (m, 1H), 2.5-2.45 (m, 1H), 2.20-2.18 (m, 2H), 1.71 (d, J = 6.4 Hz, 3H). |

TABLE 9-continued

| Example | Structure | Mass (m/z) and ¹H NMR |
|---|---|---|
| 149 | 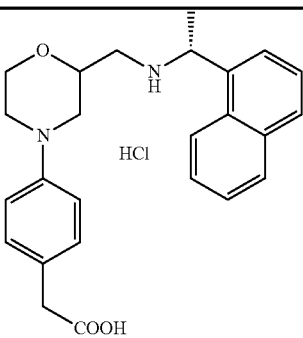<br>2-(4-(2-((((R)-1-(Naphthalen-1-yl)ethyl)amino)methyl)morpholino)phenyl) acetic acid hydrochloride | m/z 405.2; ¹H NMR (400 MHz, DMSO: δ 10.2 ( bs, 1H), 9.5 (bs, 1H), 8.19-8.17 (m, 1H), 7.87 (d, J = 7.2 Hz, 1H), 7.85-7.75 (m, 1H), 7.71-7.68 (m, 1H), 7.50-7.47 (m, 3H), 7.155-7.12 (m, 2H), 6.81-6.78 (m, 2H), 4.65 (m, 1H), 4.03-4.0 (m, 1H), 3.64 (m, 1H), 3.8-3.74 (m, 4H), 3.66-3.65 (m, 1H), 3.52-3.5 (m, 1H), 2.83-2.79 (m, 1H), 2.67-2.61 (m, 1H), 1.9 (m, 1H), 1.49 (d, 3H). |
| 150 | 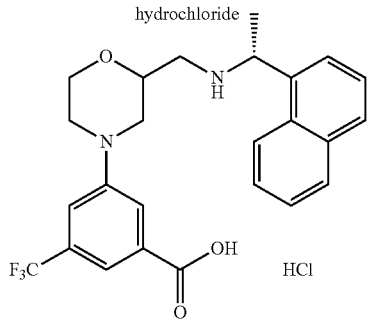<br>3-(2-((((R)-1-(Naphthalen-1-yl)ethyl)amino)methyl)morpholino)-5-(trifluoromethyl)benzoic acid hydrochloride | m/z 459.11; 150a: ¹H NMR (400 MHz, DMSO): δ 13.75-13.02 (m, 1H), 10.17 (bs, 1H), 9.26 (bs, 1H) 8.24 (d, J = 8.0 Hz, 1H), 8.02-7.97 (m, 2H), 7.66-7.54 (m, 3H), 7.50 (s, 1H), 7.42 (s, 1H), 5.37 (s, 1H), 4.04-4.02 (m, 2H), 3.81-3.61 (m, 3H), 3.39-3.34 (m, 1H), 3.30-3.23 (m, 1H), 2.81-2.50 (m, 2H), 1.72 (d, J = 8.0 Hz, 3H).<br>150b: ¹H NMR (400 MHz, DMSO): δ 13.49-13.12 (bs, 1H), 9.70 (bs, 1H), 9.51 (bs, 1H) 8.25 (d, J = 8.0 Hz, 1H), 8.03-7.99 (m, 2H), 7.67-7.58 (m, 3H), 7.55 (s, 1H), 7.43 (s, 1H), 5.36-5.35 (m, 1H), 4.03 (d, J = 8.0 Hz, 2H), 3.86-3.34 (m, 4H), 3.09 (s, 2H), 2.84-2.78 (m, 1H), 1.70 (d, J = 8.0 Hz, 3H). |

The below list of examples 151 to 156 given in Table-10 were prepared by following the similar procedure as described in Step-1 of Example-49a, 49b followed by Boc deprotection by following the similar procedure as described in Step-2 of Example-49a, 49b using Intermediate-9, Intermediate-10, Intermediate-14 or Intermediate-15. Further, hydrochloride salts of these compounds were prepared by following the similar hydrochloride salt procedure as described in Example-1.

TABLE 10

| Example | Structure | Mass (m/z) and ¹H NMR |
|---|---|---|
| 151 | 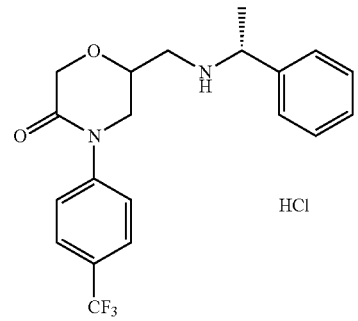<br>6-((((R)-1-Phenylethyl)amino)methyl)-4-(4-(trifluoromethyl)phenyl)morpholin-3-one hydrochloride | m/z 375.47: ¹H NMR (400 MHz, DMSO): δ 10.17 (bs, 1H), 9.65 (bs, 2H), 7.80 (d, J = 8.8 Hz, 1H), 7.64-7.58 (m, 4H), 7.47-7.39 (m, 3H), 7.47-7.39 (m, 3H), 4.48-4.29 (m, 3H), 3.82-3.66 (m, 1H), 3.14-3.11 (m, 2H), 3.02-2.95 (m, 2H), 2.71-2.69 (m, 1H), 1.63-1.61 (m, 3H). |

TABLE 10-continued

| Example | Structure | Mass (m/z) and ¹H NMR |
|---|---|---|
| 152a, 152b | 4-(3,4-Difluorophenyl)-6-((((R)-1-(4-fluoro-3-methoxyphenyl)ethyl)amino)methyl)morpholin-3-one hydrochloride | m/z 395.1: 152a: ¹H NMR (400 MHz, DMSO): δ 9.65 (bs, 2H), 9.47 (bs, 1H), 7.58-7.46 (m, 3H), 7.30-7.23 (m, 2H), 7.11-7.08 (m, 1H), 4.40-4.25 (m, 3H), 3.87 (s, 3H), 3.68 (d, J = 6 Hz, 2H), 3.00-2.89 (m, 3H), 1.61 (d, J = 6.4 Hz, 3H). 152b; ¹H NMR (400 MHz, DMSO): δ 9.62 (bs, 2H), 9.45 (bs, 1H), 7.58-7.46 (m, 3H), 7.30-7.23 (m, 2H), 7.11-7.08 (m, 1H), 4.40-4.25 (m, 3H), 3.87 (s, 3H), 3.68 (d, J = 6.4 Hz, 2H), 3.00-2.86 (m, 3H), 1.61 (d, J = 6.8 Hz, 3H). |
| 153 | 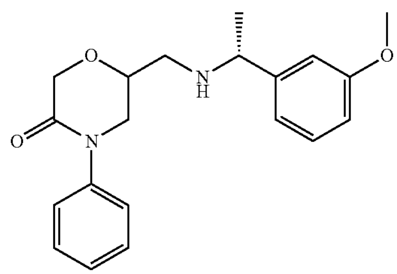 [SMILES: COc1cccc([C@@H](C)NCC2CN(c3ccccc3)C(=O)CO2)c1] | 6-((((R)-1-(3-Methoxyphenyl)ethyl)amino)methyl)-4-phenylmorpholin-3-one |
| 154 | 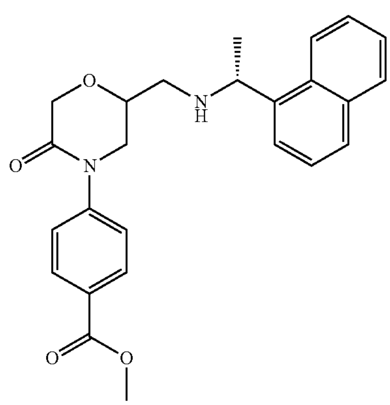 [SMILES: COC(=O)c1ccc(N2CC(CN[C@H](C)c3cccc4ccccc34)OCC2=O)cc1] | Methyl 4-(2-((((R)-1-(naphthalen-1-yl)ethyl)amino)methyl)-5-oxomorpholino)benzoate |
| 155 | 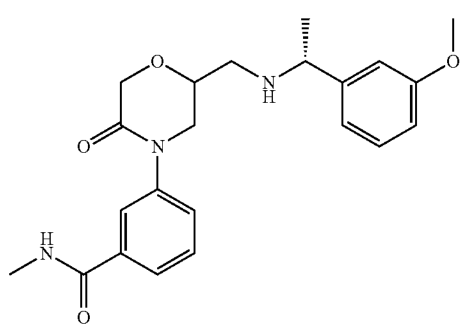 | 3-(2-((((R)-1-(3-Methoxyphenyl)ethyl)amino)methyl)-5-oxomorpholino)-N-methylbenzamide |

TABLE 10-continued

| Example | Structure | Mass (m/z) and ¹H NMR |
|---|---|---|
| 156 | 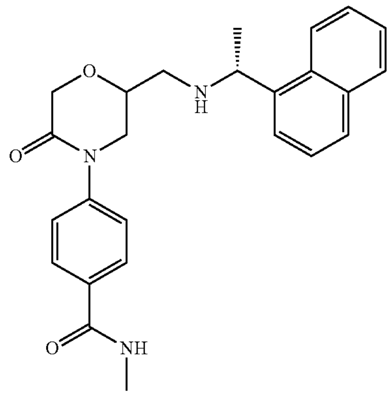 [SMILES: CNC(=O)c1ccc(N2CC(CN[C@H](C)c3cccc4ccccc34)OCC2=O)cc1] | N-Methyl-4-(2-((((R)-1-(naphthalen-1-yl)ethyl)amino)methyl)-5-oxomorpholino)benzamide |

The below list of Examples-157 to 160 given in Table-11 were prepared by following the similar procedure as described in Step-1 of Example-69a, 69b then Boc deprotection by following the similar procedure as described in Step-2 of Example-69a, 69b using Intermediate-14 or Intermediate-15. Further, hydrochloride salts of these compounds were prepared by following the similar hydrochloride salt procedure as described in Example-1.

TABLE 11

| Example | Structure | Mass (m/z) and ¹H NMR |
|---|---|---|
| 157 | 4-(Cyclopropylmethyl)-6-((((R)-1-phenylethyl)amino)methyl)morpholin-3-one hydrochloride | m/z 347.1; ¹H NMR (400 MHz, DMSO): δ 10.17 (bs, 1H), 9.65 (bs, 1H), 7.59-7.56 (m, 2H), 7.47-7.38 (m, 3H), 4.38 (s, 2H), 4.20-4.04 (m, 3H), 3.40-3.27 (m, 2H), 3.03-2.98 (m, 3H), 1.61-1.59 (m, 3H), 0.91-0.89 (m, 1H), 0.45-0.42 (m, 2H), 0.20-0.17 (m, 2H). |
| 158 | 6-((((R)-1-(4-Fluoro-3-methoxyphenyl)ethyl)amino)methyl)-4-(4-fluorophenethyl)morpholin-3-one hydrochloride | m/z 405.1; ¹H NMR (400 MHz, DMSO): δ 9.90 (bs, 1H), 9.25 (bs, 1H), 7.54-7.49 (m, 1H), 7.31-7.22 (m, 3H), 7.12-7.07 (m, 3H), 4.39-4.37 (m, 1H), 4.17-4.05 (m, 4H), 3.87 (s, 3H), 3.57-3.52 (m, 1H), 3.24-3.21 (m, 2H), 2.98-2.93 (m, 1H), 2.81-2.73 (m, 2H), 2.73-2.67 (m, 1H), 1.60 (d, J = 6.4 Hz, 3H). |

TABLE 11-continued

| Example | Structure | Mass (m/z) and ¹H NMR |
|---|---|---|
| 159a, 159b | 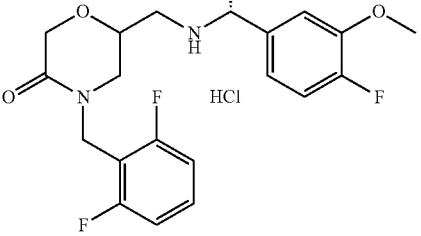<br>4-(2,6-Difluorobenzyl)-6-((((R)-1-(4-fluoro-3-methoxyphenyl)ethyl)amino)methyl)morpholin-3-one hydrochloride | m/z 409.29; 159a: ¹H NMR (400 MHz, DMSO): δ9.59 (bs, 1H), 9.33 (bs, 1H), 7.50-7.39 (m, 2H), 7.27-7.22 (m, 1H), 7.14-7.04 (m, 3H), 4.74 (d, J = 14.4 Hz, 1H), 4.49 (d, J = 14.4 Hz, 1H), 4.34-4.22 (m, 2H), 4.16-4.08 (m, 2H), 3.87 (s, 3H), 3.20-3.06 (m, 2H), 2.94-2.89 (m, 2H), 1.56 (d, J = 6.4 Hz, 3H). <br>159b: ¹H NMR (400 MHz, DMSO): δ9.98 (bs, 1H), 9.36 (bs, 1H), 7.45-7.39 (m, 2H), 7.27-7.22 (m, 1H), 7.13-7.05 (m, 3H), 4.74 (d, J = 14.8 Hz, 1H), 4.49 (d, J = 14.4 Hz, 1H), 4.33-4.12 (m, 4H), 3.85 (s, 3H), 3.16-2.99 (m, 3H), 2.94-2.86 (m, 1H), 1.56 (d, J = 6.4 Hz, 3H). |
| 160 | 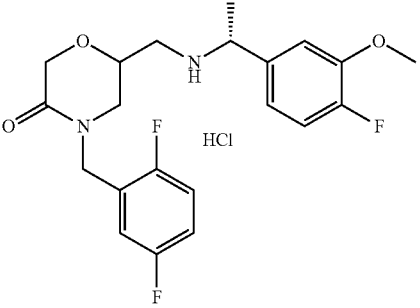<br>4-(2,5-Difluorobenzyl)-6-((((R)-1-(4-fluoro-3-methoxyphenyl)ethyl)amino)methyl)morpholin-3-one hydrochloride | m/z 409.29; 160a: ¹H NMR (400 MHz, DMSO): δ 9.55 (bs, 1H), 9.36 (bs, 1H), 7.50 (d, J = 6.8 Hz, 1H), 7.30-7.19 (m, 3H), 7.12-7.10 (m, 2H), 4.60-4.49 (m, 2H), 4.35-4.27 (m, 2H), 4.21-4.17 (m, 2H), 3.87 (s, 3H), 3.30-3.17 (m, 2H), 2.94-2.87 (m, 2H), 1.58 (d, J = 6.4 Hz, 3H). <br>160b: ¹H NMR (400 MHz, DMSO): δ 9.98 (bs, 1H), 9.25 (bs, 1H), 7.46-7.40 (m, 1H), 7.30-7.16 (m, 3H), 7.15-7.12 (m, 2H), 4.61-4.48 (m, 2H), 4.36-4.21 (m, 2H), 3.84 (s, 3H), 3.23-3.21 (m, 2H), 3.03-2.98 (m, 2H), 2.69-2.66 (m, 2H), 1.58 (d, J = 6.8 Hz, 3H). |

Example-161

6-((((S)-1-(Naphthalen-1-yl)ethyl)amino)methyl)-4-(4-(trifluoromethyl)phenyl)morpholin-3-one hydrochloride

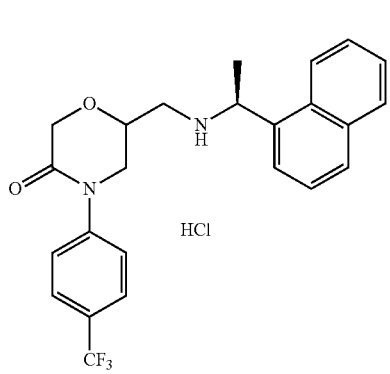 [SMILES: C[C@H](NCC1CN(c2ccc(C(F)(F)F)cc2)C(=O)CO1)c1cccc2ccccc12 ; Cl]

The title compound was prepared by following the similar procedure as described in step-1 of Example-49a, 49b by using Intermediate-17 and 1-bromo-4-(trifluoromethyl)benzene then Boc deprotection as described in step-2 Example-49a, 49b. m/z 429.20.

Example-162

(1S)-1-(Naphthalen-1-yl)-N-((4-(4-(trifluoromethyl)phenyl)morpholin-2-yl)methyl)ethanamine hydrochloride

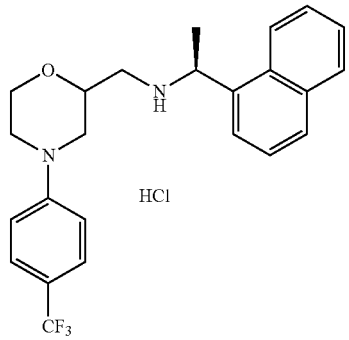 [SMILES: C[C@H](NCC1CN(c2ccc(C(F)(F)F)cc2)CCO1)c1cccc2ccccc12 ; Cl]

The title compound was prepared by following the similar reduction procedure as described in Step-2 of Example-3 by using Example-161 and borane-dimethyl sulfide complex. Further HCl salt of this example was prepared by following the similar hydrochloride salt procedure as described in Example-1. m/z 415.20.

Example-163

(1R)-N-((4-(Cyclopentylmethyl)morpholin-2-yl)methyl)-1-(4-fluoro-3-methoxyphenyl) ethanamine hydrochloride

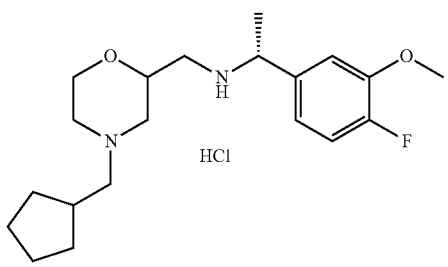 [SMILES: COc1cc([C@@H](C)NCC2CN(CC3CCCC3)CCO2)ccc1F ; Cl]

The title compound was prepared by following the similar reduction procedure as described in Step-2 of Example-3 by using Example-90 and borane-dimethyl sulfide complex. Further HCl salt of these exampleswere prepared by following the similar hydrochloride salt procedure as described in Example-1. Further HCl salt of these exampleswere prepared by following the similar hydrochloride salt procedure as described in Example-1.

m/z 351.47; $^1$H NMR (400 MHz, DMSO): δ 10.2 (bs, 1H), 9.2 (bs, 1H), 7.59 (d, J=6.8 Hz, 1H), 7.51 (d, J=8.4 Hz, 1H), 7.30-7.24 (m, 1H), 7.11-7.09 (m, 1H), 4.37-4.33 (m, 2H), 4.03 (m, 2H), 3.87 (S, 3H), 3.57-3.54 (m, 1H), 3.48-3.37 (m, 2H), 3.06-3.01 (m, 4H), 2.80-2.75 (m, 1H), 2.25-2.20 (m, 1H), 1.81-1.75 (m, 2H), 1.59 (d, J=6.8 Hz, 3H), 1.50-1.47 (m, 2H), 1.27-1.23 (m, 3H).

Example-164

2-Methyl-4-((2-((((R)-1-(naphthalen-1-yl)ethyl)amino)methyl)morpholino)methyl)benzoic acid hydrochloride

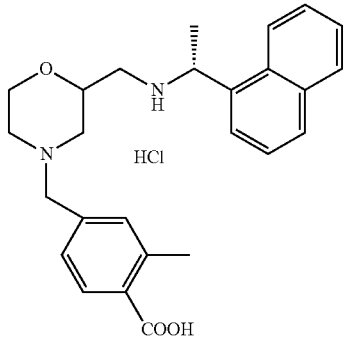 [SMILES: Cc1cc(CN2CCOC(CN[C@H](C)c3cccc4ccccc34)C2)ccc1C(=O)O ; Cl]

The title compound was prepared by following the similar procedure as described in Step-1 then Step-2 of Example-115a, 115b by taking Intermediate-13 and appropriately substituted halobenzyls. Further, hydrochloride salts of these compounds were prepared by following the similar hydrochloride salt procedure as described in Example-1.

m/z 418.97; $^1$H NMR (400 MHz, DMSO): 13.1 (bs, 1H), 9.6 (bs, 1H), 9.1 (bs, 1H), 8.09 (d, J=8.8 Hz 1H), 7.98-7.96 (m, 2H), 7.81 (d, J=8 Hz, 1H), 7.73-7.70 (m, 1H), 7.61-7.55 (m, 3H), 7.37-7.33 (m, 2H), 5.26 (m, 1H), 4.58-4.48 (m, 2H), 3.75-3.69 (m, 1H), 3.66-3.64 (m, 1H), 3.38-3.33 (m, 3H), 2.98-2.8 (m, 1H), 2.70 (s, 3H), 1.63 (d, J=8 Hz, 3H).

The below list of examples 165 to 197 given in Table-12a can be prepared by following the similar procedure as described in Step-1 then step-2 of Example-102a, 102b by taking Intermediate-13 and appropriately substituted halobenzene.

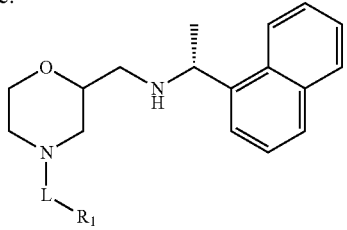

L and R$_1$ are as defined herein above;

TABLE 12a

| Example | L—R$_1$ | Chemical name |
|---|---|---|
| 165 | | 3-(2-((((R)-1-(Naphthalen-1-yl)ethyl)amino)methyl)morpholino)-5-(trifluoromethoxy)benzoic acid |

TABLE 12a-continued

| Example | L—R1 | Chemical name |
|---|---|---|
| 166 |  | 2-(3-(2-((((R)-1-(Naphthalen-1-yl)ethyl)amino)methyl)morpholino)-5-(trifluoromethyl)phenoxy)acetic acid |
| 167 |  | 3-Methyl-5-(2-((((R)-l-(naphthalen-1-yl)ethyl)amino)methyl)morpholino)benzoic acid |
| 168 |  | 3-Fluoro-5-(2-((((R)-1-(naphthalen-1-yl)ethyl)amino)methyl)morpholino)benzoic acid |
| 169 |  | 2-(3-Methyl-5-(2-((((R)-1-(naphthalen-1-yl)ethyl)amino)methyl)morpholino)phenoxy)acetic acid |
| 170 |  | 2-(3-Fluoro-5-(2-((((R)-1-(naphthalen-1-yl)ethyl)amino)methyl)morpholino)phenoxy)acetic acid |
| 171 |  | 3-(2-((((R)-1-(Naphthalen-1-yl)ethyl)amino)methyl)morpholino)-4-(trifluoromethyl)benzoic acid |

TABLE 12a-continued

| Example | L—R₁ | Chemical name |
| --- | --- | --- |
| 172 | | 5-(2-((((R)-1-(Naphthalen-1-yl)ethyl)amino)methyl)morpholino)-2-(trifluoromethyl)benzoic acid |
| 173 | | 4-(2-((((R)-1-(Naphthalen-1-yl)ethyl)amino)methyl)morpholino)-2-(trifluoromethyl)benzoic acid |
| 174 | | 2-(5-(2-((((R)-1-(Naphthalen-1-yl)ethyl)amino)methyl)morpholino)-2-(trifluoromethyl)phenoxy)acetic acid |
| 175 | | 2-(4-(2-((((R)-1-(Naphthalen-1-yl)ethyl)amino)methyl)morpholino)-2-(trifluoromethyl)phenoxy)acetic acid |
| 176 | | 2-(3-(2-((((R)-1-(Naphthalen-1-yl)ethyl)amino)methyl)morpholino)-2-(trifluoromethyl)phenoxy)acetic acid |

TABLE 12a-continued

| Example | L—R₁ | Chemical name |
|---|---|---|
| 177 | | 2-(4-(2-((((R)-1-(Naphthalen-1-yl)ethyl)amino)methyl)morpholino)-3-(trifluoromethyl)phenoxy)acetic acid |
| 178 | | 2-(2-Fluoro-5-(2-((((R)-1-(naphthalen-1-yl)ethyl)amino)methyl)morpholino)phenoxy)acetic acid |
| 179 | | 2-(2,6-Difluoro-3-(2-((((R)-1-(naphthalen-1-yl)ethyl)amino)methyl)morpholino)phenoxy)acetic acid |
| 180 | | 2-(2-Fluoro-3-(2-((((R)-1-(naphthalen-1-yl)ethyl)amino)methyl)morpholino)phenoxy)acetic acid |
| 181 | | 2-(4-Fluoro-3-(2-((((R)-1-(naphthalen-1-yl)ethyl)amino)methyl)morpholino)phenoxy)acetic acid |
| 182 | | 2-Fluoro-5-(2-((((R)-1-(naphthalen-1-yl)ethyl)amino)methyl)morpholino)benzoic acid |

TABLE 12a-continued

| Example | L—R₁ | Chemical name |
|---|---|---|
| 183 |  | 2,6-Difluoro-3-(2-((((R)-1-(naphthalen-1-yl)ethyl)amino)methyl)morpholino)benzoic acid |
| 184 |  | 2-Fluoro-3-(2-((((R)-1-(naphthalen-1-yl)ethyl)amino)methyl)morpholino)benzoic acid |
| 185 |  | 4-Fluoro-3-(2-((((R)-1-(naphthalen-1-yl)ethyl)amino)methyl)morpholino)benzoic acid |
| 186 |  | 2-Methyl-3-(2-((((R)-1-(naphthalen-1-yl)ethyl)amino)methyl)morpholino)benzoic acid |
| 187 |  | 4-Methyl-3-(2-((((R)-1-(naphthalen-1-yl)ethyl)amino)methyl)morpholino)benzoic acid |
| 188 |  | 2-Fluoro-4-(2-((((R)-1-(naphthalen-1-yl)ethyl)amino)methyl)morpholino)benzoic acid |

TABLE 12a-continued

| Example | L—R₁ | Chemical name |
| --- | --- | --- |
| 189 | | 3-Fluoro-4-(2-((((R)-1-(naphthalen-1-yl)ethyl)amino)methyl)morpholino)benzoic acid |
| 190 | | 3-Methyl-4-(2-((((R)-1-(naphthalen-1-yl)ethyl)amino)methyl)morpholino)benzoic acid |
| 191 | | 2-(3-Methyl-4-(2-((((R)-1-(naphthalen-1-yl)ethyl)amino)methyl)morpholino)phenoxy)acetic acid |
| 192 | | 2-(2-Methyl-4-(2-((((R)-1-(naphthalen-1-yl)ethyl)amino)methyl)morpholino)phenoxy)acetic acid |
| 193 | | 2-(2-Methyl-5-(2-((((R)-1-(naphthalen-1-yl)ethyl)amino)methyl)morpholino)phenoxy)acetic acid |

TABLE 12a-continued

| Example | L—R₁ | Chemical name |
|---|---|---|
| 194 | 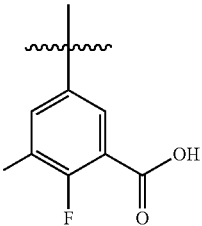 | 2,3-Difluoro-5-(2-((((R)-1-(naphthalen-1-yl)ethyl)amino)methyl)morpholino)benzoic acid |
| 195 | 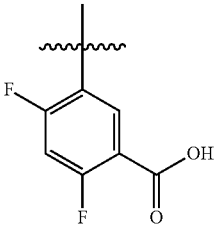 | 2,4-Difluoro-5-(2-((((R)-1-(naphthalen-1-yl)ethyl)amino)methyl)morpholino)benzoic acid |
| 196 | 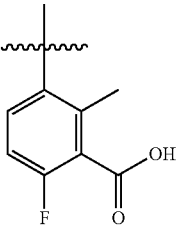 [SMILES: *c1ccc(F)c(C(=O)O)c1F] | 6-Fluoro-2-methyl-3-(2-((((R)-1-(naphthalen-1-yl)ethyl)amino)methyl)morpholino)benzoic acid |
| 197 | 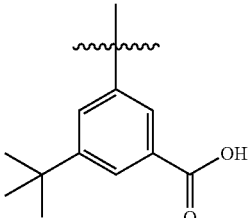 | 3-(tert-Butyl)-5-(2-((((R)-1-(naphthalen-1-yl)ethyl)amino)methyl)morpholino)benzoic acid |

The below list of examples 198 to 199 given in Table-12b can be prepared by following the similar procedure as described in Step-1 then step-2 of Example-115a, 115b by taking Intermediate-13 and appropriately substituted benzyl-halide.

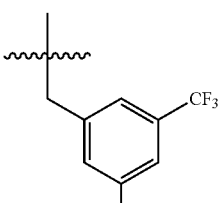

L and R₁ are as defined herein above;

TABLE 12b

| Example | L—R₁ | Chemical name |
|---|---|---|
| 198 | 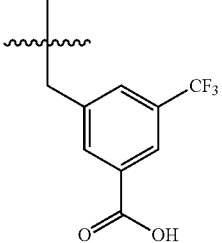 [SMILES: *Cc1cc(C(=O)O)cc(C(F)(F)F)c1] | 3-((2-((((R)-1-(Naphthalen-1-yl)ethyl)amino)methyl)morpholino)methyl)-5-(trifluoromethyl)benzoic acid |

TABLE 12b-continued

| Example | L—R₁ | Chemical name |
|---|---|---|
| 199 | | 3-methyl-5-((2-((((R)-1-(Naphthalen-1-yl)ethyl)amino)methyl)morpholino)methyl)benzoic acid |

The below list of examples 200 to 206 given in Table-12c can be prepared by following the similar procedure as described herein above.

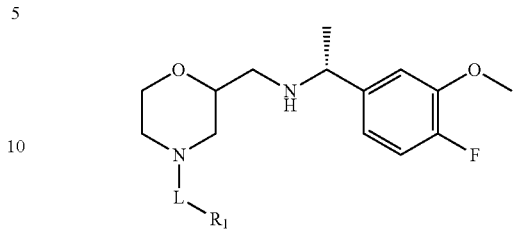

L and R₁ are as defined herein above;

TABLE 12c

| Example | L—R₁ | chemical name |
|---|---|---|
| 200 | | 3-(2-((((R)-1-(4-Fluoro-3-methoxyphenyl)ethyl)amino)methyl)morpholino)-5-(trifluoromethoxy)benzoic acid |
| 201 | | 2-(3-(2-((((R)-1-(4-Fluoro-3-methoxyphenyl)ethyl)amino)methyl)morpholino)-5-(trifluoromethyl)phenoxy)acetic acid |
| 202 | | 3-(2-((((R)-1-(4-Fluoro-3-methoxyphenyl)ethyl)amino)methyl)morpholino)-5-methylbenzoic acid |
| 203 | | 3-Fluoro-5-(2-((((R)-1-(4-fluoro-3-methoxyphenyl)ethyl)amino)methyl)morpholino)benzoic acid |

TABLE 12c-continued

| Example | L—R₁ | chemical name |
|---|---|---|
| 204 | (structure: benzoic acid with CF₃ and attachment point) | 5-(2-((((R)-1-(4-Fluoro-3-methoxyphenyl)ethyl)amino)methyl)morpholino)-2-(trifluoromethyl)benzoic acid |
| 205 | (structure: benzoic acid with CF₃ and attachment point) | 4-(2-((((R)-1-(4-Fluoro-3-methoxyphenyl)ethyl)amino)methyl)morpholino)-(trifluoromethyl)benzoic acid |
| 206 | (structure: benzoic acid with CF₃ and attachment point) | 3-(2-((((R)-1-(4-Fluoro-3-methoxyphenyl)ethyl)amino)methyl)morpholino)-5-(trifluoromethyl)benzoic acid |

The below list of examples 207 to 210 given in Table-12d can be prepared by following the similar procedure as described in Step-1 then step-2 of Example-102a, 102b by taking Intermediate-4 and appropriately substituted halobenzene.

L and R₁ are as defined herein above;

TABLE 12d

| Example | L—R₁ | Chemical name |
|---|---|---|
| 207 | (structure: benzoic acid with CF₃ and attachment point) | 3-(3-((((R)-1-(Naphthalen-1-yl)ethyl)amino)methyl)morpholino)-5-(trifluoromethyl)benzoic acid |

TABLE 12d-continued

| Example | L—R$_1$ | Chemical name |
|---|---|---|
| 208 | (structure) | 2-(3-(3-((((R)-1-(Naphthalen-1-yl)ethyl)amino)methyl)morpholino)-5-(trifluoromethyl)phenoxy)acetic acid |
| 209 | (structure) | 4-(3-((((R)-1-(Naphthalen-1-yl)ethyl)amino)methyl)morpholino)-2-(trifluoromethyl)benzoic acid |
| 210 | (structure) | 5-(3-((((R)-1-(Naphthalen-1-yl)ethyl)amino)methyl)morpholino)-2-(trifluoromethyl)benzoic acid |

Pharmacological Activity

Certain illustrative compounds within the scope of the invention are screened for CaSR activity according to the procedure given below. The screening of the compounds may also be carried by other methods and procedures known to skilled in the art.

In-Vitro Assay Method of Calcimemtics Through Modulation of Calcium Sensing Receptor (CaSR):

The ability of the compounds to modulate Calcium sensing receptor is determined by measuring an increase in intracellular calcium $[Ca^{2+}{}_i]$. Stably transfected HEK293 cells expressing hCaSR_pTriEx-3 hygro vector are developed. Cells are grown overnight on a 96-well plate to 80% confluency in Ham's F12 containing 20% FBS at 37° C., 5% $CO_2$ Subsequently, cells are washed extensively with 20 mM HEPES buffer containing 126 mM $NaCl_2$, 1 mM $MgCl_2$ and 4 mM $KCl_2$ to remove serum components that might interfere with the assay. Cells are loaded with calcium sensing Fluo4NW dye in HEPES base buffer containing 0.1% BSA and 1 mg/ml glucose for 30 minutes to measure changes in intracellular calcium. The activities of the compounds are measured in FLIPR using 0.3 mM $CaCl_2$ in 20 mM HEPES base buffer. The effectiveness of the compound to modulate receptor activity is determined by calculating the $EC_{50}$ responses for that compound in an 8-point assay and plotted using GraphPad Prism 5.

The compounds prepared were tested using the above assay procedure and the results obtained are given below. The $EC_{50}$ (nM) values of few representative compounds are set forth in Table-13.

TABLE 13

| Example | $EC_{50}$ in range |
|---|---|
| 1a, 1b, 2a, 5b, 9, 10b, 11a, 25a, 26a, 27b, 28, 33a, 54, 61, 62a, 70a, 72a, 72b, 76, 81, 82, 97a, 97b, 98a, 98b, 120, 134, 135, 150a, 150b | less than 20 nM |
| 3, 4a, 6a, 7b, 15, 17, 22, 25b, 29, 33b, 35b, 50, 59, 62b, 101a, 105, 108a, 160a | between 20.01-50 nM |
| 5a, 8, 10a, 12, 27a, 32, 36a, 37b, 69a, 60, 93b, 96, 104a, 110a, 112a, 113a, 113b, 136b, 147, 152b | between 50.01-200 nM |

Through the use of above described assay method, compounds were found to exhibit agonistic activity thus to be particularly well suited for the treatment of the diseases or disorders as described herein above.

All patents, patent applications and publications cited in this application are hereby incorporated by reference in their entirety for all purposes to the same extent as if each individual patent, patent application or publication were so individually denoted.

Although certain embodiments and examples have been described in detail above, those having ordinary skill in the art will clearly understand that many modifications are possible in the embodiments and examples without departing from the teachings thereof. All such modifications are intended to be encompassed within the below claims of the invention.

The invention claimed is:

1. A compound of Formula (I):

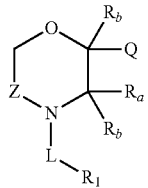

(I)

wherein,
Q is

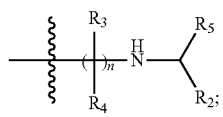

$R_a$ is hydrogen;
$R_b$ is hydrogen;
L is a bond or —$(CR_cR_d)_m$;
$R_c$ and $R_d$ are independently selected from hydrogen or substituted or unsubstituted alkyl;
$R_1$ is

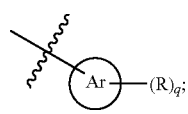

ring Ar is phenyl or naphthyl;
R, which may be same or different at each occurrence, is independently selected from halogen, nitro, cyano, substituted or unsubstituted alkyl, substituted or unsubstituted alkenyl, substituted or unsubstituted alkynyl, substituted or unsubstituted haloalkyl, —$OR_6$, —$C(O)R_6$, —$(CR_eR_f)_{0-3}$—$C(O)OR_6$, —$(CR_eR_f)_{1-2}$cycloalkylene-$C(O)OR_6$, -cycloalkylene $(CR_eR_f)_{0-2}$—$C(O)OR_6$, —$O(CR_eR_f)_{0-3}$—$C(O)OR_6$, —O-cycloalkylene-$C(O)OR_6$, —$C(O)NR_7$—$(CR_eR_f)_{1-2}$—$C(O)OR_6$, —$C(O)NR_7R_8$, —$S(O)_{0-2}R_6$, and —$S(O)_2NR_7R_8$;
$R_e$ and $R_f$ are independently hydrogen or substituted or unsubstituted alkyl;
$R_2$ is substituted or unsubstituted aryl;
$R_3$ and $R_4$ are independently selected from hydrogen, halogen, and substituted or unsubstituted alkyl;
$R_5$ is substituted or unsubstituted alkyl or haloalkyl;
$R_6$, which may be same or different at each occurrence, is independently selected from hydrogen, substituted or unsubstituted alkyl and substituted or unsubstituted haloalkyl;
$R_7$ and $R_8$, which may be same or different at each occurrence, are independently selected from hydrogen, substituted or unsubstituted alkyl, substituted or unsubstituted cycloalkyl, and substituted or unsubstituted aryl;
Z is —$CR_gR_h$—;
$R_g$ and $R_h$ are hydrogen;
'm' is an integer ranging from 1 to 3, both inclusive;
'n' is an integer ranging from 1 to 3, both inclusive; and
'q' is an integer ranging from 0 to 4, both inclusive;
or its pharmaceutically acceptable salt thereof.

2. The compound of claim 1, having the Formula (II):

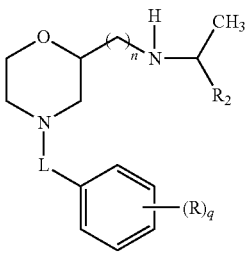

(II)

wherein,
L is a bond or —$(CR_cR_d)_m$;
$R_2$ is substituted or unsubstituted phenyl or substituted or unsubstituted naphthyl;
$R_c$, $R_d$, R, 'm', 'n' and 'q' are as defined in claim 1;
or pharmaceutically acceptable salt thereof.

3. The compound of claim 1, wherein L is a bond or —$(CR_cR_d)_m$; wherein $R_c$, $R_d$ are hydrogen or substituted or unsubstituted alkyl; and 'm' is 1 or 2.

4. The compound of claim 1, wherein $R_1$ is

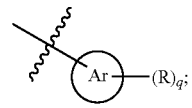

wherein ring Ar is phenyl or naphthyl;
R, which may be same or different at each occurrence, is independently selected from halogen, nitro, cyano, substituted or unsubstituted alkyl, substituted or unsubstituted alkenyl, substituted or unsubstituted alkynyl, substituted or unsubstituted haloalkyl, —$OR_6$, —$C(O)R_6$, —$(CR_eR_f)_{0-3}$—$C(O)OR_6$, —$(CR_eR_f)_{1-2}$cycloalkylene-$C(O)OR_6$, -cycloalkylene $(CR_eR_f)_{0-2}$—$C(O)OR_6$, —$O(CR_eR_f)_{0-3}$—$C(O)OR_6$, —O-cycloalkylene-$C(O)OR_6$, —$C(O)NR_7$—$(CR_eR_f)_{1-2}$—$C(O)OR_6$, —$C(O)NR_7R_8$, —$S(O)_{0-2}R_6$, and —$S(O)_2NR_7R_8$;
wherein $R_6$ is hydrogen or alkyl; $R_7$ and $R_8$ are hydrogen or substituted or unsubstituted alkyl; $R_e$ and $R_f$ are independently hydrogen or substituted or unsubstituted alkyl; and 'q' is 0 to 3;
or its pharmaceutically acceptable salt thereof.

5. The compound of claim 1, wherein Q is

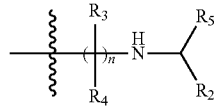

where $R_3$ and $R_4$ are hydrogen; 'n' is 1 or 2; $R_2$ is substituted or unsubstituted aryl; $R_5$ is alkyl; $R_a$ is hydrogen; and $R_b$ is hydrogen.

6. The compound of claim 5, wherein the aryl is substituted or unsubstituted wherein the substituents may be one or more, same or different and are independently selected from halogen, substituted or unsubstituted alkyl, substituted or unsubstituted haloalkyl, substituted or unsubstituted alkoxy or substituted or unsubstituted haloalkoxy.

7. The compound of claim 1, wherein L is a bond, —(CR$_c$R$_d$)$_m$, wherein R$_c$ and R$_d$ are hydrogen or substituted or unsubstituted alkyl, 'm' is 1 or 2; and R$_1$ is

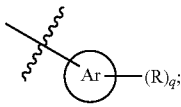

wherein ring Ar is phenyl or naphthyl;

R, which may be same or different at each occurrence, is independently selected from halogen, nitro, cyano, substituted or unsubstituted alkyl, substituted or unsubstituted alkenyl, substituted or unsubstituted alkynyl, substituted or unsubstituted haloalkyl, —OR$_6$, —C(O)R$_6$, —(CR$_e$R$_f$)$_{0-3}$—C(O)OR$_6$, —(CR$_e$R$_f$)$_{1-2}$cycloalkylene-C(O)OR$_6$, -cycloalkylene (CR$_e$R$_f$)$_{1-2}$—C(O)OR$_6$, —O(CR$_e$R$_f$)$_{0-3}$—C(O)OR$_6$, —O-cycloalkylene-C(O)OR$_6$, —C(O)NR$_7$—(CR$_e$R$_f$)$_{1-2}$—C(O)OR$_6$, —C(O)NR$_7$R$_8$, —S(O)$_{0-2}$R$_6$, and —S(O)$_2$NR$_7$R$_8$; wherein R$_6$ is hydrogen or alkyl; R$_7$ and R$_8$ are hydrogen or substituted or unsubstituted alkyl; R$_e$ and R$_f$ may be same or different and are independently hydrogen or substituted or unsubstituted alkyl; and 'q' is 0 to 3; or its pharmaceutically acceptable salt thereof.

8. The compound of claim 1, wherein Q is

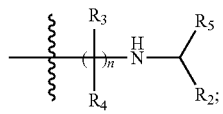

R$_a$ is hydrogen; R$_b$ is hydrogen; Z is —CH$_2$—;
L is a bond or —(CR$_c$R$_d$)$_m$;
R$_1$ is

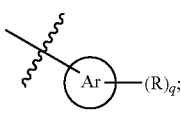

ring Ar is phenyl or naphthyl;

R, which may be same or different at each occurrence, is independently selected from halogen, nitro, cyano, substituted or unsubstituted alkyl, substituted or unsubstituted alkenyl, substituted or unsubstituted alkynyl, substituted or unsubstituted haloalkyl, —OR$_6$, —CR$_e$R$_f$)$_{0-3}$—C(O)OR$_6$, —(CR$_e$R$_f$)$_{1-2}$cycloalkylene-C(O)OR$_6$, -cycloalkylene(CR$_e$R$_f$)$_{1-2}$—C(O)OR$_6$, —O(CR$_e$R$_f$)$_{0-3}$—C(O)OR$_6$, —O-cycloalkylene-C(O)OR$_6$, —C(O)NR$_7$—(CR$_e$R$_f$)$_{1-2}$—C(O)OR$_6$, —C(O)NR$_7$R$_8$, —S(O)$_{0-2}$R$_6$, and —S(O)$_2$NR$_7$R$_8$; wherein R$_6$ is hydrogen or alkyl;

R$_7$ and R$_8$ are hydrogen or substituted or unsubstituted alkyl;

R$_e$ and R$_f$ may be same or different and are independently hydrogen or substituted or unsubstituted alkyl; 'q' is 0 to 3;

R$_2$ is substituted or unsubstituted aryl, wherein the substituent(s) may be one or more same or different and independently selected from halogen, substituted or unsubstituted alkyl, substituted or unsubstituted haloalkyl, substituted or unsubstituted alkoxy and substituted or unsubstituted haloalkoxy;

R$_3$ and R$_4$ are hydrogen; and R$_5$ is substituted or unsubstituted alkyl or substituted or unsubstituted haloalkyl; or a pharmaceutically acceptable salt thereof.

9. The compound of claim 1, wherein the pharmaceutically acceptable salt is hydrochloride salt.

10. A compound which is selected from:
(1R)-N-((4-(3-Fluorophenyl)morpholin-2-yl)methyl)-1-(naphthalen-1-yl)ethanamine hydrochloride;
(1R)-1-(Naphthalen-1-yl)-N-((4-(3-(trifluoromethyl)phenyl)morpholin-2-yl)methyl)ethanamine;
(1R)-1-(3-Methoxyphenyl)-N-((4-(3-methoxyphenyl)morpholin-2-yl)methyl)ethanamine;
(1R)-1-(3-Methoxyphenyl)-N-((4-(3-(trifluoromethyl)phenyl)morpholin-2-yl)methyl)ethanamine;
(1R)-N-((4-(3-Methoxyphenyl)morpholin-2-yl)methyl)-1-(naphthalen-1-yl)ethanamine hydrochloride;
(1R)-1-(Naphthalen-1-yl)-N-((4-phenylmorpholin-2-yl)methyl)ethanamine hydrochloride;
(1R)-1-(Naphthalen-1-yl)-N-((4-(p-tolyl)morpholin-2-yl)methyl)ethanamine hydrochloride;
(1R)-N-((4-(4-Fluorophenyl)morpholin-2-yl)methyl)-1-(naphthalen-1-yl)ethanamine hydrochloride;
(1R)-N-((4-(2-Fluorophenyl)morpholin-2-yl)methyl)-1-(naphthalen-1-yl)ethanamine hydrochloride;
(1R)-N-((4-(4-Fluoro-3-methoxyphenyl)morpholin-2-yl)methyl)-1-(naphthalen-1-yl)ethanamine hydrochloride;
(1R)-N-((4-(3-Fluorophenyl)morpholin-2-yl)methyl)-1-(3-methoxyphenyl)ethanamine dihydrochloride;
(1R)-1-(3-Methoxyphenyl)-N-((4-(3-(trifluoromethyl)phenyl)morpholin-2-yl)methyl)ethanamine hydrochloride;
(1R)-1-(Naphthalen-1-yl)-N-((4-(4-(trifluoromethyl)phenyl)morpholin-2-yl)methyl)ethanamine hydrochloride;
(1R)-N-((4-(2,4-difluorophenyl)morpholin-2-yl)methyl)-1-(3-methoxyphenyl)ethanamine hydrochloride;
2-(4-(2-(2-(((R)-1-(Naphthalen-1-yl)ethyl)amino)ethyl)morpholino)phenoxy)acetic acid hydrochloride;
2-Methyl-5-(2-(2-(((R)-1-(naphthalen-1-yl)ethyl)amino)ethyl)morpholino)benzoic acid;
2-Methyl-4-(2-(2-(((R)-1-(naphthalen-1-yl)ethyl)amino)ethyl)morpholino)benzoic acid;
(1R)-1-(Naphthalen-1-yl)-N-(2-(4-(4-(trifluoromethyl)phenyl)morpholin-2-yl)ethyl)ethanamine;
2-(2-Methyl-4-(2-(2-(((R)-1-(naphthalen-1-yl)ethyl)amino)ethyl)morpholino)phenoxy)acetic acid hydrochloride;
2-(2-Methyl-5-(2-(2-(((R)-1-(naphthalen-1-yl)ethyl)amino)ethyl)morpholino)phenoxy)acetic acid hydrochloride;
3-(2-Methyl-5-(2-(2-(((R)-1-(naphthalen-1-yl)ethyl)amino)ethyl)morpholino)phenyl)propanoic acid hydrochloride;
4-(2-(2-(((R)-1-(Naphthalen-1-yl)ethyl)amino)ethyl)morpholino)-2-(trifluoromethyl)benzoic acid hydrochloride;
5-(2-(2-(((R)-1-(Naphthalen-1-yl)ethyl)amino)ethyl)morpholino)-2-(trifluoromethyl)benzoic acid hydrochloride;
3-(2-(2-(((R)-1-(Naphthalen-1-yl)ethyl)amino)ethyl)morpholino)benzoicacid hydrochloride;
4-(2-(2-(((R)-1-(Naphthalen-1-yl)ethyl)amino)ethyl)morpholino)benzoicacid hydrochloride;
2-(3-(2-(2-(((R)-1-(Naphthalen-1-yl)ethyl)amino)ethyl)morpholino)phenoxy)acetic acid hydrochloride;

2,6-Dimethyl-3-(2-(2-(((R)-1-(naphthalen-1-yl)ethyl)amino)ethyl)morpholino)benzoic acid;
4-((2-(2-(((R)-1-(Naphthalen-1-yl)ethyl)amino)ethyl)morpholino)methyl)benzoic acid hydrochloride;
3-((2-(2-(((R)-1-(Naphthalen-1-yl)ethyl)amino)ethyl)morpholino)methyl)benzoic acid dihydrochloride;
3-Methoxy-4-(2-((((R)-1-(naphthalen-1-yl)ethyl)amino)methyl)morpholino)benzoic acid hydrochloride;
4-(2-((((R)-1-(Naphthalen-1-yl)ethyl)amino)methyl)morpholino)-2-(trifluoromethyl) benzoic acid hydrochloride;
3,5-Difluoro-4-(2-((((R)-1-(naphthalen-1-yl)ethyl)amino)methyl)morpholino)benzoic acid hydrochloride;
(1R)-1-(3-Methoxyphenyl)-N-((4-(p-tolyl)morpholin-2-yl)methyl)ethanamine hydrochloride;
(1R)-1-(3-Methoxyphenyl)-N-((4-(m-tolyl)morpholin-2-yl)methyl)ethanamine hydrochloride;
(1R)-N-((4-(3,4-Difluorophenyl)morpholin-2-yl)methyl)-1-(3-methoxyphenyl)ethanamine hydrochloride;
2-Methyl-4-(2-((((R)-1-(naphthalen-1-yl)ethyl)amino)methyl)morpholino)benzoic acid hydrochloride;
4-(2-((((R)-1-(3-Methoxyphenyl)ethyl)amino)methyl)morpholino)-N-methylbenzamide hydrochloride;
Methyl3-(2-((((R)-1-(3-methoxyphenyl)ethyl)amino)methyl)morpholino)benzoate;
Methyl 3-(2-((((R)-1-(naphthalen-1-yl)ethyl)amino)methyl)morpholino)benzoate;
Methyl 4-(2-((((R)-1-(naphthalen-1-yl)ethyl)amino)methyl)morpholino)benzoate;
3-(2-((((R)-1-(3-Methoxyphenyl)ethyl)amino)methyl)morpholino)-N,N-dimethyl benzamide;
N,N-Dimethyl-3-(2-((((R)-1-(naphthalen-1-yl)ethyl)amino)methyl)morpholino)benzamide;
4-(2-((((R)-1-(3-Methoxyphenyl)ethyl)amino)methyl)morpholino)-N,N-dimethyl benzamide hydrochloride;
N,N-Dimethyl-4-(2-((((R)-1-(naphthalen-1-yl)ethyl)amino)methyl)morpholino)benzamide;
3-(2-((((R)-1-(3-methoxyphenyl)ethyl)amino)methyl)morpholino)benzoic acid hydrochloride;
3-(2-((((R)-1-(Naphthalen-1-yl)ethyl)amino)methyl)morpholino)benzoic acid hydrochloride;
4-(2-((((R)-1-(Naphthalen-1-yl)ethyl)amino)methyl)morpholino)benzoic acid hydrochloride;
4-(2-((((R)-1-(3-Methoxyphenyl)ethyl)amino)methyl)morpholino)benzoic acid hydrochloride;
2-(4-(2-((((R)-1-(Naphthalen-1-yl)ethyl)amino)methyl)morpholino)phenyl)acetic acid hydrochloride;
3-(2-((((R)-1-(Naphthalen-1-yl)ethyl)amino)methyl)morpholino)-5-(trifluoromethyl) benzoic acid hydrochloride;
6-((((S)-1-(Naphthalen-1-yl)ethyl)amino)methyl)-4-(4-(trifluoromethyl)phenyl)morpholin-3-one hydrochloride;
(1R)-N-((4-(Cyclopentylmethyl)morpholin-2-yl)methyl)-1-(4-fluoro-3-methoxyphenyl)ethanamine hydrochloride;
2-Methyl-4-((2-((((R)-1-(naphthalen-1-yl)ethyl)amino)methyl)morpholino)methyl)benzoic acid hydrochloride;
3-(2-((((R)-1-(Naphthalen-1-yl)ethyl)amino)methyl)morpholino)-5-(trifluoromethoxy)benzoic acid;
2-(3-(2-((((R)-1-(Naphthalen-1-yl)ethyl)amino)methyl)morpholino)-5-(trifluoromethyl)phenoxy)acetic acid;
3-Methyl-5-(2-((((R)-1-(naphthalen-1-yl)ethyl)amino)methyl)morpholino)benzoic acid;
3-Fluoro-5-(2-((((R)-1-(naphthalen-1-yl)ethyl)amino)methyl)morpholino)benzoic acid;
2-(3-Methyl-5-(2-((((R)-1-(naphthalen-1-yl)ethyl)amino)methyl)morpholino)phenoxy)acetic acid;
2-(3-Fluoro-5-(2-((((R)-1-(naphthalen-1-yl)ethyl)amino)methyl)morpholino)phenoxy)acetic acid;
3-(2-((((R)-1-(Naphthalen-1-yl)ethyl)amino)methyl)morpholino)-4-(trifluoromethyl)benzoic acid;
5-(2-((((R)-1-(Naphthalen-1-yl)ethyl)amino)methyl)morpholino)-2-(trifluoromethyl)benzoic acid;
4-(2-((((R)-1-(Naphthalen-1-yl)ethyl)amino)methyl)morpholino)-2-(trifluoromethyl)benzoic acid;
2-(5-(2-((((R)-1-(Naphthalen-1-yl)ethyl)amino)methyl)morpholino)-2-(trifluoromethyl)phenoxy)acetic acid;
2-(4-(2-((((R)-1-(Naphthalen-1-yl)ethyl)amino)methyl)morpholino)-2-(trifluoromethyl)phenoxy)acetic acid;
2-(3-(2-((((R)-1-(Naphthalen-1-yl)ethyl)amino)methyl)morpholino)-2-(trifluoromethyl)phenoxy)acetic acid;
2-(4-(2-((((R)-1-(Naphthalen-1-yl)ethyl)amino)methyl)morpholino)-3-(trifluoromethyl)phenoxy)acetic acid;
2-(2-Fluoro-5-(2-((((R)-1-(naphthalen-1-yl)ethyl)amino)methyl)morpholino)phenoxy)acetic acid;
2-(2,6-Difluoro-3-(2-((((R)-1-(naphthalen-1-yl)ethyl)amino)methyl)morpholino)phenoxy)acetic acid;
2-(2-Fluoro-3-(2-((((R)-1-(naphthalen-1-yl)ethyl)amino)methyl)morpholino)phenoxy)acetic acid;
2-(4-Fluoro-3-(2-((((R)-1-(naphthalen-1-yl)ethyl)amino)methyl)morpholino)phenoxy)acetic acid;
2-Fluoro-5-(2-((((R)-1-(naphthalen-1-yl)ethyl)amino)methyl)morpholino)benzoic acid;
2,6-Difluoro-3-(2-((((R)-1-(naphthalen-1-yl)ethyl)amino)methyl)morpholino)benzoic acid;
2-Fluoro-3-(2-((((R)-1-(naphthalen-1-yl)ethyl)amino)methyl)morpholino)benzoic acid;
4-Fluoro-3-(2-((((R)-1-(naphthalen-1-yl)ethyl)amino)methyl)morpholino)benzoic acid;
2-Methyl-3-(2-((((R)-1-(naphthalen-1-yl)ethyl)amino)methyl)morpholino)benzoic acid;
4-Methyl-3-(2-((((R)-1-(naphthalen-1-yl)ethyl)amino)methyl)morpholino)benzoic acid;
2-Fluoro-4-(2-((((R)-1-(naphthalen-1-yl)ethyl)amino)methyl)morpholino)benzoic acid;
3-Fluoro-4-(2-((((R)-1-(naphthalen-1-yl)ethyl)amino)methyl)morpholino)benzoic acid;
3-Methyl-4-(2-((((R)-1-(naphthalen-1-yl)ethyl)amino)methyl)morpholino)benzoic acid;
2-(3-Methyl-4-(2-((((R)-1-(naphthalen-1-yl)ethyl)amino)methyl)morpholino)phenoxy) acetic acid;
2-(2-Methyl-4-(2-((((R)-1-(naphthalen-1-yl)ethyl)amino)methyl)morpholino)phenoxy)acetic acid;
2-(2-Methyl-5-(2-((((R)-1-(naphthalen-1-yl)ethyl)amino)methyl)morpholino)phenoxy)acetic acid;
2,3-Difluoro-5-(2-((((R)-1-(naphthalen-1-yl)ethyl)amino)methyl)morpholino)benzoic acid;
2,4-Difluoro-5-(2-((((R)-1-(naphthalen-1-yl)ethyl)amino)methyl)morpholino)benzoic acid;
6-Fluoro-2-methyl-3-(2-((((R)-1-(naphthalen-1-1)ethyl)amino)methyl)morpholino)benzoic acid;
3-(tert-butyl)-5-(2-((((R)-1-(Naphthalen-1-yl)ethyl)amino)methyl)morpholino)benzoic acid;
3-((2-((((R)-1-(Naphthalen-1-yl)ethyl)amino)methyl)morpholino)methyl)-5-(trifluoromethyl)benzoic acid;
3-Methyl-5-((2-((((R)-1-(naphthalen-1-yl)ethyl)amino)methyl)morpholino)methyl)benzoic acid;
3-(2-((((R)-1-(4-Fluoro-3-methoxyphenyl)ethyl)amino)methyl)morpholino)-5-(trifluoromethoxy)benzoic acid;
2-(3-(2-((((R)-1-(4-Fluoro-3-methoxyphenyl)ethyl)amino)methyl)morpholino)-5-(trifluoromethyl)phenoxy)acetic acid;

3-(2-((((R)-1-(4-Fluoro-3-methoxyphenyl)ethyl)amino)methyl)morpholino)-5-methylbenzoic acid;

3-Fluoro-5-(2-(((((R)-1-(4-fluoro-3-methoxyphenyl)ethyl)amino)methyl)morpholino)benzoic acid;

5-(2-((((R)-1-(4-Fluoro-3-methoxyphenyl)ethyl)amino)methyl)morpholino)-2-(trifluoromethyl)benzoic acid;

4-(2-((((R)-1-(4-Fluoro-3-methoxyphenyl)ethyl)amino)methyl)morpholino)-2-(trifluoromethyl)benzoic acid;

3-(2-((((R)-1-(4-Fluoro-3-methoxyphenyl)ethyl)amino)methyl)morpholino)-5-(trifluoromethyl)benzoic acid; and or pharmaceutically acceptable salt thereof or stereoisomer thereof.

11. A pharmaceutical composition comprising one or more compounds of Formula (I) according to claim 1, and one or more pharmaceutically acceptable excipients.

* * * * *